(12) United States Patent
Bearss et al.

(10) Patent No.: US 11,161,852 B1
(45) Date of Patent: Nov. 2, 2021

(54) INHIBITORS OF NEK7 KINASE

(71) Applicant: Halia Therapeutics, Inc., Salt Lake City, UT (US)

(72) Inventors: David James Bearss, Salt Lake City, UT (US); John Sai Keong Kauwe, III, Salt Lake City, UT (US); Alexis Henri Abel Mollard, Lehi, UT (US)

(73) Assignee: HALIA THERAPEUTICS, INC., Salt Lake City, UT (US)

( * ) Notice: Subject to any disclaimer, the term of this patent is extended or adjusted under 35 U.S.C. 154(b) by 0 days.

(21) Appl. No.: 17/315,209

(22) Filed: May 7, 2021

Related U.S. Application Data

(60) Provisional application No. 63/022,159, filed on May 8, 2020, provisional application No. 63/170,761, filed on Apr. 5, 2021.

(51) Int. Cl.
*C07D 471/04* (2006.01)
*C07D 487/04* (2006.01)
*A61P 35/02* (2006.01)

(52) U.S. Cl.
CPC ............ *C07D 487/04* (2013.01); *A61P 35/02* (2018.01); *C07D 471/04* (2013.01)

(58) Field of Classification Search
CPC ............................ C07D 471/04; C07D 487/04
USPC .................................................. 514/210.21
See application file for complete search history.

(56) References Cited

U.S. PATENT DOCUMENTS

| | | | |
|---|---|---|---|
| 5,033,252 | A | 7/1991 | Carter |
| 5,052,558 | A | 10/1991 | Carter |
| 5,323,907 | A | 6/1994 | Kalvelage |

FOREIGN PATENT DOCUMENTS

| | | |
|---|---|---|
| CN | 111646995 A | 9/2020 |
| WO | 2010/036630 A2 | 4/2010 |
| WO | 2011/022473 A1 | 2/2011 |
| WO | 2011/130628 A1 | 10/2011 |
| WO | 2013/104561 A1 | 7/2013 |
| WO | 2014/184069 A1 | 11/2014 |
| WO | 2016/075224 A1 | 5/2016 |
| WO | 2017/060874 A1 | 4/2017 |
| WO | 2017/172093 A1 | 10/2017 |
| WO | 2017/220477 A1 | 12/2017 |
| WO | 2018/015879 A1 | 1/2018 |
| WO | 2019/092170 A1 | 5/2019 |
| WO | 2019/192962 A1 | 10/2019 |

OTHER PUBLICATIONS

Yuan et al., Journal of Medicinal Chemistry (2019), 62(8), 4158-4173.*

Berge et al., "Pharmaceutical Salts," *J. Pharm. Sci.* 66(1): 1-19, 1977.
Dar et al., "Chemical genetic discovery of targets and anti-targets for cancer polypharmacology" *Nature* 486(7401):80-84, 2012.
Gottlieb et al., "NMR Chemical Shifts of Common Laboratory Solvents as Trace Impurities," *J. Org. Chem.* 62:7512-7515, 1997.
Johnson et al., "A Reliable Synthesis of 3-Amino-5-Alkyl and 5-Amino-3-Alkyl Isoxazoles," *Synthesis* 45(2): 171-173, 2013.
Rowbottom et al., "Identification of 1-(3-(6,7-Dimethoxyquinazolin-4-yloxy)phenyl)-3-(5-(1,1,1-trifluoro-2-methylpropan-2-yl)isoxazol-3-yl)urea Hydrochloride (CEP-32496), a Highly Potent and Orally Efficacious Inhibitor of V-RAF Murine Sarcoma Viral Oncogene Homologue B1 (BRAF) V600E," *J. Med. Chem.* 55(3):1082-1105, 2012.
Schmid-Burgk et al., "A Genome-wide CRISPR Screen Identifies NEK7 as an Essential Component of NLRP3 Inflammasome Activation," J. Biol. Chem., Manuscript C115.700492, p. 1-9, 2015. (12 pages).
Stella, "Pro-drugs: An Overview and Definition," *Pro-drugs as Novel Delivery Systems*, eds. Higuchi et al., A.C.S. Symposium Series, vol. 14, 1975.
Yuan et al., "Identification of Pyrrolo[2,3-d]pyrimidine-Based Derivatives as Potent and Orally Effective Fms-like Tyrosine Receptor Kinase 3 (FLT3) Inhibitors for Treating Acute Myelogenous Leukemia," *J. Med. Chem.* 62:4158-4173, 2019.
Barclay et al., "Inflammasome activation in multiple sclerosis and experimental autoimmune encephalomyelitis (EAE)," *Brain Pathology* 27:213-219, 2017.
Basiorka et al., "The NLRP3 inflammasome functions as a driver of the myelodysplastic syndrome phenotype," *Blood* 128(25):2960-2975, Dec. 22, 2016.
Booshehri et al., "CAPS and NLRP3," *Journal of Clinical Immunology* 39:277-286, 2019.
Cheng et al., "Dexmedetomidine inhibits the NF-κB pathway and NLRP3 inflammasome to attenuate papain-induced osteoarthritis in rats," *Pharm. Biol.* 57(1):649-659, 2019.

(Continued)

*Primary Examiner* — Niloofar Rahmani
(74) *Attorney, Agent, or Firm* — Seed IP Law Group LLP

(57) ABSTRACT

Compounds having activity as inhibitors of NEK7 are provided. The compounds have Structure (I):

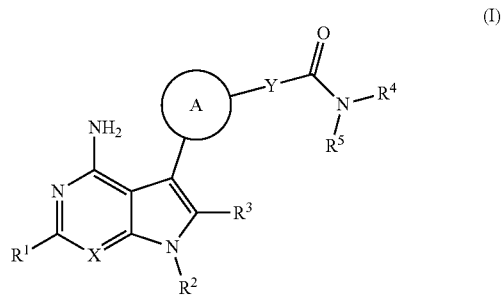

or a pharmaceutically acceptable salt, stereoisomer or prodrug thereof, wherein, A, X, Y, $R^1$, $R^2$, $R^3$, $R^4$ and $R^5$ are as defined herein. Methods associated with preparation and use of such compounds, pharmaceutical compositions comprising such compounds and methods to modulate the activity of the NLRP3 inflammasome are also provided.

27 Claims, No Drawings

(56) References Cited

OTHER PUBLICATIONS

Corcoran et al., "The NLRP3 inhibitor MCC950 inhibits IL-1β production in PBMC from 19 patients with Cryopyrin-Associated Periodic Syndrome and in 2 patients with Schnitzler's Syndrome," *Wellcome Open Research* 5(247):1-14, 2020.
Cornelius et al., "NLRP3 inflammasome inhibition attenuates sepsis-induced platelet activation and prevents multi-organ injury in cecal-ligation puncture," *PLoS One* 15(6):1-15, e0234039, Jun. 17, 2020.
Danielski et al., "The NLRP3 Inflammasome and Its Role in Sepsis Development," *Inflammation* 43(1):24-31, Feb. 1, 2020.
De Nardo et al., "New Insights into Mechanisms Controlling the NLRP3 Inflammasome and Its Role in Lung Disease," *Am. J. Pathol.* 184(1):42-54, 2014.
De Rivero Vaccari, "The Inflammasome in Reproductive Biology: A Promising Target for Novel Therapies," *Front. Endocrinol.* 11(8):1-5, Jan. 28, 2020.
Deng et al., "Inhibition of NLRP3 inflammasome-mediated pyroptosis in macrophage by cycloastragenol contributes to amelioration of imiquimod-induced psoriasis-like skin inflammation in mice," *Int. Immunopharmacol.* 74(105682):1-11, Jun. 13, 2019.
Ding et al., "Modulatory Mechanisms of the NLRP3 Inflammasomes in Diabetes," *Biomolecules* 9(850):1-15, 2019.
Freeman et al., "The pathogenic role of the inflammasome in neurodegenerative diseases," *J. Neurochem.* 136(1):29-38, 2016.
Fu et al., "NLRP3 Deficiency Alleviates Severe Acute Pancreatitis and Pancreatitis-Associated Lung Injury in a Mouse Model," *Biomed. Res. Int.* 1294951:1-10, 2018.
Grailer et al., "Critical role for the NLRP3 inflammasome during acute lung injury," *J. Immunol.* 192(12):5974-5983, Jun. 15, 2014.
Guo et al., "NLRP3 inflammasome activation contributes to the pathogenesis of rheumatoid arthritis," *Clin. Exp. Immunol.* 194:231-243, 2018.
Gupta et al., "Activation of NLRP3 inflammasome complex potentiates venous thrombosis in response to hypoxia," *PNAS* 114(18):4763-4768, May 2, 2017.
Hasegawa et al., "Nuclear DNA damage-triggered NLRP3 inflammasome activation promotes UVB-induced inflammatory responses in human keratinocytes," *Biochemical and Biophysical Research Communications* 477:329-335, 2016.
Hautem et al., "The NLRP3 Inflammasome Has a Critical Role in Peritoneal Dialysis-Related Peritonitis," *J. Am. Soc. Nephrol.* 28:2038-2052, 2017.
He et al., "Oridonin is a covalent NLRP3 inhibitor with strong anti-inflammasome activity," *Nat. Commun.* 9(2550):1-12, 2018.
Heneka et al., "NLRP3 is activated in Alzheimer's disease and contributes to pathology in APP/PS1 mice," *Nature* 493(7434):674-678, Jan. 31, 2013.
Holbrook et al., "Neurodegenerative Disease and the NLRP3 Inflammasome," *Front. Pharmacol.* 12(643254):1-15, Mar. 10, 2021.
Hutton et al., "The NLRP3 inflammasome in kidney disease and autoimmunity," *Nephrology* 21:736-744, 2016.
Ibrahim et al., "Male fertility following spinal cord injury: an update," *Andrology* 4:13-26, 2016.
Jankovic et al., "The Nlrp3 inflammasome regulates acute graft-versus-host disease," *J. Exp. Med.* 210(10):1899-1910, 2013.
Karasawa et al., "Role of NLRP3 Inflammasomes in Atherosclerosis," *J. Atheroscler. Thromb.* 24:443-451, 2017.
Klück et al., "Dapansutrile, an oral selective NLRP3 inflammasome inhibitor, for treatment of gout flares: an open-label, dose-adaptive, proof-of-concept, phase 2a trial," *Lancet Rheumatol.* 2(5):e270-e280, May 2020.
Lonnemann et al., "The NLRP3 inflammasome inhibitor OLT1177 rescues cognitive impairment in a mouse model of Alzheimer's disease," *PNAS* 117(50):32145-32154, Dec. 15, 2020.
Ma et al., "Evidence and perspective for the role of the NLRP3 inflammasome signaling pathway in ischemic stroke and its therapeutic potential (Review)," *Int. J. Mol. Med.* 42:2979-2990, 2018.

Moossavi et al., "Role of the NLRP3 inflammasome in cancer," *Mol. Cancer* 17(158):1-13, 2018.
Mridha et al., "NLRP3 inflammasome blockade reduces liver inflammation and fibrosis in experimental NASH in mice," *J. Hepatol.* 66(5):1037-1046, May 2017.
Murthy et al., "The NLRP3 inflammasome and bruton's tyrosine kinase in platelets co-regulate platelet activation, aggregation, and in vitro thrombus formation," *Biochem. Biophys. Res. Commun.* 483(1):230-236, 2017.
Negash et al., "Il-1β Production through the NLRP3 Inflammasome by Hepatic Macrophages Links Hepatitis C Virus Infection with Liver Inflammation and Disease," *PLoS Pathog.* 9(4): 1-13, e1003330, Apr. 2013.
Olcum et al., "Microglial NLRP3 inflammasome activation in multiple sclerosis," *Adv. Protein Chem. Struct. Biol.* 119:247-308, 2020.
Ozaki et al., "Targeting the NLRP3 inflammasome in chronic inflammatory diseases: current perspectives," *J Inflamm Res.* 8:15-27, Jan. 16, 2015.
Perera et al., "MCC950, a specific small molecule inhibitor of NLRP3 inflammasome attenuates colonic inflammation in spontaneous colitis mice," *Sci. Rep.* 8(8618):1-15, Jun. 5, 2018.
Poznyak et al., "NLPR3 Inflammasomes and Their Significance for Atherosclerosis," *Biomedicines* 8(205):1-11, Jul. 10, 2020.
Rheinheimer et al., "Current role of the NLRP3 inflammasome on obesity and insulin resistance: A systematic review," *Metabolism* 74:1-9, Jun. 7, 2017.
Sayan et al., "The NLRP3 inflammasome in pathogenic particle and fibre-associated lung inflammation and diseases," *Part. Fibre. Toxicol.* 13(51):1-15, 2016.
Sebastião et al., "NLRP3 Inflammasome and Allergic Contact Dermatitis: A Connection to Demystify," *Pharmaceutics* 12(867):1-16, Sep. 11, 2020.
Sendler et al., "NLRP3 Inflammasome Regulates Development of Systemic Inflammatory Response and Compensatory Anti-Inflammatory Response Syndromes in Mice With Acute Pancreatitis," *Gastroenterology* 158(1):253-269, Jan. 2020. (31 pages).
Shen et al., "NLRP3: A promising therapeutic target for autoimmune diseases," *Autoimmun. Rev.* 17:694-702, May 3, 2018.
Stienstra et al., "Inflammasome is a central player in the induction of obesity and insulin resistance," *PNAS* 108(37):15324-15329, Sep. 13, 2011.
Tang et al. "Inflammasomes in Common Immune-Related Skin Diseases," *Front. Immunol.* 11(882):1-15, May 12, 2020.
Theivanthiran et al., "A tumor-intrinsic PD-L1/NLRP3 inflammasome signaling pathway drives resistance to anti-PD-1 immunotherapy," *J. Clin. Invest.* 130(5):2570-2586, May 2020.
Theofani et al., "Targeting NLRP3 Inflammasome Activation in Severe Asthma," *J. Clin. Med.* 8(1615):1-27, Oct. 4, 2019.
Wan et al., "Interleukin-1 Receptor Signaling is Critical for the Development of Autoimmune Uveitis," *J Immunol.* 196(2):543-546, Jan. 15, 2016.
Wan et al., "Role of NLRP3 Inflammasome in the Progression of NAFLD to NASH," *Can. J. Gastroenterol. Hepatol.* 2016(6489012):1-7, Jul. 20, 2015.
Wang et al., "NLRP3 Inflammasome and Inflammatory Diseases," *Oxidative Medicine and Cellular Longevity* 2020(4063562):1-11. Feb. 18, 2020.
Weigt et al., "Inflammasomes and IL-1 biology in the pathogenesis of allograft dysfunction," *J. Clin Invest.* 127(6):2022-2029, Jun. 2017.
Wooff et al., "IL-1 Family Members Mediate Cell Death, Inflammation and Angiogenesis in Retinal Degenerative Diseases," *Front. Immunol.* 10(1618):1-21, Jul. 16, 2019.
Wu et al., "Relevance of the NLRP3 Inflammasome in the Pathogenesis of Chronic Liver Disease," *Front. Immunol.* 8(1728):1-12, Dec. 12, 2017.
Xiao et al., "NLRP3 inflammasome: A likely target for the treatment of allergic diseases," *Clin. Exp. Allergy* 48(9):1080-1091, Sep. 2018.
Xiong et al., "NLRP3 Inflammasome in Metabolic-Associated Kidney Diseases: An Update," *Front. Immunol.* 12(714340):1-9, Jul. 8, 2021.

(56) References Cited

OTHER PUBLICATIONS

Xu et al., "The role of the inflammasomes in the pathogenesis of uveitis," *Experimental Eye Research* 208(108618):1-10, May 11, 2021.

Yang et al., "A pharmacological inhibitor of NLRP3 inflammasome prevents non-alcoholic fatty liver disease in a mouse model induced by high fat diet," *Sci. Rep.* 6(24399):1-10, Apr. 14, 2016.

Zahid et al., "Pharmacological Inhibitors of the NLRP3 Inflammasome," *Front. Immunol.* 10(2538):1-10, Oct. 25, 2019.

Zhang et al., "NLRP3 inflammasome as a novel therapeutic target for Alzheimer's disease," *Signal Transduct. Target Ther.* 5(37):1-2, Apr. 1, 2020.

Zhen et al., "NLRP3 Inflammasome and Inflammatory Bowel Disease," *Frontiers in Immunology* 10(276):1-10, Feb. 28, 2019.

Zhou et al. "NLRP3: A Novel Mediator in Cardiovascular Disease," *J. Immunol. Res.* 2018(5702103):1-8, Apr. 8, 2018.

Zmora et al., "Inflammasomes and intestinal inflammation," *Mucosal. Immunol.* 10(4):865-883, Jul. 2017.

\* cited by examiner

INHIBITORS OF NEK7 KINASE

BACKGROUND

Technical Field

Embodiments of the present disclosure are generally directed to compounds and methods for their preparation and use as therapeutic or prophylactic agents, for example for treatment of inflammation.

Description of the Related Art

Inflammasomes are multi-protein complexes whose activation plays a central role in innate immunity and inflammation. To date, four inflammasomes have been described: NLRP1, NLRC4 NLRP3 and AIM2. The NLRP3 inflammasome is composed of NLRP3, ASC, and caspase-I. Its activation results in the activation of caspase-I which promotes the secretion of IL-1β and IL-18, cytokines that mediate inflammation in animal disease models of several autoimmune diseases, myocardial infarction, metabolic syndromes, inflammatory bowel disease, and macrophage activation syndrome.

NEK7 is a member of the family of NIMA-related kinases (NEKs) that act as NLRP3-binding proteins to regulate its oligomerization and activation. NEK7 is a serine/threonine kinase essential for mitotic entry, cell cycle progression, cell division, and mitotic progression. It is expressed in a variety of tissues such as the brain, heart, lung, liver, and spleen. Overexpression of NEK7 induces the production of abnormal cells, which has an intimate connection to tumors, such as retinoblastoma, gallbladder cancer and carcinoma of the head and neck.

A great number of inhibitors have been widely used to disturb effector signaling pathways involving IL-1β or IL-18 without abolishing the inflammation response. Inhibitors of NLRP3 inflammasome activation that block the NLRP3-NEK7 interaction can have therapeutic or prophylactic activity in several human diseases, such as type 2 diabetes (T2D), atherosclerosis, gout and neurodegenerative diseases. However, the exact mechanism of the NLRP-3-NEK7 is not well understood.

Accordingly, there is a need to develop inhibitors that will directly target NEK7 to affect the inflammatory response modulated by the NLRP3 inflammasome in several pathological diseases, such as gout, atherosclerosis, Type 2 diabetes, metabolic syndrome, macular degeneration, Alzheimer's disease, multiple sclerosis, and inflammatory bowel disease. Embodiments of the present disclosure fulfill this need and provide further related advantages.

BRIEF SUMMARY

In brief, embodiments of the present disclosure provide compounds, including pharmaceutically acceptable salts, stereoisomers and prodrugs thereof, which are capable of inhibiting NEK7 and/or modulating the activity of NLRP3 inflammasome.

In one aspect, the invention provides compounds of Structure (I):

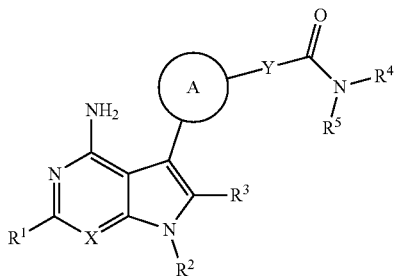

(I)

pharmaceutically acceptable salts, stereoisomers or prodrug thereof, wherein each of A, X, Y, $R^1$, $R^2$, $R^3$, $R^4$ and $R^5$ are as defined below.

In another aspect, pharmaceutical compositions comprising the disclosed compounds, and methods of use of the same for treatment of inflammation are also provided.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, the terms "about" and "approximately" mean ±20%, ±10%, ±5% or ±1% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs. As used in the specification and claims, the singular form "a", "an" and "the" include plural references unless the context clearly dictates otherwise.

"Amino" refers to the —$NH_2$ radical.
"Carboxy" or "carboxyl" refers to the —$CO_2H$ radical.
"Cyano" refers to the —CN radical.
"Hydroxy" or "hydroxyl" refers to the —OH radical.
"Nitro" refers to the —$NO_2$ radical.

"Oxo" refers to the =O substituent.

"Thiol" refers to the —SH substituent.

"Thioxo" refers to the =S substituent.

"Alkyl" refers to a saturated, straight or branched hydrocarbon chain radical consisting solely of carbon and hydrogen atoms, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), or any value within these ranges, such as $C_4$-$C_6$ alkyl and the like, and which is attached to the rest of the molecule by a single bond, e.g., methyl, ethyl, n-propyl, 1-methylethyl (iso-propyl), n-butyl, n-pentyl, 1,1-dimethylethyl (1-butyl), 3-methylhexyl, 2-methylhexyl and the like. The number of carbons referred to relates to the carbon backbone and carbon branching, but does not include carbon atoms belonging to any substituents. Unless stated otherwise specifically in the specification, an alkyl group is optionally substituted.

"Alkenyl" refers to an unsaturated, straight or branched hydrocarbon chain radical consisting solely of carbon and hydrogen atoms, which contains one or more carbon-carbon double bonds, having from two to twelve carbon atoms ($C_2$-$C_{12}$ alkenyl), two to eight carbon atoms ($C_2$-$C_8$ alkenyl) or two to six carbon atoms ($C_2$-$C_6$ alkenyl), or any value within these ranges, and which is attached to the rest of the molecule by a single bond, e.g., ethenyl, prop-1-enyl, but-1-enyl, pent-1-enyl, penta-1,4-dienyl, and the like. The number of carbons referred to relates to the carbon backbone and carbon branching, but does not include carbon atoms belonging to any substituents. Unless stated otherwise specifically in the specification, an alkenyl group is optionally substituted.

The term "alkynyl" refers to unsaturated straight or branched hydrocarbon radical, having 2 to 12 carbon atoms ($C_2$-$C_{12}$ alkynyl), two to nine carbon atoms ($C_2$-$C_9$ alkynyl), or two to six carbon atoms ($C_2$-$C_6$ alkynyl), or any value within these ranges, and having at least one carbon-carbon triple bond. Examples of alkynyl groups may be selected from the group consisting of ethynyl, propargyl, but-1-ynyl, but-2-ynyl and the like. The number of carbons referred to relates to the carbon backbone and carbon branching, but does not include carbon atoms belonging to any substituents. Unless stated otherwise specifically in the specification, an alkynyl group is optionally substituted.

"Alkoxy" refers to a radical of the formula —$OR_a$ where $R_a$ is an alkyl radical as defined above containing one to twelve carbon atoms ($C_1$-$C_{12}$ alkoxy), one to eight carbon atoms ($C_1$-$C_8$ alkoxy) or one to six carbon atoms ($C_1$-$C_6$ alkoxy), or any value within these ranges. Unless stated otherwise specifically in the specification, an alkoxy group is optionally substituted.

"Aminyl" refers to a radical of the formula —$NR_aR_b$, where $R_a$ and $R_b$ are each independently H or $C_1$-$C_6$ alkyl as defined above. When both of $R_a$ and $R_b$ are H, an "aminyl" group is the same as an "amino" group as defined above. The $C_1$-$C_6$ alkyl portion of an aminyl group is optionally substituted unless stated otherwise.

"Aminylalkylcycloalkyl" refers to a radical of the formula —$R_aR_bNR_cR_d$ where $R_a$ is cycloalkyl as defined herein, $R_b$ is $C_1$-$C_6$ alkyl, $R_c$ is H or $C_1$-$C_6$ alkyl and $R_d$ is $C_1$-$C_6$ alkyl as defined above. The cycloalkyl and each $C_1$-$C_6$ alkyl portion of an aminylalkylcycloalkyl group are optionally substituted unless stated otherwise.

"Aromatic ring" refers to a cyclic planar molecule or portion of a molecule (i.e., a radical) with a ring of resonance bonds that exhibits increased stability relative to other connective arrangements with the same sets of atoms. Generally, aromatic rings contain a set of covalently bound co-planar atoms and comprises a number of π-electrons (for example, alternating double and single bonds) that is even but not a multiple of 4 (i.e., 4n+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an "aromatic ring" includes all radicals that are optionally substituted.

"Aryl" refers to a carbocyclic ring system radical comprising 6 to 18 carbon atoms, for example 6 to 10 carbon atoms ($C_6$-$C_{10}$ aryl) and at least one carbocyclic aromatic ring. For purposes of embodiments of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Cyanoalkyl" refers to an alkyl group comprising at least one cyano substituent. The —CN substituent may be on a primary, secondary or tertiary carbon. Unless stated otherwise specifically in the specification, a cyanoalkyl group is optionally substituted.

"Carbocyclic" or "carbocycle" refers to a ring system, wherein each of the ring atoms are carbon.

"Cycloalkyl" refers to a non-aromatic monocyclic or polycyclic carbocyclic radical consisting solely of carbon and hydrogen atoms, which may include fused or bridged ring systems, having from three to fifteen ring carbon atoms ($C_3$-$C_{15}$ cycloalkyl), from three to ten ring carbon atoms ($C_3$-$C_{10}$ cycloalkyl), or from three to eight ring carbon atoms ($C_3$-$C_8$ cycloalkyl), or any value within these ranges such as three to four carbon atoms ($C_3$-$C_4$ cycloalkyl), and which is saturated or partially unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group is optionally substituted.

"Alkylcycloalkyl" refers to a radical group of the formula —$R_aR_b$ where $R_a$ is a cycloalkyl group and $R_b$ is an alkyl group as defined above. Unless otherwise stated specifically in the specification, an alkylcycloalkyl group is optionally substituted.

"Fused" refers to any ring structure described herein which is fused to another ring structure.

"Halo" refers to bromo, chloro, fluoro, or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Halocycloalkyl" refers to a cycloalkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a halocycloalkyl group is optionally substituted.

"Haloalkylcycloalkyl" refers to a radical group of the formula —$R_aR_b$ where $R_a$ is a cycloalkyl group and $R_b$ is a haloalkyl group as defined above. Unless otherwise stated specifically in the specification, a haloalkylcycloalkyl group is optionally substituted.

"Hydroxylalkyl" refers to an alkyl radical, as defined above that is substituted by one or more hydroxyl radical. The hydroxyalkyl radical is joined at the main chain through the alkyl carbon atom. Unless stated otherwise specifically in the specification, a hydroxylalkyl group is optionally substituted.

"Heterocyclyl" refers to a 3- to 18-membered, for example 3- to 10-membered or 3- to 8-membered, non-aromatic ring radical having one to ten ring carbon atoms (e.g., two to ten) and from one to six ring heteroatoms selected from the group consisting of nitrogen, oxygen and sulfur. Unless stated otherwise specifically in the specification, the heterocyclyl radical is partially or fully saturated and is a monocyclic, bicyclic, tricyclic or tetracyclic ring system, which may include fused, spirocyclic and/or bridged ring systems. Nitrogen, carbon and sulfur atoms in a heterocyclyl radical are optionally oxidized, and nitrogen atoms may be optionally quaternized. Examples of such heterocyclyl radicals include, but are not limited to, dioxolanyl, thienyl[1,3]dithianyl, decahydroisoquinolyl, furanonyl, imidazolinyl, imidazolidinyl, isothiazolidinyl, isoxazolidinyl, morpholinyl, octahydroindolyl, octahydroisoindolyl, hexahydro-1H-pyrrolizine, 2-oxopiperazinyl, 2-oxopiperidinyl, 2-oxopyrrolidinyl, oxazolidinyl, oxiranyl, piperidinyl, piperazinyl, 4-piperidonyl, azetidinyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group is optionally substituted.

"Haloheterocyclylalkyl" refers to a radical group of the formula —$R_aR_b$ where $R_a$ is an alkyl group and $R_b$ is a haloheterocyclyl group as defined herein. Unless otherwise stated specifically in the specification, a haloheterocyclylalkyl group is optionally substituted.

"Heterocyclylalkyl" refers to a radical group of the formula —$R_aR_b$ where $R_a$ is an alkyl group and $R_b$ is a heterocyclyl group as defined herein. Unless otherwise stated specifically in the specification, a heterocyclylalkyl group is optionally substituted.

"Heteroaryl" refers to a 5- to 18-membered, for example 5- to 6-membered, ring system radical comprising one to thirteen ring carbon atoms, one to six ring heteroatoms selected from the group consisting of nitrogen, oxygen and sulfur, and at least one aromatic ring. Heteroaryl radicals may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

Oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl and 1, 3, 4-thiadiazolyl refer to the following structures, respectively:

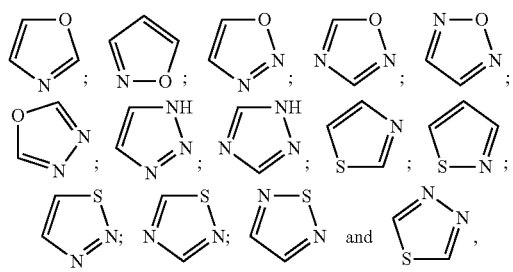

wherein the oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl, and 1, 3, 4-thiadiazolyl are attached to the remainder of the molecule by a covalent bond to one of the carbon atoms in the ring of the oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl, and 1, 3, 4-thiadiazolyl.

The term "substituted" as used herein means any of the above groups (e.g., alkyl, alkenyl, alkylene, alkylcarbonyl, alkoxy, alkoxyalkyl, aminylalkyl, aryl, cyanoalkyl, cycloalkyl, haloalkyl, heterocyclyl, heterocyclene, heterocyclylalkyl, heteroaryl, heteroarylalkyl and/or hydroxylalkyl) wherein at least one hydrogen atom (e.g., 1, 2, 3 or all hydrogen atoms) is replaced by a bond to a non-hydrogen substituent. Examples of non-hydrogen substituents include, but are not limited to: amino, carboxyl, cyano, hydroxyl, halo, nitro, oxo, thiol, thioxo, alkyl, alkenyl, alkylcarbonyl, alkoxy, aryl, cyanoalkyl, cycloalkyl, haloalkyl, heterocyclyl, heterocyclylalkyl, heteroaryl, heteroarylalkyl and/or hydroxylalkyl substituents, each of which may also be optionally substituted with one or more of the above substituents.

In some specific embodiments, the optional substitutions are independently selected from the group consisting of halo, hydroxyl, cyano, aminyl, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, $C_3$-$C_8$ halocycloalkyl, $C_6$-$C_{10}$ aryl, 5- or 6-membered heteroaryl, $C_1$-$C_6$ alkoxy and 3-8 membered heterocyclyl.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic effect and/or a prophylactic effect. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. In certain embodiments, for prophylactic benefit, the compositions are administered to a subject at risk of developing a particular disease, or to a subject reporting one or more of the physiological symptoms of a disease, even though a diagnosis of this disease may not have been made.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness of the free bases, which are biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Preferred pharmaceutically acceptable acid addition salts are those that are pharmacologically effective and suitable for contact with the tissues of patients without undue toxicity, irritation, or allergic response. Pharmaceutically acceptable acid addition salts which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness of the free acids, which are biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Preferred pharmaceutically acceptable base addition salts are those that are pharmacologically effective and suitable for contact with the tissues of patients without undue toxicity, irritation, or allergic response. Pharmaceutically acceptable base addition salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

The terms "antagonist" and "inhibitor" are used interchangeably, and they refer to a compound having the ability to inhibit a biological function of a target protein, whether by inhibiting the activity or expression of the protein, such as NLRP3 inflammasome or NEK7 or the association of NLRP3 inflammasome—NEK7. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compounds of Structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or thiol group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

Embodiments disclosed herein are also meant to encompass all pharmaceutically acceptable compounds of Structure (I).

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments include compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compounds disclosed herein. As used herein, the term "solvate" refers to an aggregate that comprises one or more compounds of the disclosure with one or more molecules of solvent. In some embodiments, the solvent is water, in which case the solvate is a hydrate. Alternatively, in other embodiments, the solvent is an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. In some aspects, the compounds of the disclosure are a true solvate, while in other cases, the compounds of the disclosure merely retain adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to formulations of compounds of the disclosure and a medium generally accepted in the art for the delivery of compounds of the disclosure to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

The compounds of the disclosure (i.e., compounds of Structure (I)) or their pharmaceutically acceptable salts may contain one or more centers of geometric asymmetry and may thus give rise to stereoisomers such as enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Embodiments of the present disclosure include all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the disclosure may exist as mixtures of atropisomers or purified or enriched for the presence of one atropisomer.

In some embodiments, the compounds of Structure (I) are a mixture of enantiomers or diastereomers. In other embodiments, the compounds of Structure (I) are substantially one enantiomer or diastereomer.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Profesional Version 17.0.0.206 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

The disclosure provides compounds including pharmaceutically acceptable salts, stereoisomers and prodrugs thereof, which are capable of inhibiting NEK7 and/or modulating the activity of NLRP3 inflammasome.

Embodiments of the present disclosure provide a compound having the following Structure (I):

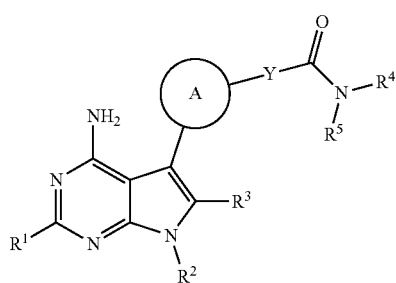

(I)

or a pharmaceutically acceptable salt, stereoisomer or prodrug thereof, wherein:

A is $C_6$-$C_{10}$ aryl, $C_3$-$C_{10}$ cycloalkyl, 3-10 membered heterocyclyl or 5-6 membered monocyclic heteroaryl, each of which is optionally substituted with one or more $R^6$.

Y is CHOH or NH;

$R^1$ is H or $C_1$-$C_6$ alkyl;

$R^2$ is $C_1$-$C_6$ alkyl, $C_2$-$C_6$ alkenyl, $C_2$-$C_6$ alkynyl, $C_3$-$C_8$ cycloalkyl, 3-8 membered heterocyclyl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3-8 membered heterocyclyl;

$R^3$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl or 5- or 6-membered heteroaryl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy;

$R^4$ is a heteroaryl selected from oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl and 1, 3, 4-thiadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, or combinations thereof;

$R^5$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl, $C_6$-$C_{10}$ aryl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy; and $R^6$ is, at each occurrence, independently halo, $C_1$-$C_6$ alkyl, cyano, $C_1$-$C_6$ hydroxylalkyl, $C_1$-$C_6$ alkoxy, or $C_1$-$C_6$ haloalkyl.

In some embodiments of Structure (I):

A is $C_6$-$C_{10}$ aryl, $C_3$-$C_{10}$ cycloalkyl, 3-10 membered heterocyclyl or 5-6 membered monocyclic heteroaryl, each of which is optionally substituted with one or more $R^6$.

Y is CHOH or NH;

$R^1$ is H or $C_1$-$C_6$ alkyl;

$R^2$ is $C_1$-$C_6$ alkyl, $C_2$-$C_6$ alkenyl, $C_2$-$C_6$ alkynyl, $C_3$-$C_8$ cycloalkyl, 3-8 membered heterocyclyl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3-8 membered heterocyclyl;

$R^3$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl or 5- or 6-membered heteroaryl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy;

$R^4$ is a heteroaryl selected from oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl and 1, 3, 4-thiadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_3$-$C_8$ halocycloalkyl;

$R^5$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl, $C_6$-$C_{10}$ aryl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy; and $R^6$ is, at each occurrence, independently halo, $C_1$-$C_6$ alkyl, or $C_1$-$C_6$ haloalkyl.

Some more specific embodiments provide a compound having the following Structure (I):

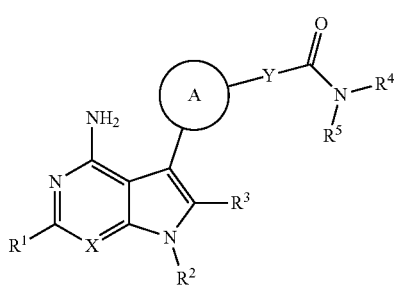

(I)

or a pharmaceutically acceptable salt, stereoisomer or prodrug thereof, wherein:

A is $C_6$-$C_{10}$ aryl, $C_3$-$C_{10}$ cycloalkyl, 3-10 membered heterocyclyl or 5-6 membered monocyclic heteroaryl, each of which is optionally substituted with one or more $R^6$.

X is CH or N;

Y is CHOH or NH;

$R^1$ is H or $C_1$-$C_6$ alkyl;

$R^2$ is $C_1$-$C_6$ alkyl, $C_2$-$C_6$ alkenyl, $C_2$-$C_6$ alkynyl, $C_3$-$C_8$ cycloalkyl, 3-8 membered heterocyclyl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3-8 membered heterocyclyl;

$R^3$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl or 5- or 6-membered heteroaryl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy;

$R^4$ is a heteroaryl selected from oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl and 1, 3, 4-thiadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl;

$R^5$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl, $C_6$-$C_{10}$ aryl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy; and $R^6$ is, at each occurrence, independently halo, $C_1$-$C_6$ alkyl, $C_1$-$C_6$ alkoxy, cyano, $C_1$-$C_6$ hydroxylalkyl or $C_1$-$C_6$ haloalkyl.

In certain embodiment, $R^1$ is H. In other embodiments, $R^1$ $C_1$-$C_6$ alkyl, such as methyl.

In one embodiment, compounds of Structure (I) are provided, where $R^2$ is branched $C_4$-$C_6$ alkyl, $C_3$-$C_4$ cycloalkyl, $C_3$-$C_8$ heterocyclyl or 5- or 6-membered heteroaryl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl.

In another embodiment, compounds of Structure (I) are provided, where $R^2$ is branched $C_4$-$C_6$ alkyl, $C_3$-$C_4$ cycloalkyl, or $C_3$-$C_8$ heterocyclyl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl.

In specific embodiments, $R^2$ is cyclopropyl or oxetanyl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl. In some embodiments, $R^2$ is cyclopropyl. In other embodiments, $R^2$ is oxetanyl. In some embodiments, $R^2$ is unsubstituted cyclopropyl or oxetanyl.

In specific embodiments, $R^2$ is cyclopropyl, cyclobutyl, pyrrolidinyl, piperidinyl, or oxetanyl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl. In some embodiments, $R^2$ is cyclopropyl. In other embodiments, $R^2$ is oxetanyl. In some embodiments, $R^2$ is unsubstituted cyclopropyl or oxetanyl. In some embodiments, $R^2$ is N-methyl substituted pyrrolidinyl. In certain specific embodiments, $R^2$ is unsubstituted cyclobutyl.

In different embodiments, $R^2$ is branched $C_4$-$C_6$ alkyl optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl. For example, in some embodiments $R^2$ is 2-methylpropyl optionally substituted with hydroxyl.

In more specific embodiments, $R^2$ has one of the following structures:

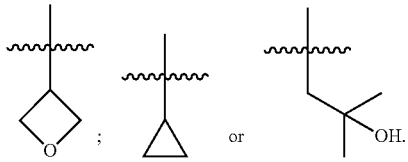

In some specific embodiments, $R^2$ has one of the following structures:

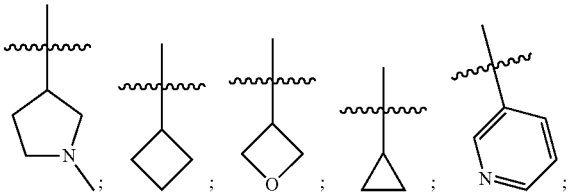

In other embodiments, $R^3$ is H. In other embodiments, $R^3$ $C_1$-$C_6$ alkyl, such as methyl.

In any of the foregoing embodiments, $R^4$ is oxazolyl, isoxazolyl, 1, 2, 3-oxadiazolyl or 1, 3, 4-oxadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxyalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof. For example, in certain embodiments, $R^4$ is isoxazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_3$-$C_8$ halocycloalkyl. In further specific embodiments, $R^4$ is substituted with $C_1$-$C_6$ alkyl, $C_1$-$C_6$ haloalkyl, $C_3$-$C_8$ cycloalkyl or $C_3$-$C_8$ halocycloalkyl.

In certain embodiments, $R^4$ is oxazolyl, isoxazolyl, 1, 2, 3-oxadiazolyl, thiazolyl, isothiazolyl, 1,2,4-thiadiazolyl, 1,3,4-thiadiazolyl, 1,2,4-triazolyl or 1, 3, 4-oxadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxyalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is isoxazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxyalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is thiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxyalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is isothiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is 1,2,4-thiadiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is 1,3,4-thiadiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is 1,2,4-triazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In certain embodiments, $R^4$ is 1, 3, 4-oxadiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, 3- to 8-membered heterocyclyl and $C_3$-$C_8$ halocycloalkyl, or combinations thereof.

In certain embodiments, $R^4$ is substituted with $C_1$-$C_6$ alkyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

In various embodiments, $R^4$ has one of the following structures:

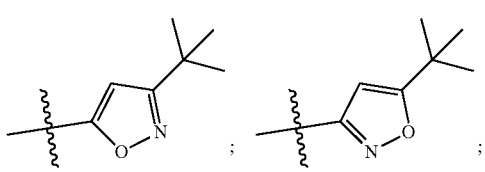

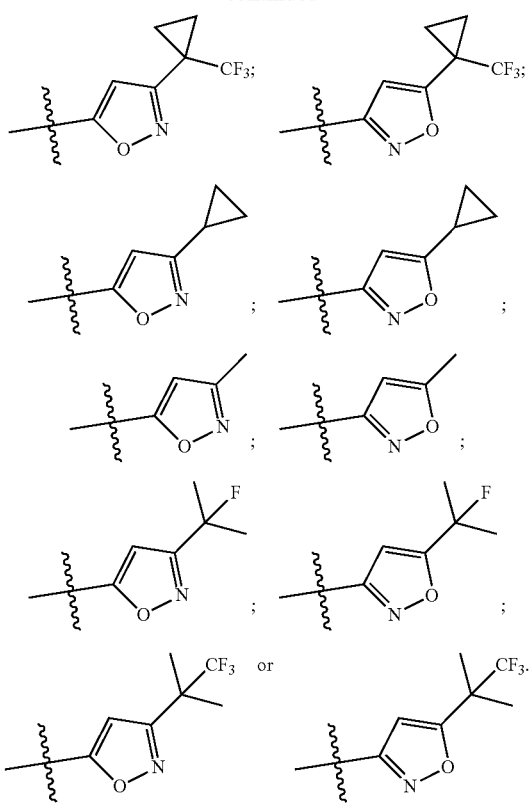
In other various embodiments, R⁴ has one of the following structures:
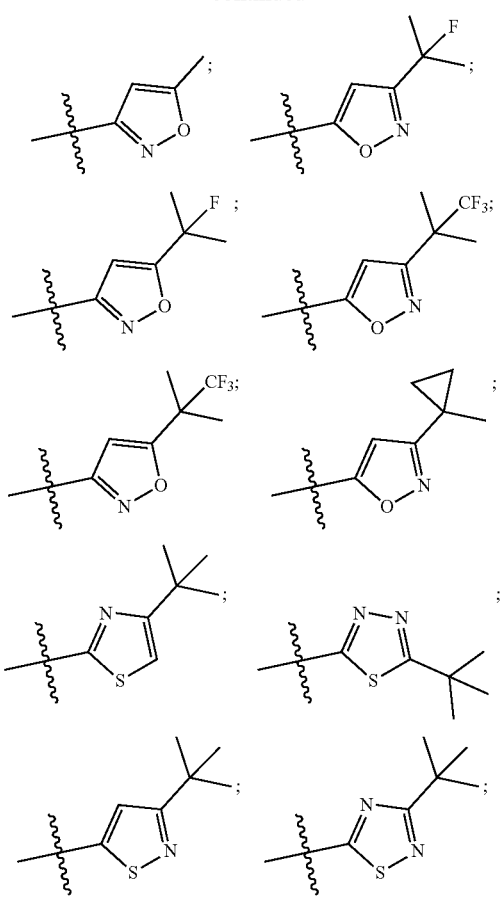
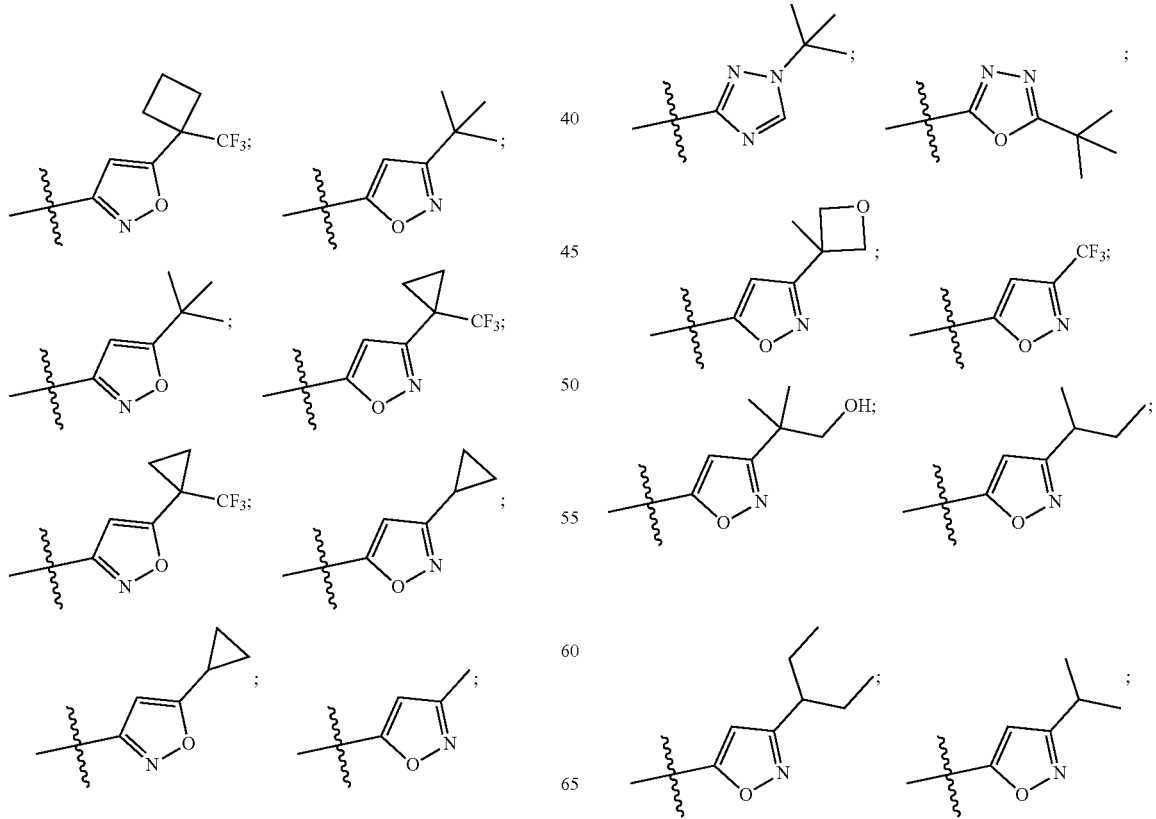

-continued
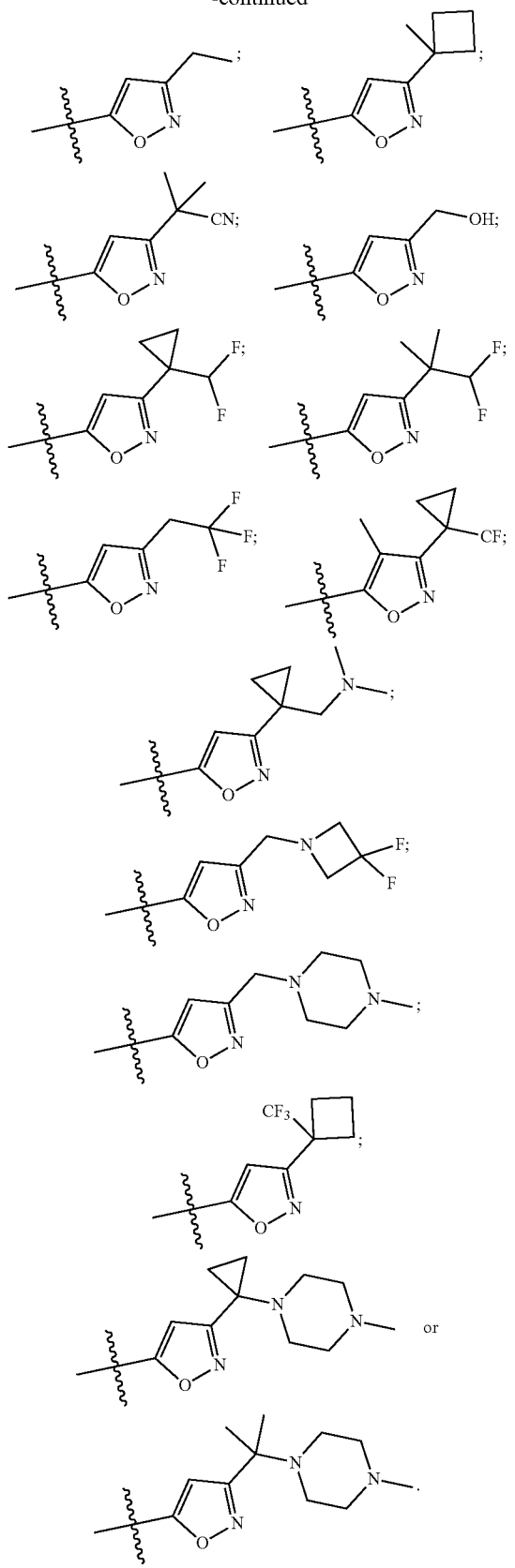
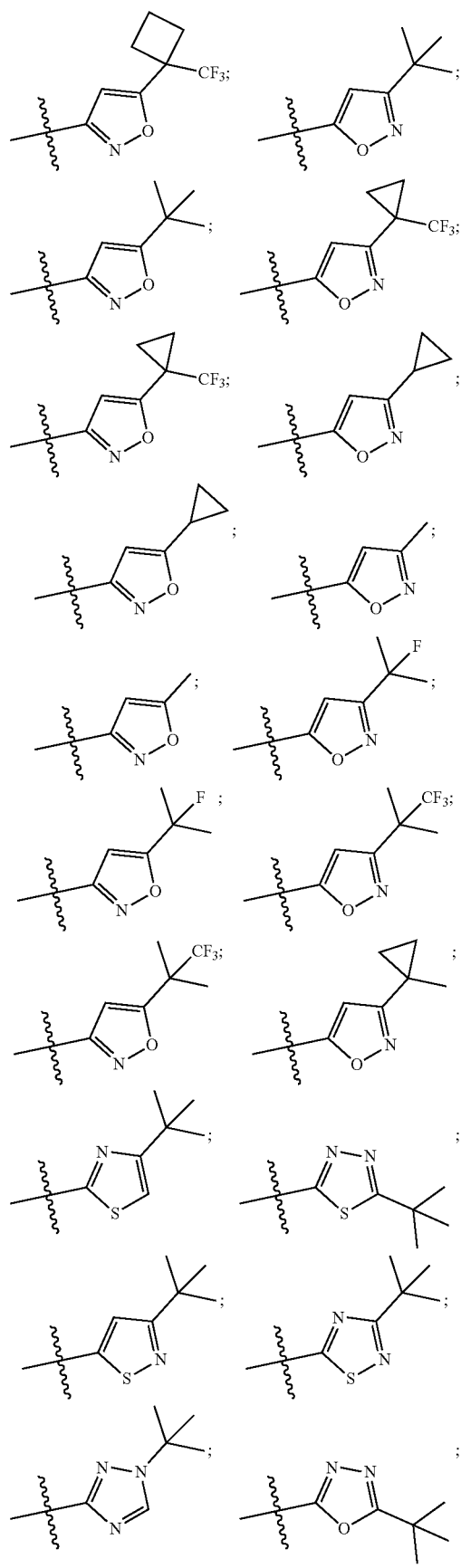
In other various embodiments, $R^4$ has one of the following structures:

-continued

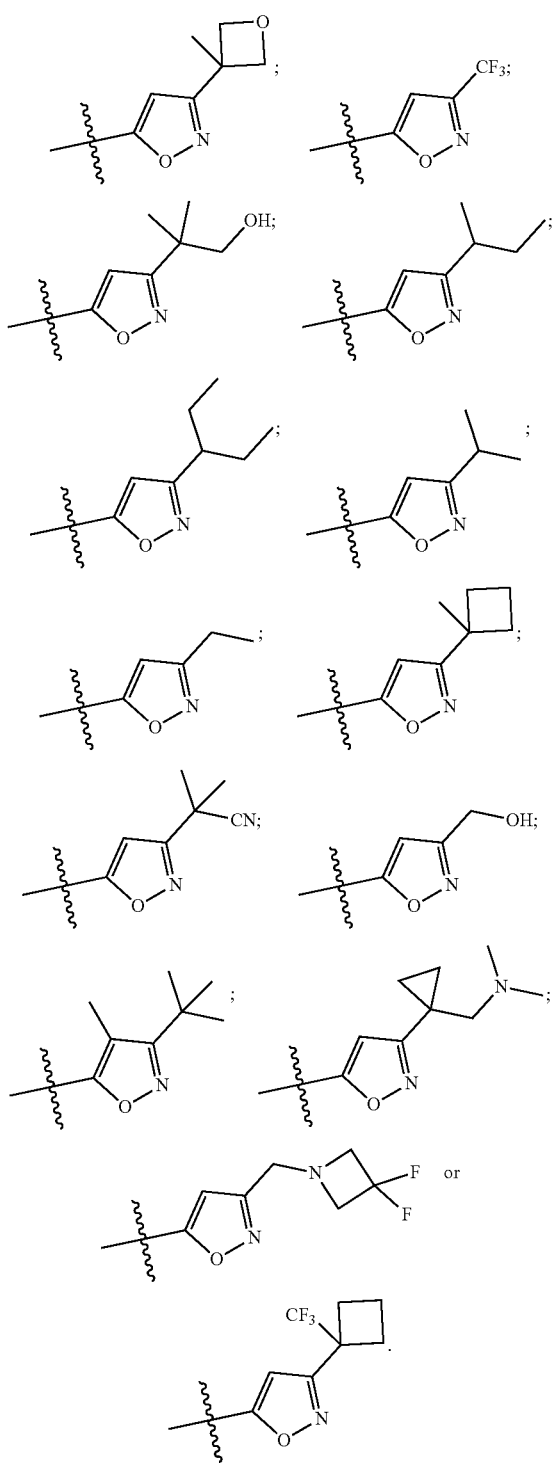

In certain specific embodiments, R² C₁-C₆ alkyl, C₂-C₆ alkenyl, C₂-C₆ alkynyl, C₃-C₈ cycloalkyl, 3-8 membered heterocyclyl or 5- or 6-membered heteroaryl, each of which is optionally substituted with one more substituents selected from halo, hydroxyl, cyano, aminyl, C₁-C₆ alkyl, C₂-C₆ alkenyl, C₂-C₆ alkynyl, C₁-C₆ alkoxy and 3-8 membered heterocyclyl; and R⁴ has one of the following structures:

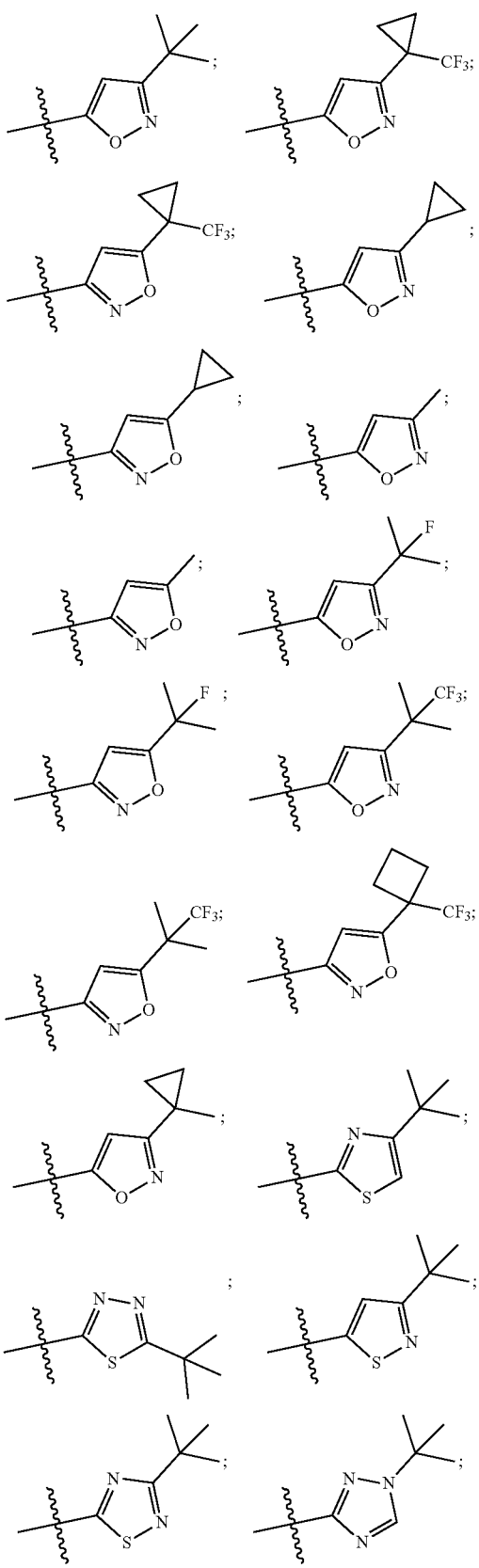

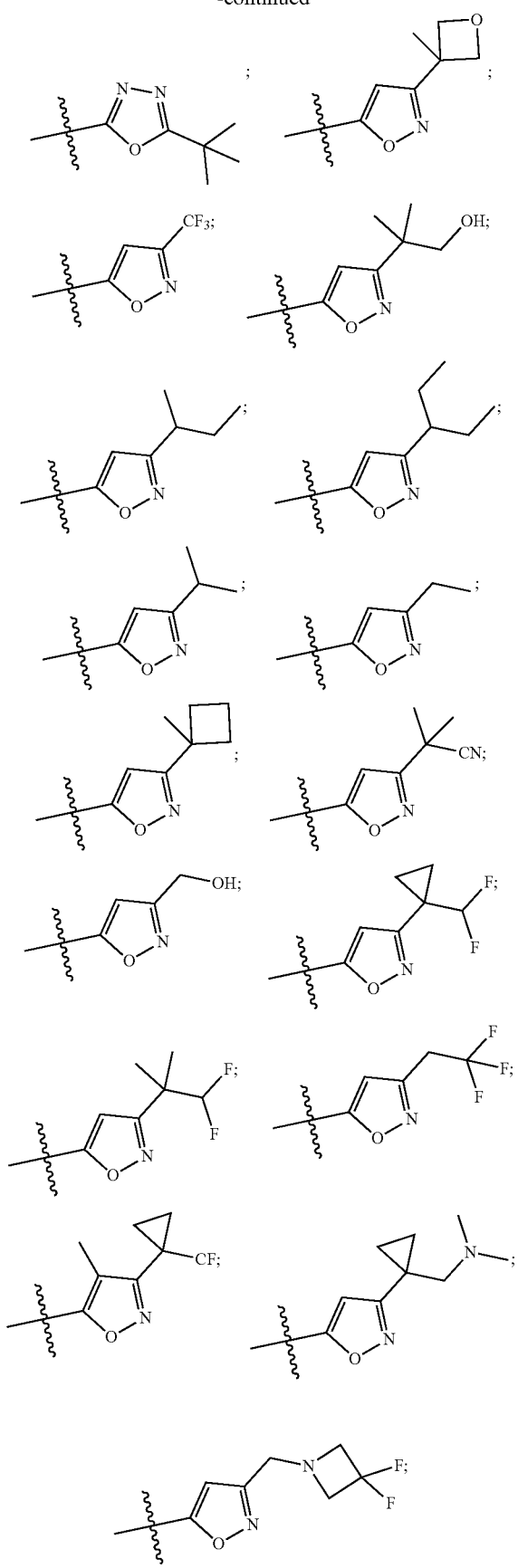
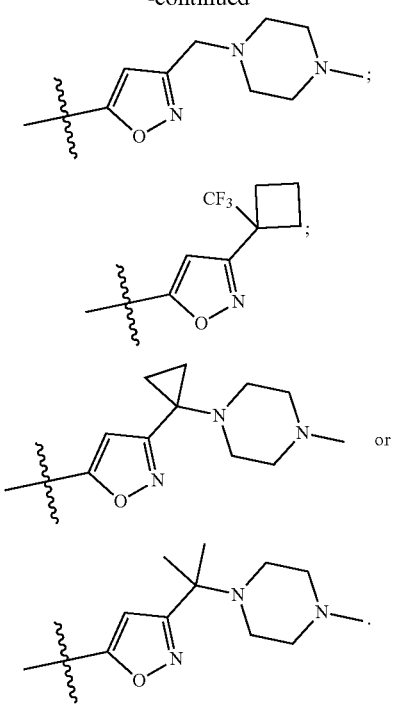
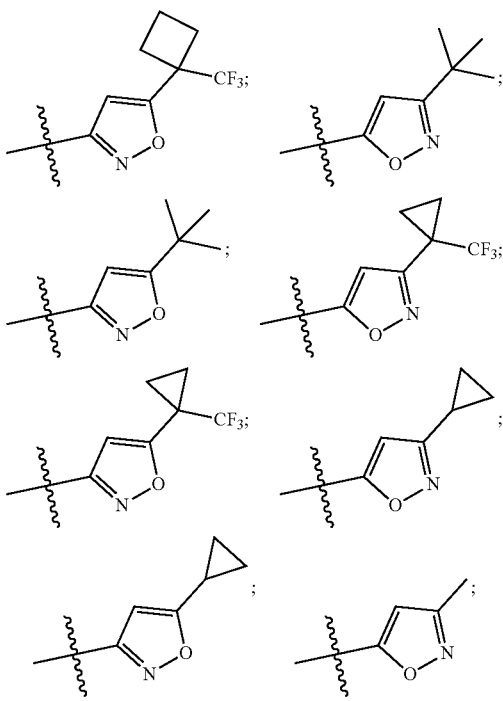

In certain specific embodiments, R² C₁-C₆ alkyl, C₂-C₆ alkenyl, C₂-C₆ alkynyl, C₃-C₈ cycloalkyl, 3-8 membered heterocyclyl or 5- or 6-membered heteroaryl, each of which is optionally substituted with one more substituents selected from halo, hydroxyl, cyano, aminyl, C₁-C₆ alkyl, C₂-C₆ alkenyl, C₂-C₆ alkynyl, C₁-C₆ alkoxy and 3-8 membered heterocyclyl; and R⁴ has one of the following structures:

-continued

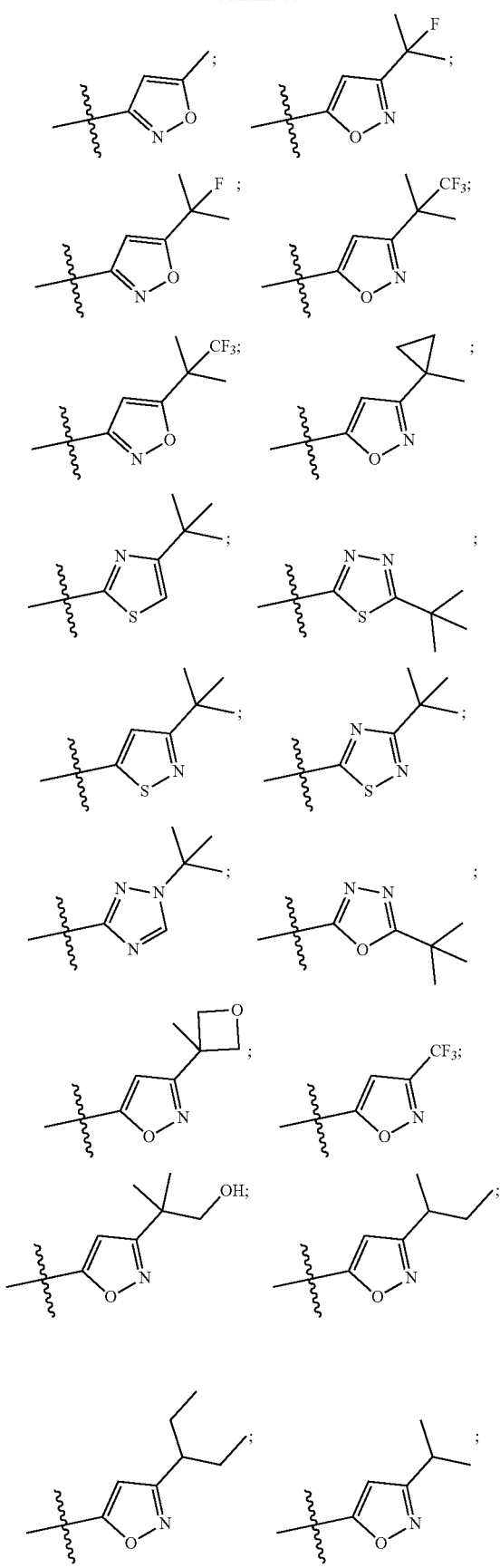

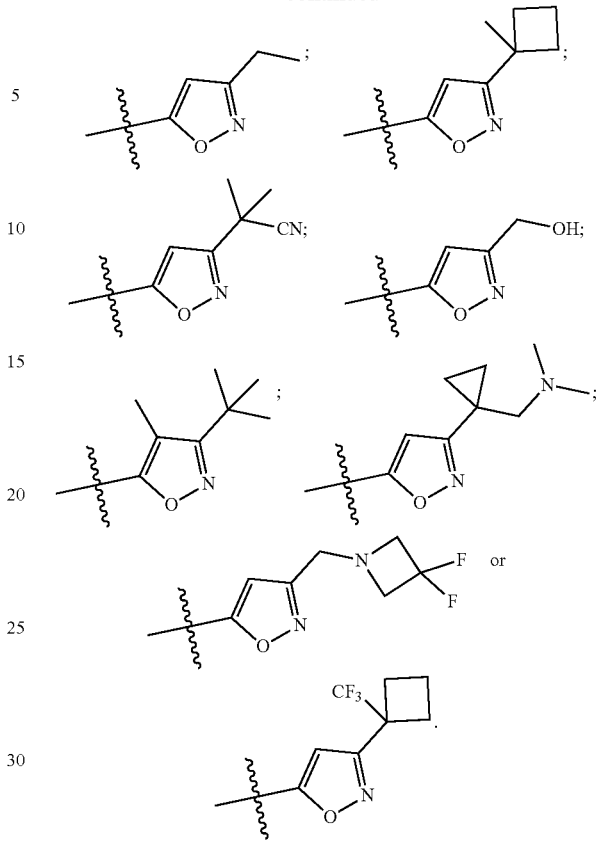

In more specific embodiments, $R^2$ is $C_1$-$C_6$ alkyl substituted with hydroxyl or $C_1$-$C_6$ alkoxy. In some embodiments, $R^2$ has one of the following structures:

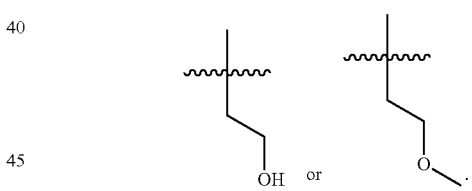

In other embodiments, $R^5$ is H. In other embodiments, $R^5$ $C_1$-$C_6$ alkyl, such as methyl.

In certain embodiments, Y is C(H)(OH). In other embodiments, Y is NH.

In various embodiments, A is $C_6$-$C_{10}$ aryl, $C_3$-$C_{10}$ cycloalkyl or 5-6 membered monocyclic heteroaryl, each of which is optionally substituted with one or more R. It is understood that A is a divalent radical.

In certain embodiments, A is a divalent optionally substituted $C_{6-10}$ aryl. In certain embodiments, A is a divalent optionally substituted 3-8 membered saturated or partially unsaturated carbocyclic ring. In certain embodiments, A is a divalent optionally substituted 3-10 membered heterocylic ring having 1-4 heteroatoms independently selected from nitrogen, oxygen, or sulfur. In certain embodiments, A is a divalent optionally substituted 5-6 membered monocyclic heteroaryl ring having 1-4 heteroatoms independently selected from nitrogen, oxygen, or sulfur.

In certain embodiments, A is a divalent group selected from phenyl, pyridinyl, cyclohexyl, and cyclohexenyl; each of which is optionally substituted. In other embodiments, A is phenyl. In different embodiments, A is saturated or unsaturated cyclohexyl. In more embodiments, A is pyridinyl.

In certain embodiments, A is pyrimidinyl, which is optionally substituted.

In any of the foregoing embodiments, A is unsubstituted. In different of the foregoing embodiments, A is substituted with one or more $R^6$. For example, in some embodiments $R^6$ is halo. In some embodiments, $R^6$ is chloro or fluoro. In other embodiments, $R^6$ is fluoro.

In some embodiments, $R^6$ is $C_1$-$C_6$ hydroxylalkyl. In some embodiments, $C_1$-$C_6$ hydroxylalkyl is —$CH_2CH_2OH$. In other embodiments, $R^6$ is cyano. In some embodiments, $R^6$ is $C_1$-$C_6$ alkoxy. In more specific embodiments, the $C_1$-$C_6$ alkoxy is methoxy.

In certain embodiments, A is a divalent group selected from phenyl, naphthyl, cyclopropyl, cyclobutyl, cyclopentyl, cyclohexyl, cyclohexenyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, dithiazinyl, tetrahydrofuranyl, furanyl, furazanyl, imidazolidinyl, imidazolinyl, imidazolyl, 1H-indazolyl, indolenyl, indolinyl, indolizinyl, indolyl, 3-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2-pyrrolyl, pyrrolyl, quinazolinyl, quinolinyl, 4H-quinolizinyl, quinoxalinyl, quinuclidinyl, tetrahydro furanyl, tetrahydroisoquinolinyl, tetrahydroquinolinyl, thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, and xanthenyl; each of which is optionally substituted.

In specific embodiments, A has one of the following structures:

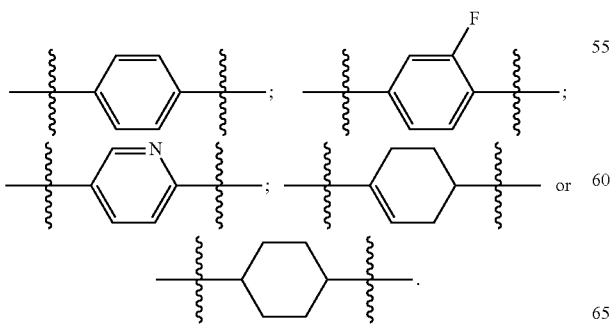

In some specific embodiments, A has one of the following structures:

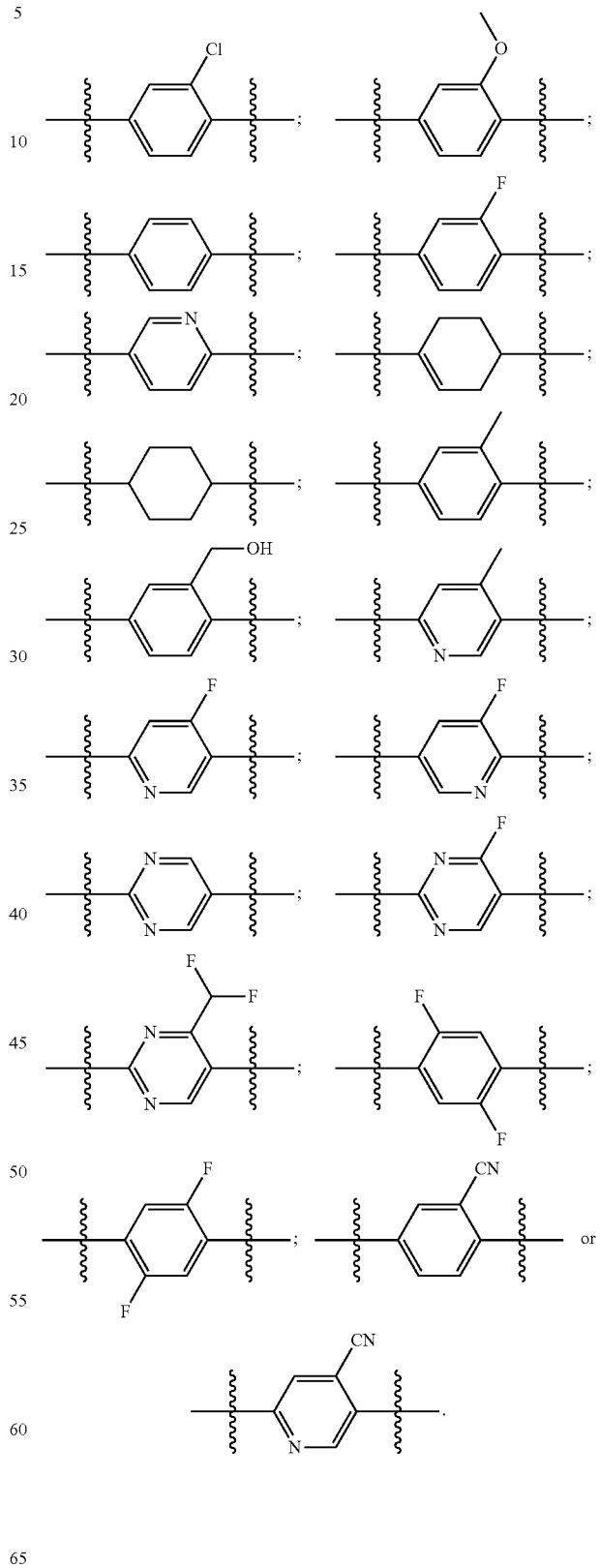

In some specific embodiments, A has one of the following structures:

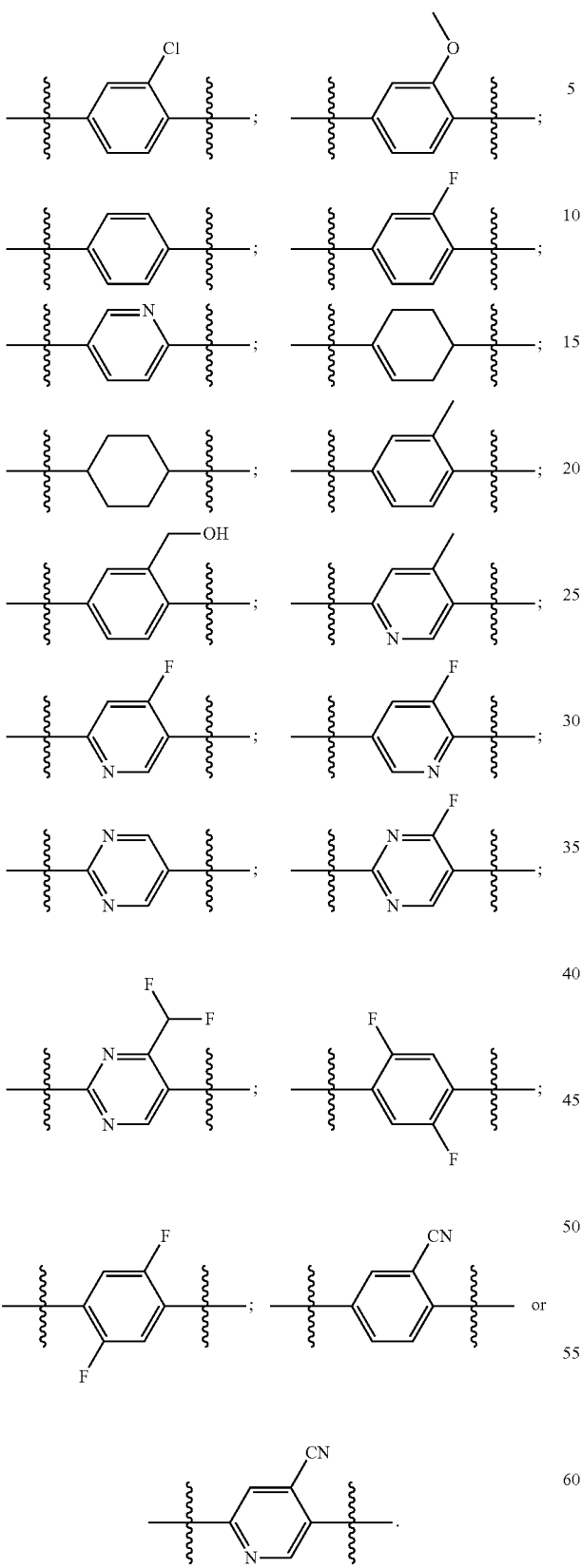

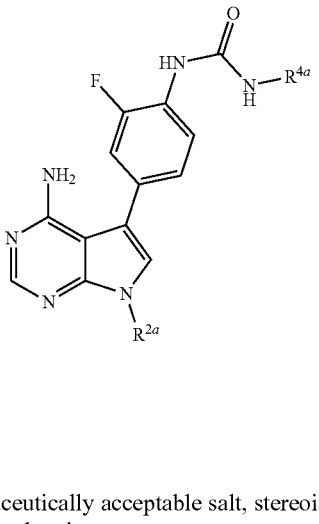

or a pharmaceutically acceptable salt, stereoisomer or prodrug thereof, wherein:

$R^{2a}$ is $C_1$-$C_6$ alkyl or $C_3$-$C_8$ cycloalkyl optionally substituted with one more substituents selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3-8 membered heterocyclyl;

$R^{4a}$ is isoxazolyl optionally substituted with one more substituents selected from $C_1$-$C_6$ haloalkyl, $C_3$-$C_8$ cycloalkyl, or $C_3$-$C_8$ haloalkylcycloalkyl.

In more specific embodiments, $R^{2a}$ is a branched $C_1$-$C_6$ alkyl substituted with hydroxyl. In some embodiments, $R^{2a}$ is $C_3$-$C_8$ cycloalkyl. In more specific embodiments, $R^{2a}$ has one of the following structures:

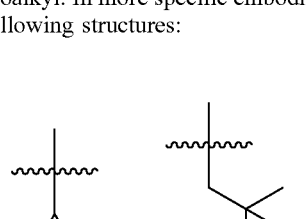

In certain embodiments, $R^{4a}$ is isoxazolyl substituted with $C_3$-$C_8$ haloalkylcycloalkyl. In some embodiments, $R^{4a}$ is $C_3$-$C_8$ fluoroalkylcycloalkyl. In still more specific embodiments, $R^{4a}$ is fluoroalkylcyclopropyl or fluoroalkylcyclobutyl. In more specific embodiments, $R^{4a}$ has one of the following structures:

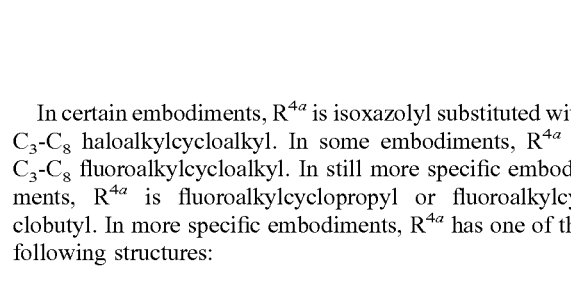

In some embodiments, X is CH. In some more specific embodiments, the compound has the following Structure (IB):

In certain embodiments, the compound has the following Structure (IA):

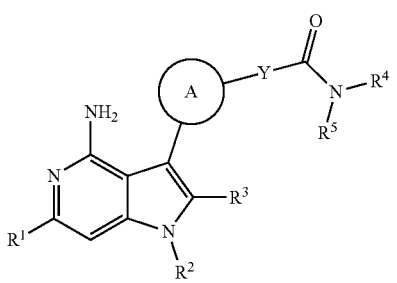

or a pharmaceutically acceptable salt, stereoisomer or prodrug thereof, wherein:

A is $C_6$-$C_{10}$ aryl, $C_3$-$C_{10}$ cycloalkyl, 3-10 membered heterocyclyl or 5-6 membered monocyclic heteroaryl, each of which is optionally substituted with one or more $R^6$.

X is CH or N;

Y is CHOH or NH;

$R^1$ is H or $C_1$-$C_6$ alkyl;

$R^2$ is $C_1$-$C_6$ alkyl, $C_2$-$C_6$ alkenyl, $C_2$-$C_6$ alkynyl, $C_3$-$C_8$ cycloalkyl, 3-8 membered heterocyclyl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3-8 membered heterocyclyl;

$R^3$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl or 5- or 6-membered heteroaryl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy;

$R^4$ is a heteroaryl selected from oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl and 1, 3, 4-thiadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl;

$R^5$ is H, $C_1$-$C_6$ alkyl, $C_2$-$C_6$ alkenyl, $C_2$-$C_6$ alkynyl, $C_3$-$C_8$ cycloalkyl, 3- to 8-membered heterocyclyl, $C_6$-$C_{10}$ aryl or 5- or 6-membered heteroaryl, each of which is optionally substituted with one more substituents selected from halo, hydroxyl, cyano, aminyl, $C_1$-$C_6$ alkyl, $C_2$-$C_6$ alkenyl, $C_2$-$C_6$ alkynyl and $C_1$-$C_6$ alkoxy; and $R^6$ is, at each occurrence, independently halo, $C_1$-$C_6$ alkyl, $C_1$-$C_6$ alkoxy, cyano, $C_1$-$C_6$ hydroxylalkyl or $C_1$-$C_6$ haloalkyl.

In a certain embodiment, the compound of Structure (I) is a modulator of the NLRP3 inflammasome.

In a specific embodiment, the compound of Structure (I) is an inhibitor of NEK7 in a patient or in a biological sample.

In various different embodiments, the compound has one of the structures set forth in Table 1 below, or a pharmaceutically acceptable salt, stereoisomer or prodrug thereof. Compounds in Table 1 were prepared as described in the Examples or methods known in the art and analyzed by mass spectrometry and/or $^1$H NMR.

TABLE 1

Representative Compounds of Structure (I)

| No. | Structure | Name |
|---|---|---|
| 1 | 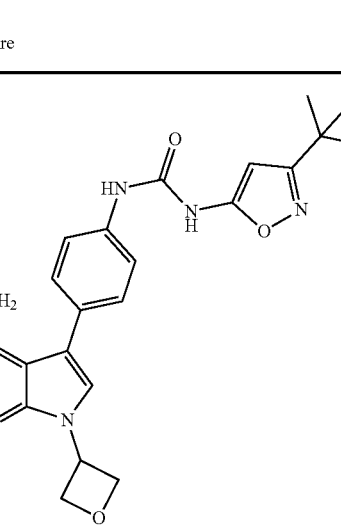 | 1-(4-(4-amino-7-(oxetan-3-yl)-7H-pyrrolo[2,3-d]pyrimidin-5-yl)phenyl)-3-(3-(tert-butyl)isoxazol-5-yl)urea |

TABLE 1-continued

Representative Compounds of Structure (I)

| No. | Structure | Name |
|---|---|---|
| 2 | 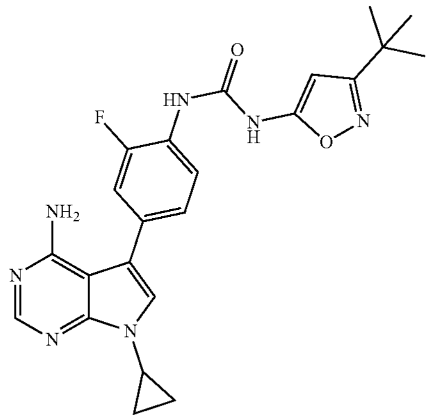 | 1-(4-(4-amino-7-cyclopropyl-7H-pyrrolo[2,3-d]pyrimidin-5-yl)-2-fluorophenyl)-3-(3-(tert-butyl)isoxazol-5-yl)urea |
| 3 | 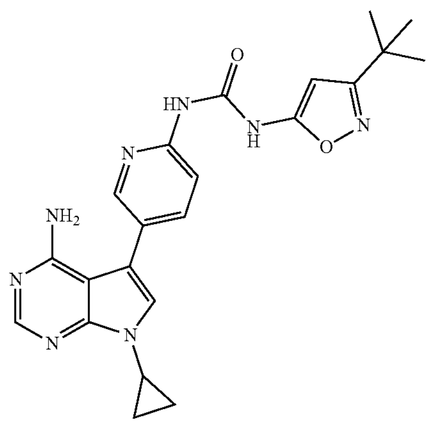 [SMILES: CC(C)(C)c1cc(NC(=O)Nc2ccc(-c3cn(C4CC4)c4ncnc(N)c34)cn2)on1] | 1-(5-(4-amino-7-cyclopropyl-7H-pyrrolo[2,3-d]pyrimidin-5-yl)pyridin-2-yl)-3-(3-(tert-butyl)isoxazol-5-yl)urea |
| 4 | 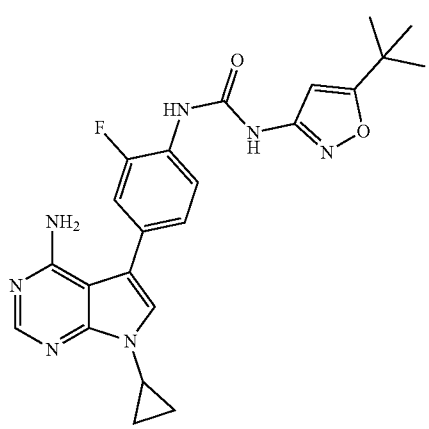 [SMILES: CC(C)(C)c1cc(NC(=O)Nc2ccc(-c3cn(C4CC4)c4ncnc(N)c34)cc2F)no1] | 1-(4-(4-amino-7-cyclopropyl-7H-pyrrolo[2,3-d]pyrimidin-5-yl)-2-fluorophenyl)-3-(5-(tert-butyl)isoxazol-3-yl)urea |

TABLE 1-continued

Representative Compounds of Structure (I)

| No. | Structure | Name |
|---|---|---|
| 5 | 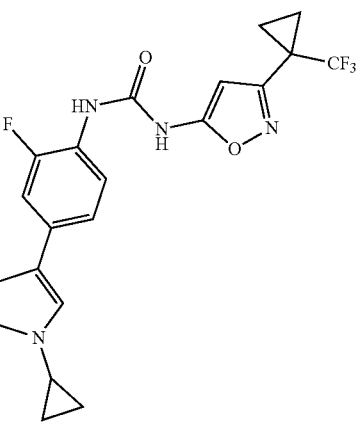 | 1-(4-(4-amino-7-cyclopropyl-7H-pyrrolo[2,3-d]pyrimidin-5-yl)-2-fluorophenyl)-3-(3-(1-(trifluoromethyl)cyclopropyl)isoxazol-5-yl)urea |
| 6 | 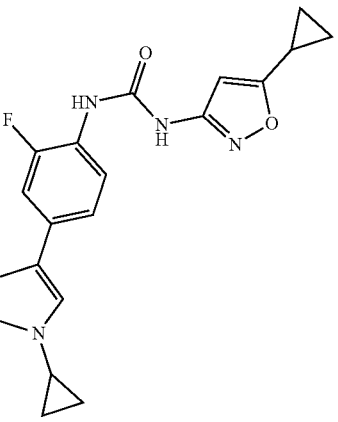 | 1-(4-(4-amino-7-cyclopropyl-7H-pyrrolo[2,3-d]pyrimidin-5-yl)-2-fluorophenyl)-3-(5-cyclopropylisoxazol-3-yl)urea |
| 7 | 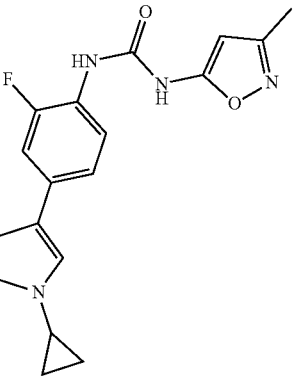 | 1-(4-(4-amino-7-cyclopropyl-7H-pyrrolo[2,3-d]pyrimidin-5-yl)-2-fluorophenyl)-3-(3-methylisoxazol-5-yl)urea |
| 8 | 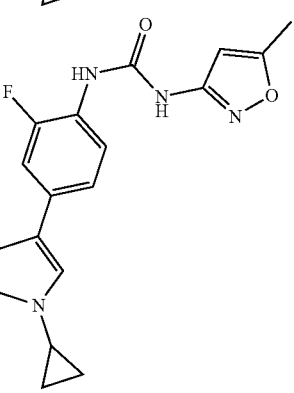 | 1-(4-(4-amino-7-cyclopropyl-7H-pyrrolo[2,3-d]pyrimidin-5-yl)-2-fluorophenyl)-3-(5-methylisoxazol-3-yl)urea |

TABLE 1-continued

Representative Compounds of Structure (I)

| No. | Structure | Name |
|---|---|---|
| 9 | 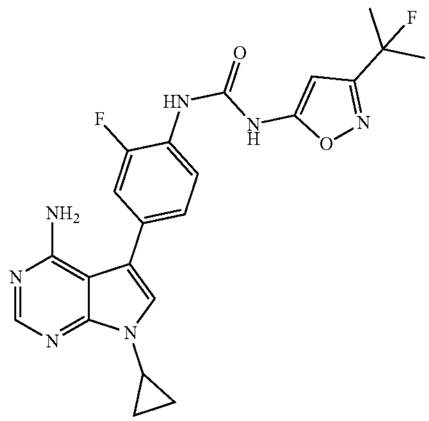 [SMILES: CC(C)(F)c1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-(2-fluoropropan-2-yl)isoxazol-5-yl)urea |
| 10 | 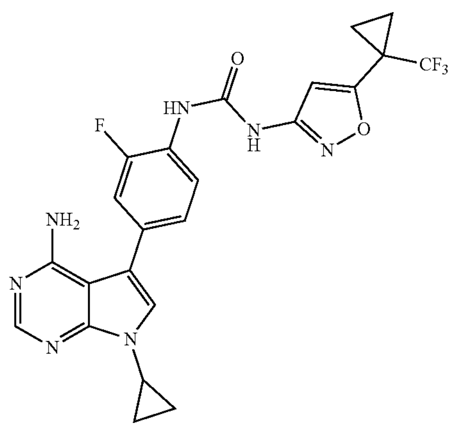 [SMILES: Nc1ncnc2c1c(-c1ccc(NC(=O)Nc3cc(C4(C(F)(F)F)CC4)on3)c(F)c1)cn2C1CC1] | 1-(4-(4-amino-7-cyclopropyl-7H-pyrrolo[2,3-d]pyrimidin-5-yl)-2-fluorophenyl)-3-(5-(1-(trifluoromethyl)cyclopropyl)isoxazol-3-yl)urea |
| 11 | 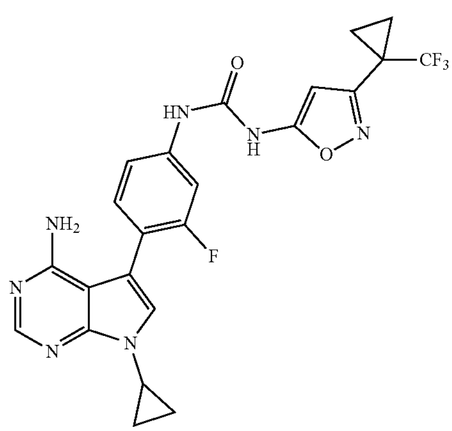 [SMILES: Nc1ncnc2c1c(-c1ccc(NC(=O)Nc3cc(C4(C(F)(F)F)CC4)no3)cc1F)cn2C1CC1] | 1-(4-(4-amino-7-cyclopropyl-7H-pyrrolo[2,3-d]pyrimidin-5-yl)-3-fluorophenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 12 | 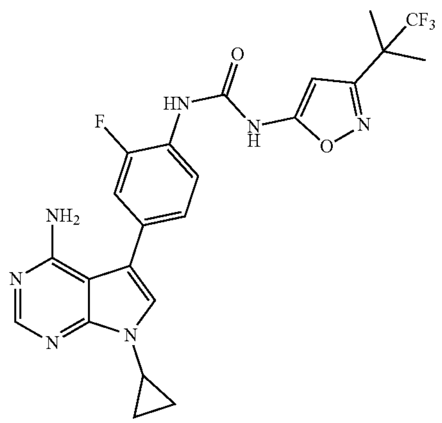 [SMILES: CC(C)(c1cc(NC(=O)Nc2ccc(-c3cn(C4CC4)c4ncnc(N)c34)cc2F)on1)C(F)(F)F] | 1-(4-(4-amino-7-cyclopropyl-7H-pyrrolo[2,3-d]pyrimidin-5-yl)-2-fluorophenyl)-3-(3-(1,1,1-trifluoro-2-methylpropan-2-yl)isoxazol-5-yl)urea |
| 13 | 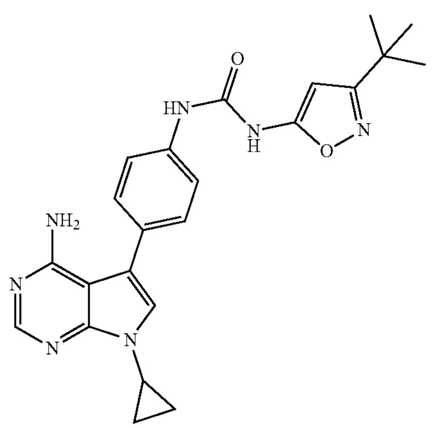 [SMILES: CC(C)(C)c1cc(NC(=O)Nc2ccc(-c3cn(C4CC4)c4ncnc(N)c34)cc2)on1] | 1-(4-(4-amino-7-cyclopropyl-7H-pyrrolo[2,3-d]pyrimidin-5-yl)phenyl)-3-(3-(tert-butyl)isoxazol-5-yl)urea |
| 14 | 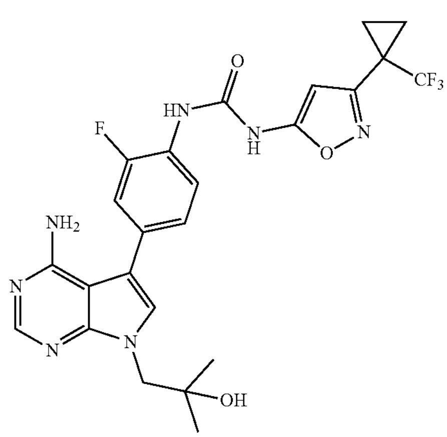 [SMILES: CC(C)(O)Cn1cc(-c2ccc(NC(=O)Nc3cc(C4(C(F)(F)F)CC4)no3)c(F)c2)c2c(N)ncnc21] | 1-(4-(4-amino-7-(2-hydroxy-2-methylpropyl)-7H-pyrrolo[2,3-d]pyrimidin-5-yl)-2-fluorophenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 15 | 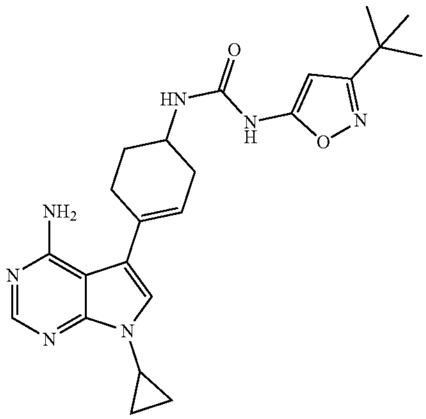 [SMILES: CC(C)(C)c1cc(NC(=O)NC2CC=C(c3cn(C4CC4)c4ncnc(N)c34)CC2)on1] | 1-(4-(4-amino-7-cyclopropyl-7H-pyrrolo[2,3-d]pyrimidin-5-yl)cyclohex-3-en-1-yl)-3-(3-(tert-butyl)isoxazol-5-yl)urea |
| 16 | 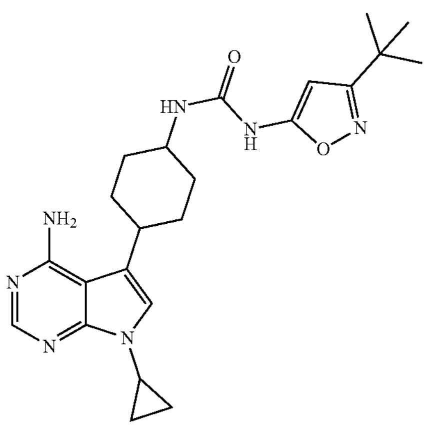 [SMILES: CC(C)(C)c1cc(NC(=O)NC2CCC(c3cn(C4CC4)c4ncnc(N)c34)CC2)on1] | 1-(4-(4-amino-7-cyclopropyl-7H-pyrrolo[2,3-d]pyrimidin-5-yl)cyclohexyl)-3-(3-(tert-butyl)isoxazol-5-yl)urea |
| 17 | 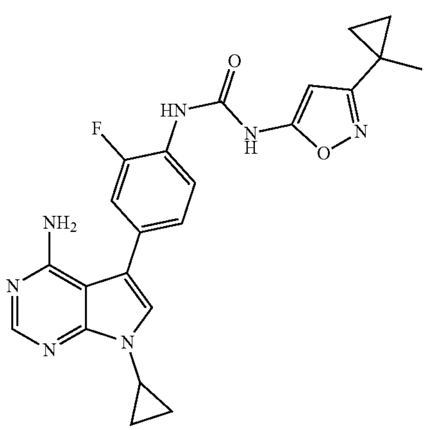 [SMILES: CC1(c2cc(NC(=O)Nc3ccc(-c4cn(C5CC5)c5ncnc(N)c45)cc3F)on2)CC1] | 1-(4-(4-amino-7-cyclopropyl-7H-pyrrolo[2,3-d]pyrimidin-5-yl)-2-fluorophenyl)-3-(3-(1-methylcyclopropyl)isoxazol-5-yl)urea |

TABLE 1-continued

Representative Compounds of Structure (I)

| No. | Structure | Name |
|---|---|---|
| 18 | 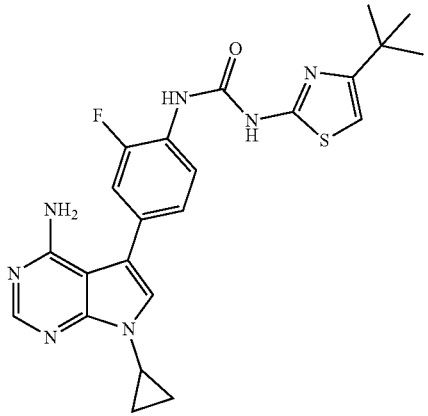 [SMILES: CC(C)(C)c1csc(NC(=O)Nc2ccc(-c3cn(C4CC4)c4ncnc(N)c34)cc2F)n1] | 1-(4-(4-amino-7-cyclopropyl-7H-pyrrolo[2,3-d]pyrimidin-5-yl)-2-fluorophenyl)-3-(4-(tert-butyl)thiazol-2-yl)urea |
| 19 | 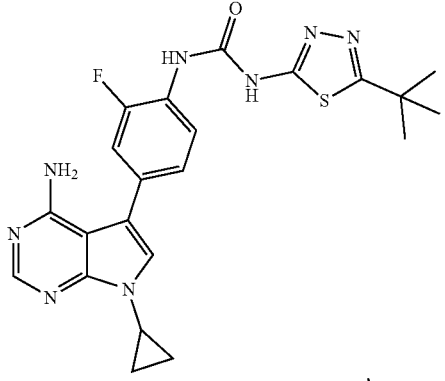 | 1-(4-(4-amino-7-cyclopropyl-7H-pyrrolo[2,3-d]pyrimidin-5-yl)-2-fluorophenyl)-3-(5-(tert-butyl)-1,3,4-thiadiazol-2-yl)urea |
| 20 | 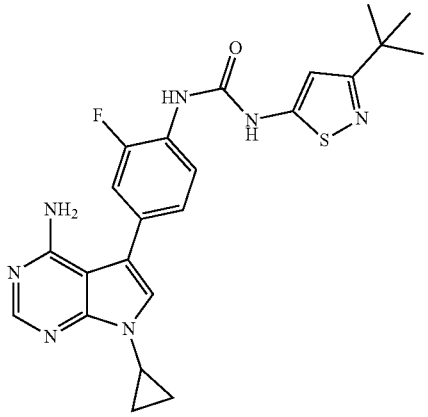 [SMILES: CC(C)(C)c1cc(NC(=O)Nc2ccc(-c3cn(C4CC4)c4ncnc(N)c34)cc2F)sn1] | 1-(4-(4-amino-7-cyclopropyl-7H-pyrrolo[2,3-d]pyrimidin-5-yl)-2-fluorophenyl)-3-(3-(tert-butyl)isothiazol-5-yl)urea |
| 21 | 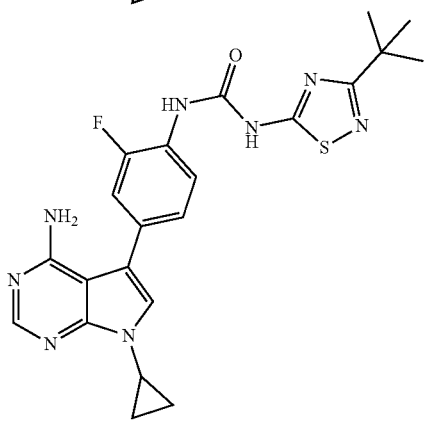 | 1-(4-(4-amino-7-cyclopropyl-7H-pyrrolo[2,3-d]pyrimidin-5-yl)-2-fluorophenyl)-3-(3-(tert-butyl)-1,2,4-thiadiazol-5-yl)urea |

TABLE 1-continued

Representative Compounds of Structure (I)

| No. | Structure | Name |
|---|---|---|
| 22 | 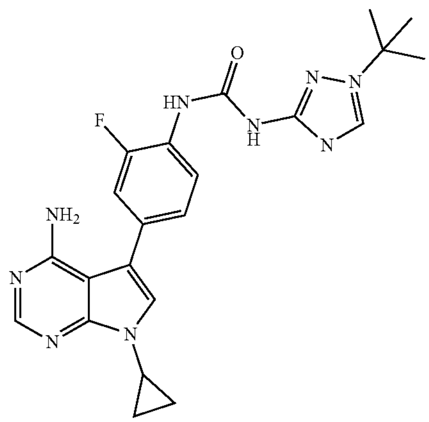 | 1-(4-(4-amino-7-cyclopropyl-7H-pyrrolo[2,3-d]pyrimidin-5-yl)-2-fluorophenyl)-3-(3-(tert-butyl)-1,2,4-thiadiazol-5-yl)urea |
| 23 | 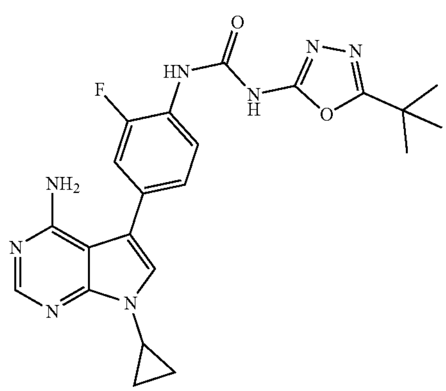 [SMILES: CC(C)(C)c1nnc(NC(=O)Nc2ccc(-c3cn(C4CC4)c4ncnc(N)c34)cc2F)o1] | 1-(4-(4-amino-7-cyclopropyl-7H-pyrrolo[2,3-d]pyrimidin-5-yl)-2-fluorophenyl)-3-(5-(tert-butyl)-1,3,4-oxadiazol-2-yl)urea |
| 24 | 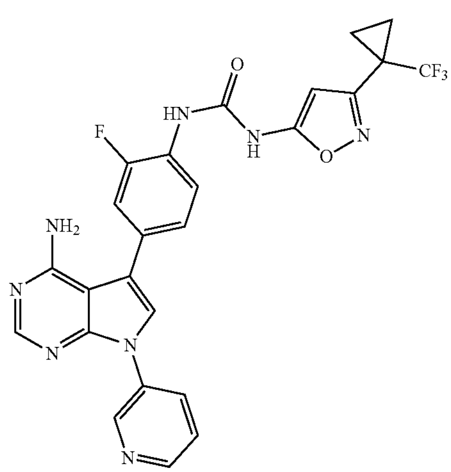 [SMILES: Nc1ncnc2c1c(-c1ccc(NC(=O)Nc3cc(C4(C(F)(F)F)CC4)no3)c(F)c1)cn2-c1cccnc1] | 1-(4-(4-amino-7-(pyridin-3-yl)-7H-pyrrolo[2,3-d]pyrimidin-5-yl)-2-fluorophenyl)-3 -(3-(1-(trifluoromethyl)cyclopropyl)isoxazol-5-yl)urea |

TABLE 1-continued

Representative Compounds of Structure (I)

| No. | Structure | Name |
|---|---|---|
| 25 | 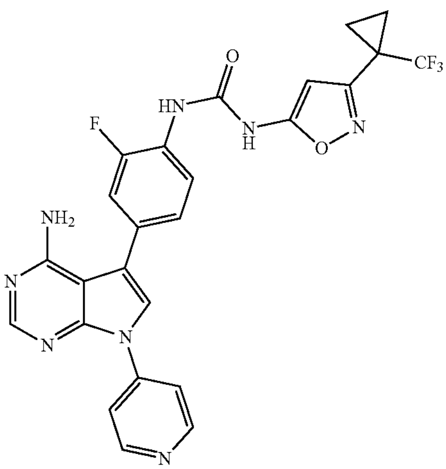 [SMILES: Nc1ncnc2c1c(-c1ccc(NC(=O)Nc3cc(C4(C(F)(F)F)CC4)no3)c(F)c1)cn2-c1ccncc1] | 1-(4-(4-amino-7-(pyridin-4-yl)-7H-pyrrolo[2,3-d]pyrimidin-5-yl)-2-fluorophenyl)-3-(3-(1-(trifluoromethyl)cyclopropyl)isoxazol-5-yl)urea |
| 26 | 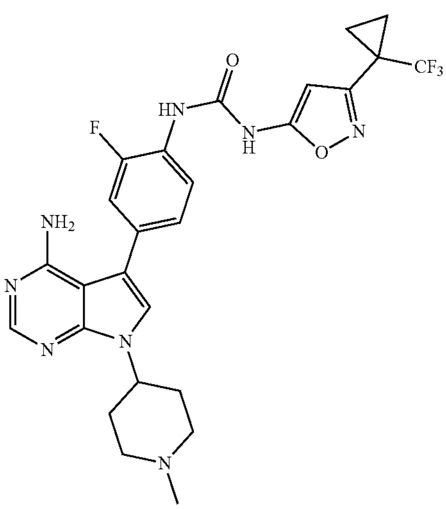 [SMILES: CN1CCC(n2cc(-c3ccc(NC(=O)Nc4cc(C5(C(F)(F)F)CC5)no4)c(F)c3)c3c(N)ncnc32)CC1] | 1-(4-(4-amino-7-(1-methylpiperidin-4-yl)-7H-pyrrolo[2,3-d]pyrimidin-5-yl)-2-fluorophenyl)-3-(3-(1-(trifluoromethyl)cyclopropyl)isoxazol-5-yl)urea |
| 27 | 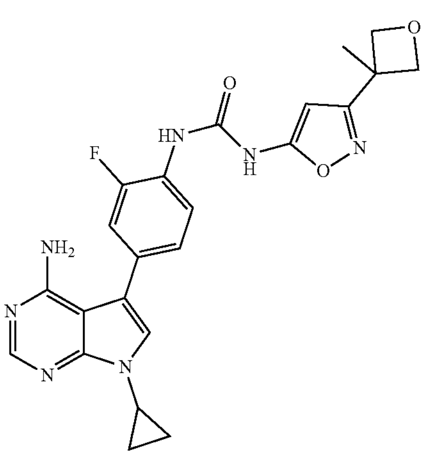 [SMILES: CC1(c2cc(NC(=O)Nc3ccc(-c4cn(C5CC5)c5ncnc(N)c45)cc3F)on2)COC1] | 1-(4-(4-amino-7-cyclopropyl-7H-pyrrolo[2,3-d]pyrimidin-5-yl)-2-fluorophenyl)-3-(3-(3-methyloxetan-3-yl)isoxazol-5-yl)urea |

TABLE 1-continued
Representative Compounds of Structure (I)
| No. | Structure | Name |
|---|---|---|
| 28 | 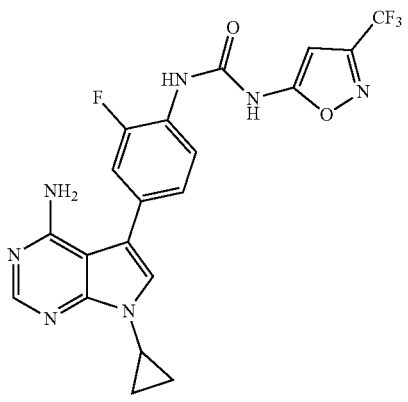 [SMILES: Nc1ncnc2c1c(-c1ccc(NC(=O)Nc3cc(C(F)(F)F)no3)c(F)c1)cn2C1CC1] | 1-(4-(4-amino-7-cyclopropyl-7H-pyrrolo[2,3-d]pyrimidin-5-yl)-2-fluorophenyl)-3-(3-(trifluoromethyl)isoxazol-5-yl)urea |
| 29 | 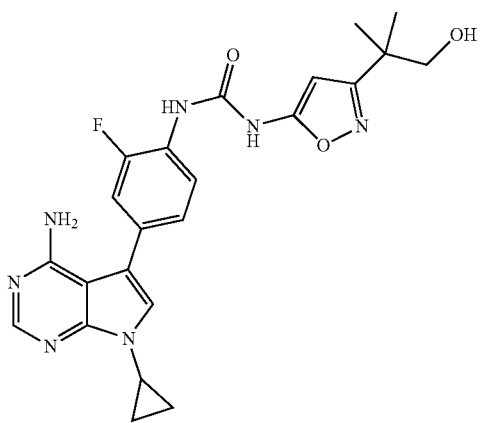 [SMILES: CC(C)(CO)c1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-(1-hydroxy-2-methylpropan-2-yl)isoxazol-5-yl)urea |
| 30 | 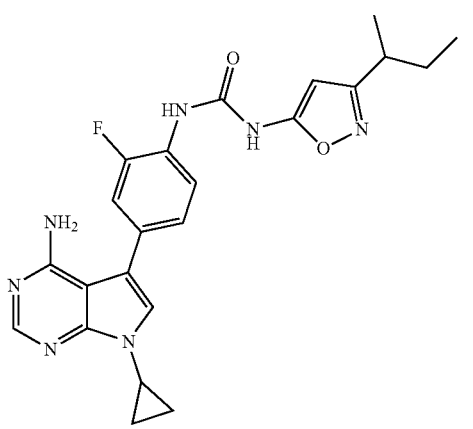 [SMILES: CCC(C)c1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-(sec-butyl)isoxazol-5-yl)urea |

TABLE 1-continued

Representative Compounds of Structure (I)

| No. | Structure | Name |
|---|---|---|
| 31 | 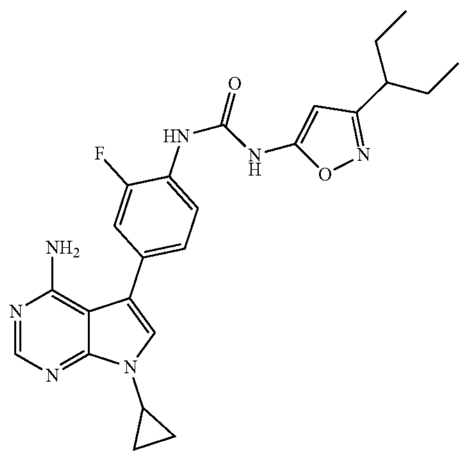 [SMILES: CCC(CC)c1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-(pentan-3-yl)isoxazol-5-yl)urea |
| 32 | 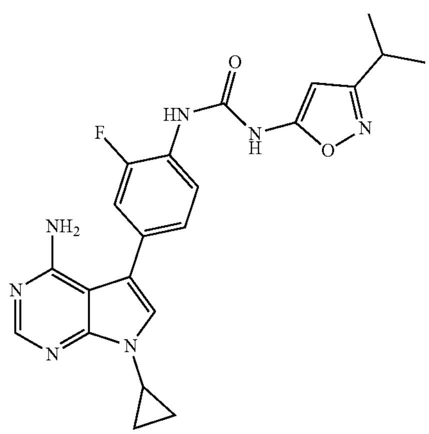 [SMILES: CC(C)c1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-isopropylisoxazol-5-yl)urea |
| 33 | 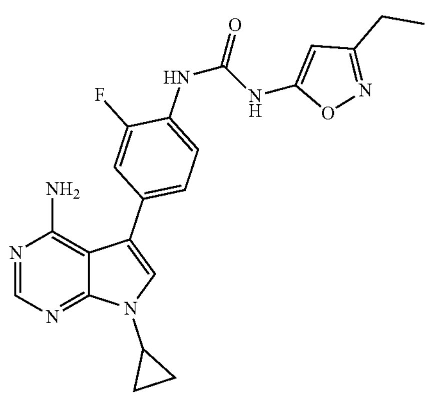 [SMILES: CCc1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-ethylisoxazol-5-yl) |

TABLE 1-continued

Representative Compounds of Structure (I)

| No. | Structure | Name |
|---|---|---|
| 34 | 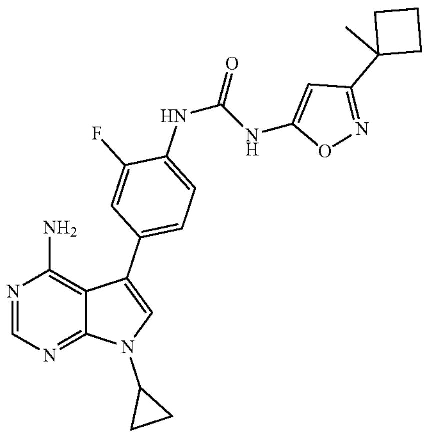 [SMILES: CC1(c2cc(NC(=O)Nc3ccc(-c4cn(C5CC5)c5ncnc(N)c45)cc3F)on2)CCC1] | 1-(4-(4-amino-7-cyclopropyl-7H-pyrrolo[2,3-d]pyrimidin-5-yl)-2-fluorophenyl)-3-(3-(1-methylcyclobutyl)isoxazol-5-yl)urea |
| 35 | 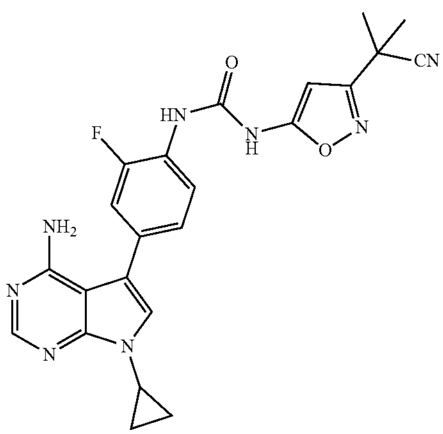 [SMILES: CC(C)(C#N)c1cc(NC(=O)Nc2ccc(-c3cn(C4CC4)c4ncnc(N)c34)cc2F)on1] | 1-(4-(4-amino-7-cyclopropyl-7H-pyrrolo[2,3-d]pyrimidin-5-yl)-2-fluorophenyl)-3-(3-(2-cyanopropan-2-yl)isoxazol-5-yl)urea |
| 36 | 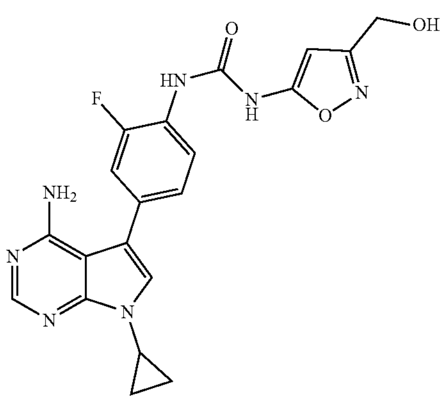 [SMILES: Nc1ncnc2c1c(-c1ccc(NC(=O)Nc3cc(CO)no3)c(F)c1)cn2C1CC1] | 1-(4-(4-amino-7-cyclopropyl-7H-pyrrolo[2,3-d]pyrimidin-5-yl)-2-fluorophenyl)-3-(3-(hydroxymethyl)isoxazol-5-yl)urea |

TABLE 1-continued

Representative Compounds of Structure (I)

| No. | Structure | Name |
|---|---|---|
| 37 | 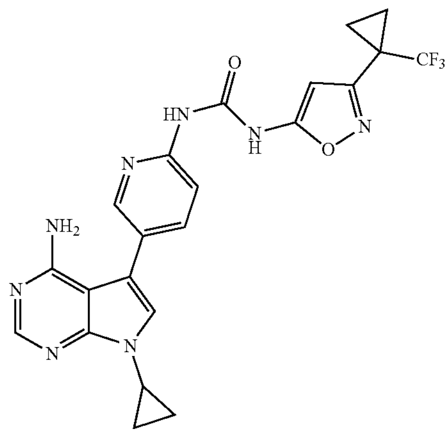 [SMILES: Nc1ncnc2c1c(-c1ccc(NC(=O)Nc3cc(C4(C(F)(F)F)CC4)no3)nc1)cn2C1CC1] | 1-(5-(4-amino-7-cyclopropyl-7H-pyrrolo[2,3-d]pyrimidin-5-yl)pyridin-2-yl)-3-(3-(trifluoromethyl)cyclopropyl)isoxazol-5-yl)urea |
| 38 | 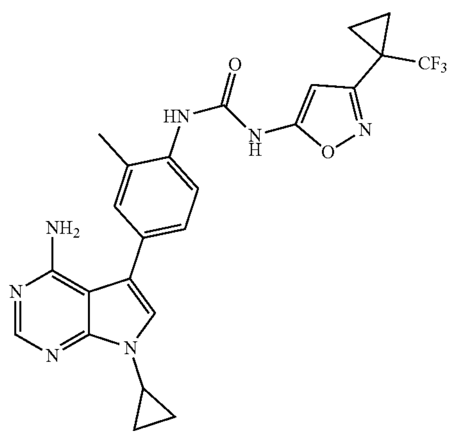 [SMILES: Cc1cc(-c2cn(C3CC3)c3ncnc(N)c23)ccc1NC(=O)Nc1cc(C2(C(F)(F)F)CC2)no1] | 1-(4-(4-amino-7-cyclopropyl-7H-pyrrolo[2,3-d]pyrimidin-5-yl)-2-methylphenyl)-3-(3-(1-(trifluoromethyl)cyclopropyl)isoxazol-5-yl)urea |
| 39 | 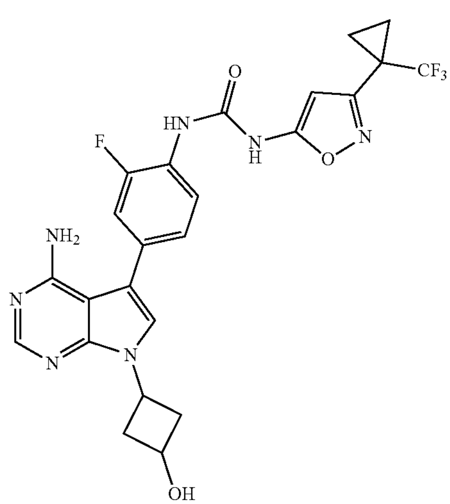 [SMILES: Nc1ncnc2c1c(-c1ccc(NC(=O)Nc3cc(C4(C(F)(F)F)CC4)no3)c(F)c1)cn2C1CC(O)C1] | 1-(4-(4-amino-7-(3-hydroxycyclobutyl)-7H-pyrrolo[2,3-d]pyrimidin-5-yl)-2-fluorophenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 40 | 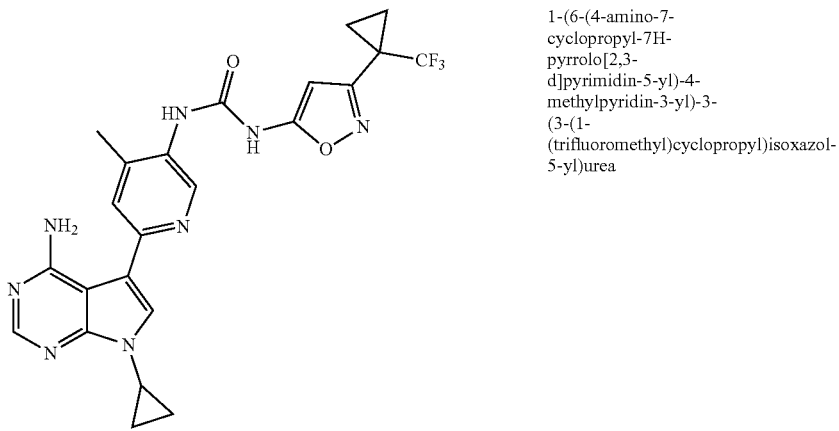 | 1-(6-(4-amino-7-cyclopropyl-7H-pyrrolo[2,3-d]pyrimidin-5-yl)-4-methylpyridin-3-yl)-3-(3-(1-(trifluoromethyl)cyclopropyl)isoxazol-5-yl)urea |
| 41 | 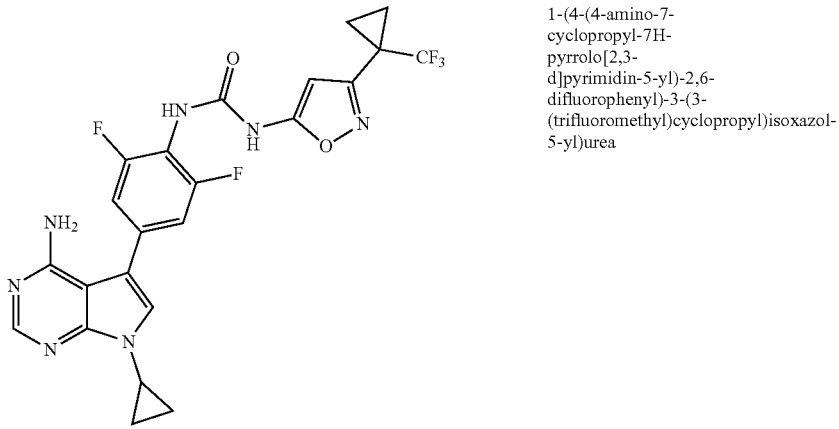 | 1-(4-(4-amino-7-cyclopropyl-7H-pyrrolo[2,3-d]pyrimidin-5-yl)-2,6-difluorophenyl)-3-(3-(1-(trifluoromethyl)cyclopropyl)isoxazol-5-yl)urea |
| 42 | 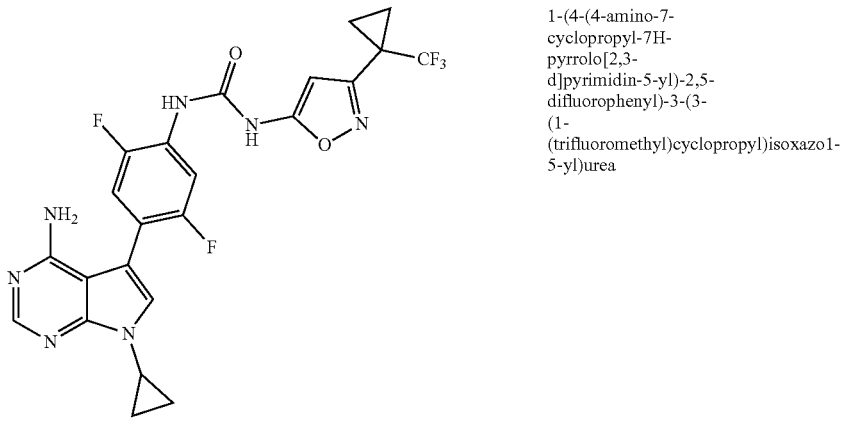 | 1-(4-(4-amino-7-cyclopropyl-7H-pyrrolo[2,3-d]pyrimidin-5-yl)-2,5-difluorophenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 43 | 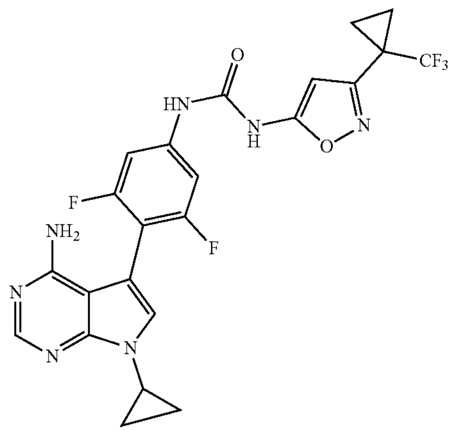 [SMILES: Nc1ncnc2c1c(-c1c(F)cc(NC(=O)Nc3cc(C4(C(F)(F)F)CC4)no3)cc1F)cn2C1CC1] | 1-(4-(4-amino-7-cyclopropyl-7H-pyrrolo[2,3-d]pyrimidin-5-yl)-3,5-difluorophenyl)-3-(3-(1-(trifluoromethyl)cyclopropyl)isoxazol-5-yl)urea |
| 44 | 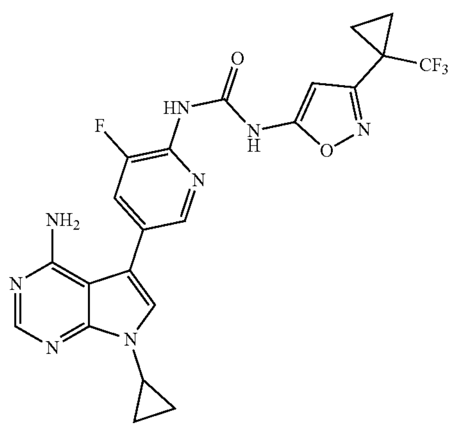 [SMILES: Nc1ncnc2c1c(-c1cnc(NC(=O)Nc3cc(C4(C(F)(F)F)CC4)no3)c(F)c1)cn2C1CC1] | 1-(5-(4-amino-7-cyclopropyl-7H-pyrrolo[2,3-d]pyrimidin-5-yl)-3-fluoropyridin-2-yl)-3-(3-(1-(trifluoromethyl)cyclopropyl)isoxazol-5-yl)urea |
| 45 | 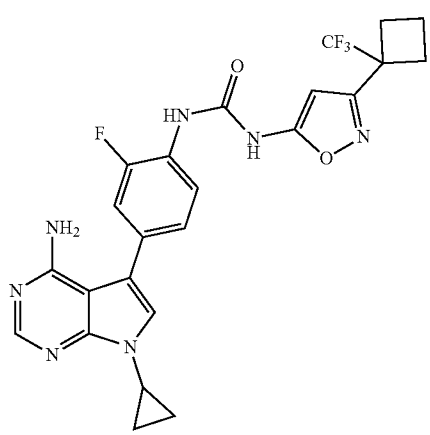 [SMILES: Nc1ncnc2c1c(-c1ccc(NC(=O)Nc3cc(C4(C(F)(F)F)CCC4)no3)c(F)c1)cn2C1CC1] | 1-(4-(4-amino-7-cyclopropyl-7H-pyrrolo[2,3-d]pyrimidin-5-yl)-2-fluorophenyl)-3-(3-(1-(trifluoromethyl)cyclobutyl)isoxazol-5-yl)urea |

TABLE 1-continued

Representative Compounds of Structure (I)

| No. | Structure | Name |
|---|---|---|
| 46 | 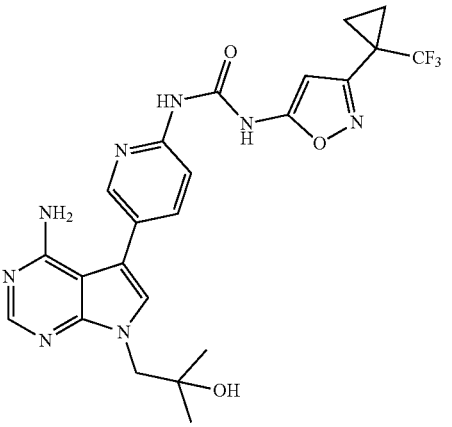 [SMILES: CC(C)(O)Cn1cc(-c2ccc(NC(=O)Nc3cc(C4(C(F)(F)F)CC4)no3)nc2)c2c(N)ncnc21] | 1-(5-(4-amino-7-(2-hydroxy-2-methylpropyl)-7H-pyrrolo[2,3-d]pyrimidin-5-yl)pyridin-2-yl)-3-(3-(1-(trifluoromethyl)cyclopropyl)isoxazol-5-yl)urea |
| 47 | 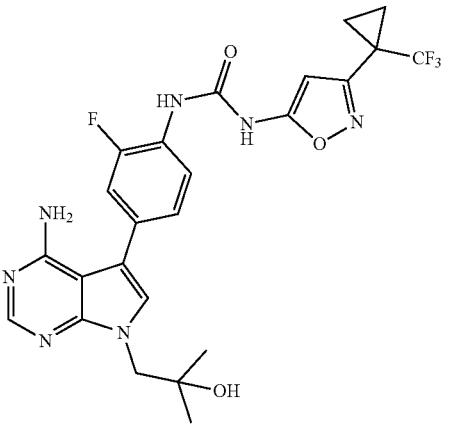 [SMILES: CC(C)(O)Cn1cc(-c2ccc(NC(=O)Nc3cc(C4(C(F)(F)F)CC4)no3)c(F)c2)c2c(N)ncnc21] | 1-(4-(4-amino-7-(2-hydroxy-2-methylpropyl)-7H-pyrrolo[2,3-d]pyrimidin-5-yl)-2-fluorophenyl)-3-(3-(1-(trifluoromethyl)cyclopropyl)isoxazol-5-yl)urea |
| 48 | 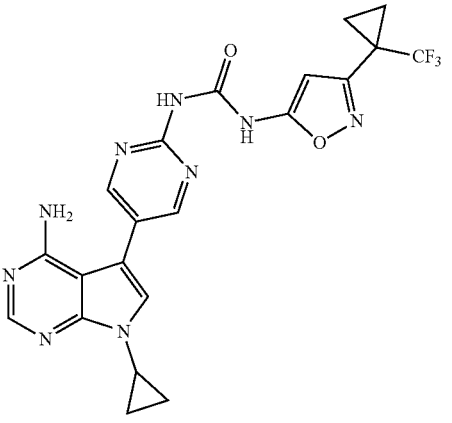 [SMILES: Nc1ncnc2c1c(-c1cnc(NC(=O)Nc3cc(C4(C(F)(F)F)CC4)no3)nc1)cn2C1CC1] | 1-(5-(4-amino-7-cyclopropyl-7H-pyrrolo[2,3-d]pyrimidin-5-yl)pyrimidin-2-yl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 49 | 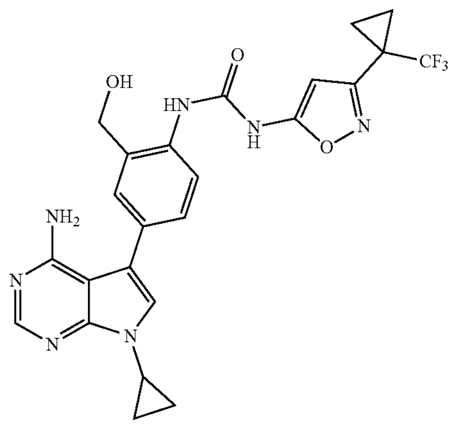 [SMILES: Nc1ncnc2c1c(-c1ccc(NC(=O)Nc3cc(C4(C(F)(F)F)CC4)no3)c(CO)c1)cn2C1CC1] | 1-(4-(4-amino-7-cyclopropyl-7H-pyrrolo[2,3-d]pyrimidin-5-yl)-2-(hydroxymethyl)phenyl)-3-(3-(1-(trifluoromethyl)cyclopropyl)isoxazol-5-yl)urea |
| 50 | 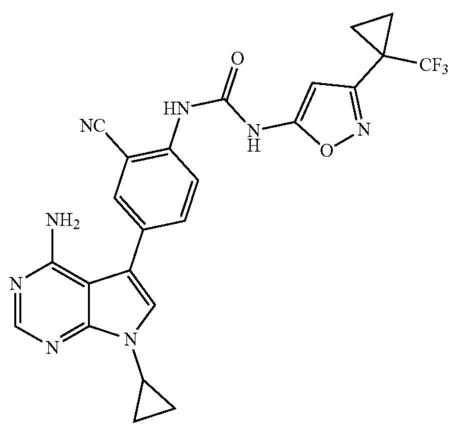 [SMILES: N#Cc1cc(-c2cn(C3CC3)c3ncnc(N)c23)ccc1NC(=O)Nc1cc(C2(C(F)(F)F)CC2)no1] | 1-(4-(4-amino-7-cyclopropyl-7H-pyrrolo[2,3-d]pyrimidin-5-yl)-2-cyanophenyl)-3-(3-(1-(trifluoromethyl)cyclopropyl)isoxazol-5-yl)urea |
| 51 | 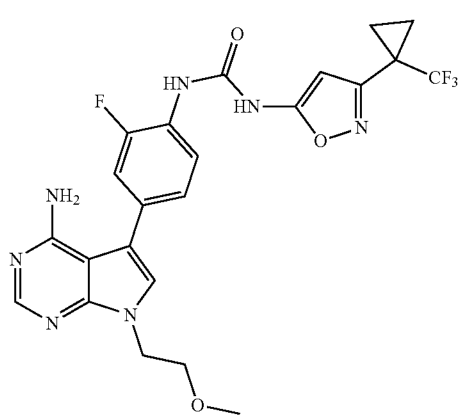 [SMILES: COCCn1cc(-c2ccc(NC(=O)Nc3cc(C4(C(F)(F)F)CC4)no3)c(F)c2)c2c(N)ncnc21] | 1-(4-(4-amino-7-(2-methoxyethyl)-7H-pyrrolo[2,3-d]pyrimidin-5-yl)-2-fluorophenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 52 | 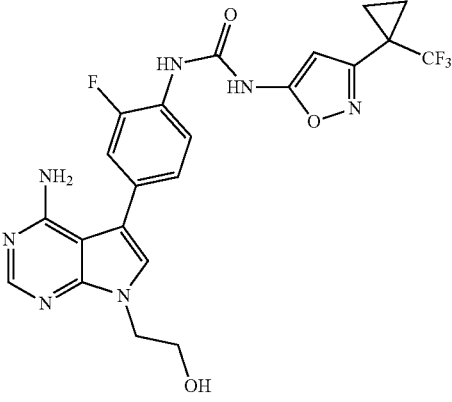 [SMILES: Nc1ncnc2c1c(-c1ccc(NC(=O)Nc3cc(C4(C(F)(F)F)CC4)no3)c(F)c1)cn2CCO] | 1-(4-(4-amino-7-(2-hydroxyethyl)-7H-pyrrolo[2,3-d]pyrimidin-5-yl)-2-fluorophenyl)-3-(3-(1-(trifluoromethyl)cyclopropyl)isoxazol-5-yl)urea |
| 53 | 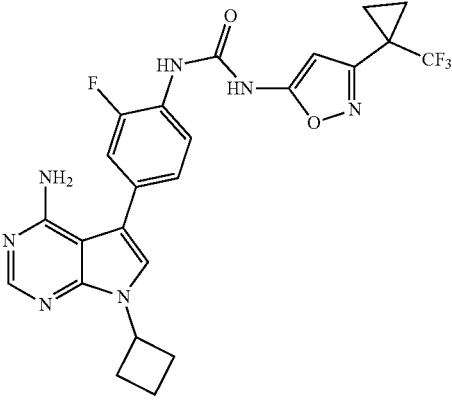 [SMILES: Nc1ncnc2c1c(-c1ccc(NC(=O)Nc3cc(C4(C(F)(F)F)CC4)no3)c(F)c1)cn2C1CCC1] | 1-(4-(4-amino-7-cyclobutyl-7H-pyrrolo[2,3-d]pyrimidin-5-yl)-2-fluorophenyl)-3-(3-(1-(trifluoromethyl)cyclopropyl)isoxazol-5-yl)urea |
| 54 | 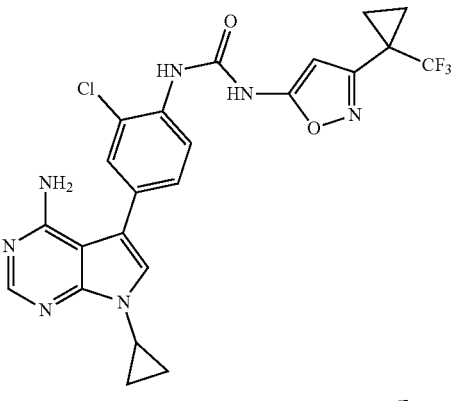 | 1-(4-(4-amino-7-cyclopropyl-7H-pyrrolo[2,3-d]pyrimidin-5-yl)-2-chlorophenyl)-3-(3-(1-(trifluoromethyl)cyclopropyl)isoxazol-5-yl)urea |
| 55 | 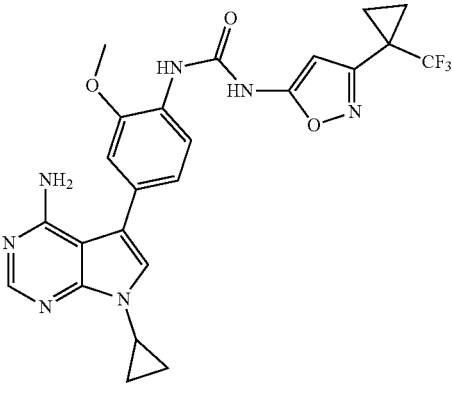 [SMILES: COc1cc(-c2cn(C3CC3)c3ncnc(N)c23)ccc1NC(=O)Nc1cc(C2(C(F)(F)F)CC2)no1] | 1-(4-(4-amino-7-cyclopropyl-7H-pyrrolo[2,3-d]pyrimidin-5-yl)-2-methoxyphenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 56 | 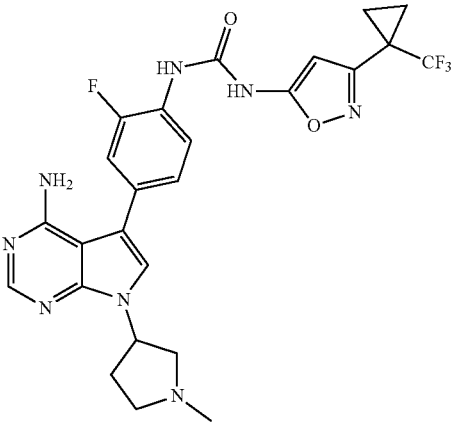 [SMILES: CN1CCC(n2cc(-c3ccc(NC(=O)Nc4cc(C5(C(F)(F)F)CC5)no4)c(F)c3)c3c(N)ncnc32)C1] | 1-(4-(4-amino-7-(1-methylpyrrolidin-3-yl)-7H-pyrrolo[2,3-d]pyrimidin-5-yl)-2-fluorophenyl)-3-(3-(1-(trifluoromethyl)cyclopropyl)isoxazol-5-yl)urea |
| 57 | 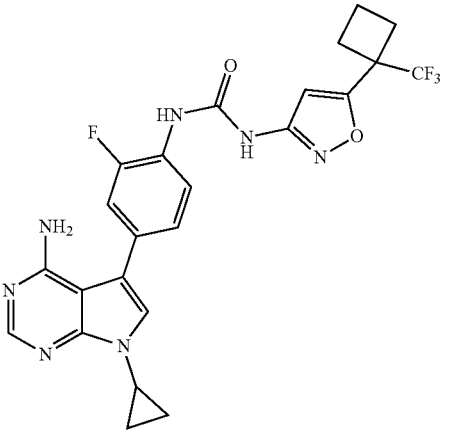 [SMILES: Nc1ncnc2c1c(-c1ccc(NC(=O)Nc3cc(C4(C(F)(F)F)CCC4)on3)c(F)c1)cn2C1CC1] | 1-(4-(4-amino-7-cyclopropyl-7H-pyrrolo[2,3-d]pyrimidin-5-yl)-2-fluorophenyl)-3-(5-(1-(trifluoromethyl)cyclobutyl)isoxazol-3-yl)urea |
| 58 | 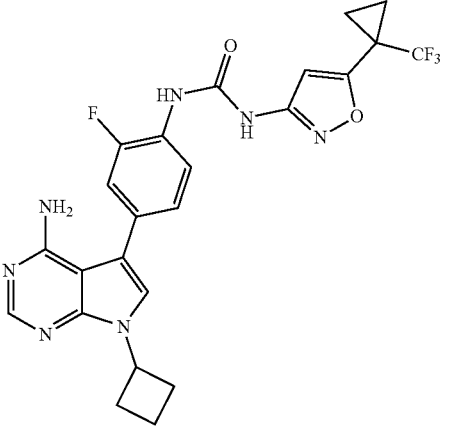 [SMILES: Nc1ncnc2c1c(-c1ccc(NC(=O)Nc3cc(C4(C(F)(F)F)CC4)on3)c(F)c1)cn2C1CCC1] | 1-(4-(4-amino-7-cyclobutyl-7H-pyrrolo[2,3-d]pyrimidin-5-yl)-2-fluorophenyl)-3-(5-(1-(trifluoromethyl)cyclopropyl)isoxazol-3-yl)urea |

TABLE 1-continued

Representative Compounds of Structure (I)

| No. | Structure | Name |
|---|---|---|
| 59 | 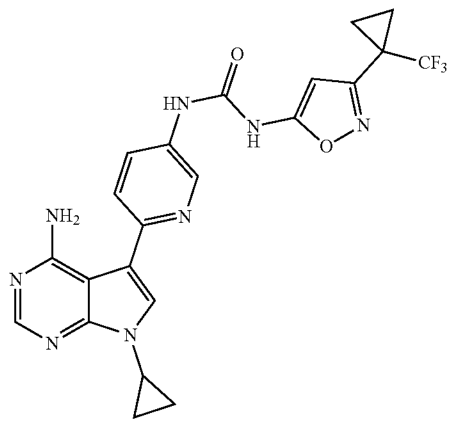 [SMILES: Nc1ncnc2c1c(-c1ccc(NC(=O)Nc3cc(C4(C(F)(F)F)CC4)no3)cn1)cn2C1CC1] | 1-(6-(4-amino-7-cyclopropyl-7H-pyrrolo[2,3-d]pyrimidin-5-yl)pyridin-3-yl)-3-(3-(1-(trifluoromethyl)cyclopropyl)isoxazol-5-yl)urea |
| 60 | 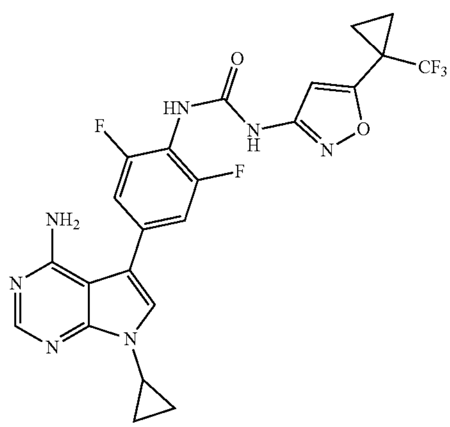 [SMILES: Nc1ncnc2c1c(-c1cc(F)c(NC(=O)Nc3cc(C4(C(F)(F)F)CC4)on3)c(F)c1)cn2C1CC1] | 1-(4-(4-amino-7-cyclopropyl-7H-pyrrolo[2,3-d]pyrimidin-5-yl)-2,6-difluorophenyl)-3-(5-(1-(trifluoromethyl)cyclopropyl)isoxazol-3-yl)urea |
| 61 | 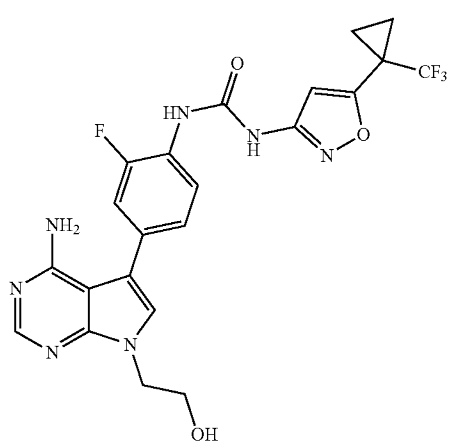 [SMILES: Nc1ncnc2c1c(-c1ccc(NC(=O)Nc3cc(C4(C(F)(F)F)CC4)on3)c(F)c1)cn2CCO] | 1-(4-(4-amino-7-(2-hydroxyethyl)-7H-pyrrolo[2,3-d]pyrimidin-5-yl)-2-fluorophenyl)-3-(5-(1-(trifluoromethyl)cyclopropyl)isoxazol-3-yl)urea |

TABLE 1-continued

Representative Compounds of Structure (I)

| No. | Structure | Name |
|---|---|---|
| 62 | 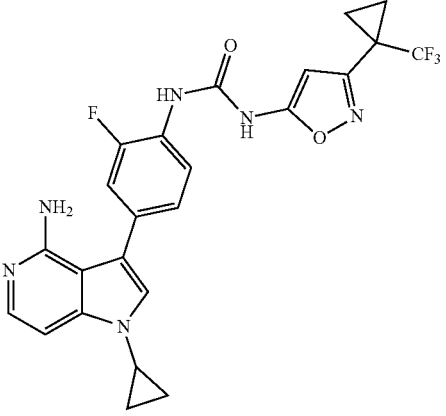 [SMILES: Nc1nccc2c1c(-c1ccc(NC(=O)Nc3cc(C4(C(F)(F)F)CC4)no3)c(F)c1)cn2C1CC1] | 1-(4-(4-amino-1-cyclopropyl-1H-pyrrolo[3,2-c]pyridin-3-yl)-2-fluorophenyl)-3-(3-(1-(trifluoromethyl)cyclopropyl)isoxazol-5-yl)urea |
| 63 | 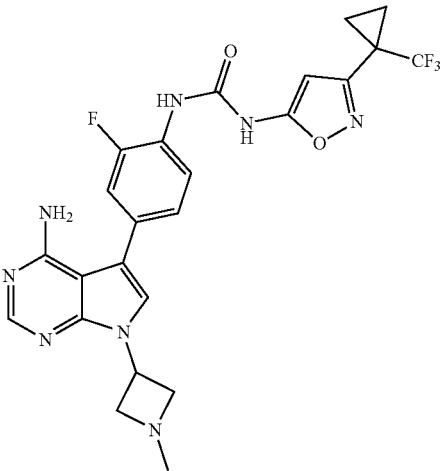 [SMILES: CN1CC(n2cc(-c3ccc(NC(=O)Nc4cc(C5(C(F)(F)F)CC5)no4)c(F)c3)c3c(N)ncnc32)C1] | 1-(4-(4-amino-7-(1-methylazetidin-3-yl)-7H-pyrrolo[2,3-d]pyrimidin-5-yl)-2-fluorophenyl)-3-(3-(1-(trifluoromethyl)cyclopropyl)isoxazol-5-yl)urea |
| 64 | 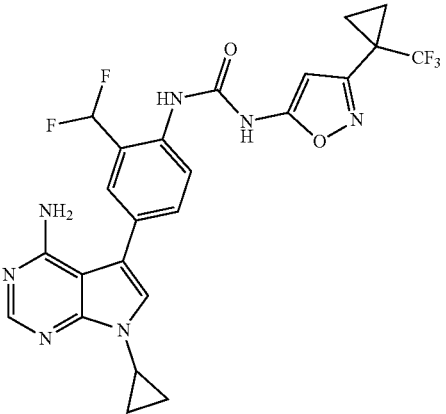 [SMILES: Nc1ncnc2c1c(-c1ccc(NC(=O)Nc3cc(C4(C(F)(F)F)CC4)no3)c(C(F)F)c1)cn2C1CC1] | 1-(4-(4-amino-7-cyclopropyl-7H-pyrrolo[2,3-d]pyrimidin-5-yl)-2-(difluoromethyl)phenyl)-3-(3-(1-(trifluoromethyl)cyclopropyl)isoxazol-5-yl)urea |

TABLE 1-continued

Representative Compounds of Structure (I)

| No. | Structure | Name |
|---|---|---|
| 65 | 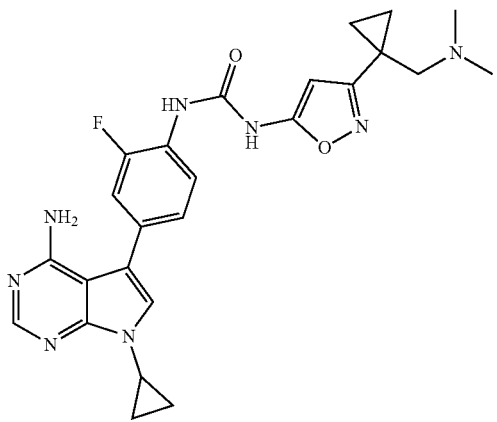 [SMILES: CN(C)CC1(c2cc(NC(=O)Nc3ccc(-c4cn(C5CC5)c5ncnc(N)c45)cc3F)on2)CC1] | 1-(4-(4-amino-7-cyclopropyl-7H-pyrrolo[2,3-d]pyrimidin-5-yl)-2-fluorophenyl)-3-(3-(1-((dimethylamino)methyl)cyclopropyl)isoxazol-5-yl)urea |
| 66 | 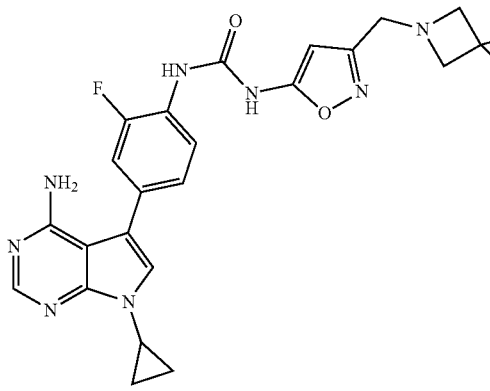 | 1-(4-(4-amino-7-cyclopropyl-7H-pyrrolo[2,3-d]pyrimidin-5-yl)-2-fluorophenyl)-3-(3-((3,3-difluoroazetidin-1-yl)methyl)isoxazol-5-yl)urea |

It is understood that in the present description, combinations of substituents and/or variables of the depicted formulae are permissible only if such contributions result in stable compounds.

In an additional embodiment, various compounds of the disclosure which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

Methods for producing the compounds described herein is provided below. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following General Reaction Schemes illustrate examples of the invention of compounds of Structure (I):

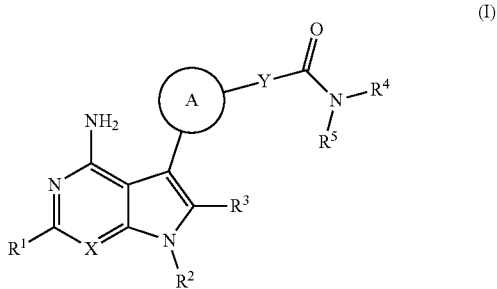

(I)

or pharmaceutically acceptable salts, stereoisomers or prodrug thereof, wherein each of A, X, Y, $R^1$, $R^2$, $R^3$, $R^4$ and $R^5$ are as defined below.

General Reaction Scheme 1

The following General Reaction Scheme, wherein $X^1$ and $X^2$ are independently halogens, and X, $R^1$, $R^2$, $R^3$ and A have the meanings described herein, illustrates examples of methods of making the amine Intermediate D:

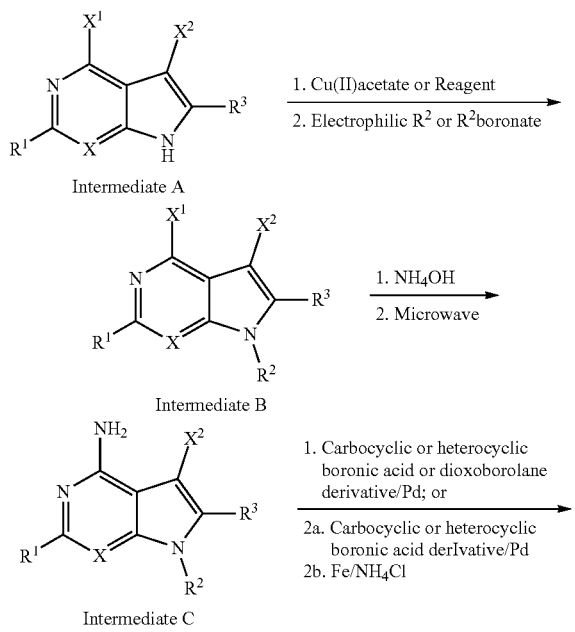

Intermediate A

Intermediate B

Intermediate C

Intermediate D

As shown in General Reaction Scheme 1, alkylation of the pyrimidine/pyridine pyrrole (i.e., Intermediate A) with a cycloalkyl boronate or an appropriate electrophile in presence of base affords the Intermediate B. This precursor is treated with ammonium hydroxide to form the pyrolopyrimidine/pyridine-4-amine derivative Intermediate C. The resulting Intermediate C can then be subject to palladium catalyzed arylation to form Intermediate D.

General Reaction Scheme 2

The following General Reaction Scheme illustrates examples of methods of making the carbamate Intermediate E:

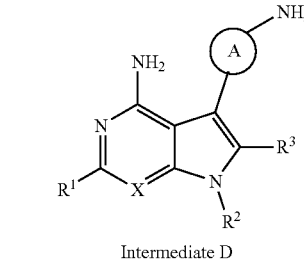

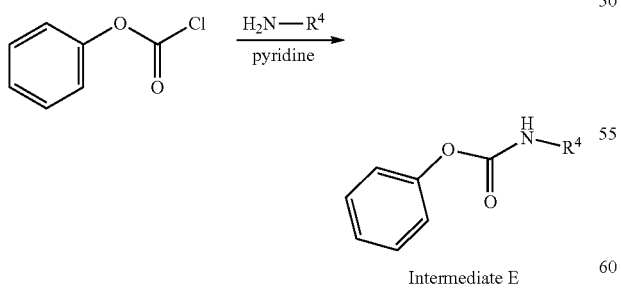

Intermediate E

As shown in General Reaction Scheme 2, Intermediate E can be prepared the in presence of base by reaction of phenyl chloroformates and the indicated heteroaryl amine (an amine-substituted analogue of $R^4$). General Reaction Scheme 2 depicts preparation of compounds wherein $R^5$ is H; however, compounds wherein $R^5$ is other than H can be prepare by similar methods by instilling $R^5$ after preparation of Intermediate E, or by using an appropriately substituted heteroaryl amine.

General Reaction Scheme 3

The following General Reaction Scheme illustrates examples of methods of making the compounds of Structure (I):

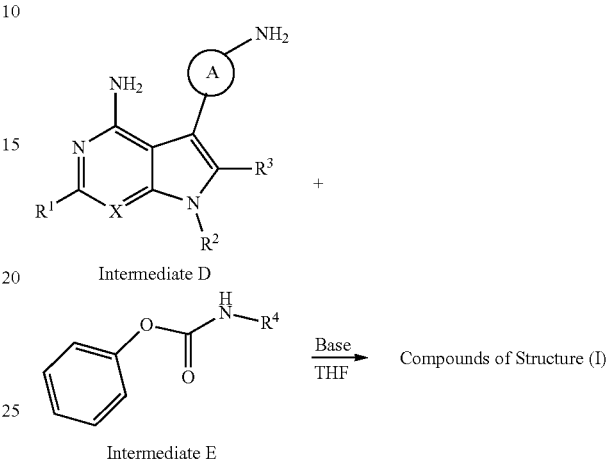

Intermediate D

Intermediate E

Intermediate D and Intermediate E are treated with a base (e.g., trimethylamine, DIPEA, DMAP, and the like) in THF to afford the compounds of Structure (I).

General Reaction Scheme 4

The following General Reaction Scheme illustrates examples of methods of making the compounds of Structure (I):

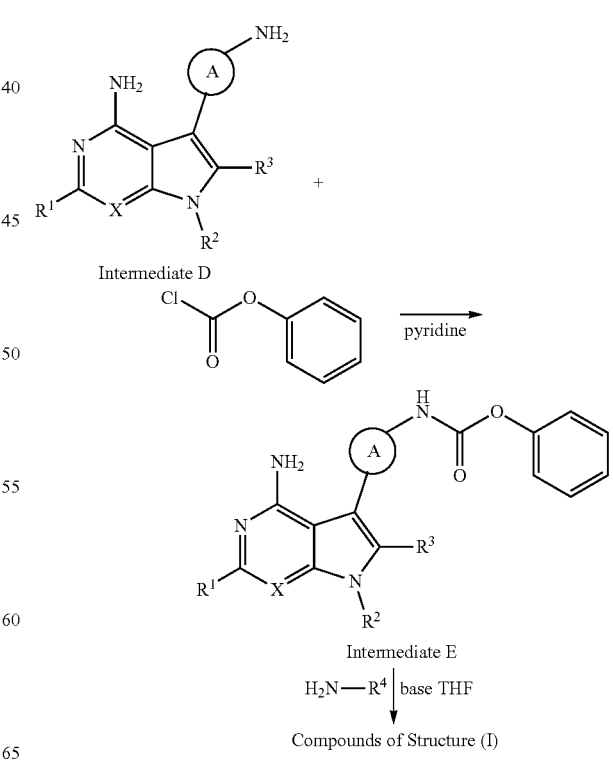

Intermediate D

Intermediate E

Compounds of Structure (I)

Intermediate D is reacted with the phenyl carbonochloridate shown under appropriate conditions to yield Intermediate E. Intermediate E is then coupled with the amine using a suitable base (e.g., trimethylamine, DIPEA, DMAP, and the like) in THF to afford the compounds of Structure (I).

Any of the above reaction scheme can be modified at any step to add and/or modify a substituent may be added or modified as appropriate during any stage of the overall synthesis of desired compounds.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the invention.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the compound is delivered in a targeted drug delivery system, for example, in a liposome coated with and organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In treatment methods according to embodiments of the invention, an effective amount of at least one compound of Structure (I) is administered to a subject suffering from or diagnosed as having such a disease, disorder, or medical condition. Effective amounts or doses may be ascertained by methods such as modeling, dose escalation studies or clinical trials, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The compounds according to the disclosure are effective over a wide dosage range. For example, in the treatment of adult humans, dosages from 10 to 5000 mg, from 100 to 5000 mg, from 1000 mg to 4000 mg per day, and from 1000 to 3000 mg per day are examples of dosages that are used in some embodiments. The exact dosage will depend upon the route of administration, the form in which the compound is administered, the subject to be treated, the body weight of the subject to be treated, and the preference and experience of the attending physician.

In some embodiments, compounds of the disclosure are administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, compounds of the disclosure are administered in multiple doses. In some embodiments, dosing is about once, twice, three times, four times, five times, six times, or more than six times per day. In other embodiments, dosing is about once a month, once every two weeks, once a week, or once every other day. In another embodiment compounds of the disclosure and another agent (e.g., anti-cancer agent) are administered together about once per day to about 6 times per day. In another embodiment the administration of compounds of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of compounds of the disclosure may continue as long as necessary. In some embodiments, compounds of the disclosure are administered for more than 1, 2, 3, 4, 5, 6, 7, 14, or 28 days. In some embodiments, compounds of the disclosure are administered for less than 28, 14, 7, 6, 5, 4, 3, 2, or 1 day. In some embodiments, compounds of the disclosure are administered chronically on an ongoing basis, e.g., for the treatment of chronic effects.

In some embodiments, the compounds of the disclosure are administered in individual dosage forms. It is known in the art that due to intersubject variability in compound pharmacokinetics, individualization of dosing regimen is necessary for optimal therapy.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the disclosed compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

Provided herein are pharmaceutical compositions comprising one or more compounds of Structure (I), and a pharmaceutically acceptable carrier.

Provided herein are pharmaceutical compositions comprising one or more compounds selected from compounds of Structure (I) and pharmaceutically acceptable diluent(s), excipient(s), and carrier(s). In certain embodiments, the compounds described are administered as pharmaceutical compositions in which one or more compounds selected from compounds of Structure (I) are mixed with other active ingredients, as in combination therapy. Encompassed herein are all combinations of actives set forth in the combination therapies section below and throughout this disclosure. In specific embodiments, the pharmaceutical compositions include one or more compounds of Structure (I).

In a certain embodiment, pharmaceutical compositions of the compounds of Structure (I) are modulators of the NLRP3 inflammasome.

In a specific embodiment, pharmaceutical compositions of the compounds of Structure (I) inhibit NEK7 when administered to a patient or a biological sample.

A pharmaceutical composition, as used herein, refers to a mixture of one or more compounds selected from compounds of Structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, therapeutically effective amounts of one or more compounds selected from compounds of Structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds selected from compounds of Structure (I) are formulated in aqueous solutions. In specific embodiments, the aqueous solution is selected from, by way of example only, a physiologically compatible buffer, such as Hank's solution, Ringer's solution, or physiological saline buffer. In other embodiments, one or more compounds selected from compounds of Structure (I) are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of one or more compounds selected from compounds of Structure (I) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions include at least one pharmaceutically acceptable carrier, diluent or excipient, and one or more compounds selected from compounds of Structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical compositions comprising one or more compounds selected from compounds of Structure (I) illustratively takes the form of a liquid where the agents are present in solution, in suspension or both. Typically when the composition is administered as a suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of one or more compounds selected from compounds of Structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers.

Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds selected from compounds of Structure (I) provided in the pharmaceutical compositions of the present disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25% 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds selected from compounds of Structure (I) provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the amount the one or more compounds selected from compounds of Structure (I) provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds selected from compounds of Structure (I) provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Packaging materials for use in packaging pharmaceutical compositions described herein include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

Embodiments of the present disclosure are useful as modulators of the NLRP3 inflammasome via the inhibition of NEK7 in a host species. Therefore, the compounds of Structure (I) are also useful in the treatment of conditions mediated by effector signaling molecules like Il-β and IL-18.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

In one embodiment, the present disclosure is useful as an inhibitor of the NLRP3 inflammasome activation mechanism. Therefore, the compounds of Structure (I) are also useful in the treatment of conditions resulting from that activation in a host species.

In another embodiment, the compounds of Structure (I) are useful as inhibitors of the NLRP3 (protein)-NEK7 (protein) interaction. Therefore, the compounds are also useful in the treatment of conditions resulting from the association of NLRP3-NEK7 in a host species.

In certain embodiments, the compounds of Structure (I) are useful in treating human conditions mediated by effectors selected from the group consisting of IL-β, IL-18, and caspase-1.

Embodiments of the invention also relate to the use of compounds according to Structure (I) and/or physiologically acceptable salts thereof for the prophylactic or therapeutic treatment and/or monitoring of diseases that are caused, mediated and/or modulated by the NLRP3 inflammasome activity. Furthermore, embodiments of the invention relate to the use of compounds according to Structure (I) and/or physiologically acceptable salts thereof for the production of a medicament for the prophylactic or therapeutic treatment and/or monitoring of diseases that are caused, mediated and/or modulated by NLRP3 inflammasome activity. In certain embodiments, the invention provides the use of a compound according to Structure I or physiologically acceptable salts thereof, for the production of a medicament for the prophylactic or therapeutic treatment of a NLRP3-mediated disorder.

In another embodiment, the present disclosure relates to a method of treating inflammatory diseases or conditions mediated by NLRP3 inflammasome by administering to a patient in need thereof a therapeutically effective amount of the compound of Structure (I).

In certain embodiments, the diseases which can be treated with a compound of Structure (I) include type II diabetes, atherosclerosis, Alzheimer's disease, aging, fatty liver, metabolic syndrome, asthma, psoriasis, obesity, acute and chronic tissue damage caused by infection, gout, arthritis, enteritis, hepatitis, peritonitis, silicosis, UV-induced skin sunburn, contact hypersensitivity, sepsis, cancer, neurodegenerative disease, multiple sclerosis, and Muckle-Wells syndrome.

In certain other embodiments, the compounds of Structure (I) are used in methods for treatment of disorders or diseases selected from auto-immune, inflammatory disorders, cardiovascular diseases, neurodegenerative disorders, bacterial and viral infections, allergy, asthma, pancreatitis, multi-organ failure, kidney diseases, platelet aggregation, transplantation, sperm motility, erythrocyte deficiency, graft rejection, lung injuries, respiratory diseases, ischemic conditions, and cancer. In some more specific embodiments, the compounds of Structure (I) are used in methods for treatment of myelodysplastic syndrome (MDS).

In some embodiments, the disorders associated with NEK7 which are treatable with a compound of Structure (I) are selected from rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, type I diabetes, type II diabetes, inflammatory bowel disease (Crohn's Disease and ulcerative colitis), hyperimmunoglobulinemia D and periodic fever syndrome, cryopyrin associated periodic syndromes, Schnitzler's syndrome, systemic juvenile idiopathic arthritis, adult's onset Still's disease, gout, pseudogout, SAPHO syndrome, Castleman's disease, sepsis, stroke, atherosclerosis, celiac disease, DIRA (Deficiency of IL-1 Receptor Antagonist), Alzheimer's disease, Parkinson's disease, and Cancer.

Also included herein are methods of treatment in which at least one compound of Structure (I) is administered in combination with an anti-inflammatory or a therapeutic agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine.

Examples of NSAIDs also include COX-2 specific inhibitors such as celecoxib, valdecoxib, lumiracoxib dnd/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The disclosure also includes embodiments in which the anti-inflammatory agent is a metabolic inhibitor such as a dihydrofolate reductase inhibitor, such as methotrexate or a dihydroorotate dehydrogenase inhibitor, such as leflunomide.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Other embodiments of the disclosure pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Therapeutic agents used in combination with the compounds of Structure (I) can also include small molecule compounds that inhibit the activation of NLRP3 inflammasomes, such as MCC950, sulforaphane, iisoliquiritigenin, p-hydroxybutyrate, flufenamic acid, mefenamic acid, 3,4-methylenedioxy-p-nitrostyrene (MNS), and parthenolide.

Still other embodiments of the disclosure pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of Structure (I) can be administered in combination with other known therapeutic agents, including anticancer agents. As used here, the term "anti-cancer agent" relates to any agent which is administered to a patient with cancer for the purposes of treating the cancer.

In some embodiments the anti-cancer agents belong to the following categories—
Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-3024, VAL-0834;
Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;
DNA altering agents: such as amrubicin, bisantrene, decitabine, mitoxantrone, procarbazine, trabectedin, clofarabine; amsacrine, brostallicin, pixantrone, laromustine 1,3;
Topoisomerase Inhibitors: such as etoposide, irinotecan, razoxane, sobuzoxane, teniposide, topotecan; amonafide, belotecan, elliptinium acetate, voreloxin;
Microtubule modifiers: such as cabazitaxel, docetaxel, eribulin, ixabepilone, paclitaxel, vinblastine, vincristine, vinorelbine, vindesine, vinflunine; fosbretabulin, tesetaxel;
Antimetabolites: such as asparaginase3, azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur2,3, trimetrexate;
Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide 1,3;
Aromatase inhibitors: such as aminoglutethimide, anastrozole, exemestane, fadrozole, letrozole, testolactone; formestane;
Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics, e.g., ipratropium, atropine or oxitropium; hormones, e.g., cortisone, hydrocortisone or prednisolone; xanthines, e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

The agents disclosed herein or other suitable agents are administered depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

In some embodiments, the compounds of Structure (I) are administered as a mono-therapy.

For identification of a signal transduction or a mechanistic pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds of embodiments of the invention can also be used as reagents for testing NEK7-dependent signal transduction pathways in animals and/or cell culture models or in the clinical diseases mentioned in this application.

The methods of embodiments of embodiments of the invention can be performed either in-vitro or in-vivo. The susceptibility of a particular cell to treatment with the compounds of Structure (I) can be particularly determined by in-vitro tests, whether in the course of research or clinical application. Typically, a culture of the cell is combined with a compound at various concentrations for a period of time which is sufficient to allow the active agents to inhibit NEK7 activity, usually between about one hour and one week. In-vitro treatment can be carried out using cultivated cells from a biopsy sample or cell line.

In some embodiments, the $IC_{50}$ of the compounds of Structure (I) to inhibit NEK7 was determined by the concentration of the compound required to inhibit 50% of the activity of the NEK kinase. The compounds of Structure (I) exhibited potency values of $IC_{50}$ of less than about 5 mM, preferably less than about 1 mM and even more preferably less than about 0.100 mM as described in further detail in the Examples.

The examples and preparations provided below further illustrate and exemplify the compounds of the present disclosure and methods of preparing and testing such compounds. It is to be understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following examples are provided for exemplary purposes.

General Procedures

All proton NMR experiments were recorded on a Bruker NEO Spectrometer equipped with a BBFO probe at 400 MHz. Deuterated solvents contained less than 0.05% v/v tetramethylsilane which was used as the reference signal (set at 0.00 ppm). When deuterated solvents did not contain tetramethylsilane, the residual nondeuterated solvent peaks were used as a reference signal, as per published guidelines (*J. Org. Chem.* 1997, 62(21), 7512-7515). Chemical shifts are expressed in parts per million (ppm, δ units). Coupling constants are in hertz (Hz). Splitting patterns describe apparent multiplicities and are designated as s (singlet), d (doublet), t (triplet), q (quartet), m (multiplet), qt (quintuplet) or brs (broad singlet).

LC/MS analyses were performed on an Agilent Technologies UHPLC 1290 Infinity II with a G6125 MS detector. Microwave reactions were conducted with a Monowave 300 by Anton Paar GmbH using standard protocols.

NEK7 Enzymatic Assay

Casein substrate (from bovine milk, hydrolyzed and partially dephosphorylated mixture of α, β and a caseins, obtained from Sigma Aldrich, catalogue #C4765, diluted in distilled water to a final concentration of 1 mg/mL) and full-length recombinant human NEK7 (expressed by baculovirus in Sf9 insect cells using a N-terminal GST tag, obtained from SignalChem, catalogue #N09-10G, 0.1 µg/µL) were mixed in assay buffer (20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, 1% DMSO). Compounds of interest (serial 3-fold dilution in DMSO from 10 µM to 0.5 nM) or vehicle (1% DMSO) were dispensed into the kinase reaction mixture by Acoustic technology (Echo550; nanoliter range). After incubation at room temperature for 20 minutes, the kinase reaction was initiated by addition of [$^{33}$P]-ATP (specific activity 10 pCi/µl) and the mixture was incubated at room temperature for 2 hours. The reaction was then stopped by spotting the reaction mixture on strips of phosphocellulose P81 paper. Following washing, the radioactivity of the P81 paper was measured and kinase activity data were expressed as the percent remaining kinase activity in test samples compared to vehicle reactions. $IC_{50}$ values and curve fits were obtained using Prism (GraphPad Software).

IL-1β Release Assay

Approximately 1.5 million THP-1 cells were plated in each well of a 6-well TC plate and incubated with 40 nM PMA in RPMI (10% FBS, 1% Penstrep) for 24 hours. The media was then removed and cells were rested in RPMI (10% FBS, 1% Penstrep) for 24 hours after which time the media was removed and cells were pre-treated for 2 hours with various concentrations of compounds of interest (typically serial 3-fold dilution in RPMI+5% FBS, concentrations ranging from 1 µM to 0.5 nM) in RPMI (5% FBS). The media was again removed and cells were incubated with 250 ng/mL LPS and compounds of interest (concentrations as above) in RMPI (5% FBS) for 2 hours. The media was removed for a last time and cells were incubated with 20 µM nigericin and compounds of interest (concentrations as above) in Opti-MEM for 30 minutes. Cell media was then collected and the amount of cleaved IL-1β was determined using a JESS instrument (Protein Simple) and standard protocols. Cleaved Il-1β antibody was obtained from Cell Signaling (catalogue #83186S) and was used at 1:20 dilution in antibody diluent 2. Protein Simple 1× anti-Rabbit HRP secondary antibody was used along with Protein Simple luminol and peroxide for chemiluminescent detection. Primary antibody incubation time was increased from 30 minutes to 60 minutes.

Abbreviations

° C. (degree Celsius); $^1$H NMR (proton Nuclear Magnetic Resonance); ACN (acetonitrile); Boc (tert-butyloxycarbonyl); DCM (dichloromethane); DIPEA (N,N-diisopropylethylamine); DMAP (4-dimethylaminopyridine); DMF (N,N-dimethylformamide); DMSO-d6 (deuterated dimethylsulfoxide); eq (equivalent); EtOAc (ethyl acetate); g (gram); h (hour); HPLC (High Performance Liquid Chromatography); LCMS (Liquid Chromatography Mass Spectrometry); MeOH (methanol); mg (milligram); min (minute); mL (milliliter); mmol (millimole); n-BuOH (1-butanol); Pd(PPh$_3$)$_4$ (palladium-tetrakis(triphenylphosphine)); PdCl$_2$(dppf) ([1,1'-bis(diphenylphosphino)ferrocene]palladium(II) dichloride); TBAF (tetra-n-butylammonium fluoride); TBDMS (tert-butyldimethylsilyl); TFA (trifluoroacetic acid); THF (tetrahydrofuran); TLC (Thin Layer Chromatography)

Preparation of Synthetic Intermediates

Intermediate A 4-chloro-5-iodo-7H-pyrrolo[2,3-d]pyrimidine

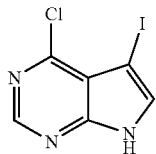 [SMILES: Clc1ncnc2[nH]cc(I)c12]

N-iodosuccinimide (1.465 g, 6.51 mmol) was added to a stirred solution of 4-chloro-7H-pyrrolo[2,3-d]pyrimidine (1.000 g, 6.51 mmol) in DMF (10 mL) at 0° C. and the resulting mixture was stirred at 25° C. for 12 h. Following completion of the reaction (as indicated by TLC), the reaction mixture was poured into ice cold water (100 mL) and stirred at 25° C. for 15 min. The resulting solid was filtered, washed with water (2×25 mL), and dried to afford the title compound as an off-white solid (1.7 g, 93% yield). $^1$H NMR (400 MHz, DMSO-d$_6$) δ=12.96 (bs, 1H), 8.60 (s, 1H), 7.95 (d, J=2.40 Hz, 1H); LCMS: 279.9 [M+H].

Intermediate B1

4-chloro-7-cyclopropyl-5-iodo-7H-pyrrolo[2,3-d]pyrimidine

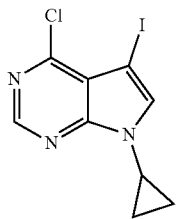 [SMILES: Clc1ncnc2c1c(I)cn2C1CC1]

Copper (II) acetate (0.650 g, 3.58 mmol), 2,2'-bipyridine (0.559 g, 3.58 mmol), and sodium bicarbonate (0.601 g, 7.16 mmol) were added to a solution of 4-chloro-5-iodo-7H-pyrrolo[2,3-d]pyrimidine (A1, 1.000 g, 3.58 mmol) and cyclopropylboronic acid (0.615 g, 7.16 mmol) in dichloroethane (10 mL) and the resulting mixture was stirred at 70° C. under oxygen atmosphere for 12 h. Following completion of the reaction (as indicated by TLC), the reaction mixture was filtered through a pad of celite which was then rinsed with DCM (2×20 mL). The combined filtrates were washed with water (20 mL) and brine (25 mL), dried over Na$_2$SO$_4$, filtered, and concentrated under reduced pressure to give crude material which was purified by flash chromatography (silica gel 230-400 mesh, eluting with 15% EtOAc in petroleum ether), affording the title compound as an off-white solid (0.7 g, 61% yield). $^1$H NMR (400 MHz, DMSO-d$_6$) δ=8.67 (s, 1H), 7.96 (s, 1H), 3.63-3.69 (m, 1H), 1.06-1.10 (m, 4H). LCMS: 319.9 [M+H].

Intermediate B2

4-chloro-5-iodo-7-(oxetan-3-yl)-7H-pyrrolo[2,3-d]pyrimidine

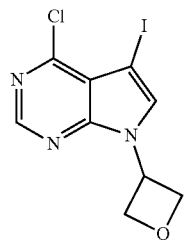 [SMILES: Clc1ncnc2c1c(I)cn2C1COC1]

K$_2$CO$_3$ (0.40 g, 2.86 mmol) and 3-iodooxetane (0.32 g, 1.71 mmol) were added to a solution of 4-chloro-5-iodo-7H-pyrrolo[2,3-d]pyrimidine (A, 0.40 g, 1.43 mmol) in DMF (5 mL) and the resulting mixture was stirred at 90° C. for 16 h in a sealed tube. Following completion of the reaction (as indicated by TLC), the reaction mixture was poured into crushed ice (50 g) and stirred for 15 min. The resulting solid was filtered, washed with water (2×5 mL), and dried to afford the title compound as an off-white solid (0.2 g, 42% yield). LCMS: 335.7 [M+H].

Intermediate B3

1-(4-chloro-5-iodo-7H-pyrrolo[2,3-d]pyrimidin-7-yl)-2-memylpropan-2-ol

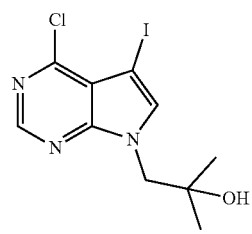 [SMILES: CC(C)(O)Cn1cc(I)c2c(Cl)ncnc21]

NaH$_2$PO$_4$ (0.105 g, 0.877 mmol) was added to a mixture of 4-chloro-5-iodo-7H-pyrrolo[2,3-d]pyrimidine (A1, 0.250 g, 0.895 mmol), 2,2-dimethyloxirane (0.157 ml, 1.762 mmol), and K$_2$CO$_3$ (0.121 g, 0.877 mmol) in ACN (3 mL) and water (1 mL). The resulting mixture was subjected to microwave irradiation at 150° C. for 1 h in a sealed tube. Following completion of the reaction (as indicated by TLC), the reaction mixture was concentrated under reduced pressure and the resulting crude material was purified by flash chromatography (silica gel 230-400 mesh, eluting with 18% EtOAc in petroleum ether), affording the title compound as a pale brown solid (0.1 g, 17% yield). LCMS: 351.9 [M+H].

Intermediate B4

4-chloro-5-iodo-7-(pyridin-3-yl)-7H-pyrrolo[2,3-d]pyrimidine

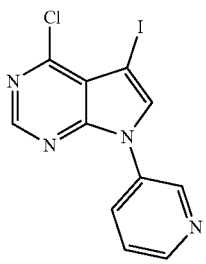 [SMILES: Clc1ncnc2c1c(I)cn2-c1cccnc1]

Triethylamine (0.905 g, 8.95 mmol) and copper (II) acetate (0.975 g, 5.37 mmol) were added to a solution of 4-chloro-5-iodo-7H-pyrrolo[2,3-d]pyrimidine (A, 1.000 g, 3.58 mmol) and 3-pyridinylboronic acid (0.880 g, 7.16 mmol) in DCM (25 mL) and the resulting mixture was stirred at 40° C. under oxygen atmosphere for 40 h. Following completion of the reaction (as indicated by LCMS), the reaction mixture was filtered through a pad of celite which was then rinsed with DCM (2×50 mL). The combined filtrates were washed with water (10 mL) and brine (10 mL), dried over $Na_2SO_4$, filtered, and concentrated under reduced pressure to give crude material. This was stirred with 30% diethyl ether in petroleum ether for 30 minutes at 25° C., filtered, and dried to afford the title compound as a brown solid (0.4 g, 29% yield). $^1$H NMR (400 MHz, DMSO-$d_6$) δ=9.05 (bs, 1H), 8.73 (s, 1H), 8.67 (bs, 1H), 8.48 (s, 1H), 8.26-8.28 (m, 1H), 7.64-7.67 (m, 1H). LCMS: 356.8 [M+H].

Intermediate B5

4-chloro-5-iodo-7-(pyridin-4-yl)-7H-pyrrolo[2,3-d]pyrimidine

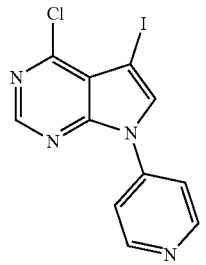 [SMILES: Clc1ncnc2c1c(I)cn2-c1ccncc1]

The title compound was obtained by following a similar procedure described for B4, starting from 4-chloro-5-iodo-7H-pyrrolo[2,3-d]pyrimidine (A, 0.50 g, 1.789 mmol) and 4-pyridinylboronic acid (0.44 g, 3.580 mmol), and was obtained as a brown solid (0.21 g, 29% yield). LCMS: 356.9 [M+H].

Intermediate B6

4-chloro-5-iodo-7-(1-methylpiperidin-4-yl)-7H-pyrrolo[2,3-d]pyrimidine

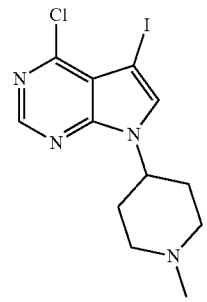 [SMILES: CN1CCC(n2cc(I)c3c(Cl)ncnc32)CC1]

The title compound was prepared as reported in PCT Pub. No. WO 2017/220477.

Intermediate B7

7-(3-(benzyloxy)cyclobutyl)-4-chloro-5-iodo-7H-pyrrolo[2,3-d]pyrimidine

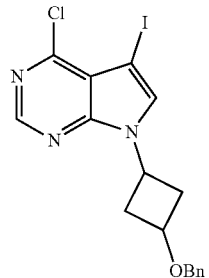 [SMILES: Clc1ncnc2c1c(I)cn2C1CC(OCc2ccccc2)C1]

$Cs_2CO_3$ (0.583 g, 1.789 mmol) and 3-(benzyloxy)cyclobutyl methanesulfonate (prepared as reported in PCT Pub. No. WO 2019/092170, 0.459 g, 1.789 mmol) were added to a solution of 4-chloro-5-iodo-7H-pyrrolo[2,3-d]pyrimidine (A, 0.250 g, 0.895 mmol) in DMF (5 mL) and the resulting mixture was stirred at 90° C. for 12 h. Following completion of the reaction (as indicated by TLC), the reaction mixture was poured into ice water (50 mL) and extracted with ethyl acetate (2×30 mL). The combined organic extracts were dried over $Na_2SO_4$, filtered, and concentrated under reduced pressure to give crude material which was purified by flash chromatography (silica gel 230-400 mesh, eluting with 30% EtOAc in petroleum ether), affording the title compound as a colorless gum (0.14 g, 31% yield). LCMS: 440.0 [M+H].

Intermediate B8

2-(4-chloro-5-iodo-7H-pyrrolo[2,3-d]pyrimidin-7-yl)ethan-1-ol

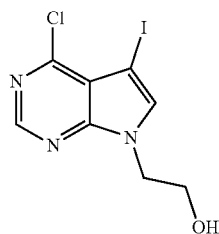 [SMILES: OCCn1cc(I)c2c(Cl)ncnc21]

K$_2$CO$_3$ (0.742 g, 5.37 mmol) and 2-bromoethan-1-ol (0.537 g, 4.29 mmol) were added to a solution of 4-chloro-5-iodo-7H-pyrrolo[2,3-d]pyrimidine (A, 1.000 g, 3.58 mmol) in DMF (6 mL) and the resulting suspension was stirred at 80° C. for 2 h. Following completion of the reaction (as indicated by TLC), the reaction mixture was poured into crushed ice (25 g). The resulting solid was filtered, washed with water (20 mL), and dried to afford the title compound as a yellow solid (0.84 g, 64% yield). LCMS: 323.9 [M+H].

Intermediate B9

4-chloro-1-cyclopropyl-3-iodo-1H-pyrrolo[3,2-c]pyridine

Step 1: synthesis of 4-chloro-1-cyclopropyl-1H-pyrrolo[3,2-c]pyridine

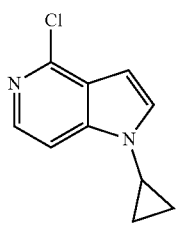 [SMILES: Clc1nccc2c1ccn2C1CC1]

Triethylamine (0.332 g, 3.280 mmol), copper (II) acetate (0.298 g, 1.638 mmol), and molecular sieves (powdered, 0.050 g) were added to a solution of 4-chloro-1H-pyrrolo[3,2-c]pyridine (0.250 g, 1.638 mmol) and cyclopropyl boronic acid (0.279 g, 3.280 mmol) in DMF (10 mL) and the resulting suspension was stirred at 60° C. for 12 h in a sealed tube. Following completion of the reaction (as indicated by TLC), the reaction mixture was filtered through a pad of celite which was then rinsed with EtOAc. The combined filtrates were concentrated under reduced pressure, giving crude material which was purified by Isolera (silica gel 230-400 mesh, eluting with 20% EtOAc in petroleum ether), affording the title compound as a yellow solid (0.19 g, 59% yield). $^1$H NMR (400 MHz, DMSO-d$_6$) δ=8.04 (d, J=5.6 Hz, 1H), 7.56-7.60 (m, 2H), 6.52-6.53 (m, 1H), 3.55-3.58 (m, 1H), 1.00-1.13 (m, 4H). LCMS: 193.1 [M+H].

Step 2: synthesis of 4-chloro-1-cyclopropyl-3-iodo-1H-pyrrolo[3,2-c]pyridine

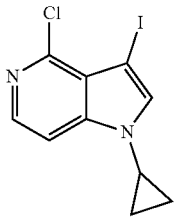

N-iodosuccinimide (0.350 g, 1.557 mmol) was added to a solution of 4-chloro-1-cyclopropyl-1H-pyrrolo[3,2-c]pyridine (0.200 g, 1.038 mmol) in DMF (5 mL) and the resulting mixture was stirred at 80° C. for an hour. Following completion of the reaction (as indicated by LCMS), the reaction mixture was poured into crushed ice (25 g) and extracted with EtOAc (2×25 mL). The combined organic extracts were washed with brine, dried over Na$_2$SO$_4$, filtered, and concentrated under reduced pressure to yield the title product (0.2 g) which was used without further purification. LCMS: 319.0 [M+H].

Intermediate C1

7-cyclopropyl-5-iodo-7H-pyrrolo[2,3-d]pyrimidin-4-amine

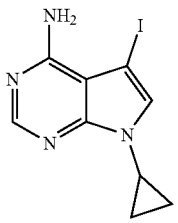 [SMILES: Nc1ncnc2c1c(I)cn2C1CC1]

A mixture of 4-chloro-7-cyclopropyl-5-iodo-7H-pyrrolo[2,3-d]pyrimidine (B1, 1.00 g, 2.191 mmol) and ammonium hydroxide (25% in water, 5 mL) was subjected to microwave irradiation at 150° C. for 1 h. Following completion of the reaction (as indicated by TLC), the reaction mixture was concentrated under reduced pressure to afford the title compound as an off-white solid (0.75 g, 80% yield). $^1$H NMR (400 MHz, DMSO-d$_6$) δ=8.12 (s, 1H), 7.39 (s, 1H), 6.57 (bs, 2H), 3.48-3.54 (m, 1H), 0.97-1.01 (m, 4H). LCMS: 301.0 [M+H].

Intermediate C2

5-iodo-7-(oxetan-3-yl)-7H-pyrrolo[2,3-d]pyrimidin-4-amine

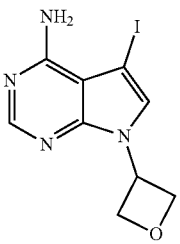 [SMILES: Nc1ncnc2c1c(I)cn2C1COC1]

The title compound was prepared via a similar procedure described for C1, starting from 4-chloro-5-iodo-7-(oxetan-3-yl)-7H-pyrrolo[2,3-d]pyrimidine (B2, 0.5 g, 1.49 mmol) and aqueous ammonium hydroxide (25% in water, 2.5 mL), and was obtained as a pale brown solid (0.27 g, 58% yield). LCMS: 316.8 [M+H].

Intermediate C3

1-(4-amino-5-iodo-7H-pyrrolo[2,3-d]pyrimidin-7-yl)-2-methylpropan-2-ol

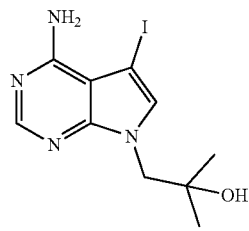 [SMILES: CC(C)(O)Cn1cc(I)c2c(N)ncnc21]

The title compound was obtained by following a similar procedure described for C1, starting from 1-(4-chloro-5-iodo-7H-pyrrolo[2,3-d]pyrimidin-7-yl)-2-methylpropan-2-ol (B3, 0.1 g, 0.284 mmol) and ammonium hydroxide (25% in water, 0.5 mL), and was obtained as an off-white solid (0.08 g, 85% yield). $^1$H NMR (400 MHz, DMSO-$d_6$) δ=8.12 (s, 1H), 7.38 (s, 1H), 4.81 (s, 1H), 4.04 (s, 2H), 1.03 (s, 6H). LCMS: 333.0 [M+H].

Intermediate C4

5-iodo-7-(pyridin-3-yl)-7H-pyrrolo[2,3-d]pyrimidin-4-amine

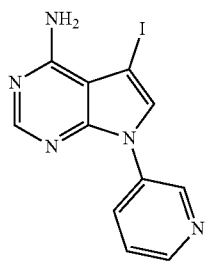 [SMILES: Nc1ncnc2c1c(I)cn2-c1cccnc1]

Ammonium hydroxide (25% in water, 1 mL) was added to a solution of 4-chloro-5-iodo-7-(pyridin-3-yl)-7H-pyrrolo[2,3-d]pyrimidine (B4, 0.30 g, 0.841 mmol) in dioxane (10 mL) and the resulting mixture was subjected to microwave irradiation at 150° C. for 2 h. Following completion of the reaction (as indicated by LCMS), the reaction mixture was concentrated under reduced pressure to yield crude material which was washed with methyl tert-butyl ether and dried, affording the title compound as an off-white solid (0.21 g, 63% yield). LCMS: 337.8 [M+H].

Intermediate C5

5-iodo-7-(pyridin-4-yl)-7H-pyrrolo[2,3-d]pyrimidin-4-amine

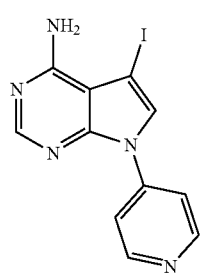 [SMILES: Nc1ncnc2c1c(I)cn2-c1ccncc1]

The title compound was obtained by following a similar procedure described for C4, starting from 4-chloro-5-iodo-7-(pyridin-4-yl)-7H-pyrrolo[2,3-d]pyrimidine (B5, 0.21 g, 0.589 mmol) and ammonium hydroxide (25% in water, 1 mL), and was obtained as an off-white solid (0.16 g, 69% yield). LCMS: 337.9 [M+H].

Intermediate C6

5-iodo-7-(1-methylpiperidin-4-yl)-7H-pyrrolo[2,3-d]pyrimidin-4-amine

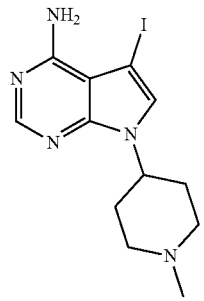 [SMILES: CN1CCC(n2cc(I)c3c(N)ncnc32)CC1]

The title compound was prepared as reported in PCT Pub. No. WO 2017/220477.

Intermediate C7

7-(3-(benzyloxy)cyclobutyl)-5-iodo-7H-pyrrolo[2,3-d]pyrimidin-4-amine

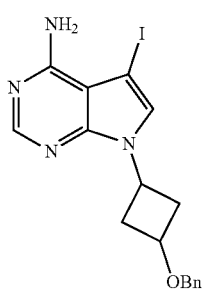 [SMILES: Nc1ncnc2c1c(I)cn2C1CC(OCc2ccccc2)C1]

The title compound was obtained by following a similar procedure described for C4, starting from 7-(3-(benzyloxy)cyclobutyl)-4-chloro-5-iodo-7H-pyrrolo[2,3-d]pyrimidine (B7, 0.140 g, 0.318 mmol) and ammonium hydroxide (25% in water, 1.4 mL), and was obtained as an off-white solid (0.06 g, 45% yield). LCMS: 421.1 [M+H].

Intermediate C8

5-iodo-7-(2-methoxyethyl)-7H-pyrrolo[2,3-d]pyrimidin-4-amine

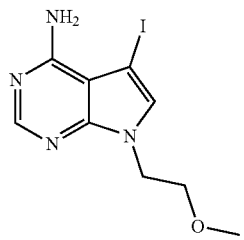

The title compound was prepared as reported in PCT Pub. No. WO 2014/184069A1.

Intermediate C9

2-(4-amino-5-iodo-7H-pyrrolo[2,3-d]pyrimidin-7-yl)ethan-1-ol

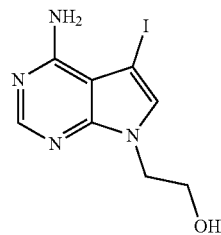 [SMILES: Nc1ncnc2c1c(I)cn2CCO]

The title compound was obtained by following a similar procedure described for C4, starting from 2-(4-chloro-5-iodo-7H-pyrrolo[2,3-d]pyrimidin-7-yl)ethan-1-ol (B8, 0.84 g, 2.61 mmol) and ammonium hydroxide (25% in water, 8 mL), and was obtained as an off-white solid (0.94 g, 69% yield). LCMS: 305.0 [M+H].

Intermediate C10

7-cyclobutyl-5-iodo-7H-pyrrolo[2,3-d]pyrimidin-4-amine

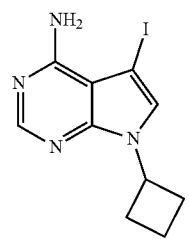 [SMILES: Nc1ncnc2c1c(I)cn2C1CCC1]

The title compound was prepared as reported in PCT Pub. No. WO 2016/075224

Intermediate C11

5-iodo-7-(1-methylpyrrolidin-3-yl)-7H-pyrrolo[2,3-d]pyrimidin-4-amine

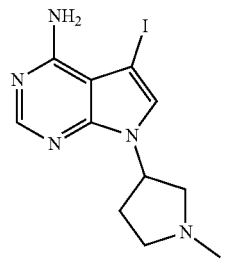 [SMILES: CN1CCC(n2cc(I)c3c(N)ncnc32)C1]

The title compound was prepared as reported in PCT Pub. No. WO 2016/075224.

Intermediate D1

5-(4-amino-3-fluorophenyl)-7-cyclopropyl-7H-pyrrolo[2,3-d]pyrimidin-4-amine

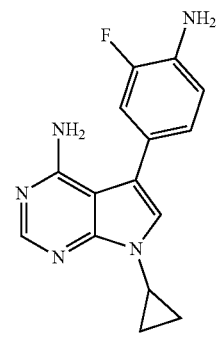

A mixture of 7-cyclopropyl-5-iodo-7H-pyrrolo[2,3-d]pyrimidin-4-amine (C1, 0.160 g, 0.533 mmol), 2-fluoro-4-(4,4,5,5-tetramethyl-1,3,2-dioxaborolan-2-yl)aniline (0.190 g, 0.800 mmol), and $K_2CO_3$ (0.221 g, 1.599 mmol) in 1,4-dioxane (1 mL) and water (0.3 mL) was purged with N2 for 10 min. Pd(PPh$_3$)$_4$ (0.062 g, 0.053 mmol) was then added and the reaction mixture was stirred at 100° C. for 12 h. Following completion of the reaction (as indicated by TLC), the mixture was filtered through a pad celite which was then rinsed with EtOAc (2×10 mL). The combined filtrates were concentrated under reduced pressure to yield crude material which was purified by flash chromatography (silica gel 230-400 mesh, eluting with 3% MeOH in DCM), affording the title compound as a yellow solid (0.110 g, 73% yield). $^1$H NMR (400 MHz, DMSO-d$_6$) δ=8.14 (s, 1H), 7.13 (s, 1H), 7.05-7.09 (m, 1H), 6.95-6.98 (m, 1H), 6.82-6.86 (m, 1H), 6.10 (bs, 2H), 5.22 (bs, 2H), 3.52-3.58 (m, 1H), 1.00-1.04 (m, 4H). LCMS: 284.1 [M+H].

101

Intermediate D2

5-(4-aminophenyl)-7-(oxetan-3-yl)-7H-pyrrolo[2,3-d]pyrimidin-4-amine

Step 1: synthesis of 5-(4-nitrophenyl)-7-(oxetan-3-yl)-7H-pyrrolo[2,3-d]pyrimidin-4-amine

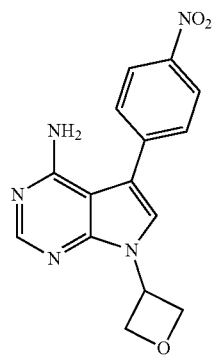 [SMILES: Nc1ccc(-c2cn(C3COC3)c3ncnc(N)c23)cc1]

The title compound was prepared via a similar procedure described for D1, starting from 4-chloro-5-iodo-7-(oxetan-3-yl)-7H-pyrrolo[2,3-d]pyrimidine (C2, 0.252 g, 0.797 mmol) and (4-nitrophenyl)boronic acid (0.200 g, 1.198 mmol), and was obtained as a pale brown solid (0.143 g, 58% yield). LCMS: 312.1 [M+H].

Step 2: synthesis of 5-(4-aminophenyl)-7-(oxetan-3-yl)-7H-pyrrolo[2,3-d]pyrimidin-4-amine

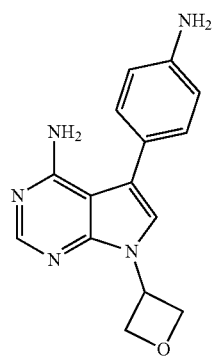

Iron powder (0.251 g, 4.5 mmol) and ammonium chloride (0.240 g, 4.5 mmol) were added to a solution of 5-(4-nitrophenyl)-7-(oxetan-3-yl)-7H-pyrrolo[2,3-d]pyrimidin-4-amine (0.14 g, 0.45 mmol) in ethanol (5 mL) and water (2 mL) and the resulting mixture was stirred at 80° C. for 3 h. Following completion of the reaction (as indicated by TLC), the reaction mixture was filtered through a pad of celite which was then rinsed with EtOAc (2×5 mL). The combined filtrates were concentrated under reduced pressure, giving a residue which was dissolved in EtOAc (25 mL), washed with brine (5 mL), dried over $Na_2SO_4$, filtered, and concentrated under reduced pressure to afford the title compound as a brown solid (0.12 g, quantitative yield) which was used without further purification. LCMS: 281.9 [M+H].

102

Intermediate D3

1-(4-amino-5-(4-amino-3-fluorophenyl)-7H-pyrrolo[2,3-d]pyrimidin-7-yl)-2-methylpropan-2-ol

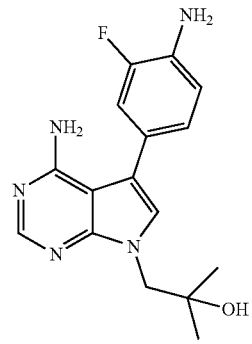 [SMILES: CC(C)(O)Cn1cc(-c2ccc(N)c(F)c2)c2c(N)ncnc21]

The title compound was prepared via a similar procedure described for D1, starting from 1-(4-amino-5-iodo-7H-pyrrolo[2,3-d]pyrimidin-7-yl)-2-methylpropan-2-ol (C3 (0.100 g, 0.301 mmol) and 2-fluoro-4-(4,4,5,5-tetramethyl-1,3,2-dioxaborolan-2-yl)aniline (0.086 g, 0.361 mmol), and was obtained as a pale yellow gum (0.05 g, 53% yield). LCMS: 316.1 [M+H].

Intermediate D4

5-(4-aminophenyl)-7-cyclopropyl-7H-pyrrolo[2,3-d]pyrimidin-4-amine

Step 1: synthesis of 7-cyclopropyl-5-(4-nitrophenyl)-7H-pyrrolo[2,3-d]pyrimidin-4-amine

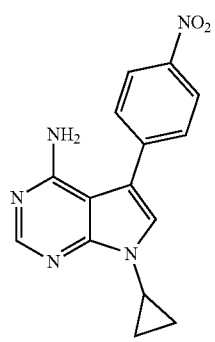 [SMILES: Nc1ncnc2c1c(-c1ccc([N+](=O)[O-])cc1)cn2C1CC1]

The title compound was obtained by following a similar procedure described for D1, starting from 7-cyclopropyl-5-iodo-7H-pyrrolo[2,3-d]pyrimidin-4-amine (C1, 0.18 g, 0.60 mmol) and (4-nitrophenyl)boronic acid (0.12 g, 0.72 mmol), and was obtained as a pale brown solid (0.10 g, 56% yield). $^1$H NMR (400 MHz, DMSO-$d_6$) δ=8.28-8.32 (m, 2H), 8.21 (s, 1H), 7.77 (s, 1H), 7.70-7.73 (m, 2H), 7.55 (s, 1H), 5.69 (bs, 2H), 3.61-3.64 (m, 1H), 1.04-1.09 (m, 4H). LCMS: 296.1 [M+H].

Step 2: synthesis of 5-(4-aminophenyl)-7-cyclopropyl-7H-pyrrolo[2,3-d]pyrimidin-4-amine

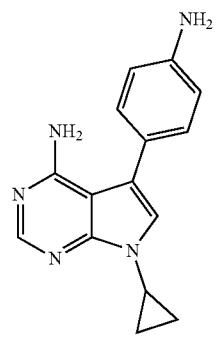

The title compound was obtained by following a similar procedure described for step 2 of D2, starting from 7-cyclopropyl-5-(4-nitrophenyl)-7H-pyrrolo[2,3-d]pyrimidin-4-amine (0.10 g, 0.33 mmol) and Fe/NH$_4$Cl, and was obtained as a brown gum (0.08 g, 90% yield) which was used without further purification. $^1$H NMR (400 MHz, DMSO-d$_6$) δ=8.13 (s, 1H), 7.04-7.11 (m, 2H), 7.04 (s, 1H), 6.63-6.67 (m, 2H), 6.05 (bs, 2H), 5.27 (bs, 2H), 3.51-3.57 (m, 1H), 0.99-1.04 (m, 4H). LCMS: 266.0 [M+H].

Intermediate D5

5-(4-amino-2-fluorophenyl)-7-cyclopropyl-7H-pyrrolo[2,3-d]pyrimidin-4-amine

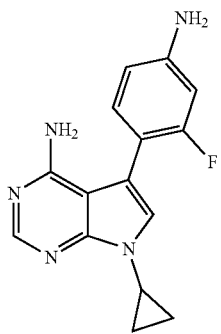 [SMILES: Nc1ccc(-c2cn(C3CC3)c3ncnc(N)c23)c(F)c1]

The title compound was obtained by following a similar procedure described for D1, starting from 7-cyclopropyl-5-iodo-7H-pyrrolo[2,3-d]pyrimidin-4-amine (C1, 0.21 g, 0.69 mmol) and 3-fluoro-4-(4,4,5,5-tetramethyl-1,3,2-dioxaborolan-2-yl)aniline (0.20 g, 0.83 mmol), and was obtained as a pale yellow gum (0.15 g, 76% yield). LCMS: 284.1 [M+H].

Intermediate D6

5-(6-aminopyridin-3-yl)-7-cyclopropyl-7H-pyrrolo[2,3-d]pyrimidin-4-amine

Step 1: synthesis of 7-cyclopropyl-5-(6-nitropyridin-3-yl)-7H-pyrrolo[2,3-d]pyrimidin-4-amine

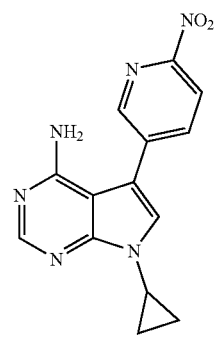 [SMILES: Nc1ncnc2c1c(-c1ccc([N+](=O)[O-])nc1)cn2C1CC1]

The title compound was obtained by following a similar procedure described for D1, starting from 7-cyclopropyl-5-iodo-7H-pyrrolo[2,3-d]pyrimidin-4-amine (C1, 0.28 g, 0.94 mmol) and 2-nitro-5-(4,4,5,5-tetramethyl-1,3,2-dioxaborolan-2-yl)pyridine (0.28 g, 1.13 mmol), and was obtained as a pale brown solid (0.16 g, 57% yield). $^1$H NMR (400 MHz, DMSO-d$_6$) δ=8.73 (d, J=2.0 Hz, 1H), 8.39 (d, J=8.8 Hz, 1H), 8.23 (s, 1H), 8.17-8.20 (m, 1H), 7.67 (s, 1H), 6.49 (bs, 2H), 3.61-3.67 (m, 1H), 1.06-1.09 (m, 4H). LCMS: 297.1 [M+H].

Step 2: synthesis of 5-(6-aminopyridin-3-yl)-7-cyclopropyl-7H-pyrrolo[2,3-d]pyrimidin-4-amine

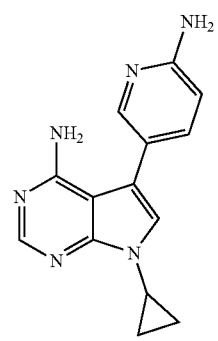 [SMILES: Nc1ccc(-c2cn(C3CC3)c3ncnc(N)c23)cn1]

The title compound was obtained by following a similar procedure described for step 2 of D2, starting from 7-cyclopropyl-5-(6-nitropyridin-3-yl)-7H-pyrrolo[2,3-d]pyrimidin-4-amine (0.16 g, 0.54 mmol) and Fe/NH$_4$Cl, and was obtained as a pale brown solid (0.1 g, 70% yield) which was used without further purification. LCMS: 267.0 [M+H].

Intermediate D7

5-(4-aminocyclohex-1-en-1-yl)-7-cyclopropyl-7H-pyrrolo[2,3-d]pyrimidin-4-amine

Step 1: synthesis of tert-butyl (4-(4-amino-7-cyclopropyl-7H-pyrrolo[2,3-d]pyrimidin-5-yl)cyclohex-3-en-1-yl)carbamate

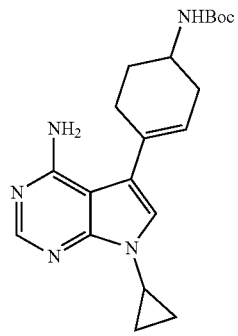 [SMILES: CC(C)(C)OC(=O)NC1CC=C(c2cn(C3CC3)c3ncnc(N)c23)CC1]

K₂CO₃ (0.318 g, 2.299 mmol) was added to a solution of 7-cyclopropyl-5-iodo-7H-pyrrolo[2,3-d]pyrimidin-4-amine (C1, 0.230 g, 0.766 mmol) and tert-butyl (4-(4,4,5,5-tetramethyl-1,3,2-dioxaborolan-2-yl)cyclohex-3-en-1-yl)carbamate (0.372 g, 1.150 mmol) in dioxane (1 mL) and water (0.3 mL). The solution was purged with N2 for 10 min then Pd(PPh₃)₄ (0.044 g, 0.038 mmol) was added and the resulting mixture was subjected to microwave irradiation at 100° C. for 1 h. Following completion of the reaction (as indicated by TLC), the reaction mixture was filtered through a pad of celite which was then rinsed with EtOAc (2×10 mL). The combined filtrates were concentrated under reduced pressure, giving crude material which was purified by preparative HPLC (mass-based, eluting with a gradient of ammonium acetate in water and ACN) to afford the title product as a pale-yellow gum (0.18 g, 62% yield). LCMS: 370.2 [M+H].

Step 2: synthesis of 5-(4-aminocyclohex-1-en-1-yl)-7-cyclopropyl-7H-pyrrolo[2,3-d]pyrimidin-4-amine

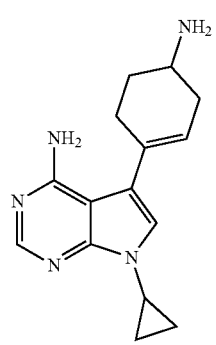 [SMILES: Nc1ncnc2c1c(C1=CCC(N)CC1)cn2C1CC1]

TFA (0.012 g, 0.108 mmol) was added to a solution of tert-butyl (4-(4-amino-7-cyclopropyl-7H-pyrrolo[2,3-d]pyrimidin-5-yl)cyclohex-3-en-1-yl)carbamate (0.040 g, 0.108 mmol) in DCM (2 mL) at 0° C. and the resulting solution was stirred at room temperature for 12 h. Following completion of the reaction (as indicated by TLC), the reaction mixture was concentrated under reduced pressure to afford the title product as a brown gum (0.029 g) which was used without further purification. LCMS: 270.1[M+H].

Intermediate D8

5-(4-amino-3-fluorophenyl)-7-(pyridin-3-yl)-7H-pyrrolo[2,3-d]pyrimidin-4-amine

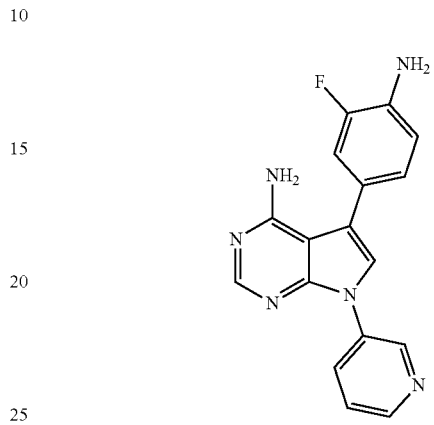

A mixture of 5-iodo-7-(pyridin-3-yl)-7H-pyrrolo[2,3-d]pyrimidin-4-amine (C4, 0.160 g, 0.475 mmol), 2-fluoro-4-(4,4,5,5-tetramethyl-1,3,2-dioxaborolan-2-yl)aniline (0.169 g, 0.712 mmol), and K₂CO₃ (0.131 g, 0.949 mmol) in dioxane (5 mL), water (2 mL), and ethanol (3 mL) was purged with N2 for 10 minutes. PdCl₂(dppf) (0.017 g, 0.024 mmol) was added and the resulting mixture was subjected to microwave irradiation at 100° C. for 1 h. Following completion of the reaction (as indicated by LCMS), the reaction mixture was filtered through a pad of celite which was then rinsed with EtOAc (5 mL). The combined filtrates were concentrated under reduced pressure to give a residue which was taken in EtOAc (50 mL), washed with water (5 mL) and brine (5 mL), dried over Na₂SO₄, filtered and concentrated under reduced pressure. The resulting crude material was purified by GRACE (silica gel 230-400 mesh, eluting with 4% MeOH in DCM) to afford the title compound as a brown solid (0.2 g, 70% yield). LCMS: 321.0 [M+H].

Intermediate D9

5-(4-amino-3-fluorophenyl)-7-(pyridin-4-yl)-7H-pyrrolo[2,3-d]pyrimidin-4-amine

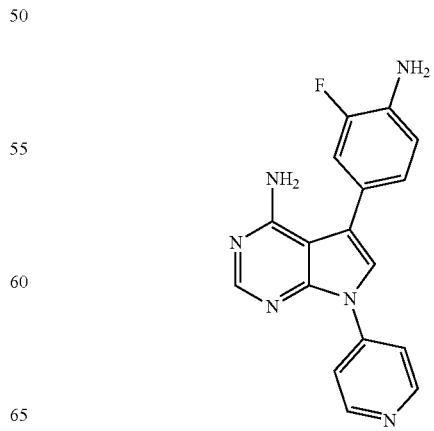

The title compound was obtained by following a similar procedure described for D8, starting from 5-iodo-7-(pyridin-4-yl)-7H-pyrrolo[2,3-d]pyrimidin-4-amine (C5, 0.160 g, 0.475 mmol) and 2-fluoro-4-(4,4,5,5-tetramethyl-1,3,2-dioxaborolan-2-yl)aniline (0.169 g, 0.712 mmol), and was obtained as a brown solid (0.08 g, 51% yield). LCMS: 321.0 [M+H].

Intermediate D10

5-(4-amino-3-fluorophenyl)-7-(1-methylpiperidin-4-yl)-7H-pyrrolo[2,3-d]pyrimidin-4-amine

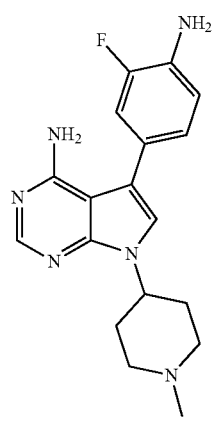 [SMILES: CN1CCC(n2cc(-c3ccc(N)c(F)c3)c3c(N)ncnc32)CC1]

The title compound was obtained by following a similar procedure described for D8, starting from 5-iodo-7-(1-methylpiperidin-4-yl)-7H-pyrrolo[2,3-d]pyrimidin-4-amine (C6, 0.180 g, 0.504 mmol) and 2-fluoro-4-(4,4,5,5-tetramethyl-1,3,2-dioxaborolan-2-yl)aniline (0.131 g, 0.554 mmol), and was obtained as a brown gum (0.15 g, 80% yield). LCMS: 341.1 [M+H].

Intermediate D11

5-(4-amino-3-methylphenyl)-7-cyclopropyl-7H-pyrrolo[2,3-d]pyrimidin-4-amine

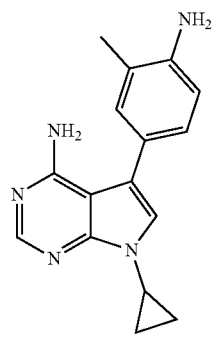 [SMILES: Cc1cc(-c2cn(C3CC3)c3ncnc(N)c23)ccc1N]

The title compound was obtained by following a similar procedure described for D8, starting from 7-cyclopropyl-5-iodo-7H-pyrrolo[2,3-d]pyrimidin-4-amine (C1, 0.250 g, 0.833 mmol) and 2-methyl-4-(4,4,5,5-tetramethyl-1,3,2-dioxaborolan-2-yl)aniline (0.214 g, 0.916 mmol), and was obtained as a brown gum (0.13 g, 56% yield). LCMS: 280.1 [M+H].

Intermediate D12

5-(4-amino-3-fluorophenyl)-7-(3-(benzyloxy)cyclobutyl)-7H-pyrrolo[2,3-d]pyrimidin-4-amine

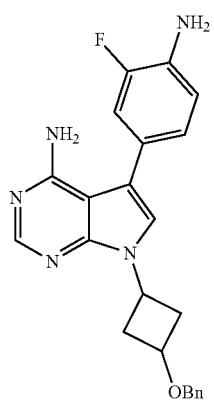 [SMILES: Nc1ccc(-c2cn(C3CC(OCc4ccccc4)C3)c3ncnc(N)c23)cc1F]

The title compound was obtained by following a similar procedure described for D8, starting from 7-(3-(benzyloxy)cyclobutyl)-5-iodo-7H-pyrrolo[2,3-d]pyrimidin-4-amine (C7, 0.060 g, 0.143 mmol) and 2-fluoro-4-(4,4,5,5-tetramethyl-1,3,2-dioxaborolan-2-yl)aniline (0.037 g, 0.157 mmol), and was obtained as a brown solid (0.03 g, 53% yield). LCMS: 404.2 [M+H].

Intermediate D13

Step 1: Synthesis of 7-cyclopropyl-5-(4,4,5,5-tetramethyl-1,3,2-dioxaborolan-2-yl)-7H-pyrrolo[2,3-d]pyrimidin-4-amine

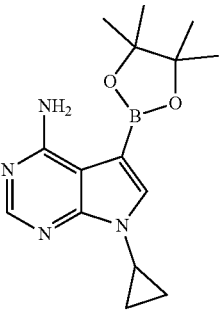 [SMILES: CC1(C)OB(c2cn(C3CC3)c3ncnc(N)c23)OC1(C)C]

Potassium acetate (0.245 g, 2.499 mmol) was added to a solution of 7-cyclopropyl-5-iodo-7H-pyrrolo[2,3-d]pyrimidin-4-amine (C1, 0.250 g, 0.833 mmol) and bis(pinacolato)diboron (0.317 g, 1.250 mmol) in DMSO (5 mL) and the resulting mixture was purged with N2 for 10 min. PdCl$_2$(dppf) (0.030 g, 0.042 mmol) was then added and the reaction mixture was stirred at 85° C. for 2 h. Following completion of the reaction, the reaction mixture was filtered through a pad of celite which was then rinsed with DCM (2×20 mL). The combined filtrates were concentrated under Step 2: synthesis of 5-(5-amino-4-methylpyridin-2-yl)-7-cyclopropyl-7H-pyrrolo[2,3-d]pyrimidin-4-amine

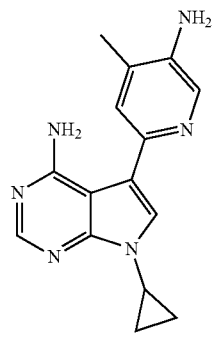

The title compound was obtained by following a similar procedure described for D8, starting from 6-bromo-4-methylpyridin-3-amine (0.142 g, 0.759 mmol) and 7-cyclopropyl-5-(4,4,5,5-tetramethyl-1,3,2-dioxaborolan-2-yl)-7H-pyrrolo[2,3-d]pyrimidin-4-amine (0.251 g, 0.835 mmol), and was obtained as a brown gum (0.05 g, 13% yield). LCMS: 281.0 [M+H].

Intermediate D14

5-(5-aminopyridin-2-yl)-7-cyclopropyl-7H-pyrrolo[2,3-d]pyrimidin-4-amine

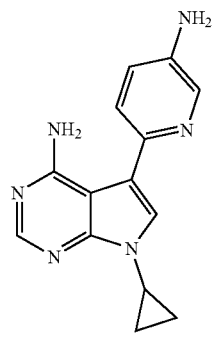 [SMILES: Nc1ccc(-c2cn(C3CC3)c3ncnc(N)c23)nc1]

The title compound was obtained by following a similar procedure described for D8, starting from 6-bromo-4-methylpyridin-3-amine (0.130 g, 0.751 mmol) and 7-cyclopropyl-5-(4,4,5,5-tetramethyl-1,3,2-dioxaborolan-2-yl)-7H-pyrrolo[2,3-d]pyrimidin-4-amine (step 1 of Intermediate D13, 0.248 g, 0.827 mmol), and was obtained as a brown gum (0.03 g, 4.5% yield). LCMS: 267.0 [M+H].

Intermediate D15

5-(4-amino-3,5-difluorophenyl)-7-cyclopropyl-7H-pyrrolo[2,3-d]pyrimidin-4-amine

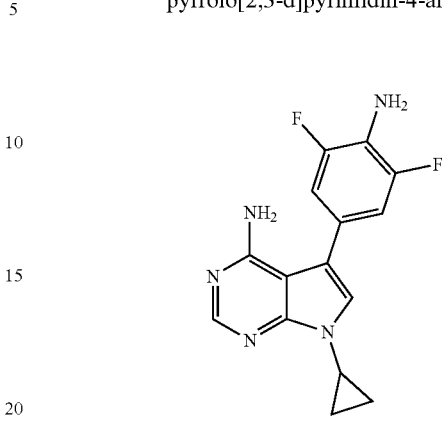

The title compound was obtained by following a similar procedure described for D8, starting from 7-cyclopropyl-5-iodo-7H-pyrrolo[2,3-d]pyrimidin-4-amine (C1, 0.500 g, 0.751 mmol) and 2,6-difluoro-4-(4,4,5,5-tetramethyl-1,3,2-dioxaborolan-2-yl)aniline (0.425 g, 1.666 mmol), and was obtained as a pale yellow solid (0.10 g, 19% yield). LCMS: 302.1 [M+H].

Intermediate D16

5-(4-amino-2,5-difluorophenyl)-7-cyclopropyl-7H-pyrrolo[2,3-d]pyrimidin-4-amine

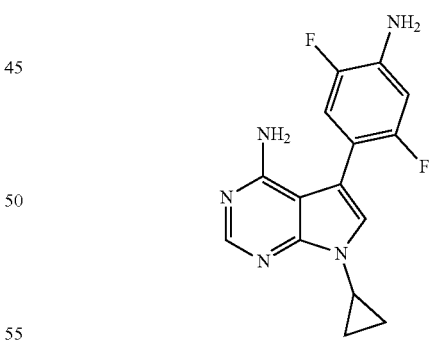

The title compound was obtained by following a similar procedure described for D8, starting from 7-cyclopropyl-5-iodo-7H-pyrrolo[2,3-d]pyrimidin-4-amine (C1, 0.125 g, 0.417 mmol) and 2,5-difluoro-4-(4,4,5,5-tetramethyl-1,3,2-dioxaborolan-2-yl)aniline (prepared as reported in PCT Pub. No. WO 2017/172093, 0.106 g, 4.17 mmol), and was obtained as a pale yellow solid (0.05 g, 40% yield). LCMS: 302.1 [M+H].

Intermediate D17

5-(4-amino-2,6-difluorophenyl)-7-cyclopropyl-7H-pyrrolo[2,3-d]pyrimidin-4-amine

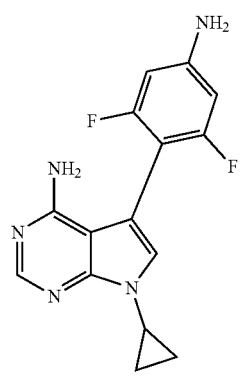 [SMILES: Nc1cc(F)c(-c2cn(C3CC3)c3ncnc(N)c23)c(F)c1]

The title compound was obtained by following a similar procedure described for D8, starting from 7-cyclopropyl-5-iodo-7H-pyrrolo[2,3-d]pyrimidin-4-amine (C1, 0.055 g, 0.183 mmol) and 3,5-difluoro-4-(4,4,5,5-tetramethyl-1,3,2-dioxaborolan-2-yl)aniline (prepared as reported in PCT Pub. No. WO 2017/172093, 0.056 g, 0.220 mmol), and was obtained as a pale brown gum (0.046 g) which was used without further purification. LCMS: 301.9 [M+H].

Intermediate D18

1-(4-amino-5-(6-aminopyridin-3-yl)-7H-pyrrolo[2,3-d]pyrimidin-7-yl)-2-methylpropan-2-ol

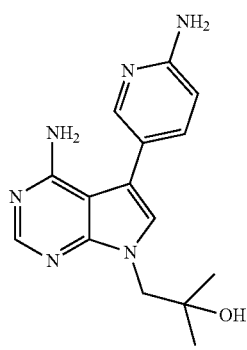 [SMILES: CC(C)(O)Cn1cc(-c2ccc(N)nc2)c2c(N)ncnc21]

The title compound was obtained by following a similar procedure described for D8, starting from 1-(4-amino-5-iodo-7H-pyrrolo[2,3-d]pyrimidin-7-yl)-2-methylpropan-2-ol (C3, 0.280 g, 0.733 mmol) and 5-(4,4,5,5-tetramethyl-1,3,2-dioxaborolan-2-yl)pyridin-2-amine (0.161 g, 0.733 mmol), and was obtained as a yellow gum (0.12 g, 50% yield). LCMS: 299.1 [M+H].

Intermediate D19

5-(2-aminopyrimidin-5-yl)-7-cyclopropyl-7H-pyrrolo[2,3-d]pyrimidin-4-amine

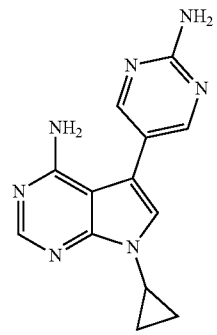

The title compound was obtained by following a similar procedure described for D8, starting from 7-cyclopropyl-5-iodo-7H-pyrrolo[2,3-d]pyrimidin-4-amine (C1, 0.25 g, 0.833 mmol) and 5-(4,4,5,5-tetramethyl-1,3,2-dioxaborolan-2-yl)pyrimidin-2-amine (0.184 g, 0.833 mmol), and was obtained as a colorless gum (0.08 g, 34% yield). LCMS: 268.2 [M+H].

Intermediate D20

(2-amino-5-(4-amino-7-cyclopropyl-7H-pyrrolo[2,3-d]pyrimidin-5-yl)phenyl)methanol

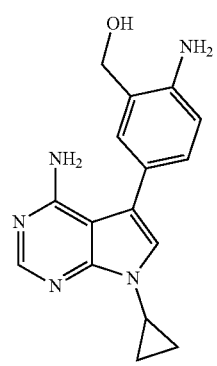 [SMILES: Nc1ccc(-c2cn(C3CC3)c3ncnc(N)c23)cc1CO]

The title compound was obtained by following a similar procedure described for D8, starting from 7-cyclopropyl-5-iodo-7H-pyrrolo[2,3-d]pyrimidin-4-amine (C1, 0.200 g, 0.666 mmol) and (2-amino-5-(4,4,5,5-tetramethyl-1,3,2-dioxolan-2-yl)phenyl)methanol (prepared as reported in PCT Pub. No. WO 2011/130628, 0.184 g, 0.733 mmol), and was obtained as a pale yellow gum (0.025 g, 13% yield). LCMS: 296.0 [M+H].

Intermediate D21

2-amino-5-(4-amino-7-cyclopropyl-7H-pyrrolo[2,3-d]pyrimidin-5-yl)benzonitrile

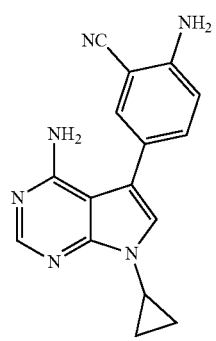 [SMILES: N#Cc1cc(-c2cn(C3CC3)c3ncnc(N)c23)ccc1N]

The title compound was obtained by following a similar procedure described for D8, starting from 7-cyclopropyl-5-iodo-7H-pyrrolo[2,3-d]pyrimidin-4-amine (C1, 0.250 g, 0.833 mmol) and 2-amino-5-(4,4,5,5-tetramethyl-1,3,2-dioxaborolan-2-yl)benzonitrile (0.203 g, 0.833 mmol), and was obtained as a yellow gum (0.13 g, 34% yield). LCMS: 291.2 [M+H].

Intermediate D22

5-(4-amino-3-fluorophenyl)-7-(2-methoxyethyl)-7H-pyrrolo[2,3-d]pyrimidin-4-amine

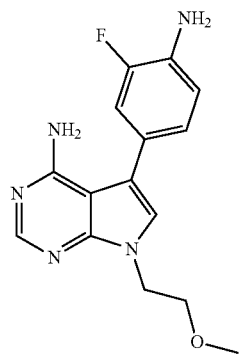 [SMILES: COCCn1cc(-c2ccc(N)c(F)c2)c2c(N)ncnc21]

The title compound was obtained by following a similar procedure described for D8, starting from 5-iodo-7-(2-methoxyethyl)-7H-pyrrolo[2,3-d]pyrimidin-4-amine (C8, 0.200 g, 0.629 mmol) and 2-fluoro-4-(4,4,5,5-tetramethyl-1,3,2-dioxaborolan-2-yl)aniline (0.149 g, 0.629 mmol), and was obtained as a pale brown solid (0.12 g, 42% yield). LCMS: 302.2 [M+H].

Intermediate D23

2-(4-amino-5-(4-amino-3-fluorophenyl)-7H-pyrrolo[2,3-d]pyrimidin-7-yl)ethan-1-ol

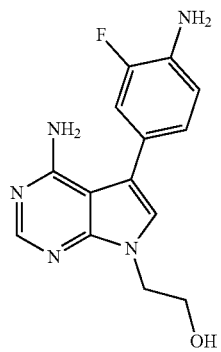 [SMILES: Nc1ccc(-c2cn(CCO)c3ncnc(N)c23)cc1F]

The title compound was obtained by following a similar procedure described for D8, starting from 2-(4-amino-5-iodo-7H-pyrrolo[2,3-d]pyrimidin-7-yl)ethan-1-ol (C9, 0.50 g, 1.644 mmol) and 2-fluoro-4-(4,4,5,5-tetramethyl-1,3,2-dioxaborolan-2-yl)aniline (0.39 g, 1.644 mmol), and was obtained as a brown solid (0.3 g, 63% yield). LCMS: 288.1 [M+H].

Intermediate D24

5-(4-amino-3-fluorophenyl)-7-cyclobutyl-7H-pyrrolo[2,3-d]pyrimidin-4-amine

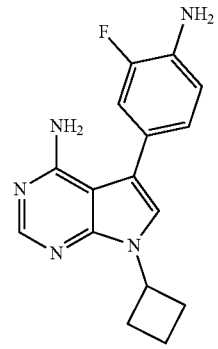 [SMILES: Nc1ccc(-c2cn(C3CCC3)c3ncnc(N)c23)cc1F]

The title compound was obtained by following a similar procedure described for D8, starting from 7-cyclobutyl-5-iodo-7H-pyrrolo[2,3-d]pyrimidin-4-amine (C10, 0.410 g, 1.305 mmol) and 2-fluoro-4-(4,4,5,5-tetramethyl-1,3,2-dioxaborolan-2-yl)aniline (0.309 g, 1.305 mmol), and was obtained as a brown solid (0.18 g, 37% yield). $^1$H NMR (400 MHz, DMSO-$d_6$) δ=8.13 (s, 1H), 7.51 (s, 1H), 7.09-7.13 (m, 1H), 6.98-7.01 (m, 1H), 6.84-6.88 (m, 1H), 6.21 (bs, 2H), 5.14-5.26 (m, 3H), 2.67-2.68 (m, 2H), 2.38-2.39 (m, 2H), 1.85-1.86 (m, 2H). LCMS: 298.0 [M+H].

Intermediate D25

5-(4-amino-3-chlorophenyl)-7-cyclopropyl-7H-pyrrolo[2,3-d]pyrimidin-4-amine

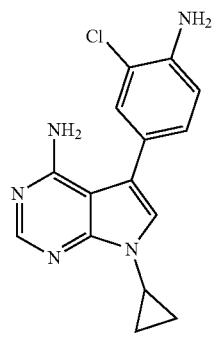 [SMILES: Nc1ccc(-c2cn(C3CC3)c3ncnc(N)c23)cc1Cl]

The title compound was obtained by following a similar procedure described for D8, starting from 7-cyclopropyl-5-iodo-7H-pyrrolo[2,3-d]pyrimidin-4-amine (C1, 0.250 g, 0.833 mmol) and 2-chloro-4-(4,4,5,5-tetramethyl-1,3,2-dioxaborolan-2-yl)aniline (0.211 g, 0.833 mmol), and was obtained as a yellow solid (0.03 g, 12% yield). LCMS: 300.1 [M+H].

Intermediate D26

5-(4-amino-3-methoxyphenyl)-7-cyclopropyl-7H-pyrrolo[2,3-d]pyrimidin-4-amine

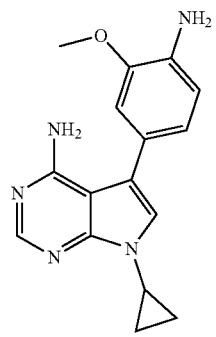 [SMILES: COc1cc(-c2cn(C3CC3)c3ncnc(N)c23)ccc1N]

The title compound was obtained by following a similar procedure described for D8, starting from 7-cyclopropyl-5-iodo-7H-pyrrolo[2,3-d]pyrimidin-4-amine (C1, 0.250 g, 0.833 mmol) and 2-methoxy-4-(4,4,5,5-tetramethyl-1,3,2-dioxaborolan-2-yl)aniline (0.208 g, 0.833 mmol), and was obtained as a pale yellow gum (0.04 g, 16% yield). LCMS: 296.1 [M+H].

Intermediate D27

5-(4-amino-3-fluorophenyl)-7-(1-methylpyrrolidin-3-yl)-7H-pyrrolo[2,3-d]pyrimidin-4-amine

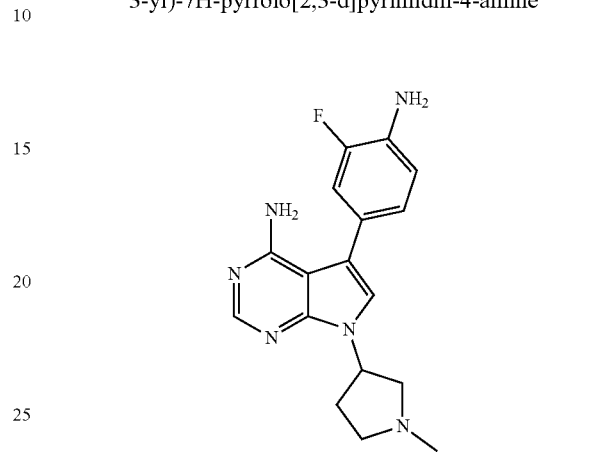

The title compound was obtained by following a similar procedure described for D8, starting from 5-iodo-7-(1-methylpyrrolidin-3-yl)-7H-pyrrolo[2,3-d]pyrimidin-4-amine (C11, 0.155 g, 0.452 mmol) and 2-fluoro-4-(4,4,5,5-tetramethyl-1,3,2-dioxaborolan-2-yl)aniline (0.107 g, 0.452 mmol), and was obtained as a brown solid (0.084 g, 27% yield). LCMS: 327.2 [M+H].

Intermediate E1-E25

General Procedure for the Synthesis of Carbamate Intermediates E:

Pyridine (1.2 eq) and phenyl chloroformate (1.5 eq) were added to a solution of amine (1.0 eq) in THF (10 vol) at 0° C. The reaction mixture was allowed to warm to 25° C. and was stirred for 12 h. Following completion of the reaction (as indicated by TLC), the mixture was diluted with EtOAc (10 mL) and washed with brine (5 mL). The organic layer was dried over Na$_2$SO$_4$, filtered, and concentrated under reduced pressure to yield crude material which was purified by flash chromatography (silica gel 230-400 mesh, eluting with 10 to 20% EtOAc in petroleum), giving the desired carbamate.

The following carbamates were prepared using the above general procedure:

| Intermediate | Carbamate structure (product) | Amine structure (starting material) | LCMS |
|---|---|---|---|
| E1 | | | 261.0 [M + H] |

-continued

| Intermediate | Carbamate structure (product) | Amine structure (starting material) | LCMS |
|---|---|---|---|
| E2 | PhO-C(=O)-NH-[3-(5-tert-butyl)isoxazolyl] | 3-amino-5-tert-butylisoxazole | 261.0 [M + H] |
| E3 | PhO-C(=O)-NH-[5-(3-methyl)isoxazolyl] | 5-amino-3-methylisoxazole | 219.1 [M + H] |
| E4 | PhO-C(=O)-NH-[3-(5-methyl)isoxazolyl] | 3-amino-5-methylisoxazole | 219.1 [M + H] |
| E5 | PhO-C(=O)-NH-[3-(5-cyclopropyl)isoxazolyl] | 3-amino-5-cyclopropylisoxazole | 245.0 [M + H] |
| E6 | PhO-C(=O)-NH-[5-(3-(1-trifluoromethylcyclopropyl))isoxazolyl] | 5-amino-3-(1-trifluoromethylcyclopropyl)isoxazole | 312.9 [M + H] |
| E7 | PhO-C(=O)-NH-[3-(5-(1-trifluoromethylcyclopropyl))isoxazolyl] | 3-amino-5-(1-trifluoromethylcyclopropyl)isoxazole | 312.9 [M + H] |
| E8 | PhO-C(=O)-NH-[5-(3-(2-trifluoro-1,1-dimethylethyl))isoxazolyl] | 5-amino-3-(2-trifluoro-1,1-dimethylethyl)isoxazole | 315.1 [M + H] |
| E9 | PhO-C(=O)-NH-[5-(3-(2-fluoro-1,1-dimethylethyl))isoxazolyl] | 5-amino-3-(2-fluoro-1,1-dimethylethyl)isoxazole | 265.1 [M + H] |

-continued

| Intermediate | Carbamate structure (product) | Amine structure (starting material) | LCMS |
|---|---|---|---|
| E10 | | | 259.1 [M + H] |
| E11 | | | 404.0 [M + H] |
| E12 | | | 278.0 [M + H] |
| E13 | | | 277.1 [M] |
| E14 | | | 273.0 [M − H] |
| E15 | | | 270.9 [M − H] |
| E16 | | | 391.2 [M + H] |

-continued

| Intermediate | Carbamate structure (product) | Amine structure (starting material) | LCMS |
|---|---|---|---|
| E17 | | | 261.0 [M + H] |
| E18 | | | 273.0 [M − H] |
| E19 | | | 247.1 [M + H] |
| E20 | | | 233.0 [M + H] |
| E21 | | | 272.5 [M + H] |
| E22 | | | 272.5 [M + H] |
| E23 | | | 349.6 [M + H] |
| E24 | | | 327.1 [M + H] |

-continued

| Intermediate | Carbamate structure (product) | Amine structure (starting material) | LCMS |
|---|---|---|---|
| E25 | 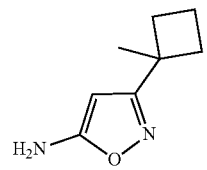 | | 327.0 [M + H] |

All amines used for the synthesis of carbamate Intermediates E are commercially available except for the following:

3-(1-(Trifluoromethyl)cyclopropyl)isoxazol-5-amine (precursor to E6) and 5-(1-(trifluoromethyl)cyclopropyl)isoxazol-3-amine (precursor to E7) were synthesized as reported in *Synthesis* 2013, 45, 171-173.

3-(1,1,1-Trifluoro-2-methylpropan-2-yl)isoxazol-5-amine (precursor to E8) and 3-(2-fluoropropan-2-yl)isoxazol-5-amine (precursor to E9) were synthesized from methyl 3,3,3-trifluoro-2,2-dimethylpropanote and methyl 2-fluoro-2-methylpropionate, respectively, followed by the procedure reported in *Synthesis* 2013, 45, 171-173.

3-(1-((Tert-butyldimethylsilyl)oxy)-2-methylpropan-2-yl)isoxazol-5-amine (precursor to E16) was synthesized as reported in PCT publication No. WO 2010/036630.

2-(5-Aminoisoxazol-3-yl)-2-methylpropanenitrile (precursor to E22) and 3-(1-(Trifluoromethyl)cyclobutyl)isoxazol-5-amine (precursor to E24) were synthesized as reported in *J. Med. Chem.* 2012, 55(3), 1082-1105

3-(((Tert-butyldiphenylsilyl)oxy)methyl)isoxazol-5-amine (precursor to E23) was synthesized as reported in PCT publication No. WO 2013/104561.

5-(1-(Trifluoromethyl)cyclobutyl)isoxazol-3-amine (precursor to E25) was synthesized as reported in PCT publication No. WO 2011/022473.

Synthesis of
3-(3-methyloxetan-3-yl)isoxazol-5-amine (precursor to E14)

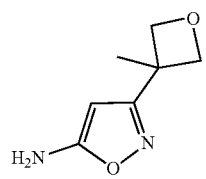

$NH_2OH \cdot H_2SO_4$ (0.520 g, 3.16 mmol) was added to a solution of 3-(3-methyloxetan-3-yl)-3-oxopropanenitrile (prepared as reported in PCT Pub. No. WO 2019/192962, 0.400 g, 2.87 mmol) and sodium hydroxide (0.126 g, 3.16 mmol) in EtOH (10 mL) and water (10 mL). The pH of the resulting mixture was adjusted to 7.5 using aqueous NaOH (1M) and the reaction mixture was stirred at 80° C. for 15 h. Following completion of the reaction (as indicated by TLC), the reaction mixture was concentrated under reduced pressure, giving a residue which was taken in EtOAc (25 mL), washed with water (10 mL), dried over $Na_2SO_4$, filtered, and concentrated under reduced pressure. The resulting crude material was purified by flash chromatography (silica gel 230-400 mesh, eluting with 30% EtOAc in petroleum ether to afford the title product as a pale brown solid (0.09 g, 20% yield). $^1H$ NMR (400 MHz, $CDCl_3$) δ=5.21 (s, 1H), 4.90-4.93 (m, 2H), 4.56-4.59 (m, 2H), 1.70 (s, 3H). LCMS: 155.1 [M+H].

Synthesis of
3-(1-methylcyclobutyl)isoxazol-5-amine (precursor to E21)

$NH_2OH \ H_2SO_4$ (0.699 g, 4.25 mmol) was added to a solution of 3-(1-methylcyclobutyl)-3-oxopropanenitrile (prepared as reported in PCT Pub. No. WO 2017/060874, 0.500 g, 3.86 mmol) and sodium hydroxide (0.170 g, 4.25 mmol) in EtOH (10 mL) and water (10 mL). The pH of the resulting mixture was adjusted to 7.5 using aqueous NaOH (1M) and the reaction mixture was stirred at 80° C. for 15 h. Following completion of the reaction (as indicated by TLC), the reaction mixture was concentrated under reduced pressure, giving a residue which was taken in DCM (25 mL), washed with water (10 mL), dried over $Na_2SO_4$, filtered, and concentrated under reduced pressure. The resulting crude material was purified by flash chromatography (silica gel 230-400 mesh, eluting with 40% EtOAc in petroleum ether to afford the title product as an off-white solid (0.110 g, 19% yield). $^1H$ NMR (400 MHz, $CDCl_3$) δ=5.04 (s, 1H), 2.43-2.49 (m, 2H), 1.96-2.02 (m, 4H), 1.50 (s, 3H). LCMS: 153.2 [M+H].

PREPARATION OF EXAMPLES

General Urea Formation Procedure for the Synthesis of Examples 1-62

Method A—Triethylamine (2.0 eq.) was added to a mixture of amine Intermediate D (1.0 eq.) and carbamate Intermediate E (1.0 eq.) in THF (10 Vol.) and the resulting mixture was stirred at 60° C. for 12 h in a sealed tube. Following completion of the reaction (as indicated by LCMS), the reaction mixture was concentrated under reduced pressure to give crude material which was purified by reverse phase preparative HPLC to afford the desired product.

Method B—DMAP (0.05 eq.) and DIPEA (1.5 eq.) were added to a solution of amine Intermediate D (1.0 eq.) and carbamate Intermediate E (1.0 eq.) in THF (10 Vol.) and the resulting mixture was stirred at 60° C. for 12 h in a sealed tube. Following completion of the reaction (as indicated by LCMS), the reaction mixture was concentrated under reduced pressure to yield the crude material which was purified by reverse phase preparative HPLC to afford the desired product.

The following compounds were prepared using the above general procedures.

Example 1

1-(4-(4-amino-7-(oxetan-3-yl)-7H-pyrrolo[2,3-d]pyrimidin-5-yl)phenyl)-3-(3-(tert-butyl)isoxazol-5-yl)urea

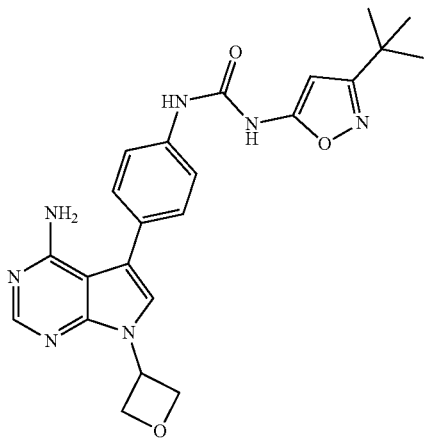 [SMILES: CC(C)(C)c1cc(NC(=O)Nc2ccc(-c3cn(C4COC4)c4ncnc(N)c34)cc2)on1]

The title compound was prepared following the general procedure for urea formation (Method A), starting from 5-(4-aminophenyl)-7-(oxetan-3-yl)-7H-pyrrolo[2,3-d]pyrimidin-4-amine (D2, 0.178 g, 0.63 mmol) and phenyl (3-(tert-butyl)isoxazol-5-yl)carbamate (E1, 0.16 g, 0.30 mmol), and was obtained as an off-white solid (0.026 g, 9% yield). $^1$H NMR (400 MHz, DMSO-$d_6$) δ=10.48 (bs, 1H), 9.34 (bs, 1H), 8.15 (s, 1H), 7.70 (s, 1H), 7.61 (d, J=8.8 Hz, 2H), 7.45 (d, J=8.8 Hz, 2H), 6.08 (bs, 2H), 6.07 (s, 1H), 5.86-5.90 (m, 1H), 4.97-5.05 (m, 4H), 1.27 (s, 9H). LCMS: 448.2 [M+H].

Example 2

1-(4-(4-amino-7-cyclopropyl-7H-pyrrolo[2,3-d]pyrimidin-5-yl)-2-fluorophenyl)-3-(3-(tert-butyl)isoxazol-5-yl)urea

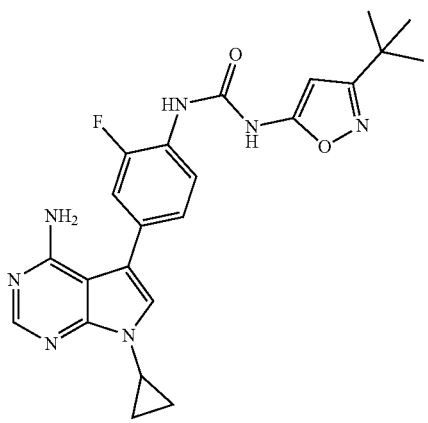

The title compound was prepared following the general procedure for urea formation (Method A), starting from 5-(4-aminophenyl)-7-(oxetan-3-yl)-7H-pyrrolo[2,3-d]pyrimidin-4-amine (D2, 0.178 g, 0.63 mmol) and phenyl (3-(tert-butyl)isoxazol-5-yl)carbamate (E1, 0.16 g, 0.30 mmol), and was obtained as an off-white solid (0.026 g, 9% yield). $^1$H NMR (400 MHz, DMSO-$d_6$) δ=10.48 (bs, 1H), 9.34 (bs, 1H), 8.15 (s, 1H), 7.70 (s, 1H), 7.61 (d, J=8.8 Hz, 2H), 7.45 (d, J=8.8 Hz, 2H), 6.08 (bs, 2H), 6.07 (s, 1H), 5.86-5.90 (m, 1H), 4.97-5.05 (m, 4H), 1.27 (s, 9H). LCMS: 448.2 [M+H].

Example 3

1-(5-(4-amino-7-cyclopropyl-7H-pyrrolo[2,3-d]pyrimidin-5-yl)pyridin-2-yl)-3-(3-(tert-butyl)isoxazol-5-yl)urea

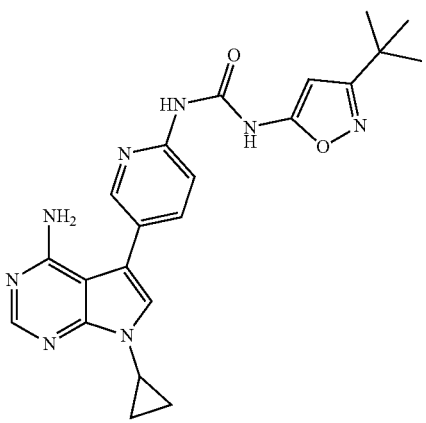 [SMILES: CC(C)(C)c1cc(NC(=O)Nc2ccc(-c3cn(C4CC4)c4ncnc(N)c34)cn2)on1]

The title compound was prepared following the general procedure for urea formation (Method A), starting from 5-(6-aminopyridin-3-yl)-7-cyclopropyl-7H-pyrrolo[2,3-d]pyrimidin-4-amine (D6, 0.100 g, 0.376 mmol) and phenyl (3-(tert-butyl)isoxazol-5-yl)carbamate (E1, 0.098 g, 0.376 mmol), and was obtained as an off-white solid (9.6 mg, 6% yield). $^1$H NMR (400 MHz, CD$_3$OD) δ=8.46-8.47 (m, 1H), 8.22 (s, 1H), 7.89-7.92 (m, 2H), 7.35-7.38 (m, 1H), 7.28 (s, 1H), 6.23 (s, 1H), 3.50-3.57 (m, 1H), 1.27 (s, 9H), 1.07-1.16 (m, 4H); LCMS: 433.2 [M+H].

Example 4

1-(4-(4-amino-7-cyclopropyl-7H-pyrrolo[2,3-d]pyrimidin-5-yl)-2-fluorophenyl)-3-(5-(tert-butyl)isoxazol-3-yl)urea

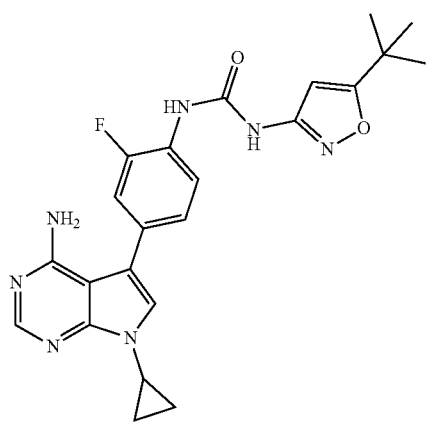 [SMILES: CC(C)(C)c1cc(NC(=O)Nc2ccc(-c3cn(C4CC4)c4ncnc(N)c34)cc2F)no1]

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.100 g, 0.35 mmol)) and phenyl (5-(tert-butyl)isoxazol-3-yl)carbamate (E2, 0.091 g, 0.35 mmol), and was obtained as an off-white solid (0.021 g, 13% yield). $^1$H NMR (400 MHz, DMSO-d$_6$) δ=9.86 (bs, 1H), 8.87 (bs, 1H), 8.17-8.21 (m, 2H), 7.24-7.35 (m, 3H), 6.51 (s, 1H), 6.17 (bs, 2H), 3.56-3.60 (m, 1H), 1.31 (s, 9H), 1.02-1.07 (m, 4H). LCMS: 450.2 [M+H].

Example 5

1-(4-(4-amino-7-cyclopropyl-7H-pyrrolo[2,3-d]pyrimidin-5-yl)-2-fluorophenyl)-3-(3-(1-(trifluoromethyl)cyclopropyl)isoxazol-5-yl)urea

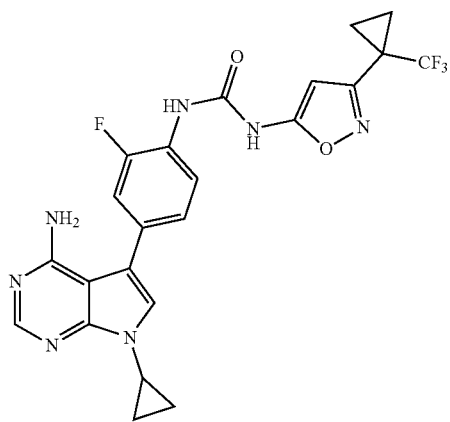 [SMILES: Nc1ncnc2c1c(-c1ccc(NC(=O)Nc3cc(C4(C(F)(F)F)CC4)no3)c(F)c1)cn2C1CC1]

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.080 g, 0.282 mmol) and phenyl (3-(1-(trifluoromethyl)cyclopropyl)isoxazol-5-yl)carbamate (E6, 0.088 g, 0.282 mmol), and was obtained as a white solid (0.031 g, 22% yield). $^1$H NMR (400 MHz, DMSO-d$_6$) δ=10.59 (bs, 1H), 8.84 (bs, 1H), 8.11-8.17 (m, 2H), 7.26-7.37 (m, 3H), 6.20 (s, 1H), 6.16 (bs, 2H), 3.55-3.61 (m, 1H), 1.45-1.49 (m, 2H), 1.38-1.43 (m, 2H), 1.03-1.08 (m, 4H). LCMS: 502.1 [M+H].

Example 6

1-(4-(4-amino-7-cyclopropyl-7H-pyrrolo[2,3-d]pyrimidin-5-yl)-2-fluorophenyl)-3-(3-(1-(trifluoromethyl)cyclopropyl)isoxazol-5-yl)urea

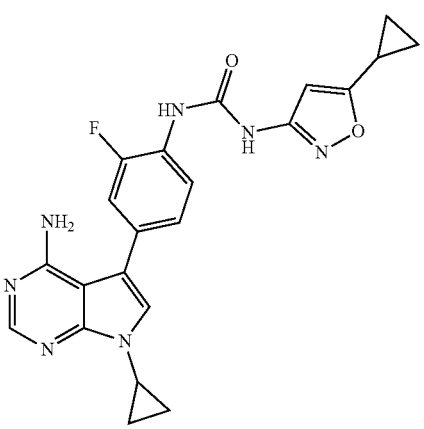 [SMILES: Nc1ncnc2c1c(-c1ccc(NC(=O)Nc3cc(C4CC4)on3)c(F)c1)cn2C1CC1]

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.060 g, 0.180 mmol) and phenyl (5-cyclopropylisoxazol-3-yl)carbamate (E5, 0.044 g, 0.282 mmol), and was obtained as an off-white solid (8.4 mg, 9% yield). $^1$H NMR (400 MHz, CD$_3$OD) δ=8.20-8.22 (m, 2H), 7.28-7.33 (m, 2H), 7.22 (s, 1H), 6.35 (s, 1H), 3.49-3.55 (m, 1H), 2.08-2.12 (m, 1H), 1.08-1.16 (m, 6H), 0.97-0.99 (m, 2H). LCMS: 434.2 [M+H].

Example 7

1-(4-(4-amino-7-cyclopropyl-7H-pyrrolo[2,3-d]pyrimidin-5-yl)-2-fluorophenyl)-3-(3-methylisoxazol-5-yl)urea

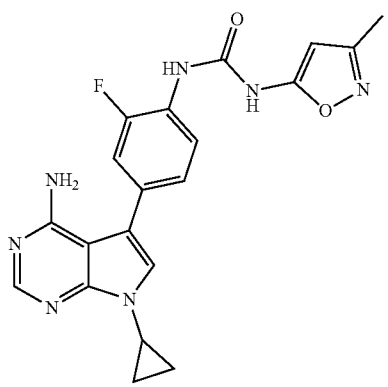 [SMILES: Cc1cc(NC(=O)Nc2ccc(-c3cn(C4CC4)c4ncnc(N)c34)cc2F)on1]

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.100 g, 0.35 mmol)) and phenyl (3-methylisoxazol-5-yl)carbamate (E3, 0.077 g, 0.35 mmol), and was obtained as an off-white solid (0.024 g, 17% yield). $^1$H NMR (400 MHz, DMSO-d$_6$) δ=10.35 (bs, 1H), 8.84 (bs, 1H), 8.10-8.18 (m, 2H), 7.25-7.36 (m, 3H), 6.13 (bs, 2H), 5.99 (s, 1H), 3.55-3.61 (m, 1H), 2.18 (s, 3H), 1.00-1.08 (m, 4H). LCMS: 408.1 [M+H].

Example 8

1-(4-(4-amino-7-cyclopropyl-7H-pyrrolo[2,3-d]pyrimidin-5-yl)-2-fluorophenyl)-3-(5-methylisoxazol-3-yl)urea

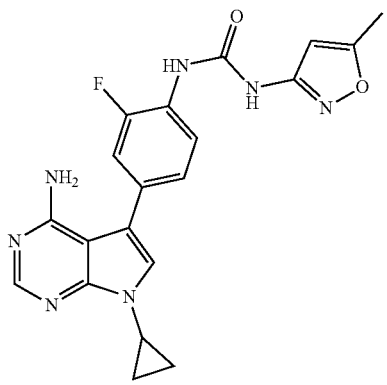 [SMILES: Cc1cc(NC(=O)Nc2ccc(-c3cn(C4CC4)c4ncnc(N)c34)cc2F)no1]

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.127 g, 0.44 mmol) and phenyl (5-methylisoxazol-3-yl)carbamate (E4, 0.097 g, 0.44 mmol), and was obtained as a white solid (0.033 g, 18% yield). $^1$H NMR (400 MHz, DMSO-d$_6$) δ=9.88 (bs, 1H), 8.96 (bs, 1H), 8.15-8.19 (m, 2H), 7.24-7.35 (m, 3H), 6.54 (s, 1H), 6.15 (bs, 2H), 3.55-3.61 (m, 1H), 2.38 (s, 3H), 1.00-1.07 (m, 4H). LCMS: 408.2 [M+H].

Example 9

1-(4-(4-amino-7-cyclopropyl-7H-pyrrolo[2,3-d]pyrimidin-5-yl)-2-fluorophenyl)-3-(3-(2-fluoropropan-2-yl)isoxazol-5-yl)urea

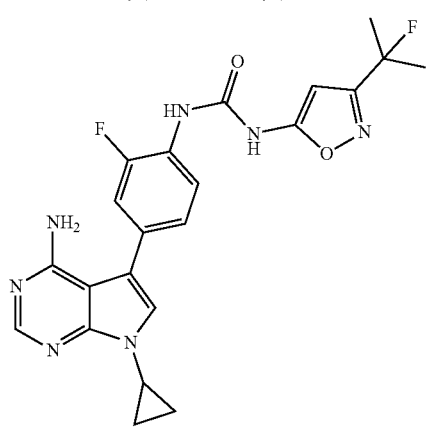

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.076 g, 0.26 mmol) and phenyl (3-(2-fluoropropan-2-yl)isoxazol-5-yl)carbamate (E9, 0.070 g, 0.26 mmol), and was obtained as a white solid (0.018 g, 14% yield). $^1$H NMR (400 MHz, DMSO-d$_6$) δ=8.99 (bs, 1H), 8.17 (s, 1H), 8.09-8.14 (m, 1H), 7.25-7.36 (m, 3H), 6.18 (s, 1H), 6.09 (bs, 2H), 3.57-3.61 (m, 1H), 1.71 (s, 3H), 1.66 (s, 3H), 1.02-1.05 (m, 4H). LCMS: 454.2 [M+H].

Example 10

1-(4-(4-amino-7-cyclopropyl-7H-pyrrolo[2,3-d]pyrimidin-5-yl)-2-fluorophenyl)-3-(5-(1-(trifluoromethyl)cyclopropyl)isoxazol-3-yl)urea

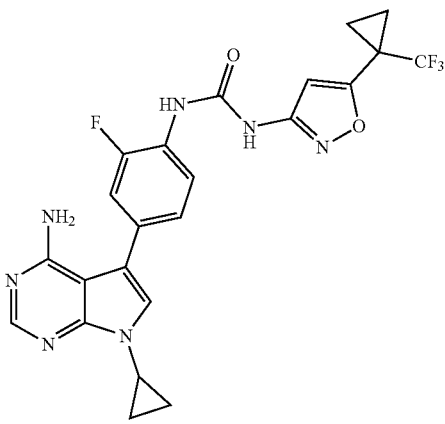 [SMILES: Nc1ncnc2c1c(-c1ccc(NC(=O)Nc3cc(C4(C(F)(F)F)CC4)on3)c(F)c1)cn2C1CC1]

The title compound was prepared following the general procedure for urea formation (Method A), starting from 5-(4-amino-3-fluorophenyl)-7-cyclopropyl-7H-pyrrolo[2,3-d]pyrimidin-4-amine (D1, 0.10 g, 0.35 mmol) and phenyl (5-(1-(trifluoromethyl)cyclopropyl)isoxazol-3-yl)carbamate (E7, 0.11 g, 0.35 mmol), and was obtained as an off-white solid (0.010 g, 6% yield). $^1$H NMR (400 MHz, DMSO-d$_6$) δ=9.99 (bs, 1H), 8.86 (bs, 1H), 8.14-8.18 (m, 2H), 7.24-7.36 (m, 3H), 6.90 (s, 1H), 6.15 (bs, 2H), 3.56-3.61 (m, 1H), 1.48-1.57 (m, 4H), 1.02-1.07 (m, 4H). LCMS: 502.2 [M+H].

Example 11

1-(4-(4-amino-7-cyclopropyl-7H-pyrrolo[2,3-d]pyrimidin-5-yl)-3-fluorophenyl)-3-(3-(1-(trifluoromethyl)cyclopropyl)isoxazol-5-yl)urea

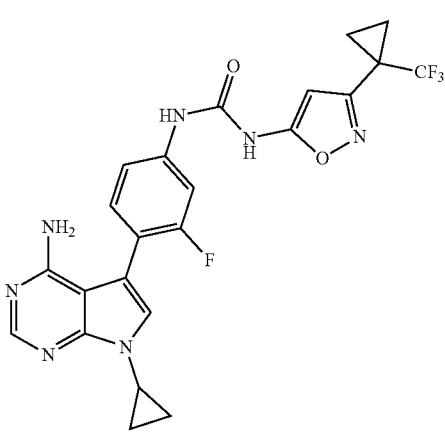 [SMILES: Nc1ncnc2c1c(-c1ccc(NC(=O)Nc3cc(C4(C(F)(F)F)CC4)no3)cc1F)cn2C1CC1]

The title compound was prepared following the general procedure for urea formation (Method A), starting from 5-(4-amino-2-fluorophenyl)-7-cyclopropyl-7H-pyrrolo[2,3-d]pyrimidin-4-amine (D5, 0.070 g, 0.24 mmol) and phenyl (3-(1-(trifluoromethyl)cyclopropyl)isoxazol-5-yl)carbamate (E6, 0.082 g, 0.24 mmol), and was obtained as an off-white solid (0.011 g, 9% yield). $^1$H NMR (400 MHz, DMSO-d$_6$) δ=10.56 (bs, 1H), 9.29 (bs, 1H), 8.16 (s, 1H), 7.58-7.62 (m, 1H), 7.27-7.36 (m, 2H), 7.22 (s, 1H), 6.20 (s, 1H), 6.00 (bs, 2H), 3.55-3.60 (m, 1H), 1.38-1.48 (m, 4H), 1.02-1.06 (m, 4H). LCMS: 502.2 [M+H].

Example 12

1-(4-(4-amino-7-cyclopropyl-7H-pyrrolo[2,3-d]pyrimidin-5-yl)-2-fluorophenyl)-3-(3-(1,1,1-trifluoro-2-methylpropan-2-yl)isoxazol-5-yl)urea

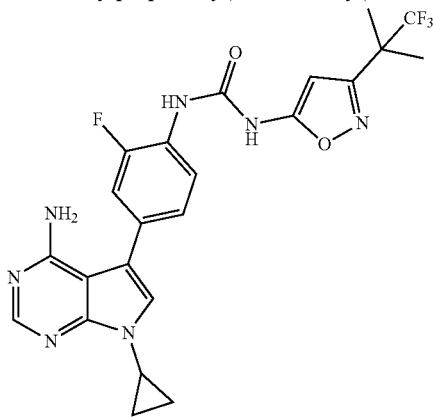

The title compound was prepared following the general procedure for urea formation (Method A), starting from 5-(4-amino-2-fluorophenyl)-7-cyclopropyl-7H-pyrrolo[2,3-d]pyrimidin-4-amine (D1, 0.050 g, 0.176 mmol) and phenyl (3-(1,1,1-trifluoro-2-methylpropan-2-yl)isoxazol-5-yl)carbamate (E8, 0.055 g, 0.176 mmol), and was obtained as an off-white solid (9.9 mg, 11% yield). $^1$H NMR (400 MHz, DMSO-d$_6$) δ=10.59 (bs, 1H), 8.83 (bs, 1H), 8.18 (s, 1H), 8.12-8.17 (m, 1H), 7.25-7.36 (m, 3H), 6.22 (s, 1H), 6.17 (bs, 2H), 3.55-3.61 (m, 1H), 1.52 (s, 6H), 1.02-1.07 (m, 4H). LCMS: 504.2 [M+H].

Example 13

1-(4-(4-amino-7-cyclopropyl-7H-pyrrolo[2,3-d]pyrimidin-5-yl)phenyl)-3-(3-(tert-butyl)isoxazol-5-yl)urea

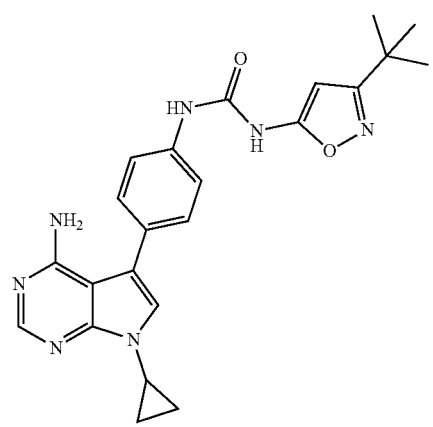 [SMILES: CC(C)(C)c1cc(NC(=O)Nc2ccc(-c3cn(C4CC4)c4ncnc(N)c34)cc2)on1]

The title compound was prepared following the general procedure for urea formation (Method A), starting from 5-(4-aminophenyl)-7-cyclopropyl-7H-pyrrolo[2,3-d]pyrimidin-4-amine (D4, 0.080 g, 0.30 mmol) and phenyl (3-(tert-butyl)isoxazol-5-yl)carbamate (E1, 0.078 g, 0.30 mmol), and was obtained as an off-white solid (0.036 g, 28% yield). $^1$H NMR (400 MHz, DMSO-d$_6$) δ=10.13 (bs, 1H), 8.93 (bs, 1H), 8.16 (s, 1H), 7.56 (d, J=8.4 Hz, 2H), 7.40 (d, J=8.8 Hz, 2H), 7.22 (s, 1H), 6.08 (s, 1H), 6.00 (bs, 2H), 3.56-3.59 (m, 1H), 1.27 (s, 9H), 1.05-1.07 (m, 4H). LCMS: 430.2 [M−H].

Example 14

1-(4-(4-amino-7-(2-hydroxy-2-methylpropyl)-7H-pyrrolo[2,3-d]pyrimidin-5-yl)-2-fluorophenyl)-3-(3-(1-(trifluoromethyl)cyclopropyl)isoxazol-5-yl)urea

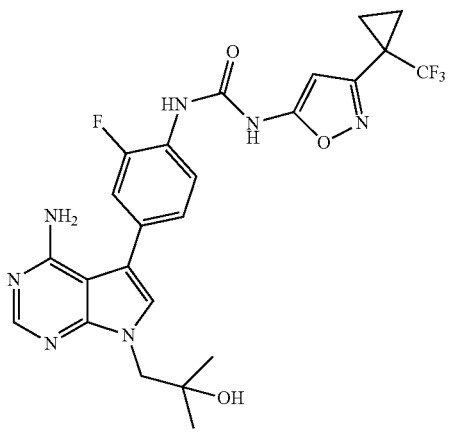 [SMILES: CC(C)(O)Cn1cc(-c2ccc(NC(=O)Nc3cc(C4(C(F)(F)F)CC4)no3)c(F)c2)c2c(N)ncnc21]

The title compound was prepared following the general procedure for urea formation (Method A), starting from 1-(4-amino-5-(4-amino-3-fluorophenyl)-7H-pyrrolo[2,3-d]pyrimidin-7-yl)-2-methylpropan-2-ol (D3, 0.086 g, 0.273 mmol) and phenyl (3-(1-(trifluoromethyl)cyclopropyl)isoxazol-5-yl)carbamate (E6, 0.085 g, 0.273 mmol), and was obtained as pale brown solid (0.011 g, 8% yield). $^1$H NMR (400 MHz, DMSO-d$_6$) δ=10.92 (bs, 1H), 9.06 (bs, 1H), 8.11-8.15 (m, 2H), 7.26-7.35 (m, 3H), 6.18 (s, 1H), 6.14 (bs, 2H), 4.86 (bs, 1H), 4.11 (bs, 2H), 1.37-1.46 (m, 4H), 1.06-1.08 (m, 6H). LCMS: 534.1 [M+H].

Example 15

1-(4-(4-amino-7-cyclopropyl-7H-pyrrolo[2,3-d]pyrimidin-5-yl)cyclohex-3-en-1-yl)-3-(3-(tert-butyl)isoxazol-5-yl)urea

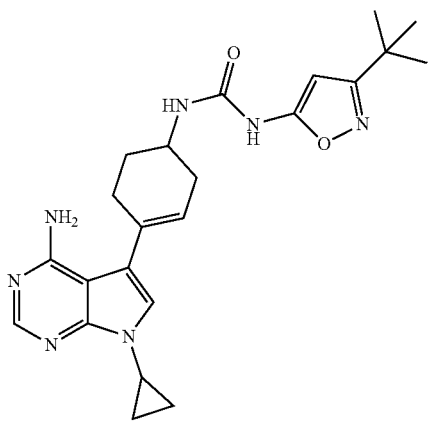 [SMILES: CC(C)(C)c1cc(NC(=O)NC2CC=C(c3cn(C4CC4)c4ncnc(N)c34)CC2)on1]

The title compound was prepared following the general procedure for urea formation (Method A), starting from 5-(4-aminocyclohex-1-en-1-yl)-7-cyclopropyl-7H-pyrrolo[2,3-d]pyrimidin-4-amine (D7, 0.120 g, 0.446 mmol) and phenyl (3-(tert-butyl)isoxazol-5-yl)carbamate (E1, 0.116 g, 0.446 mmol), and was obtained as an off-white solid (0.013 g, 7% yield). $^1$H NMR (400 MHz, DMSO-$d_6$) δ=9.83 (bs, 1H), 8.39 (bs, 1H), 7.47 (s, 1H), 6.54 (d, J=7.6 Hz, 1H), 5.93 (s, 1H), 5.67 (bs, 1H), 3.88-3.90 (m, 2H), 3.61-3.67 (m, 2H), 2.08-2.14 (m, 1H), 1.92-1.95 (m, 1H), 1.69-1.73 (m, 1H), 1.24 (s, 9H), 1.05-1.08 (m, 4H). LCMS: 436.2 [M+H].

Example 16

1-(4-(4-amino-7-cyclopropyl-7H-pyrrolo[2,3-d]pyrimidin-5-yl)cyclohexyl)-3-(3-(tert-butyl)isoxazol-5-yl)urea

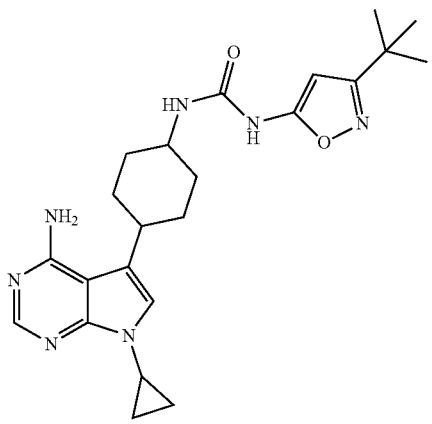 [SMILES: CC(C)(C)c1cc(NC(=O)NC2CCC(c3cn(C4CC4)c4ncnc(N)c34)CC2)on1]

Platinum oxide (0.016 g, 0.069 mmol) was added to a solution of 1-(4-(4-amino-7-cyclopropyl-7H-pyrrolo[2,3-d]pyrimidin-5-yl)cyclohex-3-en-1-yl)-3-(3-(tert-butyl)isoxazol-5-yl)urea (Example 15, 0.100 g, 0.230 mmol) in EtOAc (5 mL) and the resulting suspension was stirred at room temperature under H2 atmosphere for 12 h. Following completion of the reaction (as indicated by LCMS), the reaction mixture was filtered through a pad celite which was then rinsed with EtOAc (2×5 mL). The combined filtrates were concentrated under reduced pressure to yield crude material which was purified by preparative HPLC (mass-based, eluting with a gradient of ammonium acetate in water and ACN), giving the title product as an off white solid (2.0 mg, 2% yield). $^1$H NMR (400 MHz, CD$_3$OD) δ=8.12 (s, 1H), 6.92 (s, 1H), 6.02 (s, 1H), 3.50-3.51 (m, 1H), 2.87-2.90 (m, 1H), 2.13-2.18 (m, 6H), 1.51-1.57 (m, 3H), 1.33 (s, 9H), 0.90-1.20 (m, 4H). LCMS: 436.2 [M−H].

Example 17

1-(4-(4-amino-7-cyclopropyl-7H-pyrrolo[2,3-d]pyrimidin-5-yl)-2-fluorophenyl)-3-(3-(1-methylcyclopropyl)isoxazol-5-yl)urea

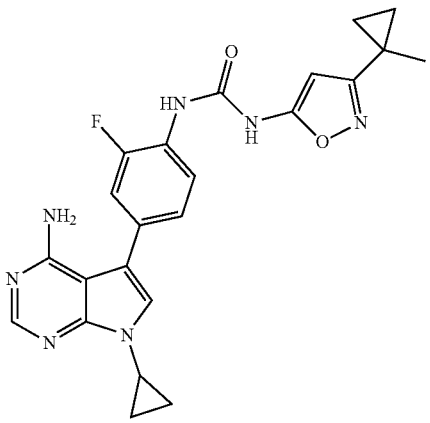 [SMILES: CC1(c2cc(NC(=O)Nc3ccc(-c4cn(C5CC5)c5ncnc(N)c45)cc3F)on2)CC1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.050 g, 0.176 mmol) and phenyl (3-(1-methylcyclopropyl)isoxazol-5-yl)carbamate (E10, 0.046 g, 0.176 mmol), and was obtained as an off-white solid (0.013 g, 16% yield). $^1$H NMR (400 MHz, DMSO-$d_6$) δ=10.40 (bs, 1H), 8.84 (bs, 1H), 8.11-8.17 (m, 2H), 7.24-7.36 (m, 3H), 6.16 (bs, 2H), 5.84 (s, 1H), 3.55-3.61 (m, 1H), 1.38 (s, 3H), 1.02-1.07 (m, 4H), 0.94-0.96 (m, 2H), 0.83-0.84 (m, 2H). LCMS: 448.2 [M+H].

Example 18

1-(4-(4-amino-7-cyclopropyl-7H-pyrrolo[2,3-d]pyrimidin-5-yl)-2-fluorophenyl)-3-(4-(tert-butyl)thiazol-2-yl)urea

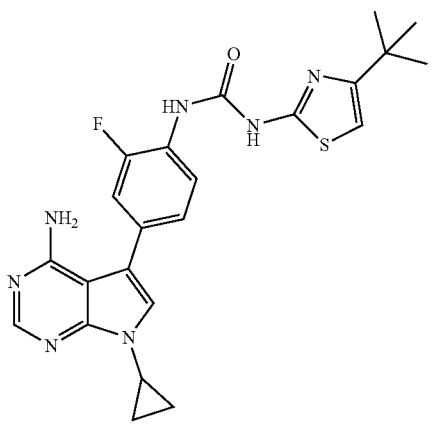 [SMILES: CC(C)(C)c1csc(NC(=O)Nc2ccc(-c3cn(C4CC4)c4ncnc(N)c34)cc2F)n1]

The title compound was obtained following the general procedure for urea formation (Method A), starting from phenyl (4-(4-amino-7-cyclopropyl-7H-pyrrolo[2,3-d]pyrimidin-5-yl)-2-fluorophenyl)carbamate (E11, 0.040 g, 0.099 mmol) and 4-(tert-butyl)thiazol-2-amine (0.015 g, 0.099 mmol), and was obtained as an off-white solid (7.0 mg, 15% yield). $^1$H NMR (400 MHz, DMSO-$d_6$) δ=10.99 (bs, 1H), 9.29 (bs, 1H), 8.46 (s, 1H), 8.26-8.30 (m, 1H), 7.67 (s, 1H), 7.38-7.41 (m, 1H), 7.27-7.30 (m, 1H), 6.70 (s, 1H), 3.71 (bs, 1H), 1.27 (s, 9H), 1.10-1.10 (m, 4H). LCMS: 466.0 [M+H].

Example 19

1-(4-(4-amino-7-cyclopropyl-7H-pyrrolo[2,3-d]pyrimidin-5-yl)-2-fluorophenyl)-3-(5-(tert-butyl)-1,3,4-thiadiazol-2-yl)urea

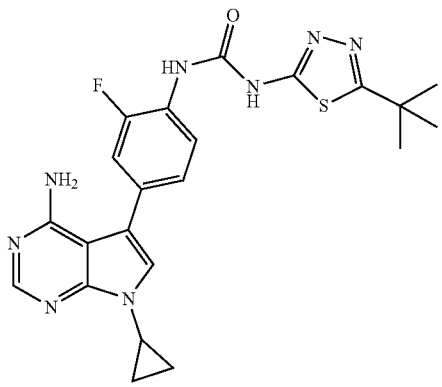 [SMILES: CC(C)(C)c1nnc(NC(=O)Nc2ccc(-c3cn(C4CC4)c4ncnc(N)c34)cc2F)s1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.050 g, 0.176 mmol) and phenyl (5-(tert-butyl)-1,3,4-thiadiazol-2-yl)carbamate (E12, 0.049 g, 0.176 mmol), and was obtained as an off-white solid (2.0 mg, 2% yield). $^1$H NMR (400 MHz, CD$_3$OD) δ=8.19-8.23 (m, 2H), 7.30-7.35 (m, 2H), 7.23 (s, 1H), 3.50-3.54 (m, 1H), 1.49 (s, 9H), 1.08-1.17 (m, 4H). LCMS: 466.9 [M+H].

Example 20

1-(4-(4-amino-7-cyclopropyl-7H-pyrrolo[2,3-d]pyrimidin-5-yl)-2-fluorophenyl)-3-(3-(tert-butyl)isothiazol-5-yl)urea

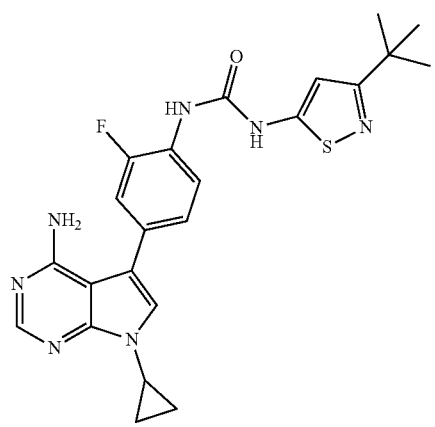 [SMILES: CC(C)(C)c1cc(NC(=O)Nc2ccc(-c3cn(C4CC4)c4ncnc(N)c34)cc2F)sn1]

The title compound was obtained following the general procedure for urea formation (Method A), starting from phenyl (4-(4-amino-7-cyclopropyl-7H-pyrrolo[2,3-d]pyrimidin-5-yl)-2-fluorophenyl)carbamate (E11, 0.040 g, 0.099 mmol) and 4-(tert-butyl)thiazol-2-amine (0.015 g, 0.099 mmol), and was obtained as an off-white solid (2.0 mg, 4% yield). $^1$H NMR (400 MHz, CD$_3$OD) δ=8.21 (s, 1H), 8.11-8.17 (m, 1H), 7.30-7.34 (m, 2H), 7.23 (s, 1H), 6.78 (s, 1H), 3.50-3.54 (m, 1H), 1.35 (s, 9H), 1.08-1.30 (m, 4H). LCMS: 466.0 [M+H].

Example 21

1-(4-(4-amino-7-cyclopropyl-7H-pyrrolo[2,3-d]pyrimidin-5-yl)-2-fluorophenyl)-3-(3-(tert-butyl)-1,2,4-thiadiazol-5-yl)urea

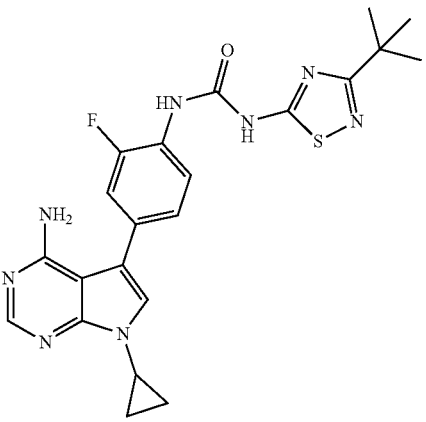 [SMILES: CC(C)(C)c1nsc(NC(=O)Nc2ccc(-c3cn(C4CC4)c4ncnc(N)c34)cc2F)n1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.050 g, 0.176 mmol) and phenyl (3-(tert-butyl)-1,2,4-thiadiazol-5-yl)carbamate (E13, 0.049 g, 0.176 mmol), and was obtained as an off-white solid (8.0 mg, 10% yield). $^1$H NMR (400 MHz, DMSO-d$_6$) δ=11.54 (bs, 1H), 9.00 (bs, 1H), 8.09-8.18 (m, 2H), 7.28-7.39 (m, 3H), 6.19 (bs, 2H), 3.57-3.61 (m, 1H), 1.34 (s, 9H), 1.03-1.05 (m, 4H). LCMS: 467.0 [M+H].

Example 22

1-(4-(4-amino-7-cyclopropyl-7H-pyrrolo[2,3-d]pyrimidin-5-yl)-2-fluorophenyl)-3-(1-(tert-butyl)-1H-1,2,4-triazol-3-yl)urea

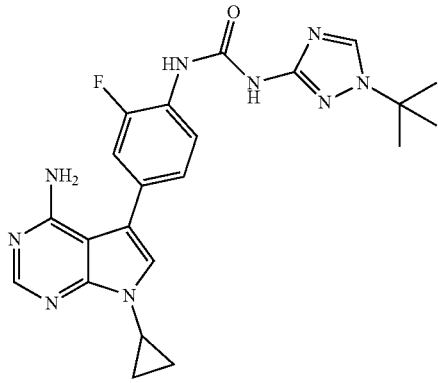 [SMILES: CC(C)(C)n1cnc(NC(=O)Nc2ccc(-c3cn(C4CC4)c4ncnc(N)c34)cc2F)n1]

The title compound was obtained following the general procedure for urea formation (Method A), starting from phenyl (4-(4-amino-7-cyclopropyl-7H-pyrrolo[2,3-d]pyrimidin-5-yl)-2-fluorophenyl)carbamate (E11, 0.040 g, 0.099 mmol) and 1-(tert-butyl)-1H-1,2,4-triazol-3-amine (0.014 g, 0.099 mmol), and was obtained as an off-white solid (3.0 mg, 6% yield). $^1$H NMR (400 MHz, DMSO-d$_6$) δ=10.70 (bs, 1H), 10.16 (bs, 1H), 8.54 (s, 1H), 8.31-8.35 (m, 1H), 8.16 (s, 1H), 7.25-7.37 (m, 3H), 6.17 (bs, 2H), 3.56-3.59 (m, 1H), 1.57 (s, 9H), 1.02-1.05 (m, 4H). LCMS: 450.0 [M+H].

Example 23

1-(4-(4-amino-7-cyclopropyl-7H-pyrrolo[2,3-d]pyrimidin-5-yl)-2-fluorophenyl)-3-(5-(tert-butyl)-1,3,4-oxadiazol-2-yl)urea

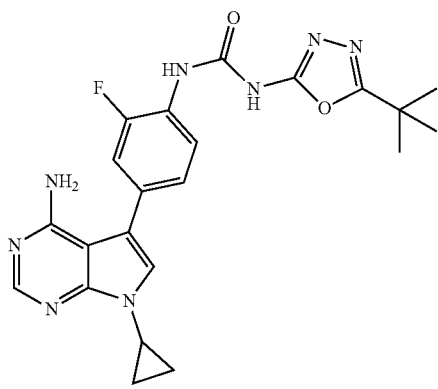 [SMILES: CC(C)(C)c1nnc(NC(=O)Nc2ccc(-c3cn(C4CC4)c4ncnc(N)c34)cc2F)o1]

The title compound was obtained following the general procedure for urea formation (Method A), starting from phenyl (4-(4-amino-7-cyclopropyl-7H-pyrrolo[2,3-d]pyrimidin-5-yl)-2-fluorophenyl)carbamate (E11, 0.040 g, 0.099 mmol) and 5-(tert-butyl)-1,3,4-oxadiazol-2-amine (0.014 g, 0.099 mmol), and was obtained as an off-white solid (2.0 mg, 4% yield). $^1$H NMR (400 MHz, CD$_3$OD) δ=8.35 (s, 1H), 8.26-8.30 (m, 1H), 7.48 (s, 1H), 7.31-7.40 (m, 2H), 3.69-3.71 (m, 1H), 1.45 (s, 9H), 1.17-1.22 (m, 4H). LCMS: 451.0 [M+H].

Example 24

1-(4-(4-amino-7-(pyridin-3-yl)-7H-pyrrolo[2,3-d]pyrimidin-5-yl)-2-fluorophenyl)-3-(3-(1-(trifluoromethyl)cyclopropyl)isoxazol-5-yl)urea

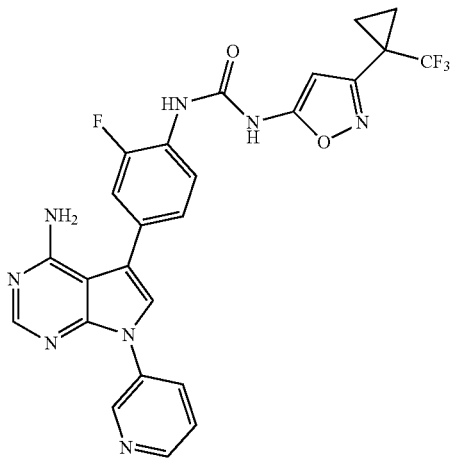 [SMILES: Nc1ncnc2c1c(-c1ccc(NC(=O)Nc3cc(C4(C(F)(F)F)CC4)no3)c(F)c1)cn2-c1cccnc1]

The title compound was obtained following the general procedure for urea formation (Method A), starting from 5-(4-amino-3-fluorophenyl)-7-(pyridin-3-yl)-7H-pyrrolo[2,3-d]pyrimidin-4-amine (D8, 0.100 g, 0.312 mmol) and phenyl (3-(1-(trifluoromethyl)cyclopropyl)isoxazol-5-yl)carbamate (E6, 0.107 g, 0.343 mmol), and was obtained as a white solid (0.023 g, 14% yield). $^1$H NMR (400 MHz, DMSO-d$_6$) δ=10.69 (bs, 1H), 9.13 (bs, 1H), 8.97 (bs, 1H), 8.62 (d, J=4.8 Hz, 1H), 8.31-8.36 (m, 2H), 8.20-8.24 (m, 1H), 7.95 (s, 1H), 7.62-7.65 (m, 1H), 7.38-7.50 (m, 2H), 6.76 (bs, 2H), 6.21 (s, 1H), 1.39-1.47 (m, 4H). LCMS: 538.8 [M+H].

Example 25

1-(4-(4-amino-7-(pyridin-4-yl)-7H-pyrrolo[2,3-d]pyrimidin-5-yl)-2-fluorophenyl)-3 (3-(1-(trifluoromethyl)cyclopropyl)isoxazol-5-yl urea

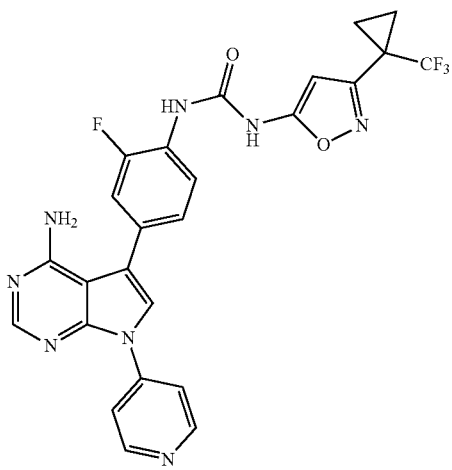 [SMILES: Nc1ncnc2c1c(-c1ccc(NC(=O)Nc3cc(C4(C(F)(F)F)CC4)no3)c(F)c1)cn2-c1ccncc1]

The title compound was obtained following the general procedure for urea formation (Method A), starting from 5-(4-amino-3-fluorophenyl)-7-(pyridin-4-yl)-7H-pyrrolo[2,3-d]pyrimidin-4-amine (D9, 0.080 g, 0.250 mmol) and phenyl (3-(1-(trifluoromethyl)cyclopropyl)isoxazol-5-yl)carbamate (E6, 0.086 g, 0.275 mmol), and was obtained as an off-white solid (0.046 g, 33% yield). $^1$H NMR (400 MHz, DMSO-d$_6$) δ=10.68 (bs, 1H), 9.00 (bs, 1H), 8.89 (d, J=6.4 Hz, 2H), 8.58 (d, J=6.4 Hz, 2H), 8.43 (s, 1H), 8.21-8.27 (m, 2H), 7.49-7.52 (m, 1H), 7.39-7.42 (m, 1H), 6.90 (bs, 2H), 6.22 (s, 1H), 1.39-1.49 (m, 4H). LCMS: 538.9 [M+H].

Example 26

1-(4-(4-amino-7-(1-methylpiperidin-4-yl)-7H-pyrrolo[2,3-d]pyrimidin-5-yl)-2-fluorophenyl)-3-(3-(1-(trifluoromethyl)cyclopropyl)isoxazol-5-yl)urea

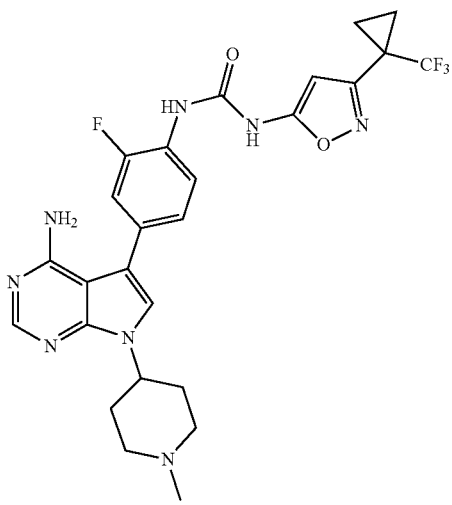 [SMILES: CN1CCC(n2cc(-c3ccc(NC(=O)Nc4cc(C5(C(F)(F)F)CC5)no4)c(F)c3)c3c(N)ncnc32)CC1]

The title compound was obtained following the general procedure for urea formation (Method A), starting from 5-(4-amino-3-fluorophenyl)-7-(1-methylpiperidin-4-yl)-7H-pyrrolo[2,3-d]pyrimidin-4-amine (D10, 0.020 g, 0.059 mmol) and phenyl (3-(1-(trifluoromethyl)cyclopropyl)isoxazol-5-yl)carbamate (E6, 0.018 g, 0.059 mmol), and was obtained as a white solid (2.4 mg, 7% yield). $^1$H NMR (400 MHz, DMSO-d$_6$) δ=10.68 (bs, 1H), 8.96 (bs, 1H), 8.32 (s, 1H), 8.16-8.20 (m, 1H), 7.55 (s, 1H), 7.38-7.41 (m, 1H), 7.29-7.31 (m, 1H), 6.98 (bs, 2H), 6.21 (s, 1H), 4.85-4.91 (m, 1H), 3.59-3.62 (m, 4H), 2.85 (s, 3H), 2.21-2.34 (m, 4H), 1.38-1.49 (m, 4H). LCMS: 559.2 [M+H].

Example 27

1-(4-(4-amino-7-cyclopropyl-7H-pyrrolo[2,3-d]pyrimidin-5-yl)-2-fluorophenyl)-3-(3-(3-methyloxetan-3-yl)isoxazol-5-yl)urea

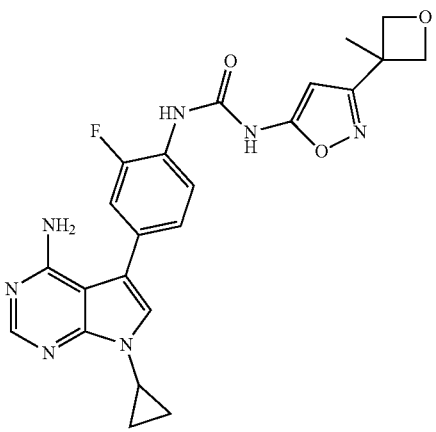 [SMILES: CC1(c2cc(NC(=O)Nc3ccc(-c4cn(C5CC5)c5ncnc(N)c45)cc3F)on2)COC1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.050 g, 0.176 mmol) and phenyl (3-(3-methyloxetan-3-yl)isoxazol-5-yl)carbamate (E14, 0.048 g, 0.176 mmol), and was obtained as a white solid (3.4 mg, 4% yield). $^1$H NMR (400 MHz, DMSO-d$_6$) δ=10.56 (s, 1H), 8.94 (bs, 1H), 8.42 (s, 1H), 8.19 (t, J=8.4 Hz, 1H), 7.57 (bs, 3H), 7.38 (d, J=10.8 Hz, 1H), 7.28 (d, J=8.4 Hz, 1H), 6.22 (s, 1H), 4.77 (d, J=5.6 Hz, 2H), 4.52 (d, J=5.6 Hz, 2H), 3.68-3.69 (m, 1H), 1.63 (s, 3H), 1.09-1.10 (m, 4H). LCMS: 464.1 [M+H].

Example 28

1-(4-(4-amino-7-cyclopropyl-7H-pyrrolo[2,3-d]pyrimidin-5-yl)-2-fluorophenyl)-3-(3-(trifluoromethyl)isoxazol-5-yl)urea

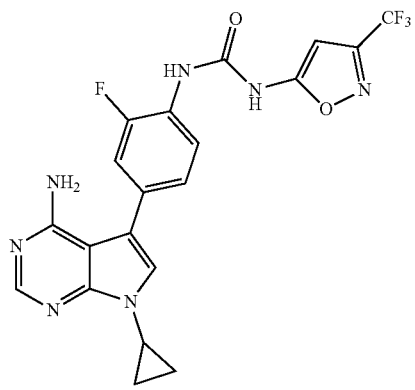 [SMILES: Nc1ncnc2c1c(-c1ccc(NC(=O)Nc3cc(C(F)(F)F)no3)c(F)c1)cn2C1CC1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.050 g, 0.176 mmol) and phenyl (3-(trifluoromethyl)isoxazol-5-yl)carbamate (E15, 0.048 g, 0.176 mmol), and was obtained as a white solid (2.9 mg, 4% yield). $^1$H NMR (400 MHz, DMSO-$d_6$) δ=11.03 (bs, 1H), 8.97 (bs, 1H), 8.19 (s, 1H), 8.10 (t, J=8.4 Hz, 1H), 7.27-7.38 (m, 3H), 6.54 (s, 1H), 6.30 (bs, 2H), 3.56-3.60 (m, 1H), 1.03-1.05 (m, 4H). LCMS: 461.9 [M+H].

Example 29

1-(4-(4-amino-7-cyclopropyl-7H-pyrrolo[2,3-d]pyrimidin-5-yl)-2-fluorophenyl)-3-(3-(1-hydroxy-2-methylpropan-2-yl)isoxazol-5-yl)urea Step 1: Synthesis of 1-(4-(4-amino-7-cyclopropyl-7H-pyrrolo[2,3-d]pyrimidin-5-yl)-2-fluorophenyl)-3-(3-(1-((tert-butyldimethylsilyl)oxy)-2-methylpropan-2-yl)isoxazol-5-yl)urea

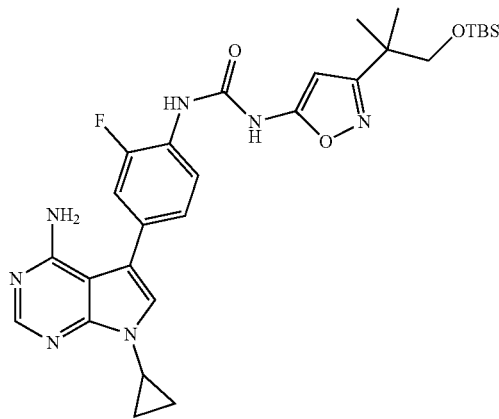 [SMILES: CC(C)(CO[Si](C)(C)C(C)(C)C)c1cc(NC(=O)Nc2ccc(-c3cn(C4CC4)c4ncnc(N)c34)cc2F)on1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.131 g, 0.461 mmol) and phenyl (3-(1-((tert-butyldimethylsilyl)oxy)-2-methylpropan-2-yl)isoxazol-5-yl)carbamate (E16, 0.180 g, 0.461 mmol), and was obtained as an off-white solid (0.013 g, 5% yield). LCMS: 580.0 [M+H].

Step 2: Synthesis of 1-(4-(4-amino-7-cyclopropyl-7H-pyrrolo[2,3-d]pyrimidin-5-yl)-2-fluorophenyl)-3-(3-(1-hydroxy-2-methylpropan-2-yl)isoxazol-5-yl)urea

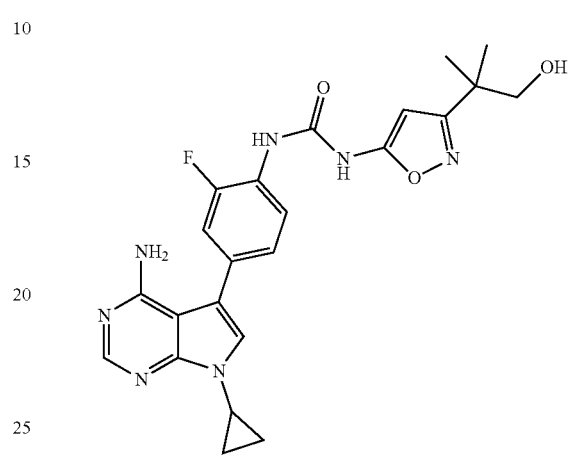

TBAF (1M in THF, 0.067 ml) was added to a solution of 1-(4-(4-amino-7-cyclopropyl-7H-pyrrolo[2,3-d]pyrimidin-5-yl)-2-fluorophenyl)-3-(3-(1-((tert-butyldimethylsilyl)oxy)-2-methylpropan-2-yl)isoxazol-5-yl)urea (0.013 g, 0.022 mmol) in THF (2 ml) at 0° C. and the resulting solution was stirred at 25° C. for 4 h. Following completion of the reaction (as indicated by TLC), the reaction mixture was concentrated under reduced pressure to give crude material which was purified by preparative HPLC to afford the title compound as a white solid (TFA salt, 2.2 mg, 21% yield). $^1$H NMR (400 MHz, CD$_3$OD) δ=8.36 (s, 1H), 8.23 (t, J=8.4 Hz, 1H), 7.49 (s, 1H), 7.30-7.38 (m, 2H), 6.20 (s, 1H), 3.69-3.72 (m, 1H), 3.61 (s, 2H), 1.32 (s, 6H), 1.18-1.24 (m, 4H). LCMS: 466.2 [M+H].

Example 30

1-(4-(4-amino-7-cyclopropyl-7H-pyrrolo[2,3-d]pyrimidin-5-yl)-2-fluorophenyl)-3-(3-(sec-butyl)isoxazol-5-yl)urea

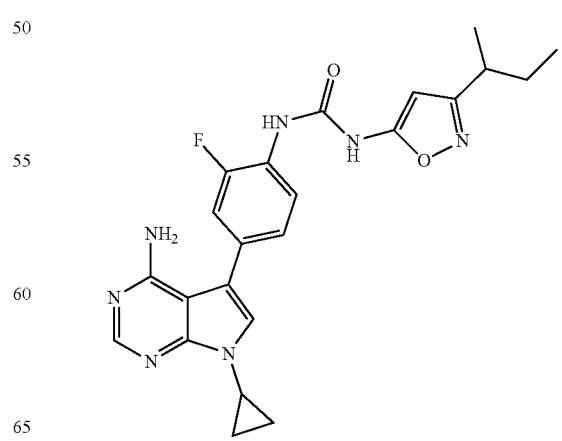

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.055 g, 0.194 mmol) and phenyl (3-(sec-butyl)isoxazol-5-yl)carbamate (E17, 0.051 g, 0.194 mmol), and was obtained as a white solid (0.012 g, 14% yield). $^1$H NMR (400 MHz, DMSO-d$_6$) δ=10.39 (bs, 1H), 8.84 (bs, 1H), 8.12-8.14 (m, 2H), 7.25-7.36 (m, 3H), 6.16 (bs, 2H), 6.02 (s, 1H), 3.56-3.59 (m, 1H), 2.68-2.73 (m, 1H), 1.56-1.60 (m, 2H), 1.18-1.20 (m, 3H), 1.01-1.10 (m, 4H), 0.81-0.89 (m, 3H). LCMS: 450.0 [M+H].

Example 31

1-(4-(4-amino-7-cyclopropyl-7H-pyrrolo[2,3-d]pyrimidin-5-yl)-2-fluorophenyl)-3-(3-(pentan-3-yl)isoxazol-5-yl)urea

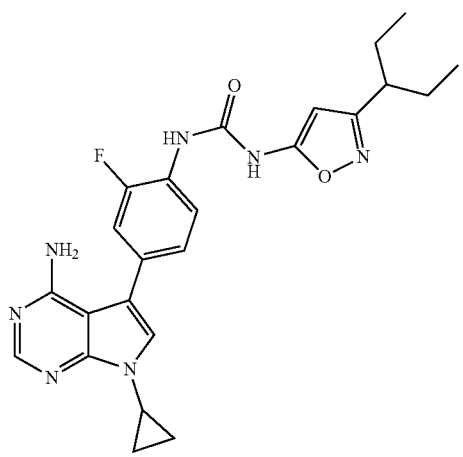 [SMILES: CCC(CC)c1cc(NC(=O)Nc2ccc(-c3cn(C4CC4)c4ncnc(N)c34)cc2F)on1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.050 g, 0.176 mmol) and phenyl (3-(pentan-3-yl)isoxazol-5-yl)carbamate (E18, 0.048 g, 0.176 mmol), and was obtained as an off-white solid (0.016 g, 19% yield). $^1$H NMR (400 MHz, DMSO-d$_6$) δ=10.65 (bs, 1H), 9.06 (bs, 1H), 8.37 (s, 1H), 8.18 (t, J=8.4 Hz, 1H), 7.51 (s, 1H), 7.35-7.38 (m, 1H), 7.26-7.28 (m, 3H), 5.98 (s, 1H), 3.65-3.68 (m, 1H), 1.49-1.68 (m, 4H), 1.07-1.09 (m, 4H), 0.79-0.82 (m, 6H). LCMS: 464.0 [M+H].

Example 32

1-(4-(4-amino-7-cyclopropyl-7H-pyrrolo[2,3-d]pyrimidin-5-yl)-2-fluorophenyl)-3-(3-isopropylisoxazol-5-yl)urea

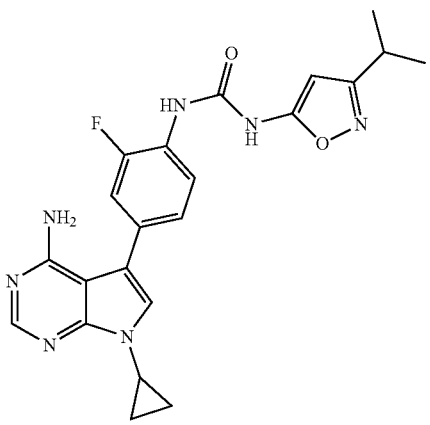 [SMILES: CC(C)c1cc(NC(=O)Nc2ccc(-c3cn(C4CC4)c4ncnc(N)c34)cc2F)on1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.056 g, 0.198 mmol) and phenyl (3-isopropylisoxazol-5-yl)carbamate (E19, 0.049 g, 0.198 mmol), and was obtained as an off-white solid (0.018 g, 21% yield). $^1$H NMR (400 MHz, DMSO-d$_6$) δ=10.34 (bs, 1H), 8.81 (bs, 1H), 8.12-8.16 (m, 2H), 7.25-7.36 (m, 3H), 6.15 (bs, 2H), 6.04 (s, 1H), 3.55-3.59 (m, 1H), 2.89-2.96 (m, 1H), 1.21-1.25 (m, 6H), 1.07-1.09 (m, 4H). LCMS: 436.0 [M+H].

Example 33

1-(4-(4-amino-7-cyclopropyl-7H-pyrrolo[2,3-d]pyrimidin-5-yl)-2-fluorophenyl)-3-(3-ethylisoxazol-5-yl)urea

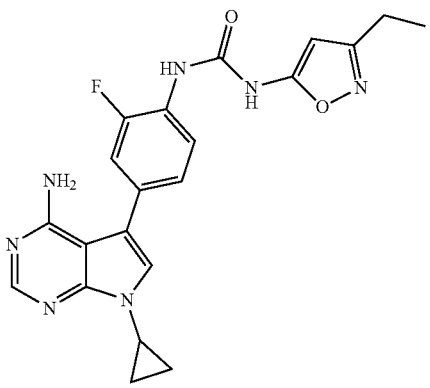 [SMILES: CCc1cc(NC(=O)Nc2ccc(-c3cn(C4CC4)c4ncnc(N)c34)cc2F)on1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.061 g, 0.215 mmol) and phenyl (3-ethylisoxazol-5-yl)carbamate (E20, 0.050 g, 0.215 mmol), and was obtained as an off-white solid (0.020 g, 22% yield). $^1$H NMR (400 MHz, DMSO-d$_6$) δ=10.31 (bs, 1H), 8.81 (bs, 1H), 8.12-8.17 (m, 2H), 7.25-7.36 (m, 3H), 6.15 (bs, 2H), 6.03 (s, 1H), 3.55-3.60 (m, 1H), 2.54-2.60 (m, 2H), 1.05-1.21 (m, 3H), 1.03-1.04 (m, 4H). LCMS: 422.0 [M+H].

Example 34

1-(4-(4-amino-7-cyclopropyl-7H-pyrrolo[2,3-d]pyrimidin-5-yl)-2-fluorophenyl)-3-(3-(1-methylcyclobutyl)isoxazol-5-yl)urea

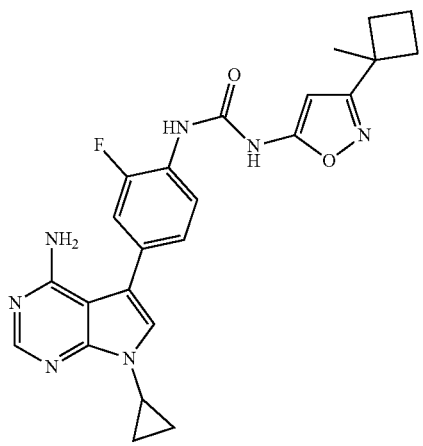 [SMILES: CC1(c2cc(NC(=O)Nc3ccc(-c4cn(C5CC5)c5ncnc(N)c45)cc3F)on2)CCC1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.075 g, 0.265 mmol) and phenyl (3-(1-methylcyclobutyl)isoxazol-5-yl)carbamate (E21, 0.072 g, 0.265 mmol), and was obtained as a white solid (6.8 mg, 5% yield). $^1$H NMR (400 MHz, DMSO-d$_6$) δ=10.42 (bs, 1H), 8.90 (bs, 1H), 8.42 (s, 1H), 8.18-8.22 (m, 1H), 7.58 (s, 1H), 7.37-7.40 (m, 1H), 7.27-7.29 (m, 1H), 6.06 (s, 1H), 3.67-3.71 (m, 1H), 2.34-2.38 (m, 2H), 1.85-2.08 (m, 4H), 1.42 (s, 3H), 1.07-1.11 (m, 4H). LCMS: 462.2 [M+H].

Example 35

1-(4-(4-amino-7-cyclopropyl-7H-pyrrolo[2,3-d]pyrimidin-5-yl)-2-fluorophenyl)-3-(3-(2-cyanopropan-2-yl)isoxazol-5-yl)urea

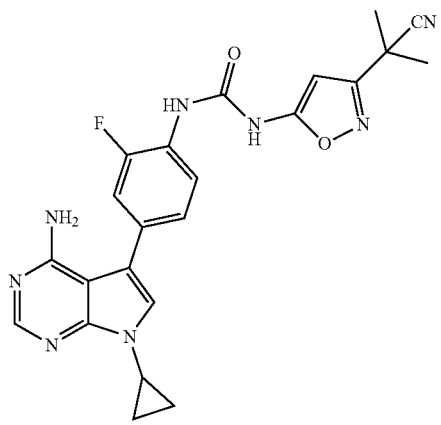 [SMILES: CC(C)(C#N)c1cc(NC(=O)Nc2ccc(-c3cn(C4CC4)c4ncnc(N)c34)cc2F)on1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.070 g, 0.247 mmol) and phenyl (3-(2-cyanopropan-2-yl)isoxazol-5-yl)carbamate (E22, 0.067 g, 0.247 mmol), and was obtained as a white solid (4.1 mg, 3% yield). $^1$H NMR (400 MHz, CD$_3$OD) δ=8.33 (s, 1H), 8.20-8.24 (m, 1H), 7.43 (s, 1H), 7.31-7.38 (m, 2H), 6.33 (s, 1H), 3.50-3.66 (m, 1H), 1.77 (s, 6H), 1.15-1.21 (m, 4H). LCMS: 461.1 [M+H].

Example 36

1-(4-(4-amino-7-cyclopropyl-7H-pyrrolo[2,3-d]pyrimidin-5-yl)-2-fluorophenyl)-3-(3-(hydroxymethyl)isoxazol-5-yl)urea

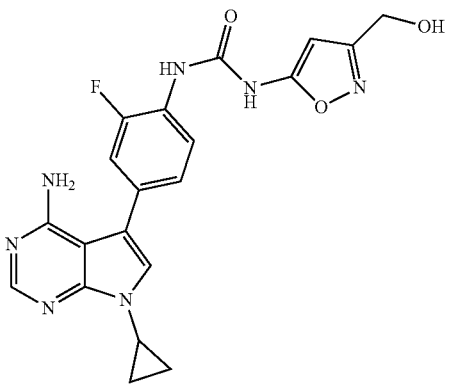 [SMILES: Nc1ncnc2c1c(-c1ccc(NC(=O)Nc3cc(CO)no3)c(F)c1)cn2C1CC1]

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.250 g, 0.882 mmol) and phenyl (3-(((tert-butyldimethylsilyl)oxy)methyl)isoxazol-5-yl)carbamate (E23, 0.308 g, 0.882 mmol), and was obtained as an off-white solid (0.029 g, 8% yield). $^1$H NMR (400 MHz, DMSO-d$_6$) δ=10.43 (bs, 1H), 8.92 (bs, 1H), 8.40 (s, 1H), 8.18-8.22 (m, 1H), 7.56 (s, 1H), 7.37-7.40 (m, 1H), 7.27-7.29 (m, 1H), 6.12 (s, 1H), 4.43 (s, 2H), 3.66-3.71 (m, 1H), 1.08-1.11 (m, 4H). LCMS: 422.0 [M−H].

Note: cleavage of the TBDMS group was observed during purification when eluting with a gradient of 10 mM ammonium acetate in water and ACN.

Example 37

1-(5-(4-amino-7-cyclopropyl-7H-pyrrolo[2,3-d]pyrimidin-5-yl)pyridin-2-yl)-3-(3-(1-(trifluoromethyl)cyclopropyl)isoxazol-5-yl)urea

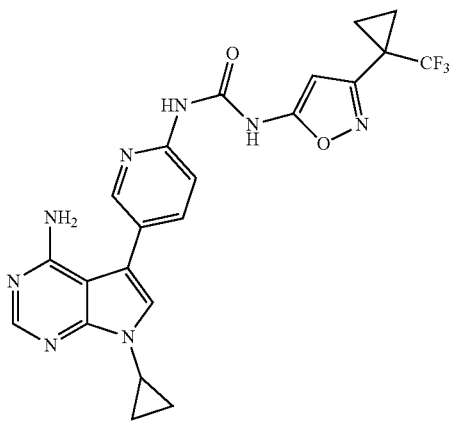 [SMILES: Nc1ncnc2c1c(-c1ccc(NC(=O)Nc3cc(C4(C(F)(F)F)CC4)no3)nc1)cn2C1CC1]

The title compound was obtained following the general procedure for urea formation (Method A), starting from 5-(6-aminopyridin-3-yl)-7-cyclopropyl-7H-pyrrolo[2,3-d]pyrimidin-4-amine (D6, 0.300 g, 1.127 mmol) and phenyl (3-(1-(trifluoromethyl)cyclopropyl)isoxazol-5-yl)carbamate (E6, 0.352 g, 1.127 mmol), and was obtained as an off-white solid (0.018 g, 3% yield). $^1$H NMR (400 MHz, DMSO-$d_6$) δ=11.77 (bs, 1H), 9.85 (bs, 1H), 8.39-8.40 (m, 1H), 8.18 (s, 1H), 7.86-7.88 (m, 1H), 7.62 (d, J=8.4 Hz, 1H), 7.34 (s, 1H), 6.26 (s, 1H), 6.23 (bs, 2H), 3.58-3.61 (m, 1H), 1.40-1.49 (m, 4H), 1.03-1.06 (m, 4H). LCMS: 485.0 [M+H].

Example 38

1-(4-(4-amino-7-cyclopropyl-7H-pyrrolo[2,3-d]pyrimidin-5-yl)-2-methylphenyl)-3-(3-(1-(trifluoromethyl)cyclopropyl)isoxazol-5-yl)urea

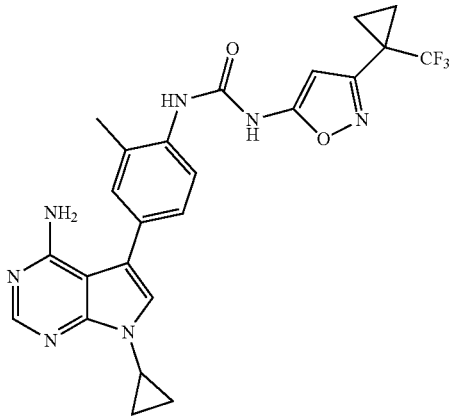 [SMILES: Cc1cc(-c2cn(C3CC3)c3ncnc(N)c23)ccc1NC(=O)Nc1cc(C2(C(F)(F)F)CC2)no1]

The title compound was obtained following the general procedure for urea formation (Method A), starting from 5-(4-amino-3-methylphenyl)-7-cyclopropyl-7H-pyrrolo[2,3-d]pyrimidin-4-amine (D11, 0.270 g, 0.967 mmol) and phenyl (3-(1-(trifluoromethyl)cyclopropyl)isoxazol-5-yl)carbamate (E6, 0.302 g, 0.967 mmol), and was obtained as an off-white solid (0.080 g, 16% yield). $^1$H NMR (400 MHz, DMSO-$d_6$) δ=10.63 (bs, 1H), 8.29 (bs, 1H), 8.16 (s, 1H), 7.87 (d, J=8.4 Hz, 1H), 7.22-7.32 (m, 3H), 6.17 (s, 1H), 6.08 (bs, 2H), 3.55-3.60 (m, 1H), 2.29 (s, 3H), 1.37-1.48 (m, 4H), 1.00-1.05 (m, 4H). LCMS: 498.1 [M+H].

Example 39

1-(4-(4-amino-7-(3-hydroxycyclobutyl)-7H-pyrrolo[2,3-d]pyrimidin-5-yl)-2-fluorophenyl)-3-(3-(1-(trifluoromethyl)cyclopropyl)isoxazol-5-yl)urea Step 1: Synthesis of 1-(4-(4-amino-7-(3-(benzyloxy)cyclobutyl)-7H-pyrrolo[2,3-d]pyrimidin-5-yl)-2-fluorophenyl)-3-(3-(1-(trifluoromethyl)cyclopropyl)isoxazol-5-yl)urea

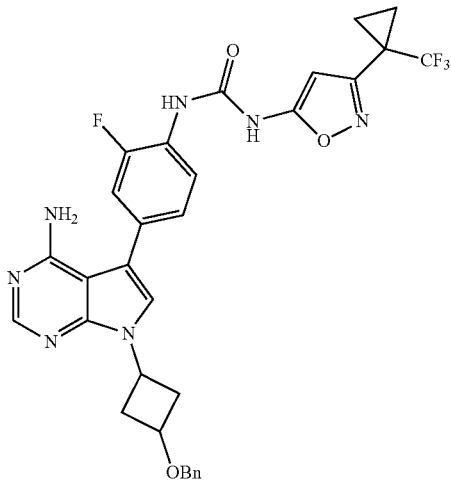 [SMILES: Nc1ncnc2c1c(-c1ccc(NC(=O)Nc3cc(C4(C(F)(F)F)CC4)no3)c(F)c1)cn2C1CC(OCc2ccccc2)C1]

The title compound was obtained following the general procedure for urea formation (Method B), starting from 5-(4-amino-3-fluorophenyl)-7-(3-(benzyloxy)cyclobutyl)-7H-pyrrolo[2,3-d]pyrimidin-4-amine (D12, 0.033 g, 0.082 mmol) and phenyl (3-(1-(trifluoromethyl)cyclopropyl)isoxazol-5-yl)carbamate (E6, 0.028 g, 0.090 mmol), and was obtained as a yellow gum (0.038 g, 29% yield). LCMS: 622.3 [M+H].

Step 2: Synthesis of 1-(4-(4-amino-7-(3-hydroxycyclobutyl)-7H-pyrrolo[2,3-d]pyrimidin-5-yl)-2-fluorophenyl)-3-(3-(1-(trifluoromethyl)cyclopropyl)isoxazol-5-yl)urea

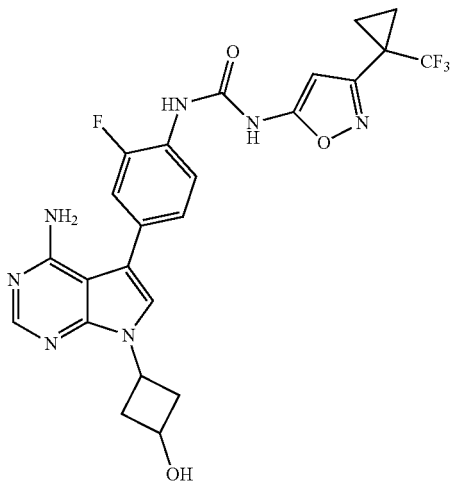 [SMILES: Nc1ncnc2c1c(-c1ccc(NC(=O)Nc3cc(C4(C(F)(F)F)CC4)no3)c(F)c1)cn2C1CC(O)C1]

Boron trichloride (1M in DCM, 0.901 mL, 0.901 mmol) was added dropwise to a solution of 1-(4-(4-amino-7-(3-(benzyloxy)cyclobutyl)-7H-pyrrolo[2,3-d]pyrimidin-5-yl)-2-fluorophenyl)-3-(3-(1-(trifluoromethyl)cyclopropyl)isoxazol-5-yl)urea (0.070 g, 0.113 mmol) in DCM (5 mL) at −60° C. and the resulting mixture was stirred at 0° C. for 3 h. Following completion of the reaction (as indicated by TLC and LCMS), the reaction mixture was cooled to −70° C., neutralized with NH$_4$OH (25% in water), and extracted with DCM (2×10 mL). The combined organic extracts were dried over Na$_2$SO$_4$, filtered, and concentrated under reduced pressure to yield crude material which was purified by preparative HPLC (eluting with a gradient of 1% TFA in water and ACN), affording the title product as a white solid (0.012 g, 20% yield). $^1$H NMR (400 MHz, CD$_3$OD) δ=8.33 (s, 1H), 8.22-8.26 (m, 1H), 7.77 (s, 1H), 7.34-7.42 (m, 2H), 6.33 (s, 1H), 5.58-5.62 (m, 1H), 4.64-4.66 (m, 1H), 2.85-2.92 (m, 2H), 2.58-2.64 (m, 2H), 1.39-1.49 (m, 4H). LCMS: 531.8 [M+H].

Example 40

1-(6-(4-amino-7-cyclopropyl-7H-pyrrolo[2,3-d]pyrimidin-5-yl)-4-methylpyridin-3-yl)-3-(3-(1-(trifluoromethyl)cyclopropyl)isoxazol-5-yl)urea

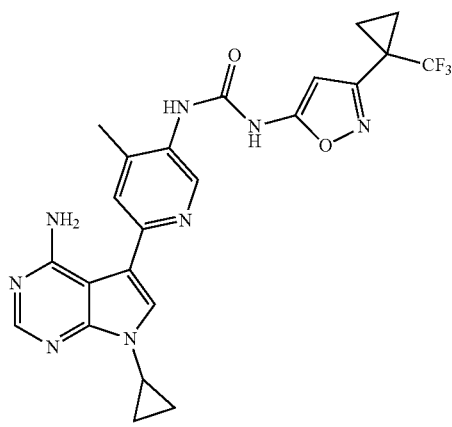 [SMILES: Cc1cc(-c2cn(C3CC3)c3ncnc(N)c23)ncc1NC(=O)Nc1cc(C2(C(F)(F)F)CC2)no1]

The title compound was obtained following the general procedure for urea formation (Method A), starting from 5-(5-amino-4-methylpyridin-2-yl)-7-cyclopropyl-7H-pyrrolo[2,3-d]pyrimidin-4-amine (D13, 0.050 g, 0.102 mmol) and phenyl (3-(1-(trifluoromethyl)cyclopropyl)isoxazol-5-yl)carbamate (E6, 0.032 g, 0.102 mmol), and was obtained as an off-white solid (8 mg, 16% yield). $^1$H NMR (400 MHz, DMSO-d$_6$) δ=9.81 (bs, 1H), 8.76 (s, 1H), 8.51 (bs, 1H), 8.08 (s, 1H), 7.93-7.94 (m, 2H), 7.12 (bs, 2H), 6.17 (s, 1H), 3.53-3.56 (m, 1H), 2.30 (s, 3H), 1.37-1.46 (m, 4H), 1.05-1.08 (m, 4H). LCMS: 499.2 [M+H].

Example 41

1-(4-(4-amino-7-cyclopropyl-7H-pyrrolo[2,3-d]pyrimidin-5-yl)-2,6-difluorophenyl)-3-(3-(1-(trifluoromethyl)cyclopropyl)isoxazol-5-yl)urea

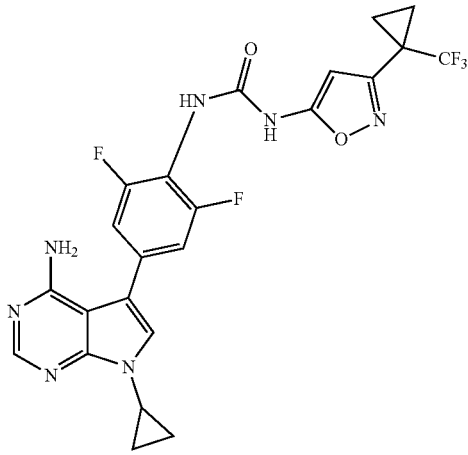 [SMILES: Nc1ncnc2c1c(-c1cc(F)c(NC(=O)Nc3cc(C4(C(F)(F)F)CC4)no3)c(F)c1)cn2C1CC1]

The title compound was obtained following the general procedure for urea formation (Method B), starting from 5-(4-amino-3,5-difluorophenyl)-7-cyclopropyl-7H-pyrrolo[2,3-d]pyrimidin-4-amine (D15, 0.080 g, 0.266 mmol) and phenyl (3-(1-(trifluoromethyl)cyclopropyl)isoxazol-5-yl)carbamate (E6, 0.083 g, 0.266 mmol), and was obtained as an off-white solid (8 mg, 5.6% yield). $^1$H NMR (400 MHz, DMSO-d$_6$) δ=10.78 (bs, 1H), 8.71 (bs, 1H), 8.42 (bs, 1H), 7.67 (s, 1H), 7.56 (bs, 2H), 7.23-7.29 (m, 2H), 6.14 (s, 1H), 3.67-3.76 (m, 1H), 1.37-1.47 (m, 4H), 1.09-1.12 (m, 4H). LCMS: 519.7 [M+H].

Example 42

1-(4-(4-amino-7-cyclopropyl-7H-pyrrolo[2,3-d]pyrimidin-5-yl)-2,5-difluorophenyl)-3-(3-(1-(trifluoromethyl)cyclopropyl)isoxazol-5-yl)urea

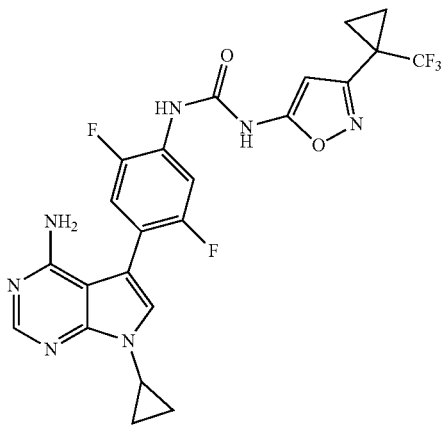 [SMILES: Nc1ncnc2c1c(-c1cc(F)c(NC(=O)Nc3cc(C4(C(F)(F)F)CC4)no3)cc1F)cn2C1CC1]

The title compound was obtained following the general procedure for urea formation (Method B), starting from 5-(4-amino-2,5-difluorophenyl)-7-cyclopropyl-7H-pyrrolo

[2,3-d]pyrimidin-4-amine (D16, 0.100 g, 0.332 mmol) and phenyl (3-(1-(trifluoromethyl)cyclopropyl)isoxazol-5-yl)carbamate (E6, 0.104 g, 0.332 mmol), and was obtained as an off-white solid (8 mg, 5% yield). ¹H NMR (400 MHz, DMSO-d₆) δ=10.63 (bs, 1H), 9.01 (bs, 1H), 8.16 (s, 1H), 8.04-8.09 (m, 1H), 7.28-7.34 (m, 2H), 6.21 (s, 1H), 6.16 (bs, 2H), 3.55-3.61 (m, 1H), 1.36-1.49 (m, 4H), 1.00-1.04 (m, 4H). LCMS: 520.1 [M+H].

Example 43

1-(4-(4-amino-7-cyclopropyl-7H-pyrrolo[2,3-d]pyrimidin-5-yl)-3,5-difluorophenyl)-3-(3-(1-(trifluoromethyl)cyclopropyl)isoxazol-5-yl)urea

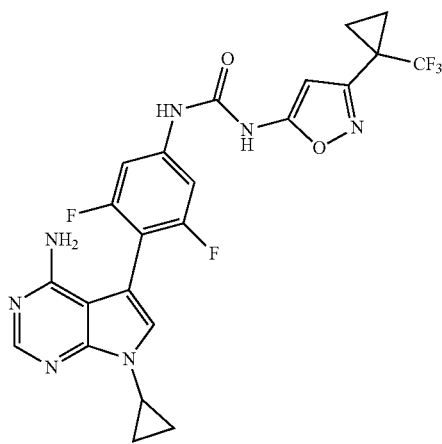 [SMILES: Nc1ncnc2c1c(-c1c(F)cc(NC(=O)Nc3cc(C4(C(F)(F)F)CC4)no3)cc1F)cn2C1CC1]

The title compound was obtained following the general procedure for urea formation (Method B), starting from 5-(4-amino-2,6-difluorophenyl)-7-cyclopropyl-7H-pyrrolo[2,3-d]pyrimidin-4-amine (D17, 0.0724 g, 0.240 mmol) and phenyl (3-(1-(trifluoromethyl)cyclopropyl)isoxazol-5-yl)carbamate (E6, 0.075 g, 0.240 mmol), and was obtained as an off-white solid (3 mg, 2% yield). ¹H NMR (400 MHz, DMSO-d₆) δ=8.14 (s, 1H), 7.39-7.42 (m, 2H), 7.24 (s, 1H), 6.15 (s, 1H), 6.02 (bs, 2H), 3.58-3.59 (m, 1H), 1.36-1.44 (m, 4H), 1.03-1.05 (m, 4H). LCMS: 520.2 [M+H].

Example 44

1-(4-(4-amino-7-cyclopropyl-7H-pyrrolo[2,3-d]pyrimidin-5-yl)-3,5-difluorophenyl)-3-(3-(1-(trifluoromethyl)cyclopropyl)isoxazol-5-yl)urea Step 1: Synthesis of 1-(5-bromo-3-fluoropyridin-2-yl)-3-(3-(1-(trifluoromethyl)cyclopropyl)isoxazol-5-yl)urea

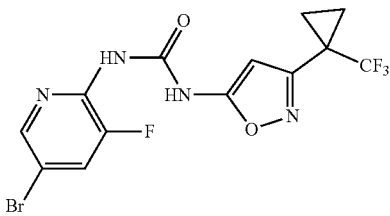 [SMILES: O=C(Nc1cc(C2(C(F)(F)F)CC2)no1)Nc1ncc(Br)cc1F]

The title compound was obtained following the general procedure for urea formation (Method B), starting from 5-bromo-3-fluoropyridin-2-amine (0.040 g, 0.209 mmol) and phenyl (3-(1-(trifluoromethyl)cyclopropyl)isoxazol-5-yl)carbamate (E6, 0.065 g, 0.209 mmol), and was obtained as a pale yellow solid (0.020 g, 23% yield). LCMS: 410.9 [M+H].

Step 2: Synthesis of 1-(4-(4-amino-7-cyclopropyl-7H-pyrrolo[2,3-d]pyrimidin-5-yl)-3,5-difluorophenyl)-3-(3-(1-(trifluoromethyl)cyclopropyl)isoxazol-5-yl)urea

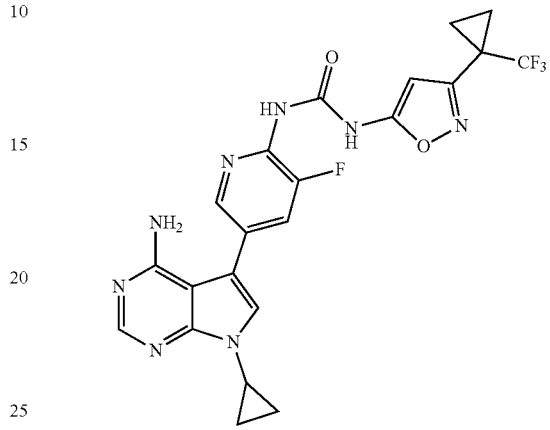

The title compound was obtained by following a similar procedure described for Intermediate D8, starting from 1-(5-bromo-3-fluoropyridin-2-yl)-3-(3-(1-(trifluoromethyl)cyclopropyl)isoxazol-5-yl)urea (0.020 g, 0.049 mmol) and tert-butyl (tert-butoxycarbonyl)(7-cyclopropyl-5-(4,4,5,5-tetramethyl-1,3,2-dioxaborolan-2-yl)-7H-pyrrolo[2,3-d]pyrimidin-4-yl)carbamate (prepared as reported in PCT Pub. No. WO 2018/015879, 0.024 g, 0.049 mmol), and was obtained as an off-white solid (2 mg, 7% yield). ¹H NMR (400 MHz, CD₃OD) δ=8.32-8.33 (m, 2H), 7.81-7.84 (m, 1H), 7.50 (s, 1H), 6.42 (s, 1H), 3.60-3.68 (m, 1H), 1.41-1.50 (m, 4H), 1.13-1.23 (m, 4H). LCMS: 503.1 [M+H]. Note: cleavage of the Boc groups was observed during the reaction.

Example 45

1-(4-(4-amino-7-cyclopropyl-7H-pyrrolo[2,3-d]pyrimidin-5-yl)-2-fluorophenyl)-3-(3-(1-(trifluoromethyl)cyclobutyl)isoxazol-5-yl)urea

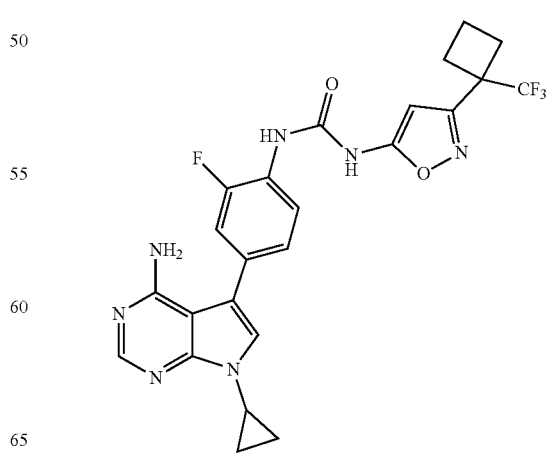

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.080 g, 0.282 mmol) and phenyl (3-(1-(trifluoromethyl)cyclobutyl)isoxazol-5-yl)carbamate (E24, 0.092 g, 0.282 mmol), and was obtained as an off-white solid (0.035 g, 22% yield). $^1$H NMR (400 MHz, DMSO-d$_6$) δ=10.66 (bs, 1H), 8.90 (bs, 1H), 8.21 (s, 1H), 8.12-8.16 (m, 1H), 7.26-7.36 (m, 3H), 6.41 (bs, 2H), 6.14 (s, 1H), 3.54-3.56 (m, 1H), 2.57-2.68 (m, 4H), 2.03-2.05 (m, 2H), 1.04-1.06 (m, 4H). LCMS: 515.9 [M+H].

Example 46

1-(5-(4-amino-7-(2-hydroxy-2-methylpropyl)-7H-pyrrolo[2,3-d]pyrimidin-5-yl)pyridin-2-yl)-3-(3-(1-(trifluoromethyl)cyclopropyl)isoxazol-5-yl)urea

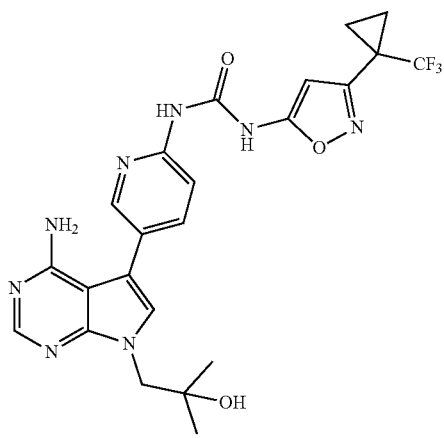 [SMILES: CC(C)(O)Cn1cc(-c2ccc(NC(=O)Nc3cc(C4(C(F)(F)F)CC4)no3)nc2)c2c(N)ncnc21]

The title compound was obtained following the general procedure for urea formation (Method B), starting from 1-(4-amino-5-(6-aminopyridin-3-yl)-7H-pyrrolo[2,3-d]pyrimidin-7-yl)-2-methylpropan-2-ol (D18, 0.100 g, 0.335 mmol) and phenyl (3-(1-(trifluoromethyl)cyclopropyl)isoxazol-5-yl)carbamate (E6, 0.105 g, 0.335 mmol), and was obtained as an off-white solid (0.010 g, 6% yield). $^1$H NMR (400 MHz, DMSO-d$_6$) δ=11.74 (bs, 1H), 9.91 (bs, 1H), 8.41-8.43 (m, 2H), 7.89-7.92 (m, 1H), 7.80 (bs, 2H), 7.68-7.71 (m, 1H), 7.59 (s, 1H), 6.26 (s, 1H), 4.20 (s, 2H), 1.38-1.50 (m, 4H), 1.11-1.12 (m, 6H). LCMS: 516.9 [M+H].

Example 47

1-(4-(4-amino-7-(2-hydroxy-2-methylpropyl)-7H-pyrrolo[2,3-d]pyrimidin-5-yl)-2-fluorophenyl)-3-(5-(1-(trifluoromethyl)cyclopropyl)isoxazol-3-yl)urea

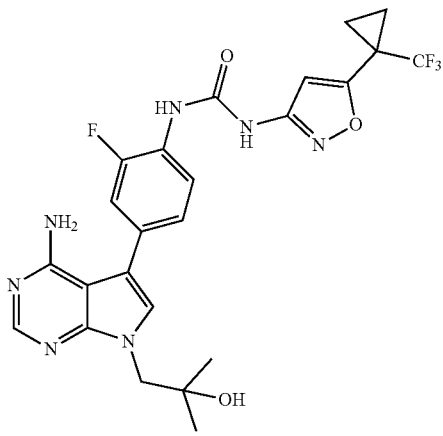 [SMILES: CC(C)(O)Cn1cc(-c2ccc(NC(=O)Nc3cc(C4(C(F)(F)F)CC4)on3)c(F)c2)c2c(N)ncnc21]

The title compound was obtained following the general procedure for urea formation (Method B), starting from 1-(4-amino-5-(4-amino-3-fluorophenyl)-7H-pyrrolo[2,3-d]pyrimidin-7-yl)-2-methylpropan-2-ol (D3, 0.120 g, 0.381 mmol) and phenyl (5-(1-(trifluoromethyl)cyclopropyl)isoxazol-3-yl)carbamate (E7, 0.119 g, 0.381 mmol), and was obtained as an off-white solid (0.028 g, 13% yield). $^1$H NMR (400 MHz, DMSO-d$_6$) δ=10.04 (bs, 1H), 8.94 (bs, 1H), 8.41 (s, 1H), 8.23-8.27 (m, 1H), 7.55 (s, 1H), 7.36-7.40 (m, 1H), 7.27-7.30 (m, 1H), 6.91 (s, 1H), 4.18 (s, 2H), 1.51-1.58 (m, 4H), 1.07-1.11 (m, 6H). LCMS: 534.2 [M+H].

Example 48

1-(5-(4-amino-7-cyclopropyl-7H-pyrrolo[2,3-d]pyrimidin-5-yl)pyrimidin-2-yl)-3-(3-(1-(trifluoromethyl)cyclopropyl)isoxazol-5-yl)urea

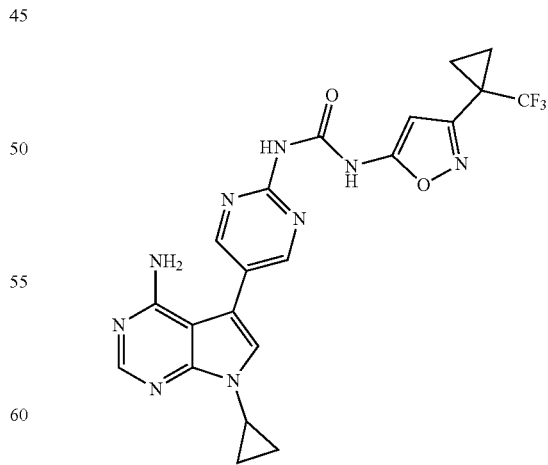

The title compound was obtained following the general procedure for urea formation (Method B), starting from 5-(2-aminopyrimidin-5-yl)-7-cyclopropyl-7H-pyrrolo[2,3-d]pyrimidin-4-amine (D19, 0.080 g, 0.299 mmol) and phenyl (3-(1-(trifluoromethyl)cyclopropyl)isoxazol-5-yl)carbamate (E6, 0.093 g, 0.299 mmol), and was obtained as an off-white solid (4 mg, 3% yield). $^1$H NMR (400 MHz, DMSO-$d_6$) δ=10.76 (bs, 1H), 9.04 (bs, 1H), 8.65 (bs, 1H), 8.34 (bs, 2H), 7.61 (s, 1H), 6.66 (bs, 2H), 6.10 (s, 1H), 3.66-3.71 (m, 1H), 1.37-1.45 (m, 4H), 1.11-1.11 (m, 4H). LCMS: 485.9 [M+H].

Example 49

1-(4-(4-amino-7-cyclopropyl-7H-pyrrolo[2,3-d]pyrimidin-5-yl)-2-(hydroxymethyl)phenyl)-3-(3-(1-(trifluoromethyl)cyclopropyl)isoxazol-5-yl)urea

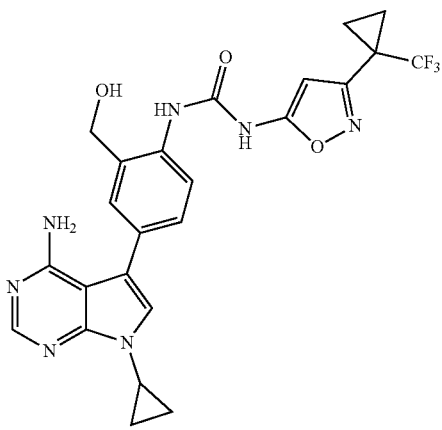 [SMILES: Nc1ncnc2c1c(-c1ccc(NC(=O)Nc3cc(C4(C(F)(F)F)CC4)no3)c(CO)c1)cn2C1CC1]

The title compound was obtained following the general procedure for urea formation (Method A), starting from (2-amino-5-(4-amino-7-cyclopropyl-7H-pyrrolo[2,3-d]pyrimidin-5-yl)phenyl)methanol (D20, 0.020 g, 0.068 mmol) and phenyl (3-(1-(trifluoromethyl)cyclopropyl)isoxazol-5-yl)carbamate (E6, 0.021 g, 0.068 mmol), and was obtained as an off-white solid (3 mg, 8% yield). $^1$H NMR (400 MHz, DMSO-$d_6$) δ=10.96 (bs, 1H), 8.56 (bs, 1H), 8.17 (s, 1H), 7.91-7.93 (m, 1H), 7.34-7.42 (m, 2H), 7.21 (s, 1H), 6.04-6.17 (m, 3H), 5.49 (bs, 1H), 4.57 (bs, 2H), 3.56-3.61 (m, 1H), 1.37-1.47 (m, 4H), 1.00-1.06 (m, 4H). LCMS: 514.1 [M+H].

Example 50

1-(4-(4-amino-7-cyclopropyl-7H-pyrrolo[2,3-d]pyrimidin-5-yl)-2-cyanophenyl)-3-(3-(1-(trifluoromethyl)cyclopropyl)isoxazol-5-yl)urea

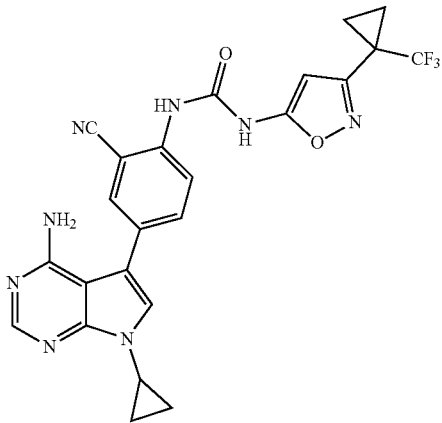

The title compound was obtained following the general procedure for urea formation (Method B), starting from 2-amino-5-(4-amino-7-cyclopropyl-7H-pyrrolo[2,3-d]pyrimidin-5-yl)benzonitrile (D21, 0.130 g, 0.287 mmol) and phenyl (3-(1-(trifluoromethyl)cyclopropyl)isoxazol-5-yl)carbamate (E6, 0.089 g, 0.287 mmol), and was obtained as an off-white solid (5 mg, 3% yield). $^1$H NMR (400 MHz, DMSO-$d_6$) δ=8.62 (s, 1H), 7.43-7.52 (m, 3H), 6.86 (s, 1H), 6.05 (s, 1H), 3.67-3.70 (m, 1H), 1.38-1.46 (m, 4H), 1.08-1.10 (m, 4H). LCMS: 509.2 [M+H].

Example 51

1-(4-(4-amino-7-(2-methoxyethyl)-7H-pyrrolo[2,3-d]pyrimidin-5-yl)-2-fluorophenyl)-3-(3-(1-(trifluoromethyl)cyclopropyl)isoxazol-5-yl)urea

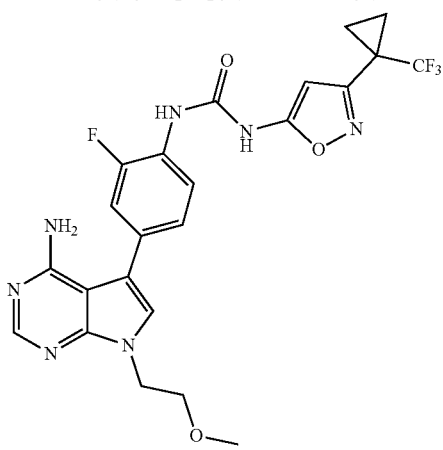 [SMILES: COCCn1cc(-c2ccc(NC(=O)Nc3cc(C4(C(F)(F)F)CC4)no3)c(F)c2)c2c(N)ncnc21]

The title compound was obtained following the general procedure for urea formation (Method B), starting from 5-(4-amino-3-fluorophenyl)-7-(2-methoxyethyl)-7H-pyrrolo[2,3-d]pyrimidin-4-amine (D22, 0.075 g, 0.249 mmol) and phenyl (3-(1-(trifluoromethyl)cyclopropyl)isoxazol-5-yl)carbamate (E6, 0.078 g, 0.249 mmol), and was obtained as an off-white solid (0.037 g, 28% yield). $^1$H NMR (400 MHz, DMSO-$d_6$) δ=10.63 (bs, 1H), 8.88 (bs, 1H), 8.13-8.18 (m, 2H), 7.42 (s, 1H), 7.26-7.36 (m, 2H), 6.35 (bs, 2H), 6.20 (s, 1H), 4.34 (t, J=5.6 Hz, 2H), 3.72 (t, J=5.2 Hz, 2H), 3.26 (s, 3H), 1.38-1.49 (m, 4H). LCMS: 520.2 [M+H].

Example 52

1-(4-(4-amino-7-(2-hydroxyethyl)-7H-pyrrolo[2,3-d]pyrimidin-5-yl)-2-fluorophenyl)-3-(3-(1-(trifluoromethyl)cyclopropyl)isoxazol-5-yl)urea The title compound was obtained following the general procedure for urea formation (Method B), starting from 2-(4-amino-5-(4-amino-3-fluorophenyl)-7H-pyrrolo[2,3-d]pyrimidin-7-yl)ethan-1-ol (D23, 0.080 g, 0.278 mmol) and phenyl (3-(1-(trifluoromethyl)cyclopropyl)isoxazol-5-yl) carbamate (E6, 0.087 g, 0.278 mmol), and was obtained as an off-white solid (0.011 g, 7% yield). $^1$H NMR (400 MHz, DMSO-d$_6$) δ=10.53 (bs, 1H), 8.78 (bs, 1H), 8.05-8.09 (m, 2H), 7.32 (s, 1H), 7.19-7.28 (m, 2H), 6.18 (bs, 2H), 6.13 (s, 1H), 4.90 (t, J=5.2 Hz, 1H), 4.14 (t, J=6.0 Hz, 2H), 3.66-3.69 (m, 2H), 1.31-1.41 (m, 4H). LCMS: 506.2 [M+H].

Example 53

1-(4-(4-amino-7-cyclobutyl-7H-pyrrolo[2,3-d]pyrimidin-5-yl)-2-fluorophenyl)-3-(3-(1-(trifluoromethyl)cyclopropyl)isoxazol-5-yl)urea

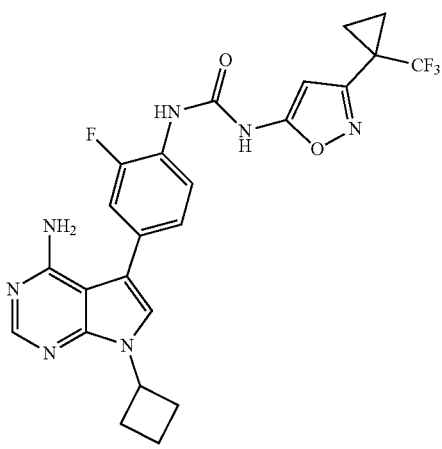 [SMILES: Nc1ncnc2c1c(-c1ccc(NC(=O)Nc3cc(C4(C(F)(F)F)CC4)no3)c(F)c1)cn2C1CCC1]

The title compound was obtained following the general procedure for urea formation (Method B), starting from 5-(4-amino-3-fluorophenyl)-7-cyclobutyl-7H-pyrrolo[2,3-d]pyrimidin-4-amine (D24, 0.150 g, 0.504 mmol) and phenyl (3-(1-(trifluoromethyl)cyclopropyl)isoxazol-5-yl)carbamate (E6, 0.158 g, 0.504 mmol), and was obtained as an off-white solid (0.111 g, 38% yield). $^1$H NMR (400 MHz, DMSO-d$_6$) δ=10.67 (bs, 1H), 8.96 (bs, 1H), 8.38 (s, 1H), 8.18-8.22 (m, 1H), 7.93 (s, 1H), 7.43 (bs, 2H), 7.41 (d, J=1.6 Hz, 1H), 7.32 (d, J=8.4 Hz, 1H), 6.21 (s, 1H), 5.23-5.27 (m, 1H), 2.51-2.68 (m, 4H), 1.84-1.89 (m, 2H), 1.38-1.49 (m, 4H). LCMS: 516.1 [M+H].

Example 54

1-(4-(4-amino-7-cyclopropyl-7H-pyrrolo[2,3-d]pyrimidin-5-yl)-2-chlorophenyl)-3-(3-(1-(trifluoromethyl)cyclopropyl)isoxazol-5-yl)urea

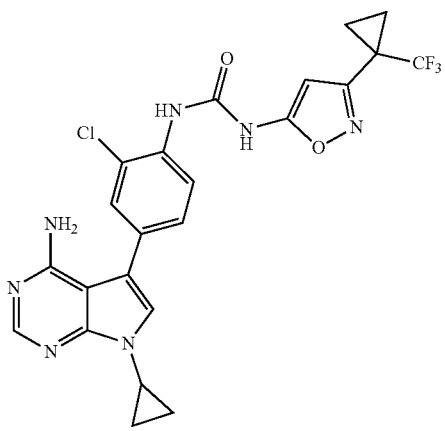 [SMILES: Nc1ncnc2c1c(-c1ccc(NC(=O)Nc3cc(C4(C(F)(F)F)CC4)no3)c(Cl)c1)cn2C1CC1]

The title compound was obtained following the general procedure for urea formation (Method B), starting from 5-(4-amino-3-chlorophenyl)-7-cyclopropyl-7H-pyrrolo[2,3-d]pyrimidin-4-amine (D25, 0.050 g, 0.167 mmol) and phenyl (3-(1-(trifluoromethyl)cyclopropyl)isoxazol-5-yl)carbamate (E6, 0.052 g, 0.167 mmol), and was obtained as an off-white solid (6 mg, 7% yield). $^1$H NMR (400 MHz, DMSO-d$_6$) δ=11.04 (bs, 1H), 8.67 (bs, 1H), 8.40 (s, 1H), 8.23-8.25 (m, 1H), 7.58-7.60 (m, 2H), 7.42-7.44 (m, 1H), 6.21 (s, 1H), 3.67-3.73 (m, 1H), 1.46-2.33 (m, 2H), 1.37-1.38 (m, 2H), 1.11-1.13 (m, 4H). LCMS: 518.2 [M+H].

Example 55

1-(4-(4-amino-7-cyclopropyl-7H-pyrrolo[2,3-d]pyrimidin-5-yl)-2-methoxyphenyl)-3-(3-(1-(trifluoromethyl)cyclopropyl)isoxazol-5-yl)urea

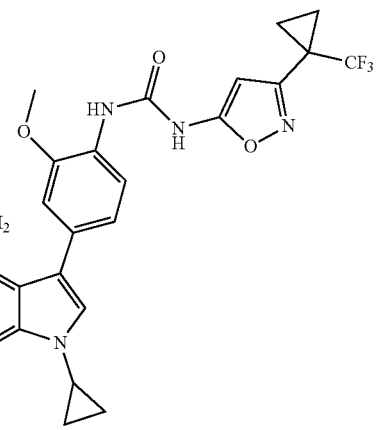

The title compound was obtained following the general procedure for urea formation (Method B), starting from 5-(4-amino-3-methoxyphenyl)-7-cyclopropyl-7H-pyrrolo[2,3-d]pyrimidin-4-amine (D26, 0.020 g, 0.068 mmol) and phenyl (3-(1-(trifluoromethyl)cyclopropyl)isoxazol-5-yl) carbamate (E6, 0.021 g, 0.068 mmol), and was obtained as an off-white solid (7 mg, 19% yield). $^1$H NMR (400 MHz, DMSO-d$_6$) δ=10.96 (bs, 1H), 8.65 (bs, 1H), 8.23 (s, 1H), 8.17 (d, J=8.4 Hz, 1H), 7.30 (s, 1H), 7.12-7.17 (m, 1H), 7.01-7.04 (m, 1H), 6.47 (bs, 2H), 6.19 (s, 1H), 3.94 (s, 3H), 3.60-3.62 (m, 1H), 1.45-1.48 (m, 2H), 1.36-1.38 (m, 2H), 1.04-1.07 (m, 4H). LCMS: 513.9 [M+H].

Example 56

1-(4-(4-amino-7-(1-methylpyrrolidin-3-yl)-7H-pyrrolo[2,3-d]pyrimidin-5-yl)-2-fluorophenyl)-3-(3-(1-(trifluoromethyl)cyclopropyl)isoxazol-5-yl)urea

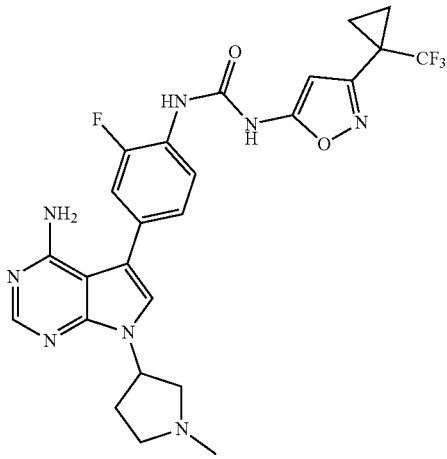 [SMILES: CN1CCC(n2cc(-c3ccc(NC(=O)Nc4cc(C5(C(F)(F)F)CC5)no4)c(F)c3)c3c(N)ncnc32)C1]

The title compound was obtained following the general procedure for urea formation (Method B), starting from 5-(4-amino-3-fluorophenyl)-7-(1-methylpyrrolidin-3-yl)-7H-pyrrolo[2,3-d]pyrimidin-4-amine (D27, 0.040 g, 0.123 mmol) and phenyl (3-(1-(trifluoromethyl)cyclopropyl) isoxazol-5-yl)carbamate (E6, 0.036 g, 0.115 mmol), and was obtained as a white solid (0.015 mg, 24% yield). $^1$H NMR (400 MHz, DMSO-d$_6$) δ=10.82 (bs, 1H), 9.07 (bs, 1H), 8.39 (s, 1H), 8.19-8.23 (m, 1H), 7.84 (s, 1H), 7.14-7.40 (m, 2H), 6.21 (s, 1H), 5.55-5.66 (m, 1H), 3.90-4.09 (m, 2H), 2.95 (bs, 4H), 2.08 (s, 3H), 1.38-1.49 (m, 4H). LCMS: 545.3 [M+H].

Example 57

1-(4-(4-amino-7-cyclopropyl-7H-pyrrolo[2,3-d]pyrimidin-5-yl)-2-fluorophenyl)-3-(5-(1-(trifluoromethyl)cyclobutyl)isoxazol-3-yl)urea

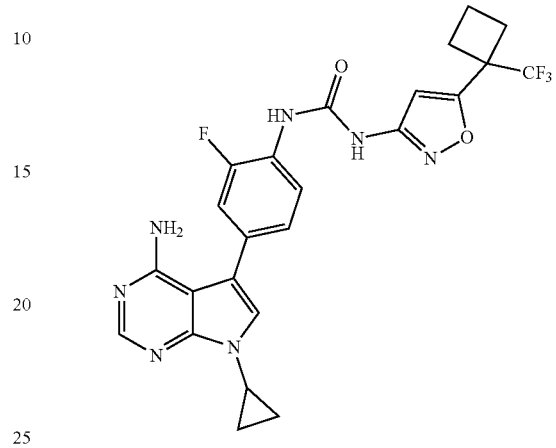

The title compound was obtained following the general procedure for urea formation (Method A), starting from 5-(4-amino-3-fluorophenyl)-7-cyclopropyl-7H-pyrrolo[2,3-d]pyrimidin-4-amine (D1, 0.160 g, 0.565 mmol) and phenyl (5-(1-(trifluoromethyl)cyclobutyl)isoxazol-3-yl)carbamate (E25, 0.184 g, 0.565 mmol), and was obtained as a white solid (0.081 mg, 28% yield). $^1$H NMR (400 MHz, DMSO-d$_6$) δ=10.02 (bs, 1H), 8.87 (bs, 1H), 8.15-8.20 (m, 2H), 7.25-7.36 (m, 3H), 6.96 (s, 1H), 6.16 (bs, 2H), 3.55-3.61 (m, 1H), 2.59-2.68 (m, 4H), 2.03-2.11 (m, 2H), 1.02-1.11 (m, 4H). LCMS: 516.2 [M+H].

Example 58

1-(4-(4-amino-7-cyclobutyl-7H-pyrrolo[2,3-d]pyrimidin-5-yl)-2-fluorophenyl)-3-(5-(1-(trifluoromethyl)cyclopropyl)isoxazol-3-yl)urea

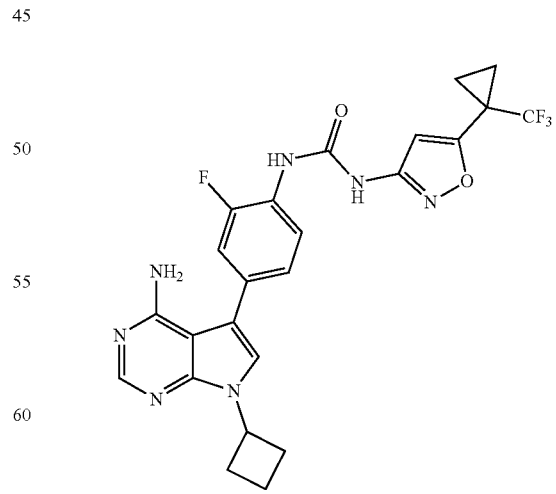

The title compound was obtained following the general procedure for urea formation (Method B), starting from 5-(4-amino-3-fluorophenyl)-7-cyclobutyl-7H-pyrrolo[2,3- d]pyrimidin-4-amine (D24, 0.204 g, 0.686 mmol) and phenyl (5-(1-(trifluoromethyl)cyclopropyl)isoxazol-3-yl)carbamate (E7, 0.214 g, 0.686 mmol), and was obtained as an off-white solid (0.096 g, 27% yield). $^1$H NMR (400 MHz, DMSO-$d_6$) δ=10.01 (bs, 1H), 8.87 (bs, 1H), 8.14-8.20 (m, 2H), 7.66 (s, 1H), 7.28-7.39 (m, 2H), 6.91 (s, 1H), 6.18 (bs, 2H), 5.18-5.23 (m, 1H), 2.39-2.41 (m, 4H), 1.81-1.90 (m, 2H), 1.54-1.55 (m, 4H). LCMS: 516.2 [M+H].

Example 59

1-(6-(4-amino-7-cyclopropyl-7H-pyrrolo[2,3-d]pyrimidin-5-yl)pyridin-3-yl)-3-(3-(1-(trifluoromethyl)cyclopropyl)isoxazol-5-yl)urea

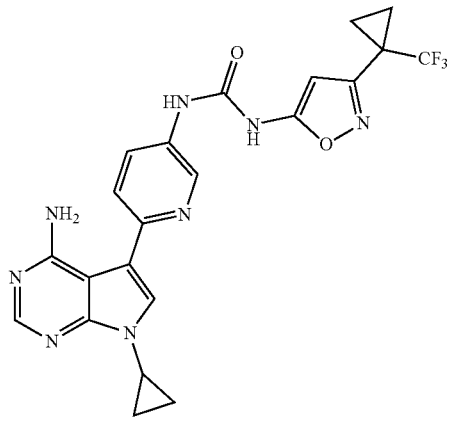 [SMILES: Nc1ncnc2c1c(-c1ccc(NC(=O)Nc3cc(C4(C(F)(F)F)CC4)no3)cn1)cn2C1CC1]

The title compound was obtained following the general procedure for urea formation (Method B), starting from 5-(5-aminopyridin-2-yl)-7-cyclopropyl-7H-pyrrolo[2,3-d]pyrimidin-4-amine (D14, 0.030 g, 0.045 mmol) and phenyl (3-(1-(trifluoromethyl)cyclopropyl)isoxazol-5-yl)carbamate (E6, 0.014 g, 0.045 mmol), and was obtained as an off-white solid (5 mg, 23% yield). $^1$H NMR (400 MHz, DMSO-$d_6$) δ=10.67 (bs, 1H), 9.68 (bs, 1H), 9.12 (s, 1H), 8.59-8.60 (m, 1H), 8.09 (s, 1H), 7.92-8.00 (m, 2H), 7.17 (bs, 2H), 6.20 (s, 1H), 3.58-3.63 (m, 1H), 1.36-1.48 (m, 4H), 1.06-1.10 (m, 4H). LCMS: 485.2 [M+H].

Example 60

1-(4-(4-amino-7-cyclopropyl-7H-pyrrolo[2,3-d]pyrimidin-5-yl)-2,6-difluorophenyl)-3-(5-(1-(trifluoromethyl)cyclopropyl)isoxazol-3-yl)urea

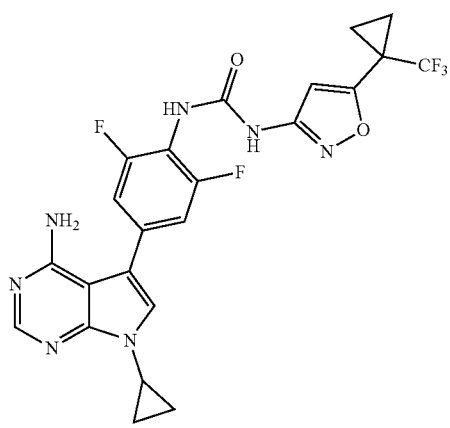 [SMILES: Nc1ncnc2c1c(-c1cc(F)c(NC(=O)Nc3cc(C4(C(F)(F)F)CC4)on3)c(F)c1)cn2C1CC1]

The title compound was obtained following the general procedure for urea formation (Method A), starting from 5-(4-amino-3,5-difluorophenyl)-7-cyclopropyl-7H-pyrrolo[2,3-d]pyrimidin-4-amine (D15, 0.150 g, 0.498 mmol) and phenyl (5-(1-(trifluoromethyl)cyclopropyl)isoxazol-3-yl)carbamate (E7, 0.155 g, 0.498 mmol), and was obtained as a white solid (0.015 g, 6% yield). $^1$H NMR (400 MHz, DMSO-$d_6$) δ=11.47 (bs, 1H), 10.17 (bs, 1H), 8.18 (s, 1H), 7.42 (s, 1H), 7.18-7.22 (m, 2H), 6.82 (s, 1H), 6.27 (bs, 2H), 3.51-3.55 (m, 1H), 1.46-1.51 (m, 4H), 1.04-1.05 (m, 4H). LCMS: 520.2 [M+H].

Example 61

1-(4-(4-amino-7-(2-hydroxyethyl)-7H-pyrrolo[2,3-d]pyrimidin-5-yl)-2-fluorophenyl)-3-(5-(1-(trifluoromethyl)cyclopropyl)isoxazol-3-yl)urea

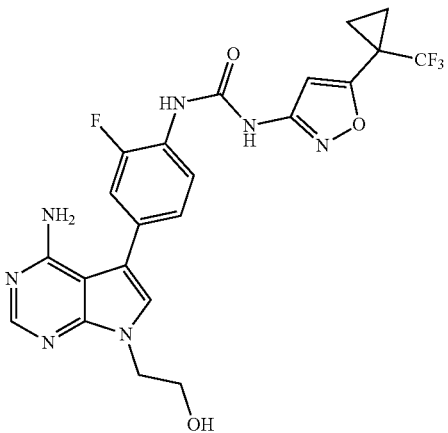 [SMILES: Nc1ncnc2c1c(-c1ccc(NC(=O)Nc3cc(C4(C(F)(F)F)CC4)on3)c(F)c1)cn2CCO]

The title compound was obtained following the general procedure for urea formation (Method B), starting from 2-(4-amino-5-(4-amino-3-fluorophenyl)-7H-pyrrolo[2,3-d]pyrimidin-7-yl)ethan-1-ol (D23, 0.100 g, 0.348 mmol) and phenyl (5-(1-(trifluoromethyl)cyclopropyl)isoxazol-3-yl)carbamate (E7, 0.109 g, 0.348 mmol), and was obtained as a white solid (0.035 mg, 20% yield). $^1$H NMR (400 MHz, CD$_3$OD) δ=8.35 (s, 1H), 8.23-8.27 (m, 1H), 7.58 (s, 1H), 7.32-7.39 (m, 2H), 6.81 (s, 1H), 4.47 (t, J=10.8 Hz, 2H), 3.95-3.98 (m, 2H), 1.49-1.59 (m, 4H). LCMS: 506.2 [M+H].

Example 62

1-(4-(4-amino-1-cyclopropyl-1H-pyrrolo[3,2-c]pyridin-3-yl)-2-fluorophenyl)-3-(3-(1-(trifluoromethyl)cyclopropyl)isoxazol-5-yl)urea Step 1: Synthesis of 1-cyclopropyl-N-(2,4-dimethoxybenzyl)-3-iodo-1H-pyrrolo[3,2-c]pyridin-4-amine

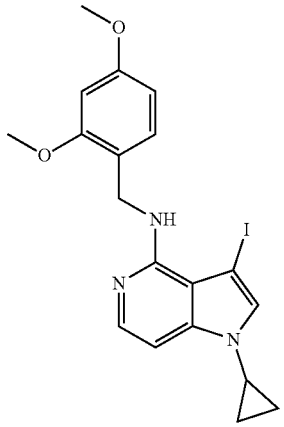 [SMILES: COc1ccc(CNc2nccc3c2c(I)cn3C2CC2)c(OC)c1]

A mixture of 4-chloro-1-cyclopropyl-3-iodo-1H-pyrrolo[3,2-c]pyridine (B9, 0.300 g, 0.942 mmol) and (2,5-dimethoxyphenyl)methanamine (0.429 mL, 2.83 mmol) in n-BuOH (10 mL) was stirred at 110° C. for 12 h. Following completion of the reaction (as indicated by LCMS), the reaction mixture was concentrated under reduced pressure to give crude material which was purified by Isolera (silica gel 230-400 mesh, eluting with 30% EtOAc in petroleum ether). Affording the title product as a yellow gum (0.10 g, 19% yield). LCMS: 450.0 [M+H].

Step 2: Synthesis of 3-(4-amino-3-fluorophenyl)-1-cyclopropyl-N-(2,4-dimethoxybenzyl)-1H-pyrrolo[3,2-c]pyridin-4-amine

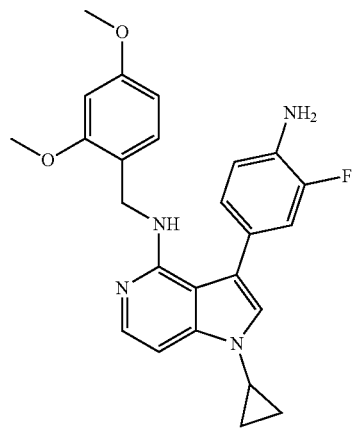 [SMILES: COc1ccc(CNc2nccc3c2c(-c2ccc(N)c(F)c2)cn3C2CC2)c(OC)c1]

The title compound was obtained by following a similar procedure described for Intermediate D8, starting from 1-cyclopropyl-N-(2,4-dimethoxybenzyl)-3-iodo-1H-pyrrolo[3,2-c]pyridin-4-amine (0.190 g, 0.423 mmol) and 2-fluoro-4-(4,4,5,5-tetramethyl-1,3,2-dioxaborolan-2-yl)aniline (0.100 g, 0.423 mmol), and was obtained as a brown gum (0.080 g, 41% yield). LCMS: 433.2 [M+H].

Step 3: Synthesis of 1-(4-(1-cyclopropyl-4-((2,4-dimethoxybenzyl)amino)-1H-pyrrolo[3,2-c]pyridin-3-yl)-2-fluorophenyl)-3-(3-(1-(trifluoromethyl)cyclopropyl)isoxazol-5-yl)urea

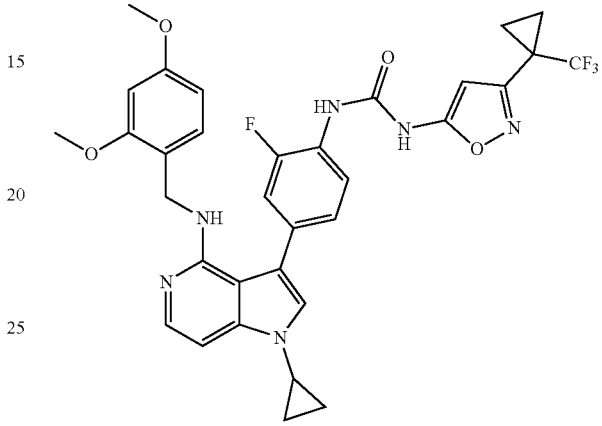

The title compound was obtained following the general procedure for urea formation (Method B), starting from 3-(4-amino-3-fluorophenyl)-1-cyclopropyl-N-(2,4-dimethoxybenzyl)-1H-pyrrolo[3,2-c]pyridin-4-amine (0.080 g, 0.185 mmol) and phenyl (3-(1-(trifluoromethyl)cyclopropyl)isoxazol-5-yl)carbamate (E6, 0.058 g, 0.185 mmol), and was obtained as an off-white solid (0.027 g, 17% yield). LCMS: 651.3 [M+H].

Step 4: Synthesis of 1-(4-(4-amino-1-cyclopropyl-1H-pyrrolo[3,2-c]pyridin-3-yl)-2-fluorophenyl)-3-(3-1-(trifluoromethyl)cyclopropyl)isoxazol-5-yl)urea

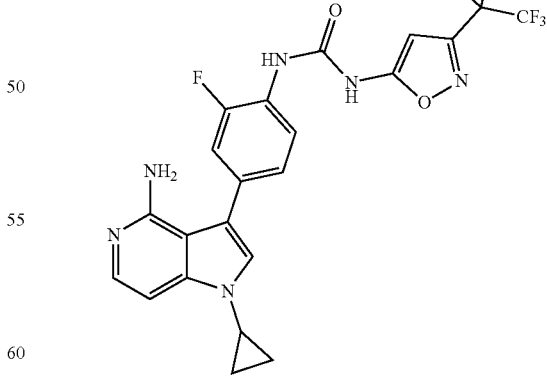

Triethylsilane (4.8 mg, 0.041 mmol) and TFA (4.7 mg, 0.041 mmol) were added to a solution of 1-(4-(1-cyclopropyl-4-((2,4-dimethoxybenzyl)amino)-1H-pyrrolo[3,2-c]pyridin-3-yl)-2-fluorophenyl)-3-(3-(1-(trifluoromethyl)cyclopropyl)isoxazol-5-yl)urea (0.027 g, 0.041 mmol) in DCM (2 mL) at 0° C. and the resulting mixture was stirred at 25° C. for 12 h. Following completion of the reaction (as indicated by LCMS), the reaction mixture was concentrated under reduced pressure to give crude material which was purified by preparative HPLC (eluting with a gradient of 0.1% TFA in water and), affording the title product as an off-white solid (5 mg, 24% yield). $^1$H NMR (400 MHz, CD$_3$OD) δ=8.21-8.25 (m, 1H), 7.64-7.66 (m, 1H), 7.51 (s, 1H), 7.30-7.38 (m, 3H), 6.33 (s, 1H), 3.59-3.62 (m, 1H), 1.39-1.49 (m, 4H), 1.13-1.26 (m, 4H). LCMS: 501.2 [M+H].

Biological Example 1

Biochemical Assay of the Compounds

Representative compounds were tested for inhibitory activity against NEK7 and IL-1p release according to the procedures described above. Results are given in the following table.

TABLE 2

Activity of Representative Compounds

| Compound No. | NEK7 IC$_{50}$ (nM) | IL-1β release IC$_{50}$ (nM) |
|---|---|---|
| 1 | **** | – |
| 2 | ***** | ++++ |
| 3 | ***** | +++ |
| 4 | ***** | – |
| 5 | ***** | ++++ |
| 6 | *** | – |
| 7 | ** | – |
| 8 | ** | – |
| 9 | ***** | +++ |
| 10 | **** | ++++ |
| 11 | *** | – |
| 12 | **** | – |
| 13 | *** | – |
| 14 | **** | ++++ |
| 15 | * | + |
| 16 | * | – |
| 17 | ***** | ++++ |
| 18 | * | – |
| 19 | *** | – |
| 20 | * | – |
| 21 | * | – |
| 22 | * | – |
| 23 | *** | – |
| 24 | ** | – |
| 25 | ** | – |
| 26 | *** | – |
| 27 | ***** | – |
| 28 | **** | – |
| 29 | *** | – |
| 30 | **** | – |
| 31 | *** | – |
| 32 | ***** | – |
| 33 | ***** | – |
| 34 | ***** | ++++ |
| 35 | **** | +++ |
| 36 | ** | – |
| 37 | ***** | ++++ |
| 38 | ** | ++ |
| 39 | ***** | ++++ |
| 40 | * | – |
| 41 | * | – |
| 42 | ** | – |
| 43 | * | – |
| 44 | ** | – |
| 45 | **** | – |
| 46 | ***** | – |
| 47 | ***** | – |
| 48 | * | – |
| 49 | * | – |
| 50 | * | – |
| 51 | ***** | – |

TABLE 2-continued

Activity of Representative Compounds

| Compound No. | NEK7 IC$_{50}$ (nM) | IL-1β release IC$_{50}$ (nM) |
|---|---|---|
| 52 | ***** | – |
| 53 | *** | – |
| 54 | * | – |
| 55 | * | – |
| 56 | *** | – |
| 57 | ***** | – |
| 58 | ** | – |
| 59 | * | – |
| 60 | * | – |
| 61 | ***** | – |
| 62 | * | – |

For NEK7 IC$_{50}$ activity in Table 2:
* IC$_{50}$ greater than 1500 nM
** IC$_{50}$ range from 501-1500 nM
*** IC$_{50}$ range from 301-500 nM
**** IC$_{50}$ range from 151-300 nM
***** IC$_{50}$ less than 150 nM
For IL-1β IC$_{50}$ activity in Table 2:
+ IC$_{50}$ greater than 1000 nM
++ IC$_{50}$ range from 301-500 nM
+++ IC$_{50}$ from 151-300 nM
++++ IC$_{50}$ less than 150 nM
– denotes a value was not determined The various embodiments described above can be combined to provide further 15 embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further 20 embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full 25 scope of equivalents to which such claims are entitled. Accordingly, the claims are not limited by the disclosure.

The invention claimed is:

1. A compound having the following Structure (I):

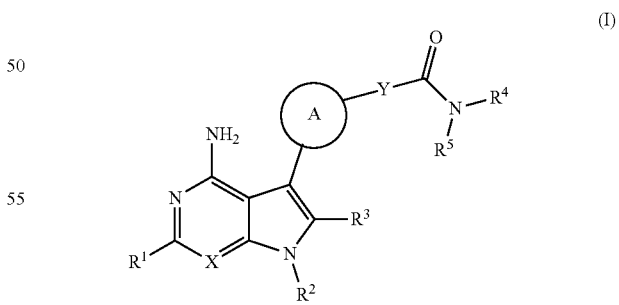

or a pharmaceutically acceptable salt, stereoisomer or prodrug thereof, wherein:

A is $C_6$-$C_{10}$ aryl, $C_3$-$C_{10}$ cycloalkyl, 3-10 membered heterocyclyl or 5-6 membered monocyclic heteroaryl, each of which is optionally substituted with one or more $R^6$;

X is CH or N;

Y is NH;

$R^1$ is H;

$R^2$ is $C_3$-$C_4$ cycloalkyl, $C_3$-$C_8$ heterocyclyl or 5- or 6-membered heteroaryl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl;

$R^3$ is H;

$R^4$ is a heteroaryl selected from oxazolyl, isoxazolyl, 1, 2, 3-oxadiazolyl, 1, 2, 4-oxadiazolyl, 1, 2, 5-oxadiazolyl, 1, 3, 4-oxadiazolyl, 1, 2, 3-triazolyl, 1, 2, 4-triazolyl, thiazolyl, isothiazolyl, 1, 2, 3-thiadiazolyl, 1, 2, 4-thiadiazolyl, 1, 2, 5-thiadiazolyl and 1, 3, 4-thiadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl;

$R^5$ is H; and $R^6$ is, at each occurrence, independently halo, $C_1$-$C_6$ alkyl, $C_1$-$C_6$ alkoxy, cyano, $C_1$-$C_6$ hydroxylalkyl or $C_1$-$C_6$ haloalkyl.

2. The compound of claim 1, wherein $R^2$ is cyclopropyl, cyclobutyl, pyrrolidinyl, piperidinyl, or oxetanyl, each of which is optionally substituted with one more substituent selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3- to 8-membered heterocyclyl.

3. The compound of claim 2, wherein $R^2$ is unsubstituted.

4. The compound of claim 1, wherein $R^2$ has one of the following structures:

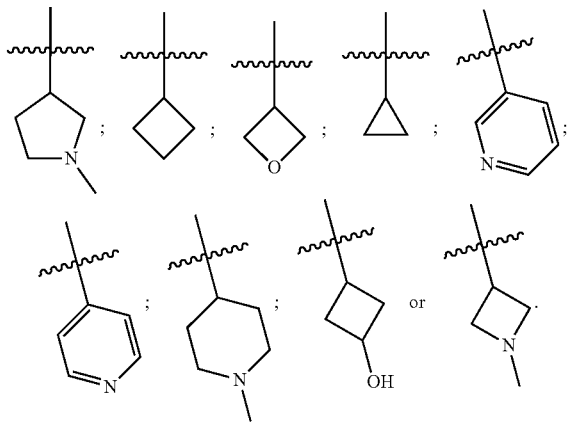

5. The compound of claim 1, wherein $R^4$ is oxazolyl, isoxazolyl, 1, 2, 3-oxadiazolyl, thiazolyl, isothiazolyl, 1,2,4-thiadiazolyl, 1,3,4-thiadiazolyl, 1,2,4-triazolyl or 1, 3, 4-oxadiazolyl, each of which is optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

6. The compound of claim 5, wherein $R^4$ is isoxazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

7. The compound of claim 5, wherein $R^4$ is thiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

8. The compound of claim 5, wherein $R^4$ is isothiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

9. The compound of claim 5, wherein $R^4$ is 1,2,4-thiadiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

10. The compound of claim 5, wherein $R^4$ is 1,3,4-thiadiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

11. The compound of claim 5, wherein $R^4$ is 1,2,4-triazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

12. The compound of claim 5, wherein $R^4$ is 1, 3, 4-oxadiazolyl optionally substituted with one more substituents selected from halo, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, and $C_3$-$C_8$ halocycloalkyl, and combinations thereof.

13. The compound of claim 1, wherein $R^4$ is substituted with $C_1$-$C_6$ alkyl, $C_1$-$C_6$ haloalkyl, $C_3$-$C_8$ cycloalkyl, cyano, aminyl, $C_1$-$C_6$ hydroxylalkyl, $C_1$-$C_6$ cyanoalkyl, 3- to 8-membered heterocyclyl, $C_3$-$C_8$ haloalkylcycloalkyl, $C_3$-$C_8$ aminylalkylcycloalkyl, $C_3$-$C_8$ alkylcycloalkyl, 3- to 8-membered heterocyclylalkyl, 3- to 8-membered alkylheterocyclylcycloalkyl, 3- to 8-membered haloheterocyclylalkyl, or $C_3$-$C_8$ halocycloalkyl, or combinations thereof.

14. The compound of claim 1, wherein $R^4$ has one of the following structures:

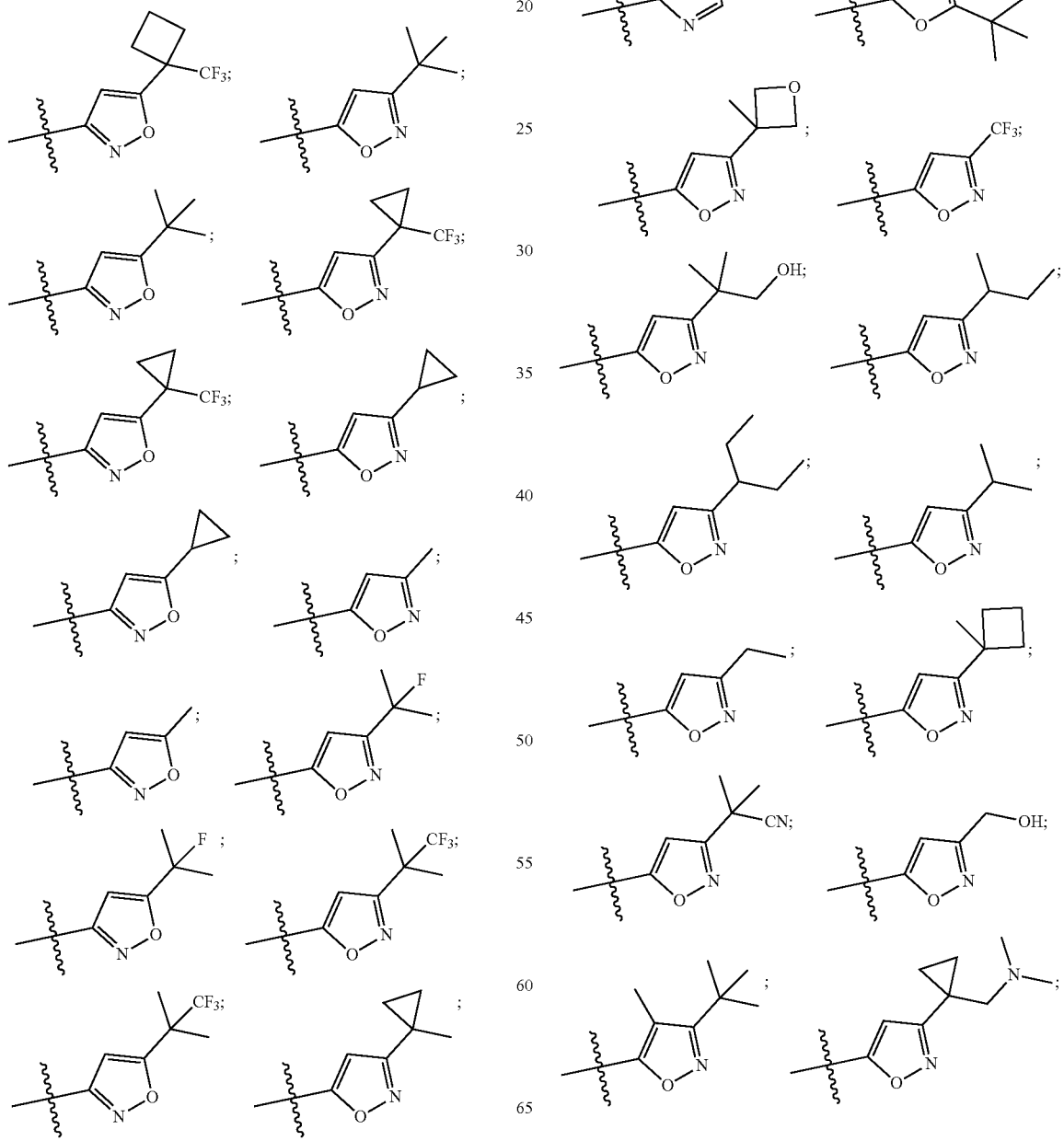

-continued

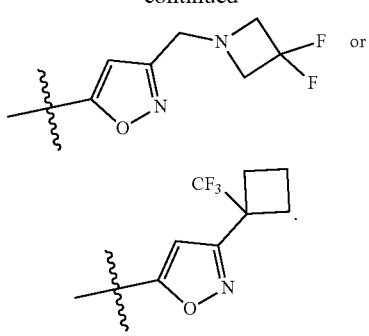

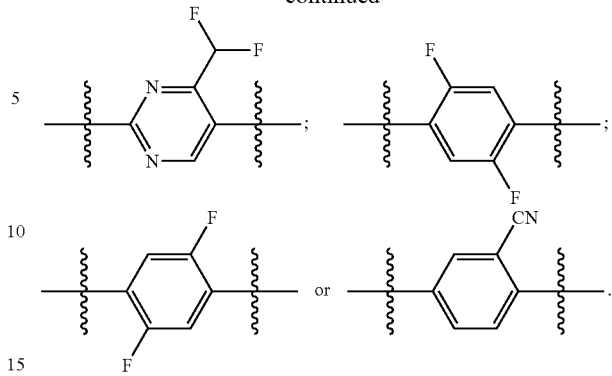

15. The compound of claim 1, wherein A is $C_6$-$C_{10}$ aryl, $C_3$-$C_{10}$ cycloalkyl or 5-6 membered monocyclic heteroaryl, each of which is optionally substituted with one or more $R^6$.

16. The compound of claim 15, wherein A is phenyl.

17. The compound of claim 1, wherein A is unsubstituted.

18. The compound of claim 1, wherein A is substituted with one or more $R^6$.

19. The compound of claim 18, wherein $R^6$ is chloro, fluoro, —CH$_2$CH$_2$OH, cyano, or methoxy.

20. The compound of claim 1, wherein A has one of the following structures:

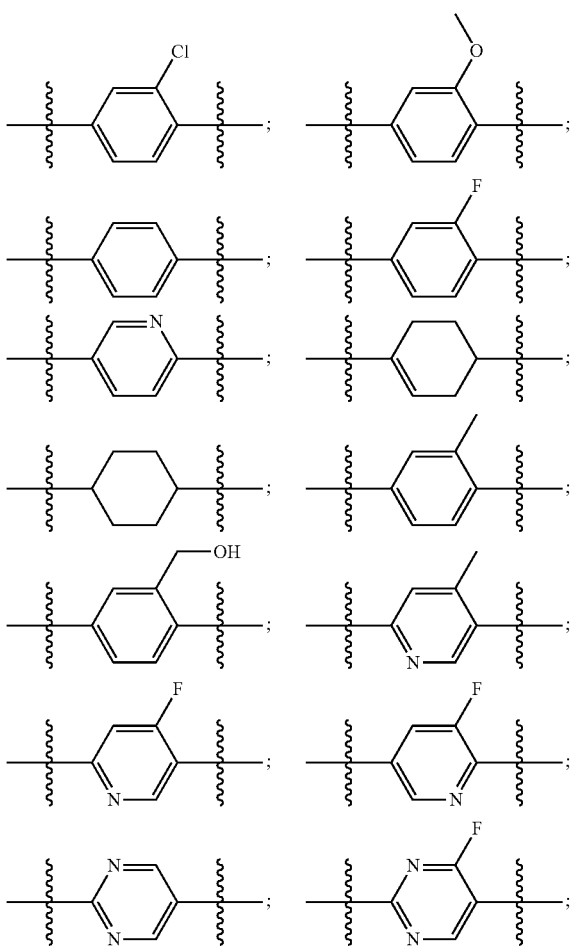

21. The compound of claim 1, wherein the compound has the following Structure (IA):

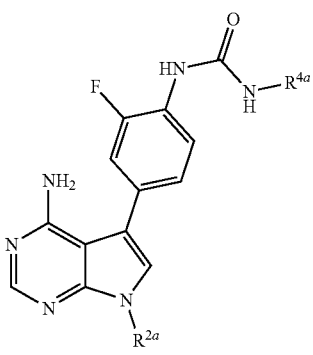

(IA)

or a pharmaceutically acceptable salt, stereoisomer or prodrug thereof, wherein:
$R^{2a}$ is $C_3$-$C_4$ cycloalkyl optionally substituted with one more substituents selected from halo, hydroxyl, cyano, aminyl, $C_1$-$C_6$ alkyl, $C_2$-$C_6$ alkenyl, $C_2$-$C_6$ alkynyl, $C_1$-$C_6$ alkoxy and 3-8 membered heterocyclyl;
$R^{4a}$ is isoxazolyl optionally substituted with one more substituents selected from $C_1$-$C_6$ haloalkyl, $C_3$-$C_8$ cycloalkyl or $C_3$-$C_8$ haloalkylcycloalkyl.

22. The compound of claim 21, wherein $R^{2a}$ has the following structure:

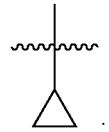

23. The compound of claim 21, wherein $R^{4a}$ has one of the following structures:

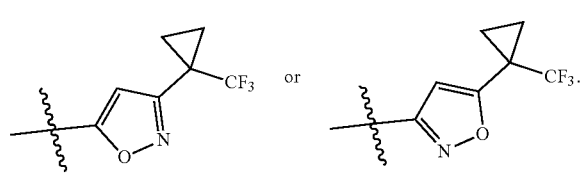 [SMILES: *c1cc(C2(C(F)(F)F)CC2)no1 ; *c1cc(C2(C(F)(F)F)CC2)on1]

24. The compound of claim 1, wherein the compound has one of the following structures:
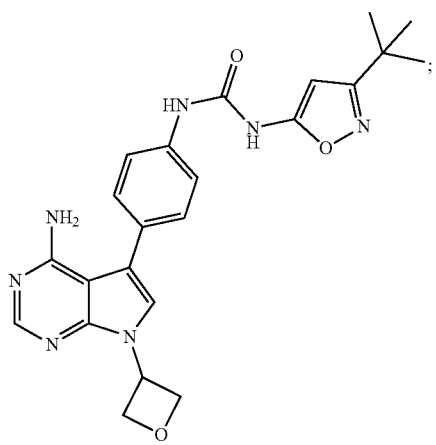
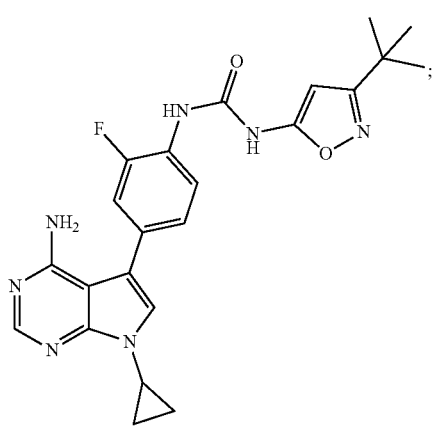
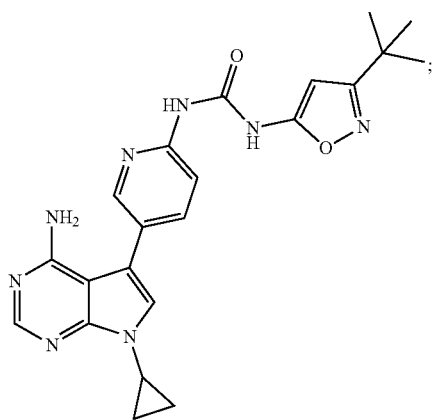
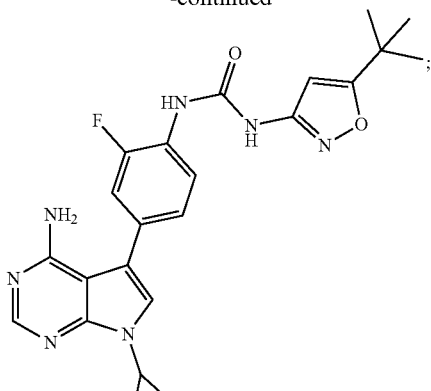
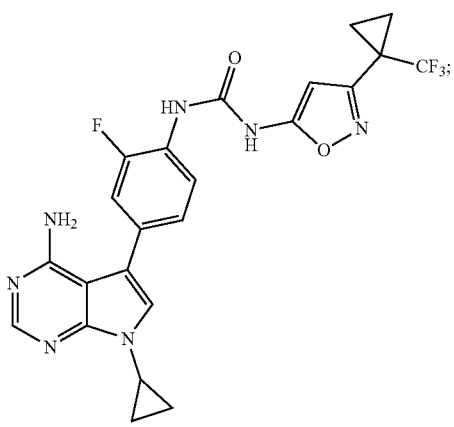
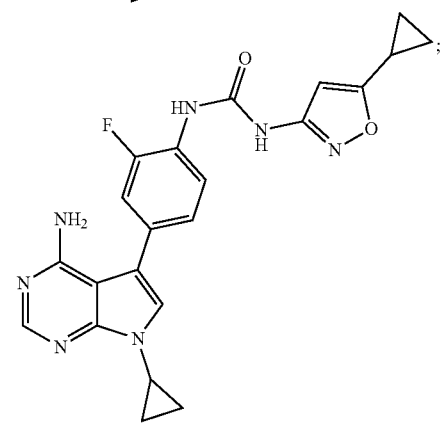
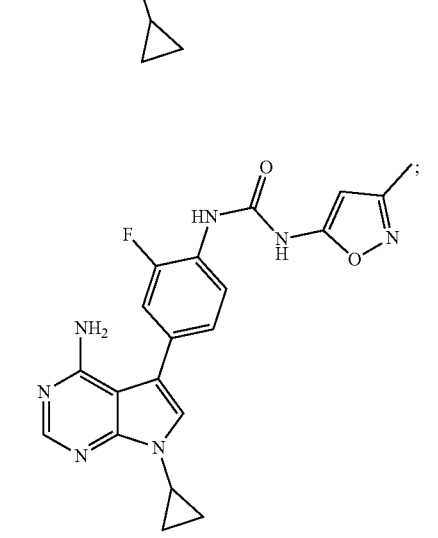

175
-continued
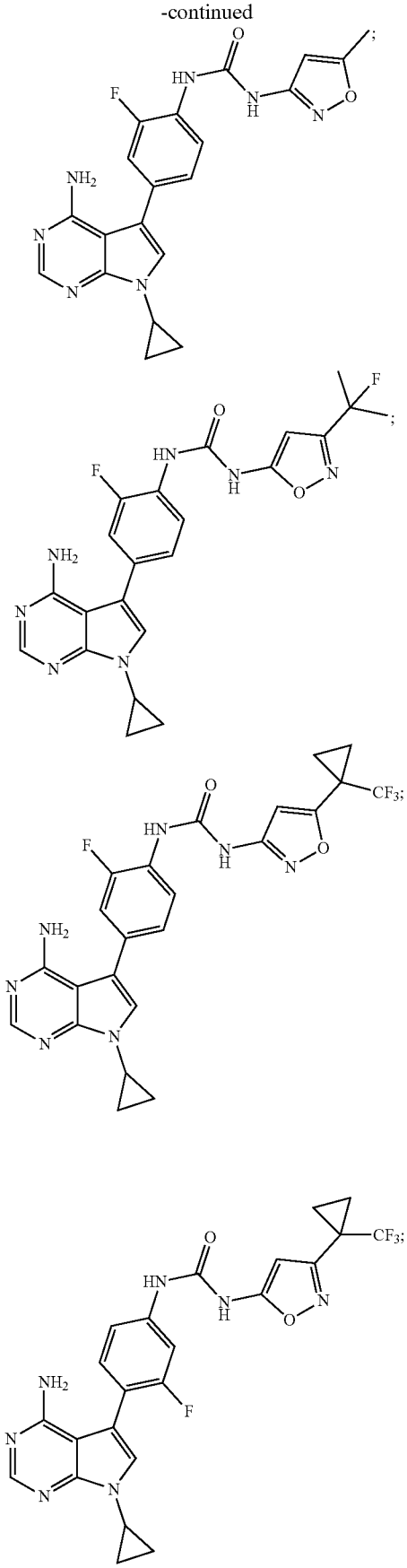
176
-continued
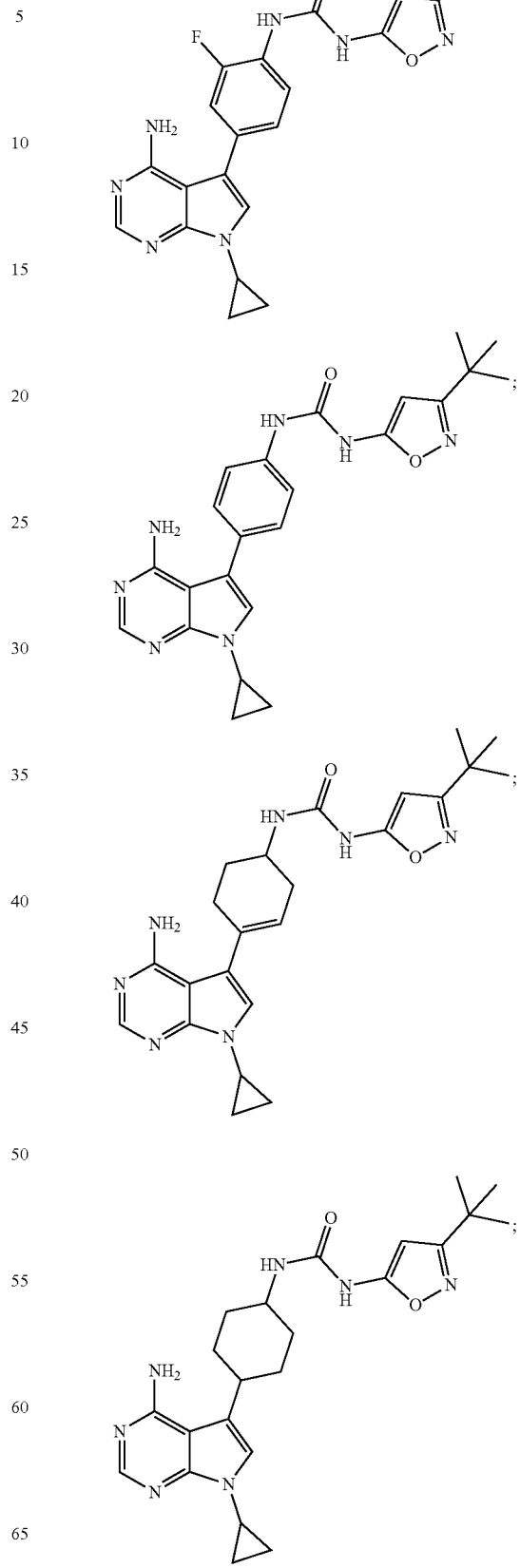

177
-continued
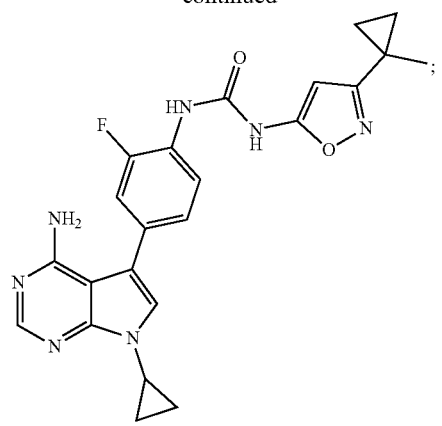
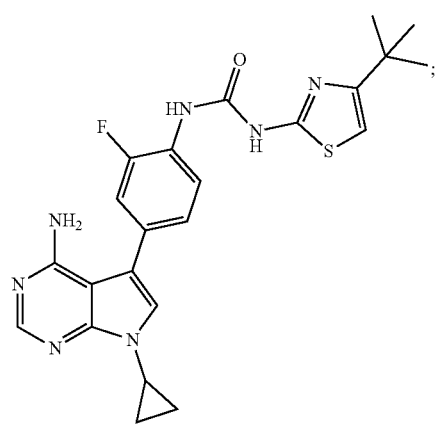
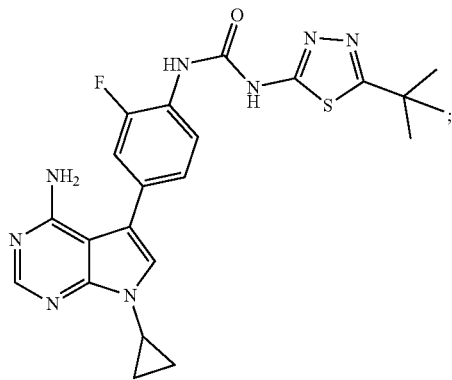
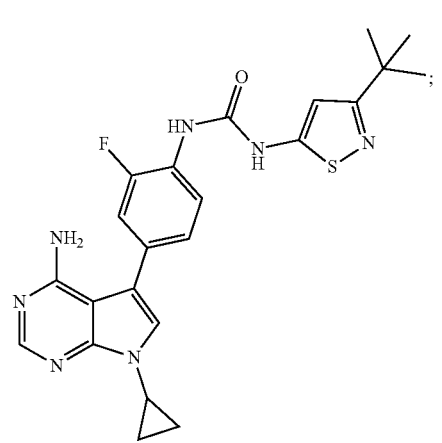
178
-continued
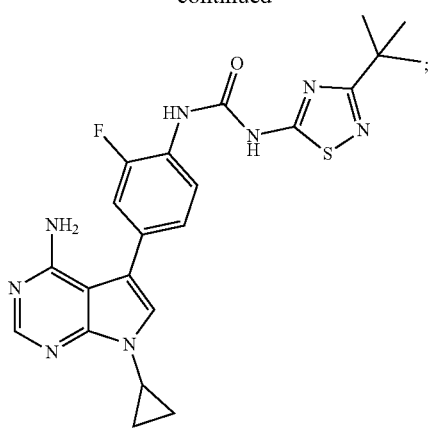
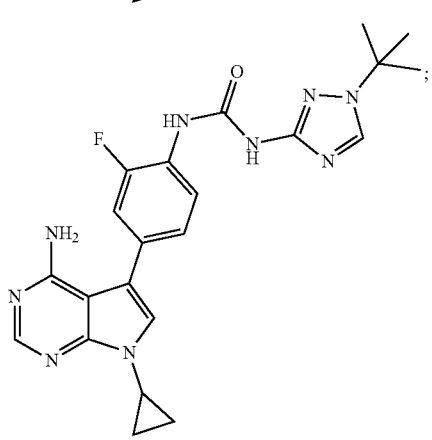
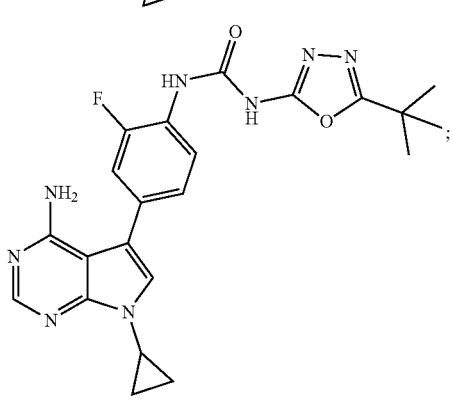
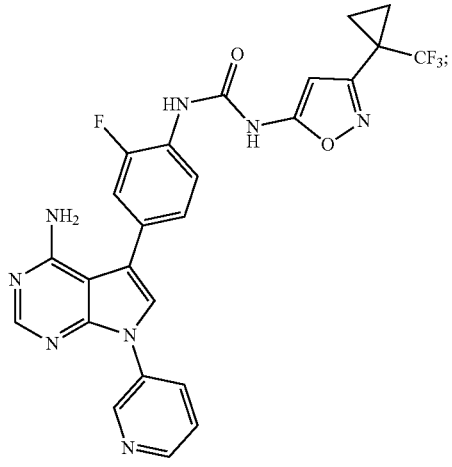

179
-continued
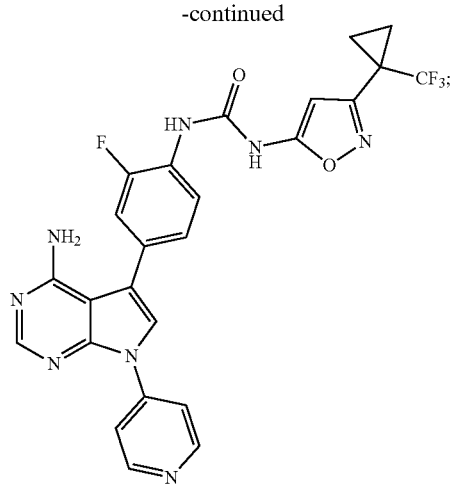
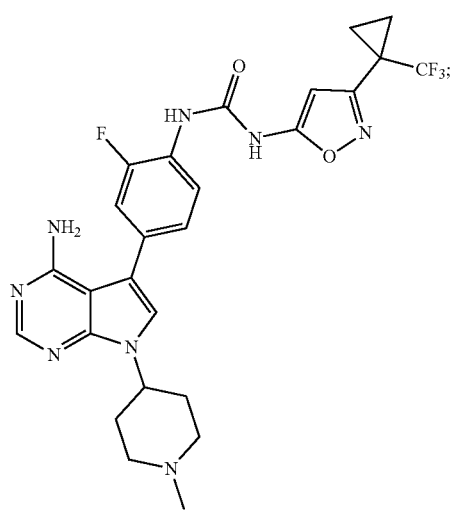
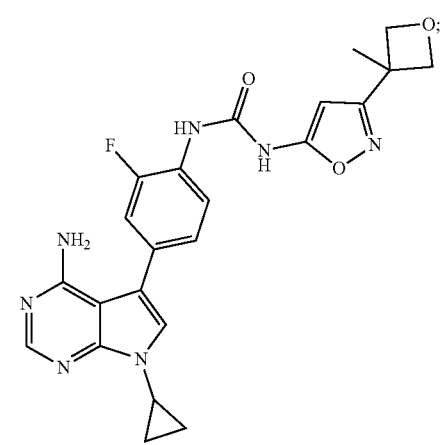
180
-continued
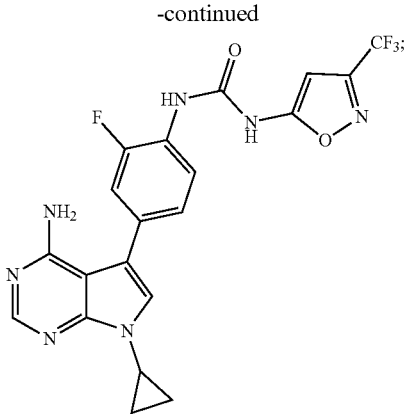
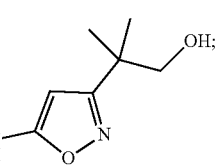
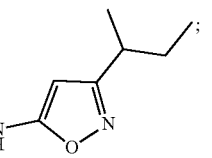
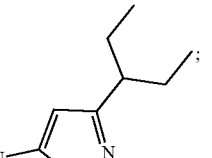

181
-continued
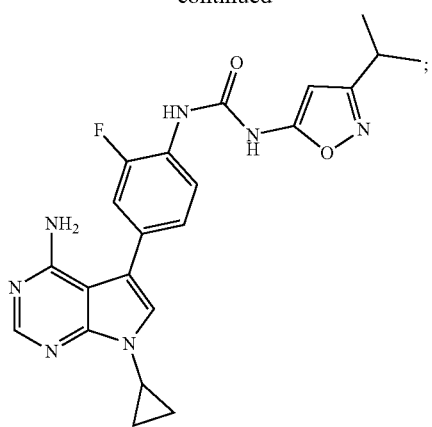
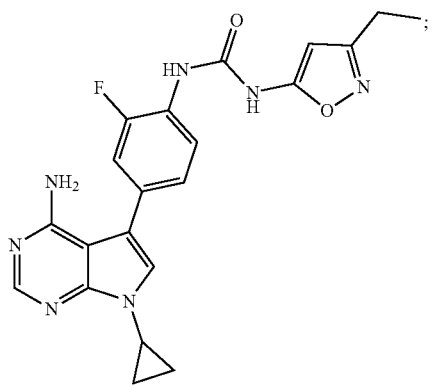
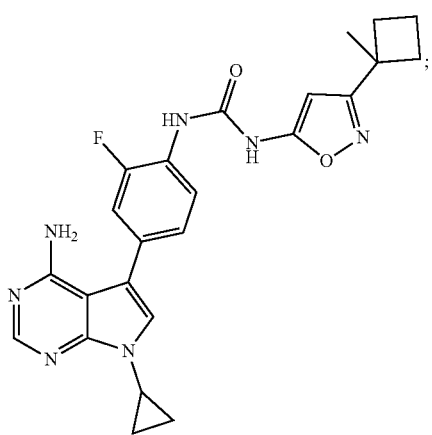
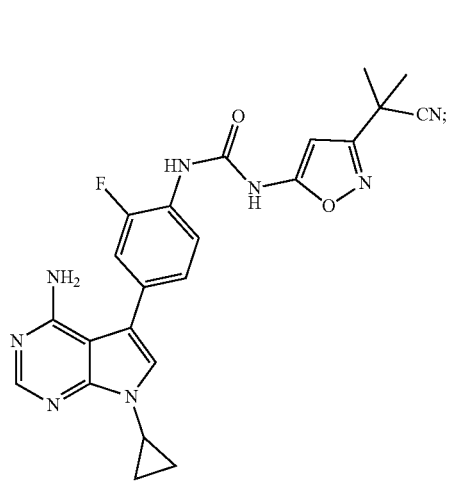
182
-continued
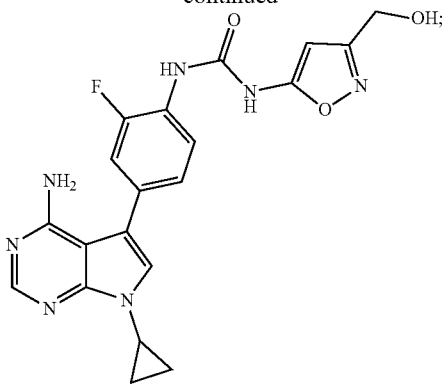
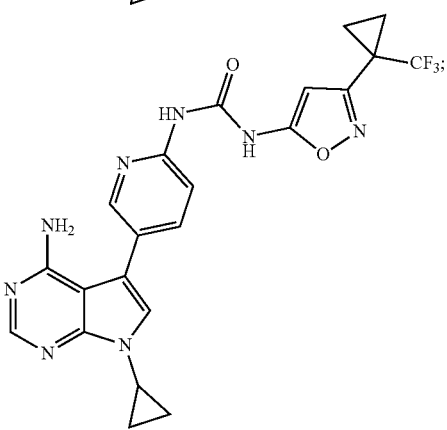
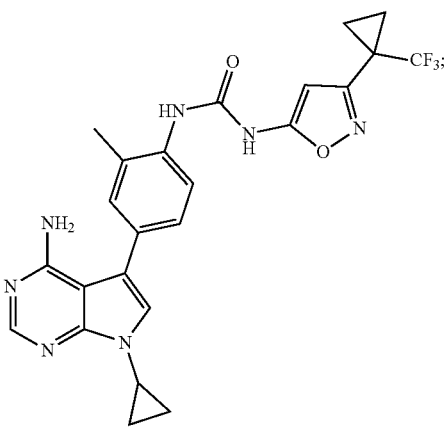
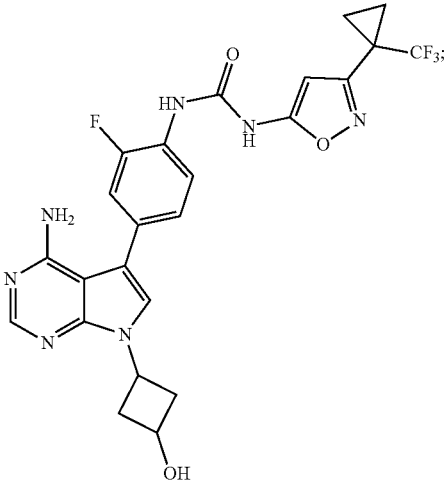

-continued
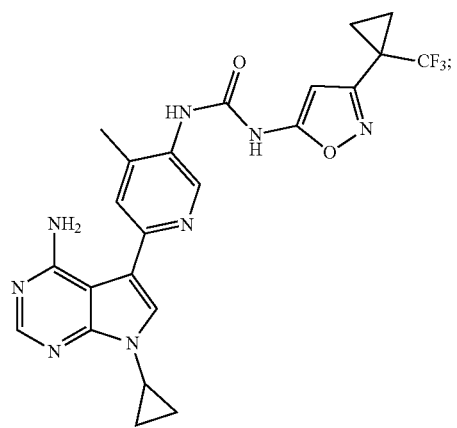
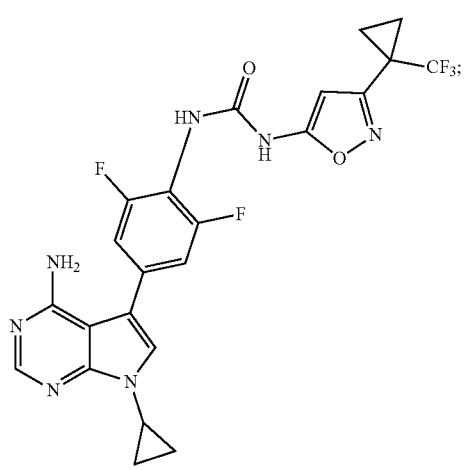
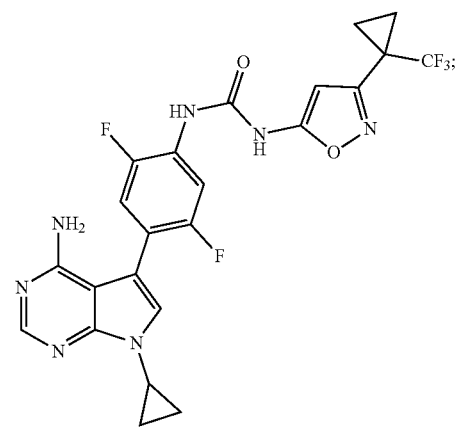
-continued
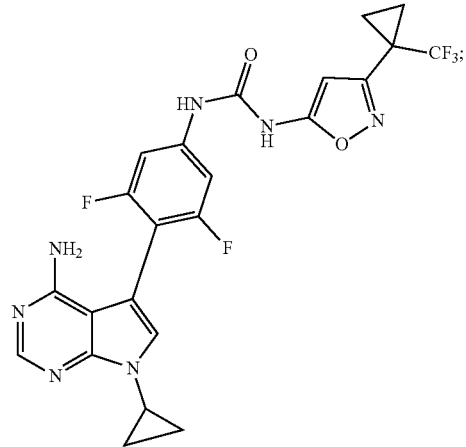
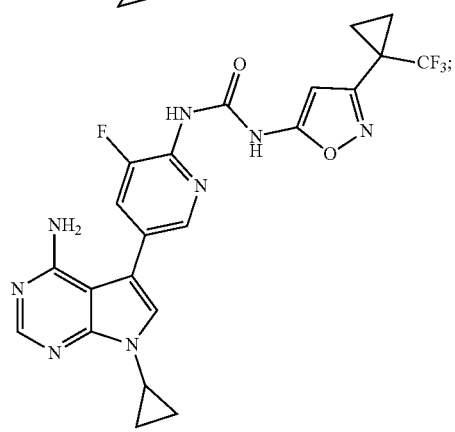
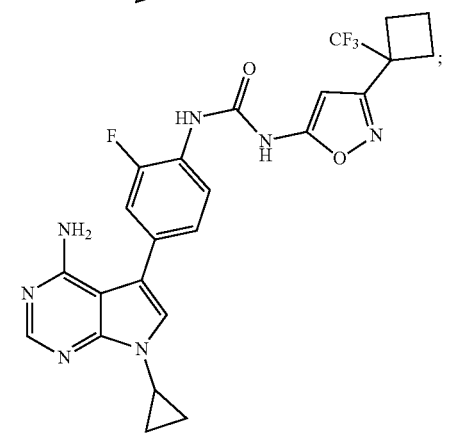
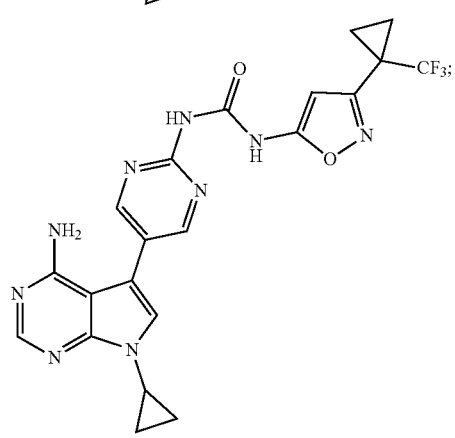

185
-continued
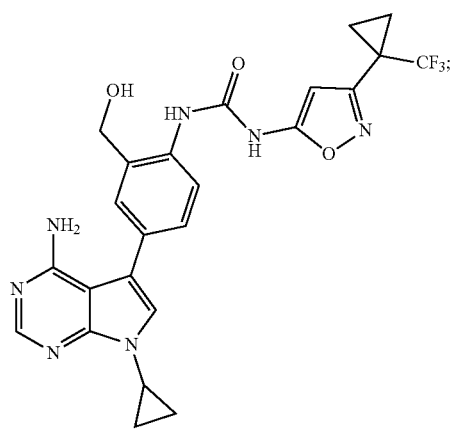
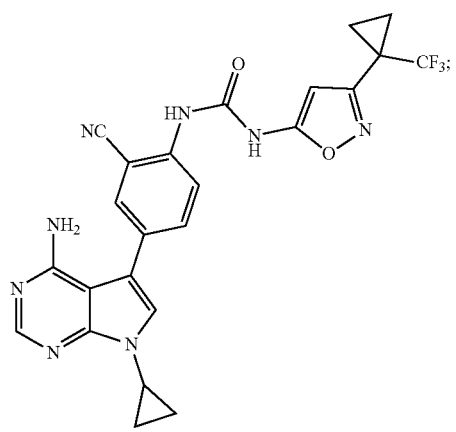
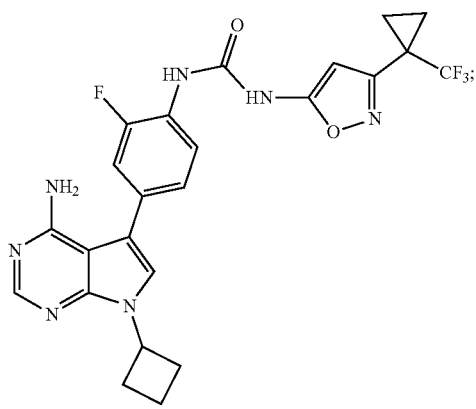
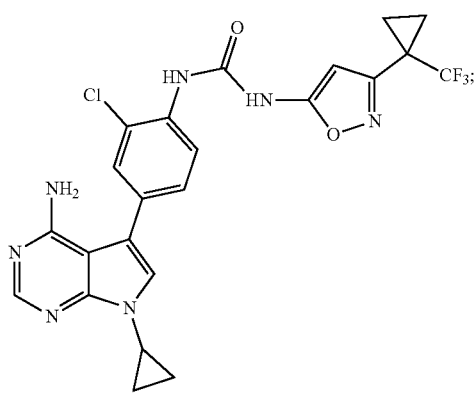
186
-continued
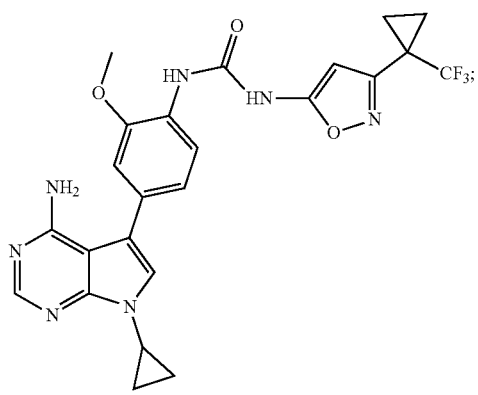
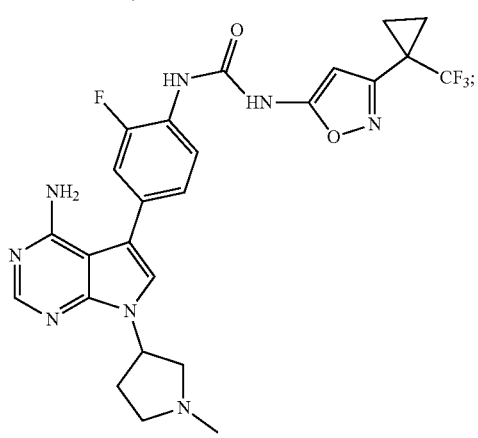
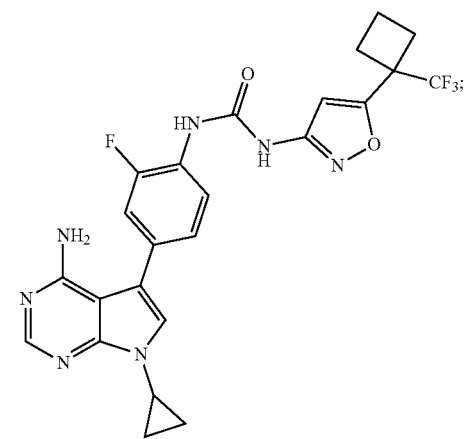
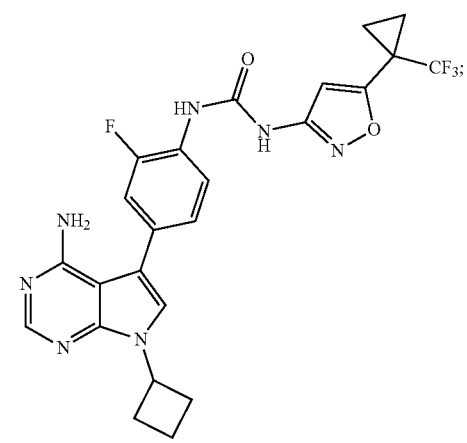

187
-continued

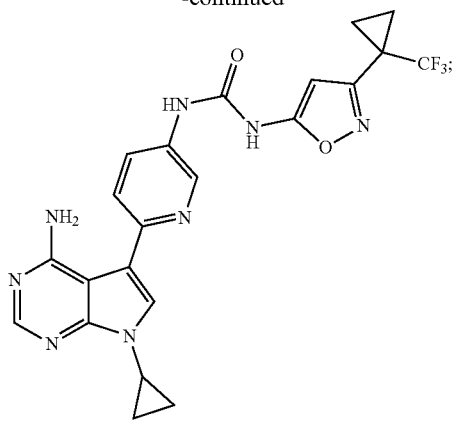

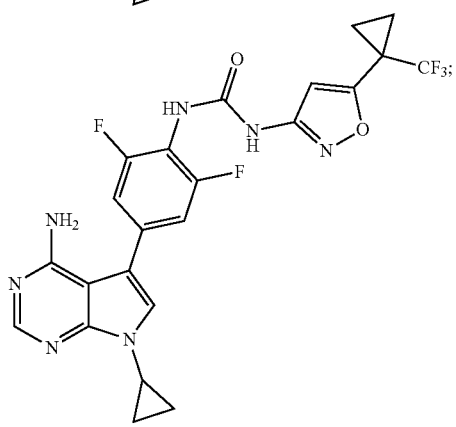

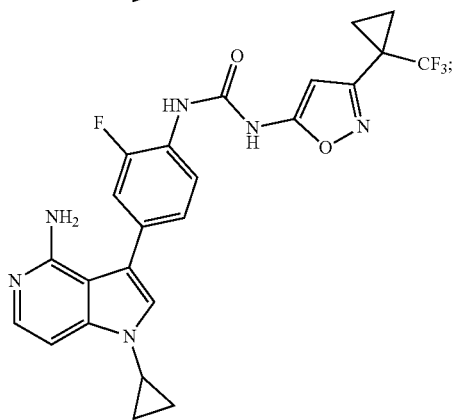

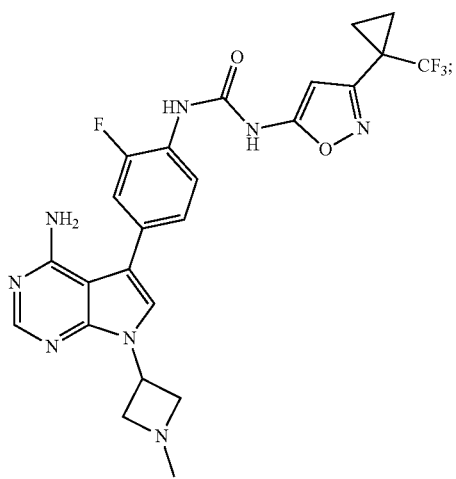

188
-continued

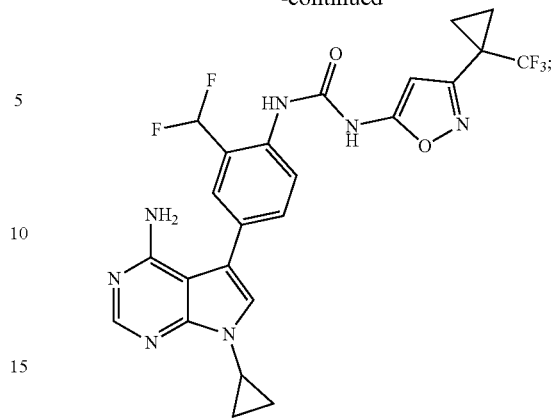

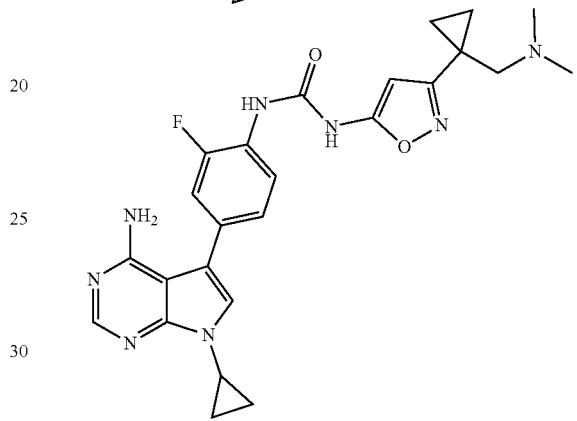

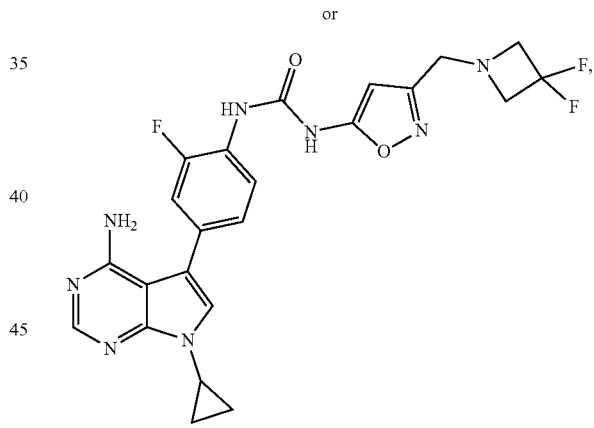

or or a pharmaceutically acceptable salt, stereoisomer, or prodrug thereof.

25. A pharmaceutical composition comprising the compound of claim 1, and a pharmaceutically acceptable carrier, diluent, or excipient.

26. A method of treating a NLRP3-mediated disorder, comprising administering a therapeutically effective amount of a compound of claim 1 to a subject in need thereof wherein the disorder is selected from type II diabetes, atherosclerosis, Alzheimer's disease, fatty liver, asthma, psoriasis, obesity, acute and chronic tissue damage caused by infection, gout, arthritis, macular degeneration, enteritis, hepatitis, peritonitis, silicosis, UV-induced skin sunburn, contact hypersensitivity, sepsis, cancer, neurodegenerative disease, multiple sclerosis, and Muckle-Wells syndrome.

27. A method of treating a NLRP3-mediated disorder, comprising administering a therapeutically effective amount of a compound of claim 1 to a subject in need thereof wherein the disorder is myelodysplastic syndrome (MDS).

* * * * *

UNITED STATES PATENT AND TRADEMARK OFFICE
CERTIFICATE OF CORRECTION

| | | |
|---|---|---|
| PATENT NO. | : 11,161,852 B1 | Page 1 of 1 |
| APPLICATION NO. | : 17/315209 | |
| DATED | : November 2, 2021 | |
| INVENTOR(S) | : David James Bearss et al. | |

It is certified that error appears in the above-identified patent and that said Letters Patent is hereby corrected as shown below:

In the Claims

Column 172, Claim 20, Lines 1-5:

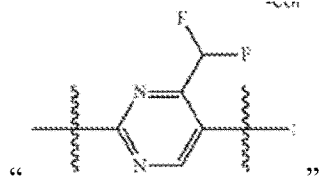

Should read:

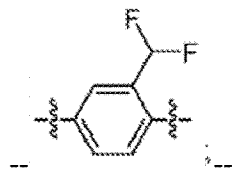

Column 172, Claim 20, Lines 1-5:

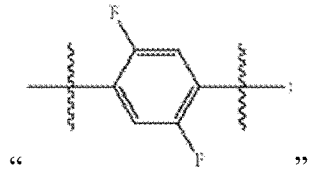

Should read:

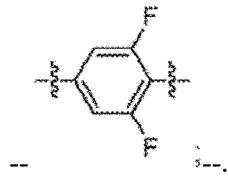

Signed and Sealed this
Twenty-eighth Day of February, 2023

Katherine Kelly Vidal
*Director of the United States Patent and Trademark Office*